(12) United States Patent
Bannister et al.

(10) Patent No.: US 7,501,404 B2
(45) Date of Patent: Mar. 10, 2009

(54) SUBSTITUTED AZETIDINONES

(75) Inventors: Thomas Bannister, Palm Beach Gardens, FL (US); Cassandra Celatka, Hull, MA (US); Nizal S. Chandrakumar, North Grafton, MA (US); Hongfeng Deng, Acton, MA (US); Zihong Guo, Southbury, CT (US); Lei Jin, Wellesley, MA (US); Tsvetelina Lazarova, Brookline, MA (US); Jian Lin, Walpole, MA (US); Scott T. Moe, Marlborough, MA (US); Pamela Nagafuji, Cambridge, MA (US); Manuel Navia, Lexington, MA (US); Amy Ripka, Winthrop, MA (US); Michael J. Rynkiewicz, Boston, MA (US); Kerry L. Spear, Concord, MA (US); James E. Stickler, Milton, MA (US); Roger Xie, Southborough, MA (US)

(73) Assignee: DAIMED, Cambridge, MA (US)

( * ) Notice: Subject to any disclaimer, the term of this patent is extended or adjusted under 35 U.S.C. 154(b) by 51 days.

(21) Appl. No.: 11/398,438

(22) Filed: Apr. 4, 2006

(65) Prior Publication Data

US 2007/0105832 A1    May 10, 2007

Related U.S. Application Data

(60) Provisional application No. 60/668,325, filed on Apr. 4, 2005.

(51) Int. Cl.
| | |
|---|---|
| C07D 205/08 | (2006.01) |
| C07D 205/085 | (2006.01) |
| C07D 401/14 | (2006.01) |
| C07D 401/12 | (2006.01) |
| C07D 401/06 | (2006.01) |
| C07D 403/12 | (2006.01) |
| C07D 403/14 | (2006.01) |
| C07D 403/04 | (2006.01) |
| A61K 31/397 | (2006.01) |
| A61K 31/506 | (2006.01) |
| A61K 31/4427 | (2006.01) |
| A61K 31/41 | (2006.01) |

(52) U.S. Cl. .................. 514/210.02; 514/210.05; 540/200; 540/354; 540/355; 540/360; 540/362; 540/363; 540/364

(58) Field of Classification Search ............. 540/200, 540/355, 360; 514/210.02, 210.15
See application file for complete search history.

(56) References Cited

U.S. PATENT DOCUMENTS

| | | | |
|---|---|---|---|
| 5,037,819 A | 8/1991 | Han et al. | |
| 6,297,233 B1 | 10/2001 | Stein et al. | |
| 6,335,324 B1 | 1/2002 | Bisacchi et al. | |
| 6,344,450 B1 | 2/2002 | Bisacchi et al. | |
| 6,358,960 B1 | 3/2002 | Senokuchi et al. | |
| 6,476,015 B1 * | 11/2002 | Turos et al. ............ | 514/210.15 |
| 2003/0191108 A1 * | 10/2003 | Turos .................... | 514/210.15 |
| 2004/0147502 A1 | 7/2004 | Bisacchi et al. | |
| 2004/0180855 A1 | 9/2004 | Schumacher et al. | |

OTHER PUBLICATIONS

Adlington, "Design and Synthesis of Novel Monocyclic β-Lactam Inhibitors of Prostate Specific Antigen," *Bioorganic & Medicinal Chemistry Letters*, 7(13):1689-1694 (Jul. 8, 1997).
Briggs, "Side Chain Selectivity and Kinetics of Penicillin G Amidase in Acylating Acis-Racemic Beta-Lactam Intermediate in the Synthesis of Loracarbef," *New Journal of Chemistry*, 18(3):425-434 (1994).
Yoshida, "Studies on Monocyclic Beta-Lactam Antibiotics. IV. Synthesis and Antibacterial Activity of (3S,4R)-3-[2-(2-aminothiazol-4-yl)-(Z)-2-(O-substituted oxyimino)acetamido]-4-methyl-1-(1H-tetrazol-5-yl)-2-azetidinones," *J. Antibiotics* (Tokyo), 39(1):90-100 (1986).
Bisacchi et al., Bioorganic & Medicinal Chemistry Letters vol. 14, Issue 9, May 3, 2004, pp. 2227-2231.*

* cited by examiner

*Primary Examiner*—Mark L Berch
(74) *Attorney, Agent, or Firm*—Morgan, Lewis and Bockius, LLP

(57) ABSTRACT

Compounds are provided which have the structure

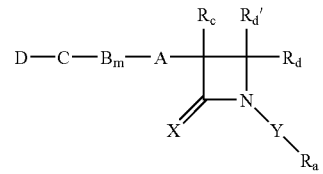

Wherein A, B, C, D, m, Y, Ra, Rc, Rd, and Rd' are as described herein, and which are useful as inhibitors of tryptase, thrombin, trypsin, Factor Xa, Factor VIIa, Factor XIa, and urokinase-type plasminogen activator and may be employed in preventing and/or treating asthma, chronic asthma, allergic rhinitis, and thrombotic disorders.

17 Claims, 136 Drawing Sheets

FIG. 1B

| | | | | | |
|---|---|---|---|---|---|
| A11 | 2-aminopyridine-4-C(O)NH- | H | -C(O)OH | H | -C(O)CH2-phenyl |
| A12 | 2-aminopyridine-4-C(O)NH- | H | -C(O)OH | H | -C(O)N(H)-CH(CH3)-phenyl (S) |
| A13 | H2N-C(=NH)-NH-CH(R5)-C(O)- | H | -C(O)OH | H | -(CH2)3-phenyl |
| A14 | H2N-C(=NH)-NH-CH(R5)-C(O)- | H | -C(O)OH | H | -C(O)-CH2CH2-phenyl |
| A15 | H2N-C(=NH)-NH-CH(R5)-C(O)- | H | -C(O)OH | H | -CH2CH2-phenyl |
| A16 | H2N-C(=NH)-NH-CH(R5)-C(O)- | H | -C(O)OH | H | -C(O)-CH2-phenyl |
| A17 | 2-aminopyridine-4-CH2-NH- | H | -C(O)O-ethyl | H | -(CH2)3-phenyl |
| A18 | 2-aminopyridine-4-CH2-NH- | H | -C(O)O-ethyl | H | -C(O)CH2CH2-phenyl |
| A19 | 2-aminopyridine-4-CH2-NH- | H | -C(O)O-ethyl | H | -CH2CH2-phenyl |
| A20 | 2-aminopyridine-4-CH2-NH- | H | -C(O)O-ethyl | H | -C(O)CH2-phenyl |
| A21 | 2-aminopyridine-4-CH2- | H | -C(O)O-ethyl | H | -(CH2)3-phenyl |
| A22 | 2-aminopyridine-4-CH2- | H | -C(O)O-ethyl | H | -C(O)CH2CH2-phenyl |
| A23 | 2-aminopyridine-4-CH2- | H | -C(O)O-ethyl | H | -CH2CH2-phenyl |

FIG. 1C

| | | | | | |
|---|---|---|---|---|---|
| A24 | 2-aminopyridin-4-ylmethyl | H | ethyl ester | H | benzyl ketone |
| A25 | 2-aminoisonicotinamide-N-yl | H | ethyl ester | H | 3-phenylpropyl |
| A26 | 2-aminoisonicotinamide-N-yl | H | ethyl ester | H | 3-phenylpropanone |
| A27 | 2-aminoisonicotinamide-N-yl | H | ethyl ester | H | 2-phenylethyl |
| A28 | 2-aminoisonicotinamide-N-yl | H | ethyl ester | H | benzyl ketone |
| A29 | 2-aminoisonicotinamide-N-yl | H | ethyl ester | H | (S)-N-(1-phenylethyl)amide |
| A30 | guanidino-CHR5-C(O)- | H | ethyl ester | H | 3-phenylpropyl |
| A31 | guanidino-CHR5-C(O)- | H | ethyl ester | H | 3-phenylpropanone |
| A32 | guanidino-CHR5-C(O)- | H | ethyl ester | H | 2-phenylethyl |
| A33 | guanidino-CHR5-C(O)- | H | ethyl ester | H | benzyl ketone |
| A34 | (2-aminopyridin-4-yl)methylamino | H | cyclobutyl ester | H | 3-phenylpropyl |
| A35 | (2-aminopyridin-4-yl)methylamino | H | cyclobutyl ester | H | 3-phenylpropanone |
| A36 | (2-aminopyridin-4-yl)methylamino | H | cyclobutyl ester | H | 2-phenylethyl |

FIG. 1D

| | | | | | |
|---|---|---|---|---|---|
| A50 |  | H |  | H |  |
| A51 |  | H |  | H |  |
| A52 |  | H |  | H |  |
| A53 |  | H |  | H |  |
| A54 |  | H |  | H |  |
| A55 |  | H |  | H |  |
| A56 |  | H |  | H |  |
| A57 |  | H |  | H |  |
| A58 |  | H |  | H |  |
| A59 |  | H |  | H |  |
| A60 |  | H |  | H |  |
| A61 |  | H |  | H |  |

| | | | | | |
|---|---|---|---|---|---|
| A75 | 2-aminopyridin-4-yl-CH₂– | H | –CH₂COOH | H | –C(O)CH₂-phenyl |
| A76 | 2-amino-pyridine-4-carboxamide | H | –CH₂COOH | H | –(CH₂)₃-phenyl |
| A77 | 2-amino-pyridine-4-carboxamide | H | –CH₂COOH | H | –C(O)CH₂CH₂-phenyl |
| A78 | 2-amino-pyridine-4-carboxamide | H | –CH₂COOH | H | –(CH₂)₂-phenyl |
| A79 | 2-amino-pyridine-4-carboxamide | H | –CH₂COOH | H | –C(O)CH₂-phenyl |
| A80 | 2-amino-pyridine-4-carboxamide | H | –CH₂COOH | H | –C(O)NH–CH(CH₃)-phenyl |
| A81 | guanidino-CH(R⁵)-C(O)NH– | H | –CH₂COOH | H | –(CH₂)₃-phenyl |
| A82 | guanidino-CH(R⁵)-C(O)NH– | H | –CH₂COOH | H | –C(O)CH₂CH₂-phenyl |
| A83 | guanidino-CH(R⁵)-C(O)NH– | H | –CH₂COOH | H | –(CH₂)₂-phenyl |
| A84 | guanidino-CH(R⁵)-C(O)NH– | H | –CH₂COOH | H | –C(O)CH₂-phenyl |
| A85 | 2-aminopyridin-4-yl-CH₂NH– | H | H | H | –(CH₂)₃-phenyl |
| A86 | 2-aminopyridin-4-yl-CH₂NH– | H | H | H | –C(O)CH₂CH₂-phenyl |
| A87 | 2-aminopyridin-4-yl-CH₂NH– | H | H | H | –(CH₂)₂-phenyl |

| | | | | | |
|---|---|---|---|---|---|
| A88 |  | H | H | H |  |
| A89 |  | H | H | H |  |
| A90 |  | H | H | H |  |
| A91 |  | H | H | H |  |
| A92 |  | H | H | H |  |
| A93 |  | H | H | H |  |
| A94 |  | H | H | H |  |
| A95 |  | H | H | H |  |
| A96 |  | H | H | H |  |
| A97 |  | H | H | H |  |
| A98 |  | H | H | H |  |
| A99 |  | H | H | H |  |

| | | | | | |
|---|---|---|---|---|---|
| A113 | pyridine-CONH- with H₂N on pyridine | CH₃ | H | H | -C(O)-CH₂-phenyl |
| A114 | pyridine-CONH- with H₂N on pyridine | CH₃ | H | H | -C(O)-NH-CH(CH₃)-phenyl (S) |
| A115 | H₂N-C(=NH)-NH-CH(R⁵)-C(O)- | CH₃ | H | H | -(CH₂)₃-phenyl |
| A116 | H₂N-C(=NH)-NH-CH(R⁵)-C(O)- | CH₃ | H | H | -C(O)-CH₂-CH₂-phenyl |
| A117 | H₂N-C(=NH)-NH-CH(R⁵)-C(O)- | CH₃ | H | H | -CH₂-CH₂-phenyl |
| A118 | H₂N-C(=NH)-NH-CH(R⁵)-C(O)- | CH₃ | H | H | -C(O)-CH₂-phenyl |

FIG. 1K

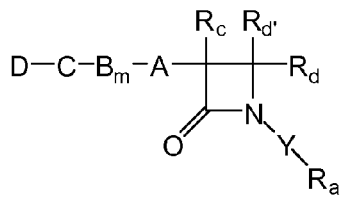

| Index | DCB$_m$A | R$_c$ | R$_d$ | R$_{d'}$ | Y-R$_a$ |
|---|---|---|---|---|---|
| A119 | 2-amino-pyridin-4-yl-CH$_2$ | H | -CH$_2$CH$_2$-NH-SO$_2$-CH$_3$ | H | -C(O)-NH-CH(Ph)- |
| A120 | 2-amino-pyridin-4-yl-CH$_2$ | H | -CH$_2$CH$_2$-NH-SO$_2$-(4-methylphenyl) | H | -C(O)-NH-CH(Ph)- |
| A121 | 2-amino-pyridin-4-yl-CH$_2$ | H | -CH$_2$CH$_2$-NH-SO$_2$-(4-fluorophenyl) | H | -C(O)-NH-CH(Ph)- |
| A122 | 2-amino-pyridin-4-yl-CH$_2$ | H | -CH$_2$CH$_2$-NH-SO$_2$-(4-methoxyphenyl) | H | -C(O)-NH-CH(Ph)- |
| A123 | 2-amino-pyridin-4-yl-CH$_2$ | H | -CH$_2$CH$_2$-NH-CH$_2$-Ph | H | -C(O)-NH-CH(Ph)- |
| A124 | 2-amino-pyridin-4-yl-CH$_2$ | H | -CH$_2$CH$_2$-NH-Et | H | -C(O)-NH-CH(Ph)- |
| A125 | 2-amino-pyridin-4-yl-CH$_2$ | H | -CH$_2$CH$_2$-NH-C(O)-CH$_3$ | H | -C(O)-NH-CH(Ph)- |
| A126 | 2-amino-pyridin-4-yl-CH$_2$ | H | -CH$_2$CH$_2$-NH-C(O)-Ph | H | -C(O)-NH-CH(Ph)- |
| A127 | 2-amino-pyridin-4-yl-CH$_2$ | H | -CH$_2$CH$_2$-NH-C(O)-NH-Ph | H | -C(O)-NH-CH(Ph)- |

FIG. 1L

| A140 |  | CH₃ |  | H |  |
| A141 |  | CH₃ |  | H |  |
| A142 |  | CH₃ |  | H |  |
| A143 |  | CH₃ |  | H |  |
| A144 |  | H |  | H |  |
| A145 |  | H |  | H |  |
| A146 |  | H |  | H |  |
| A147 |  | H |  | H |  |
| A148 |  | CH₃ |  | H |  |
| A149 |  | CH₃ |  | H |  |
| A150 |  | CH₃ |  | H |  |
| A151 |  | CH₃ |  | H |  |

| A152 |  | H |  | H |  |
| A153 |  | H |  | H |  |
| A154 |  | H |  | H |  |
| A155 |  | H |  | H |  |

| Index | DCBmA | Rc | Rd | Rd' | Y-Ra |
|---|---|---|---|---|---|
| A156 | imidazole-NH2, N=CH- | H | -COOH | H | -C(O)NH-CH(Ph) |
| A157 | imidazole-NH2, N=CH- | CH3 | -COOH | H | -C(O)NH-CH(Ph) |
| A158 | imidazole-NH2, N=CH- | H | -COOH | H | -C(O)NH-CH(Ph) |
| A159 | imidazole-NH2, N=CH- | H | -COOH | H | -C(O)NH-CH(Ph) |
| A160 | imidazole-NH2, N=CH- | H | -COOH | H | -C(O)NH-CH(Ph) |
| A161 | imidazole-NH2, N=CH- | CH3 | -COOH | CH3 | -C(O)NH-CH(Ph) |
| A162 | imidazole-NH2, N=CH- | H | -C(O)OEt | H | -C(O)NH-CH(Ph) |
| A163 | imidazole-NH2, N=CH- | H | -C(O)OEt | H | -C(O)NH-CH(Ph) |
| A164 | imidazole-NH2, N=CH- | H | -C(O)OEt | H | -C(O)NH-CH(Ph) |

| | | | | | | |
|---|---|---|---|---|---|---|
| A165 |  | H |  | H |  |
| A166 |  | H |  | H |  |
| A167 |  | H |  | H |  |
| A168 |  | H |  | H |  |
| A169 |  | CH₃ |  | H |  |
| A170 |  | H |  | H |  |
| A171 |  | H |  | H |  |
| A172 |  | H |  | H |  |
| A173 |  | CH₃ |  | H |  |
| A174 |  | H |  | H |  |
| A175 |  | H |  | H |  |
| A176 |  | H |  | H |  |

| | | | | | |
|---|---|---|---|---|---|
| A177 |  | CH₃ |  | H |  |
| A178 |  | H |  | H |  |
| A179 |  | CH₃ |  | H |  |
| A180 |  | H |  | H |  |
| A181 |  | CH₃ |  | H |  |
| A182 |  | H |  | H |  |
| A183 |  | H |  | H |  |
| A184 |  | H |  | H |  |
| A185 |  | CH₃ |  | H |  |
| A186 |  | H |  | H |  |
| A187 |  | H |  | H |  |

| | | | | | |
|---|---|---|---|---|---|
| A210 | HN-C(=NH)-NH-O-CH2CH2- (guanidinyloxyethyl) | H | -C(=O)-O-CH2CH3 | H | -C(=O)-NH-CH(phenyl) (R) |
| A211 | HN-C(=NH)-NH-O-CH2CH2- | H | -C(=O)-O-CH2-C(CH3)3 | H | -C(=O)-NH-CH(phenyl) (R) |
| A212 | HN-C(=NH)-NH-O-CH2CH2- | H | -C(=O)-O-cyclopentyl | H | -C(=O)-NH-CH(phenyl) (R) |
| A213 | HN-C(=NH)-NH-O-CH2CH2- | H | -C(=O)-O-cyclopentyl | H | -C(=O)-NH-CH(phenyl) (R) |
| A214 | HN-C(=NH)-NH-O-CH2CH2- | H | -C(=O)-O-cyclopentyl | H | -C(=O)-NH-CH(phenyl) (R) |
| A215 | HN-C(=NH)-NH-O-CH2CH2- | CH3 | -C(=O)-O-cyclopentyl | H | -C(=O)-NH-CH(phenyl) (R) |
| A216 | HN-C(=NH)-NH-O-CH2CH2- | H | -C(=O)-O-cyclobutyl | H | -C(=O)-NH-CH(phenyl) (R) |
| A217 | HN-C(=NH)-NH-O-CH2CH2- | H | -C(=O)-O-cyclobutyl | H | -C(=O)-NH-CH(phenyl) (R) |
| A218 | HN-C(=NH)-NH-O-CH2CH2- | H | -C(=O)-O-cyclobutyl | H | -C(=O)-NH-CH(phenyl) (R) |
| A219 | HN-C(=NH)-NH-O-CH2CH2- | CH3 | -C(=O)-O-cyclobutyl | H | -C(=O)-NH-CH(phenyl) (R) |
| A220 | HN-C(=NH)-NH-O-CH2CH2- | H | -C(=O)-O-CH(CH3)2 | H | -C(=O)-NH-CH(phenyl) (R) |
| A221 | HN-C(=NH)-NH-O-CH2CH2- | H | -C(=O)-O-CH(CH3)2 | H | -C(=O)-NH-CH(phenyl) (R) |

| | | | | | |
|---|---|---|---|---|---|
| A234 | HN-C(=NH)-NH-O-CH2CH2- (guanidine-O-ethyl) | H | morpholine-N-C(=O)- | H | -C(=O)-NH-CH(CH3)-Ph (R) |
| A235 | HN-C(=NH)-NH-O-CH2CH2- | CH3 | morpholine-N-C(=O)- | H | -C(=O)-NH-CH(CH3)-Ph (R) |
| A236 | HN-C(=NH)-NH-O-CH2CH2- | H | -CH2-C(=O)-OH | H | -C(=O)-NH-CH(CH3)-Ph (R) |
| A237 | HN-C(=NH)-NH-O-CH2CH2- | CH3 | -CH2-C(=O)-O-Et | H | -C(=O)-NH-CH(CH3)-Ph (R) |
| A238 | HN-C(=NH)-NH-O-CH2CH2- | H | -CH2-C(=O)-N(Et)2 | H | -C(=O)-NH-CH(CH3)-Ph (R) |
| A239 | HN-C(=NH)-NH-O-CH2CH2- | H | -CH2-C(=O)-N(Et)2 | H | -C(=O)-NH-CH(CH3)-Ph (R) |
| A240 | HN-C(=NH)-NH-O-CH2CH2- | H | -CH2-C(=O)-N(Et)2 | H | -C(=O)-NH-CH(CH3)-Ph (R) |
| A241 | HN-C(=NH)-NH-O-CH2CH2- | CH3 | -CH2-C(=O)-N(Et)2 | H | -C(=O)-NH-CH(CH3)-Ph (R) |
| A242 | HN-C(=NH)-NH-O-CH2CH2- | H | -C(=O)-N(H)-S(=O)2-CH3 | H | -C(=O)-NH-CH(CH3)-Ph (R) |
| A243 | HN-C(=NH)-NH-O-CH2CH2- | CH3 | -C(=O)-N(H)-S(=O)2-CH3 | H | -C(=O)-NH-CH(CH3)-Ph (R) |
| A244 | HN-C(=NH)-NH-O-CH2CH2- | H | tetrazole | H | -C(=O)-NH-CH(CH3)-Ph (R) |
| A245 | HN-C(=NH)-NH-O-CH2CH2- | H | tetrazole | H | -C(=O)-NH-CH(CH3)-Ph (R) |

FIG. 1W

| | | | | | |
|---|---|---|---|---|---|
| A246 | guanidine-O-CH2CH2- | H | tetrazole | H | -C(O)-NH-CH(Ph)- |
| A247 | guanidine-O-CH2CH2- | CH3 | tetrazole | H | -C(O)-NH-CH(Ph)- |
| A248 | guanidine-C(O)-CH2CH2- | CH3 | -C(O)OH | H | -C(O)-NH-CH(Ph)- |
| A249 | guanidine-C(O)-CH2CH2- | H | -C(O)OH | H | -C(O)-NH-CH(Ph)- |
| A250 | guanidine-C(O)-CH2CH2- | H | -C(O)OH | H | -C(O)-NH-CH(Ph)- |
| A251 | guanidine-C(O)-CH2CH2- | H | -C(O)OH | H | -C(O)-NH-CH(Ph)- |
| A252 | guanidine-C(O)-CH2CH2- | CH3 | -C(O)OH | CH3 | -C(O)-NH-CH(Ph)- |
| A253 | guanidine-C(O)-CH2CH2- | H | -C(O)OEt | H | -C(O)-NH-CH(Ph)- |
| A254 | guanidine-C(O)-CH2CH2- | H | -C(O)OEt | H | -C(O)-NH-CH(Ph)- |
| A255 | guanidine-C(O)-CH2CH2- | H | -C(O)OEt | H | -C(O)-NH-CH(Ph)- |
| A256 | guanidine-C(O)-CH2CH2- | H | -C(O)O-CH2-C(CH3)3 | H | -C(O)-NH-CH(Ph)- |
| A257 | guanidine-C(O)-CH2CH2- | H | -C(O)O-cyclopentyl | H | -C(O)-NH-CH(Ph)- |

| | | | | | |
|---|---|---|---|---|---|
| A258 |  | H |  | H |  |
| A259 |  | H |  | H |  |
| A260 |  | CH₃ |  | H |  |
| A261 |  | H |  | H |  |
| A262 |  | H |  | H |  |
| A263 |  | H |  | H |  |
| A264 |  | CH₃ |  | H |  |
| A265 |  | H |  | H |  |
| A266 |  | H |  | H |  |
| A267 |  | H |  | H |  |
| A268 |  | CH₃ |  | H |  |
| A269 |  | H |  | H |  |

FIG. 1Y

| | | | | | |
|---|---|---|---|---|---|
| A270 | guanidinyl-propyl | CH₃ | CH₂-NH-S(O)₂-CH₃ | H | C(O)-NH-CH(Ph) |
| A271 | guanidinyl-propyl | H | C(O)-N-cyclopropyl | H | C(O)-NH-CH(Ph) |
| A272 | guanidinyl-propyl | CH₃ | C(O)-N-cyclopropyl | H | C(O)-NH-CH(Ph) |
| A273 | guanidinyl-propyl | H | C(O)-pyrrolidinyl | H | C(O)-NH-CH(Ph) |
| A274 | guanidinyl-propyl | H | C(O)-pyrrolidinyl | H | C(O)-NH-CH(Ph) |
| A275 | guanidinyl-propyl | H | C(O)-pyrrolidinyl | H | C(O)-NH-CH(Ph) |
| A276 | guanidinyl-propyl | CH₃ | C(O)-pyrrolidinyl | H | C(O)-NH-CH(Ph) |
| A277 | guanidinyl-propyl | H | C(O)-morpholinyl | H | C(O)-NH-CH(Ph) |
| A278 | guanidinyl-CH(R⁶)-CH(R⁵)-C(O) | H | C(O)-morpholinyl | H | C(O)-NH-CH(Ph) |
| A279 | guanidinyl-propyl | H | C(O)-morpholinyl | H | C(O)-NH-CH(Ph) |
| A280 | guanidinyl-propyl | CH₃ | C(O)-morpholinyl | H | C(O)-NH-CH(Ph) |
| A281 | guanidinyl-propyl | H | CH₂-C(O)-OH | H | C(O)-NH-CH(Ph) |

| | | | | | |
|---|---|---|---|---|---|
| A282 |  | CH₃ |  | H |  |
| A283 |  | H |  | H |  |
| A284 |  | H |  | H |  |
| A285 |  | H |  | H |  |
| A286 |  | CH₃ |  | H |  |
| A287 |  | H |  | H |  |
| A288 |  | CH₃ |  | H |  |
| A289 |  | H |  | H |  |
| A290 |  | H |  | H |  |
| A291 |  | H |  | H |  |
| A292 |  | CH₃ |  | H |  |
| A293 |  | H |  | H |  |

FIG. 1AA

| | | | | | |
|---|---|---|---|---|---|
| A294 | guanidine-propanamide | CH₃ | COOH | H | N-phenyl amide (S) |
| A295 | guanidine-propanamide | H | COOH | H | N-phenyl amide (S) |
| A296 | guanidine-propanamide | H | COOH | H | N-phenyl amide (S) |
| A297 | guanidine-propanamide | H | COOH | H | N-phenyl amide (S) |
| A298 | guanidine-propanamide | CH₃ | COOH | CH₃ | N-phenyl amide (S) |
| A299 | guanidine-propanamide | H | COOEt | H | N-phenyl amide (S) |
| A300 | guanidine-propanamide | H | COOEt | H | N-phenyl amide (S) |
| A301 | guanidine-propanamide | H | COOEt | H | N-phenyl amide (S) |
| A302 | guanidine-propanamide | H | COO-neopentyl | H | N-phenyl amide (S) |
| A303 | guanidine-propanamide | H | COO-cyclopentyl | H | N-phenyl amide (S) |
| A304 | guanidine-propanamide | H | COO-cyclopentyl | H | N-phenyl amide (S) |
| A305 | guanidine-propanamide | H | COO-cyclopentyl | H | N-phenyl amide (S) |

FIG. 1AB

| ID | R1 | R2 | R3 | R4 | R5 |
|---|---|---|---|---|---|
| A306 | HN=C(NH₂)-NH-C(=O)-CH₂-⁀ | CH₃ | -O-C(=O)-O-cyclopentyl | H | -C(=O)-NH-CH(CH₃)-Ph |
| A307 | HN=C(NH₂)-NH-C(=O)-CH₂-⁀ | H | -O-C(=O)-O-cyclobutyl | H | -C(=O)-NH-CH(CH₃)-Ph |
| A308 | HN=C(NH₂)-NH-C(=O)-CH₂-⁀ | H | -O-C(=O)-O-cyclobutyl | H | -C(=O)-NH-CH(CH₃)-Ph |
| A309 | HN=C(NH₂)-NH-C(=O)-CH₂-⁀ | H | -O-C(=O)-O-cyclobutyl | H | -C(=O)-NH-CH(CH₃)-Ph |
| A310 | HN=C(NH₂)-NH-C(=O)-CH₂-⁀ | CH₃ | -O-C(=O)-O-cyclobutyl | H | -C(=O)-NH-CH(CH₃)-Ph |
| A311 | HN=C(NH₂)-NH-C(=O)-CH₂-⁀ | H | -O-C(=O)-O-iPr | H | -C(=O)-NH-CH(CH₃)-Ph |
| A312 | HN=C(NH₂)-NH-C(=O)-CH₂-⁀ | H | -O-C(=O)-O-iPr | H | -C(=O)-NH-CH(CH₃)-Ph |
| A313 | HN=C(NH₂)-NH-C(=O)-CH₂-⁀ | H | -O-C(=O)-O-iPr | H | -C(=O)-NH-CH(CH₃)-Ph |
| A314 | HN=C(NH₂)-NH-C(=O)-CH₂-⁀ | CH₃ | -O-C(=O)-O-iPr | H | -C(=O)-NH-CH(CH₃)-Ph |
| A315 | HN=C(NH₂)-NH-C(=O)-CH₂-⁀ | H | -CH₂-NH-S(=O)₂-CH₃ | H | -C(=O)-NH-CH(CH₃)-Ph |
| A316 | HN=C(NH₂)-NH-C(=O)-CH₂-⁀ | CH₃ | -CH₂-NH-S(=O)₂-CH₃ | H | -C(=O)-NH-CH(CH₃)-Ph |
| A317 | HN=C(NH₂)-NH-C(=O)-CH₂-⁀ | H | -C(=O)-N(cyclopropyl) | H | -C(=O)-NH-CH(CH₃)-Ph |

FIG. 1AC

| A318 | ![guanidine-propanoyl] | CH₃ | ![N-cyclopropyl carbonyl] | H | ![(R)-phenylglycyl] |
| --- | --- | --- | --- | --- | --- |
| A319 | ![guanidine-propanoyl] | H | ![pyrrolidinyl carbonyl] | H | ![(R)-phenylglycyl] |
| A320 | ![guanidine-propanoyl] | H | ![pyrrolidinyl carbonyl] | H | ![(R)-phenylglycyl] |
| A321 | ![guanidine-propanoyl] | H | ![pyrrolidinyl carbonyl] | H | ![(R)-phenylglycyl] |
| A322 | ![guanidine-propanoyl] | CH₃ | ![pyrrolidinyl carbonyl] | H | ![(R)-phenylglycyl] |
| A323 | ![guanidine-propanoyl] | H | ![morpholinyl carbonyl] | H | ![(R)-phenylglycyl] |
| A324 | ![guanidine-propanoyl] | H | ![morpholinyl carbonyl] | H | ![(R)-phenylglycyl] |
| A325 | ![guanidine-propanoyl] | H | ![morpholinyl carbonyl] | H | ![(R)-phenylglycyl] |
| A326 | ![guanidine-propanoyl] | CH₃ | ![morpholinyl carbonyl] | H | ![(R)-phenylglycyl] |
| A327 | ![guanidine-propanoyl] | H | ![carboxymethyl] | H | ![(R)-phenylglycyl] |
| A328 | ![guanidine-propanoyl] | CH₃ | ![ethoxycarbonylmethyl] | H | ![(R)-phenylglycyl] |
| A329 | ![guanidine-propanoyl] | H | ![N,N-diethyl carbamoylmethyl] | H | ![(R)-phenylglycyl] |

| | | | | | |
|---|---|---|---|---|---|
| A330 |  | H |  | H |  |
| A331 |  | H |  | H |  |
| A332 |  | CH₃ |  | H |  |
| A333 |  | H |  | H |  |
| A334 |  | CH₃ |  | H |  |
| A335 |  | H |  | H |  |
| A336 |  | H |  | H |  |
| A337 |  | H |  | H |  |
| A338 |  | CH₃ |  | H |  |

FIG. 1AE

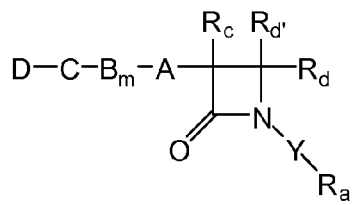

| Index | DCB$_m$A | R$_c$ | R$_d$ | R$_{d'}$ | Y-R$_a$ |
|---|---|---|---|---|---|
| A339 | H$_2$N-C(=NH)-NH-S(=O)$_2$-CH(R$^5$)- | H | -C(=O)OH | H | -C(=O)-NH-CH(Ph)- |
| A340 | H$_2$N-C(=NH)-NH-S(=O)$_2$-CH(R$^5$)- | CH$_3$ | -C(=O)OH | H | -C(=O)-NH-CH(Ph)- |
| A341 | H$_2$N-C(=NH)-NH-S(=O)$_2$-CH(R$^5$)- | H | -C(=O)OH | CH$_3$ | -C(=O)-NH-CH(Ph)- |
| A342 | H$_2$N-C(=NH)-NH-S(=O)$_2$-CH(R$^5$)- | CH$_3$ | -C(=O)OH | CH$_3$ | -C(=O)-NH-CH(Ph)- |
| A343 | H$_2$N-C(=NH)-NH-S(=O)$_2$-CH(R$^5$)- | H | -C(=O)OEt | H | -C(=O)-NH-CH(Ph)- |
| A344 | H$_2$N-C(=NH)-NH-S(=O)$_2$-CH(R$^5$)- | CH$_3$ | -C(=O)OEt | H | -C(=O)-NH-CH(Ph)- |
| A345 | H$_2$N-C(=NH)-NH-S(=O)$_2$-CH(R$^5$)- | H | -C(=O)OEt | CH$_3$ | -C(=O)-NH-CH(Ph)- |
| A346 | H$_2$N-C(=NH)-NH-S(=O)$_2$-CH(R$^5$)- | CH$_3$ | -C(=O)OEt | CH$_3$ | -C(=O)-NH-CH(Ph)- |
| A347 | H$_2$N-C(=NH)-NH-S(=O)$_2$-CH(R$^5$)- | H | -C(=O)OCH$_2$C(CH$_3$)$_3$ | H | -C(=O)-NH-CH(Ph)- |
| A348 | H$_2$N-C(=NH)-NH-S(=O)$_2$-CH(R$^5$)- | CH$_3$ | -C(=O)OCH$_2$C(CH$_3$)$_3$ | H | -C(=O)-NH-CH(Ph)- |

| | | | | | |
|---|---|---|---|---|---|
| A349 |  | H |  | CH₃ |  |
| A350 |  | CH₃ |  | CH₃ |  |
| A351 |  | H |  | H |  |
| A352 |  | CH₃ |  | H |  |
| A353 |  | H |  | CH₃ |  |
| A354 |  | CH₃ |  | CH₃ |  |
| A355 |  | H |  | H |  |
| A356 |  | CH₃ |  | H |  |
| A357 |  | H |  | CH₃ |  |
| A358 |  | CH₃ |  | CH₃ |  |
| A359 |  | H |  | H |  |
| A360 |  | CH₃ |  | H |  |

FIG. 1AG

| | | | | | |
|---|---|---|---|---|---|
| A361 | H₂N-C(=NH)-NH-S(=O)(=NH)-CH(R⁵)- | H | -C(=O)O-CH(CH₃)₂ | CH₃ | -C(=O)-NH-CH(CH₃)-Ph |
| A362 | H₂N-C(=NH)-NH-S(=O)(=NH)-CH(R⁵)- | CH₃ | -C(=O)O-CH(CH₃)₂ | CH₃ | -C(=O)-NH-CH(CH₃)-Ph |
| A363 | H₂N-C(=NH)-NH-S(=O)(=NH)-CH(R⁵)- | H | -CH₂-O-CH₂-Ph | H | -C(=O)-NH-CH(CH₃)-Ph |
| A364 | H₂N-C(=NH)-NH-S(=O)(=NH)-CH(R⁵)- | CH₃ | -CH₂-O-CH₂-Ph | H | -C(=O)-NH-CH(CH₃)-Ph |
| A365 | H₂N-C(=NH)-NH-S(=O)(=NH)-CH(R⁵)- | H | -CH₂-O-CH₂-Ph | CH₃ | -C(=O)-NH-CH(CH₃)-Ph |
| A366 | H₂N-C(=NH)-NH-S(=O)(=NH)-CH(R⁵)- | CH₃ | -CH₂-O-CH₂-Ph | CH₃ | -C(=O)-NH-CH(CH₃)-Ph |
| A367 | H₂N-C(=NH)-NH-S(=O)(=NH)-CH(R⁵)- | H | -CH₂-O-S(=O)₂-CH₃ | H | -C(=O)-NH-CH(CH₃)-Ph |
| A368 | H₂N-C(=NH)-NH-S(=O)(=NH)-CH(R⁵)- | CH₃ | -CH₂-O-S(=O)₂-CH₃ | H | -C(=O)-NH-CH(CH₃)-Ph |
| A369 | H₂N-C(=NH)-NH-S(=O)(=NH)-CH(R⁵)- | H | -CH₂-O-S(=O)₂-CH₃ | CH₃ | -C(=O)-NH-CH(CH₃)-Ph |
| A370 | H₂N-C(=NH)-NH-S(=O)(=NH)-CH(R⁵)- | CH₃ | -CH₂-O-S(=O)₂-CH₃ | CH₃ | -C(=O)-NH-CH(CH₃)-Ph |

FIG. 1AH

| | | | | | |
|---|---|---|---|---|---|
| A371 | H₂N-C(=NH)-NH-S(=O)₂-CH(R⁵)- | H | -CH₂-NH-S(=O)₂-CH₃ | H | -C(=O)-NH-CH(phenyl) |
| A372 | H₂N-C(=NH)-NH-S(=O)₂-CH(R⁵)- | CH₃ | -CH₂-NH-S(=O)₂-CH₃ | H | -C(=O)-NH-CH(phenyl) |
| A373 | H₂N-C(=NH)-NH-S(=O)₂-CH(R⁵)- | H | -CH₂-NH-S(=O)₂-CH₃ | CH₃ | -C(=O)-NH-CH(phenyl) |
| A374 | H₂N-C(=NH)-NH-S(=O)₂-CH(R⁵)- | CH₃ | -CH₂-NH-S(=O)₂-CH₃ | CH₃ | -C(=O)-NH-CH(phenyl) |
| A375 | H₂N-C(=NH)-NH-S(=O)₂-CH(R⁵)- | H | -C(=O)-N(cyclopropyl) | H | -C(=O)-NH-CH(phenyl) |
| A376 | H₂N-C(=NH)-NH-S(=O)₂-CH(R⁵)- | CH₃ | -C(=O)-N(cyclopropyl) | H | -C(=O)-NH-CH(phenyl) |
| A377 | H₂N-C(=NH)-NH-S(=O)₂-CH(R⁵)- | H | -C(=O)-N(cyclopropyl) | CH₃ | -C(=O)-NH-CH(phenyl) |
| A378 | H₂N-C(=NH)-NH-S(=O)₂-CH(R⁵)- | CH₃ | -C(=O)-N(cyclopropyl) | CH₃ | -C(=O)-NH-CH(phenyl) |
| A379 | H₂N-C(=NH)-NH-S(=O)₂-CH(R⁵)- | H | -C(=O)-N(pyrrolidinyl) | H | -C(=O)-NH-CH(phenyl) |
| A380 | H₂N-C(=NH)-NH-S(=O)₂-CH(R⁵)- | CH₃ | -C(=O)-N(pyrrolidinyl) | H | -C(=O)-NH-CH(phenyl) |
| A381 | H₂N-C(=NH)-NH-S(=O)₂-CH(R⁵)- | H | -C(=O)-N(pyrrolidinyl) | CH₃ | -C(=O)-NH-CH(phenyl) |
| A382 | H₂N-C(=NH)-NH-S(=O)₂-CH(R⁵)- | CH₃ | -C(=O)-N(pyrrolidinyl) | CH₃ | -C(=O)-NH-CH(phenyl) |

FIG. 1AI

| | | | | | |
|---|---|---|---|---|---|
| A395 |  | H |  | H |  |
| A396 |  | CH₃ |  | H |  |
| A397 |  | H |  | CH₃ |  |
| A398 |  | CH₃ |  | CH₃ |  |
| A399 |  | H |  | H |  |
| A400 |  | CH₃ |  | H |  |
| A401 |  | H |  | CH₃ |  |
| A402 |  | CH₃ |  | CH₃ |  |
| A403 |  | H |  | H |  |
| A404 |  | CH₃ |  | H |  |
| A405 |  | H |  | CH₃ |  |
| A406 |  | CH₃ |  | CH₃ |  |

| A407 |  | H |  | H |  |
| --- | --- | --- | --- | --- | --- |
| A408 |  | CH₃ |  | H |  |
| A409 |  | H |  | CH₃ |  |
| A410 |  | CH₃ |  | CH₃ |  |
| A411 |  | H |  | H |  |
| A412 |  | CH₃ |  | H |  |
| A413 |  | H |  | CH₃ |  |
| A414 |  | CH₃ |  | CH₃ |  |

FIG. 1AL

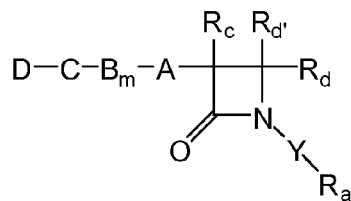

| Index | DCB$_m$A | R$_c$ | R$_d$ | R$_{d'}$ | Y-R$_a$ |
|---|---|---|---|---|---|
| A415 | pyridin-3-yloxy | H | COOH | H | C(O)NH-CH(Ph) |
| A416 | pyridin-3-yloxy | CH$_3$ | COOH | H | C(O)NH-CH(Ph) |
| A417 | pyridin-3-yloxy | H | COOH | CH$_3$ | C(O)NH-CH(Ph) |
| A418 | pyridin-3-yloxy | CH$_3$ | COOH | CH$_3$ | C(O)NH-CH(Ph) |
| A419 | pyridin-3-yloxy | H | C(O)OEt | H | C(O)NH-CH(Ph) |
| A420 | pyridin-3-yloxy | CH$_3$ | C(O)OEt | H | C(O)NH-CH(Ph) |
| A421 | pyridin-3-yloxy | H | C(O)OEt | CH$_3$ | C(O)NH-CH(Ph) |
| A422 | pyridin-3-yloxy | CH$_3$ | C(O)OEt | CH$_3$ | C(O)NH-CH(Ph) |
| A423 | pyridin-3-yloxy | H | C(O)OCH$_2$C(CH$_3$)$_3$ | H | C(O)NH-CH(Ph) |
| A424 | pyridin-3-yloxy | CH$_3$ | C(O)OCH$_2$C(CH$_3$)$_3$ | H | C(O)NH-CH(Ph) |

FIG. 1AM

| | | | | | |
|---|---|---|---|---|---|
| A425 | pyridin-3-yloxy | H | neopentyl ester | CH₃ | (R)-N-(1-phenylethyl)amide |
| A426 | pyridin-3-yloxy | CH₃ | neopentyl ester | CH₃ | (R)-N-(1-phenylethyl)amide |
| A427 | pyridin-3-yloxy | H | cyclopentyl ester | H | (R)-N-(1-phenylethyl)amide |
| A428 | pyridin-3-yloxy | CH₃ | cyclopentyl ester | H | (R)-N-(1-phenylethyl)amide |
| A429 | pyridin-3-yloxy | H | cyclopentyl ester | CH₃ | (R)-N-(1-phenylethyl)amide |
| A430 | pyridin-3-yloxy | CH₃ | cyclopentyl ester | CH₃ | (R)-N-(1-phenylethyl)amide |
| A431 | pyridin-3-yloxy | H | cyclobutyl ester | H | (R)-N-(1-phenylethyl)amide |
| A432 | pyridin-3-yloxy | CH₃ | cyclobutyl ester | H | (R)-N-(1-phenylethyl)amide |
| A433 | pyridin-3-yloxy | H | cyclobutyl ester | CH₃ | (R)-N-(1-phenylethyl)amide |
| A434 | pyridin-3-yloxy | CH₃ | cyclobutyl ester | CH₃ | (R)-N-(1-phenylethyl)amide |
| A435 | pyridin-3-yloxy | H | isopropyl ester | H | (R)-N-(1-phenylethyl)amide |
| A436 | pyridin-3-yloxy | CH₃ | isopropyl ester | H | (R)-N-(1-phenylethyl)amide |

| | | | | | |
|---|---|---|---|---|---|
| A437 |  | H |  | CH₃ |  |
| A438 |  | CH₃ |  | CH₃ |  |
| A439 |  | H |  | H |  |
| A440 |  | CH₃ |  | H |  |
| A441 |  | H |  | CH₃ |  |
| A442 |  | CH₃ |  | CH₃ |  |
| A443 |  | H |  | H |  |
| A444 |  | CH₃ |  | H |  |
| A445 |  | H |  | CH₃ |  |
| A446 |  | CH₃ |  | CH₃ |  |

| | | | | | |
|---|---|---|---|---|---|
| A447 |  | H |  | H |  |
| A448 |  | CH₃ |  | H |  |
| A449 |  | H |  | CH₃ |  |
| A450 |  | CH₃ |  | CH₃ |  |
| A451 |  | H |  | H |  |
| A452 |  | CH₃ |  | H |  |
| A453 |  | H |  | CH₃ |  |
| A454 |  | CH₃ |  | CH₃ |  |
| A455 |  | H |  | H |  |
| A456 |  | CH₃ |  | H |  |
| A457 |  | H |  | CH₃ |  |
| A458 |  | CH₃ |  | CH₃ |  |

| | | | | | |
|---|---|---|---|---|---|
| A459 |  | H |  | H |  |
| A460 |  | CH₃ |  | H |  |
| A461 |  | H |  | CH₃ |  |
| A462 |  | CH₃ |  | CH₃ |  |
| A463 |  | H |  | H |  |
| A464 |  | CH₃ |  | H |  |
| A465 |  | H |  | CH₃ |  |
| A466 |  | CH₃ |  | CH₃ |  |
| A467 |  | H |  | H |  |
| A468 |  | CH₃ |  | H |  |
| A469 |  | H |  | CH₃ |  |
| A470 |  | CH₃ |  | CH₃ |  |

FIG. 1AQ

| | | | | | |
|---|---|---|---|---|---|
| A471 | pyridin-3-yloxy | H | ethyl propanoate | H | (S)-N-(1-phenylethyl)carboxamide |
| A472 | pyridin-3-yloxy | CH₃ | ethyl propanoate | H | (S)-N-(1-phenylethyl)carboxamide |
| A473 | pyridin-3-yloxy | H | ethyl propanoate | CH₃ | (S)-N-(1-phenylethyl)carboxamide |
| A474 | pyridin-3-yloxy | CH₃ | ethyl propanoate | CH₃ | (S)-N-(1-phenylethyl)carboxamide |
| A475 | pyridin-3-yloxy | H | N,N-diethylpropanamide | H | (S)-N-(1-phenylethyl)carboxamide |
| A476 | pyridin-3-yloxy | CH₃ | N,N-diethylpropanamide | H | (S)-N-(1-phenylethyl)carboxamide |
| A477 | pyridin-3-yloxy | H | N,N-diethylpropanamide | CH₃ | (S)-N-(1-phenylethyl)carboxamide |
| A478 | pyridin-3-yloxy | CH₃ | N,N-diethylpropanamide | CH₃ | (S)-N-(1-phenylethyl)carboxamide |
| A479 | pyridin-3-yloxy | H | N-ethylpropanamide | H | (S)-N-(1-phenylethyl)carboxamide |
| A480 | pyridin-3-yloxy | CH₃ | N-ethylpropanamide | H | (S)-N-(1-phenylethyl)carboxamide |
| A481 | pyridin-3-yloxy | H | N-ethylpropanamide | CH₃ | (S)-N-(1-phenylethyl)carboxamide |
| A482 | pyridin-3-yloxy | CH₃ | N-ethylpropanamide | CH₃ | (S)-N-(1-phenylethyl)carboxamide |

| | | | | | |
|---|---|---|---|---|---|
| A483 |  | H |  | H |  |
| A484 |  | CH₃ |  | H |  |
| A485 |  | H |  | CH₃ |  |
| A486 |  | CH₃ |  | CH₃ |  |
| A487 |  | H |  | H |  |
| A488 |  | CH₃ |  | H |  |
| A489 |  | H |  | CH₃ |  |
| A490 |  | CH₃ |  | CH₃ |  |

FIG. 1AS

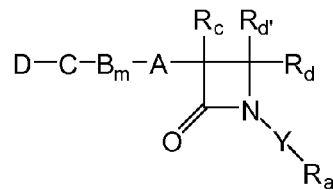

| Index | DCBmA | $R_c$ | $R_d$ | $R_{d'}$ | Y-$R_a$ |
|---|---|---|---|---|---|
| A491 | H2N-pyridine-O- | H | -COOH | H | -C(O)-NH-CH(Ph) |
| A492 | H2N-pyridine-O- | CH3 | -COOH | H | -C(O)-NH-CH(Ph) |
| A493 | H2N-pyridine-O- | H | -COOH | CH3 | -C(O)-NH-CH(Ph) |
| A494 | H2N-pyridine-O- | CH3 | -COOH | CH3 | -C(O)-NH-CH(Ph) |
| A495 | H2N-pyridine-O- | H | -C(O)OEt | H | -C(O)-NH-CH(Ph) |
| A496 | H2N-pyridine-O- | CH3 | -C(O)OEt | H | -C(O)-NH-CH(Ph) |
| A497 | H2N-pyridine-O- | H | -C(O)OEt | CH3 | -C(O)-NH-CH(Ph) |
| A498 | H2N-pyridine-O- | CH3 | -C(O)OEt | CH3 | -C(O)-NH-CH(Ph) |
| A499 | H2N-pyridine-O- | H | -C(O)OCH2C(CH3)3 | H | -C(O)-NH-CH(Ph) |
| A500 | H2N-pyridine-O- | CH3 | -C(O)OCH2C(CH3)3 | H | -C(O)-NH-CH(Ph) |

FIG. 1AT

| A513 |  | H |  | CH₃ |  |
| A514 |  | CH₃ |  | CH₃ |  |
| A515 |  | H |  | H |  |
| A516 |  | CH₃ |  | H |  |
| A517 |  | H |  | CH₃ |  |
| A518 |  | CH₃ |  | CH₃ |  |
| A519 |  | H |  | H |  |
| A520 |  | CH₃ |  | H |  |
| A521 |  | H |  | CH₃ |  |
| A522 |  | CH₃ |  | CH₃ |  |

FIG. 1AV

| | | | | | |
|---|---|---|---|---|---|
| A523 | 2-amino-pyridin-5-yloxy | H | CH₂NHS(O)₂CH₃ | H | C(O)NH-CH(CH₃)-phenyl |
| A524 | 2-amino-pyridin-5-yloxy | CH₃ | CH₂NHS(O)₂CH₃ | H | C(O)NH-CH(CH₃)-phenyl |
| A525 | 2-amino-pyridin-5-yloxy | H | CH₂NHS(O)₂CH₃ | CH₃ | C(O)NH-CH(CH₃)-phenyl |
| A526 | 2-amino-pyridin-5-yloxy | CH₃ | CH₂NHS(O)₂CH₃ | CH₃ | C(O)NH-CH(CH₃)-phenyl |
| A527 | 2-amino-pyridin-5-yloxy | H | C(O)N-cyclopropyl | H | C(O)NH-CH(CH₃)-phenyl |
| A528 | 2-amino-pyridin-5-yloxy | CH₃ | C(O)N-cyclopropyl | H | C(O)NH-CH(CH₃)-phenyl |
| A529 | 2-amino-pyridin-5-yloxy | H | C(O)N-cyclopropyl | CH₃ | C(O)NH-CH(CH₃)-phenyl |
| A530 | 2-amino-pyridin-5-yloxy | CH₃ | C(O)N-cyclopropyl | CH₃ | C(O)NH-CH(CH₃)-phenyl |
| A531 | 2-amino-pyridin-5-yloxy | H | C(O)N-pyrrolidinyl | H | C(O)NH-CH(CH₃)-phenyl |
| A532 | 2-amino-pyridin-5-yloxy | CH₃ | C(O)N-pyrrolidinyl | H | C(O)NH-CH(CH₃)-phenyl |
| A533 | 2-amino-pyridin-5-yloxy | H | C(O)N-pyrrolidinyl | CH₃ | C(O)NH-CH(CH₃)-phenyl |
| A534 | 2-amino-pyridin-5-yloxy | CH₃ | C(O)N-pyrrolidinyl | CH₃ | C(O)NH-CH(CH₃)-phenyl |

| | | | | | |
|---|---|---|---|---|---|
| A535 |  | H |  | H |  |
| A536 |  | CH₃ |  | H |  |
| A537 |  | H |  | CH₃ |  |
| A538 |  | CH₃ |  | CH₃ |  |
| A539 |  | H |  | H |  |
| A540 |  | CH₃ |  | H |  |
| A541 |  | H |  | CH₃ |  |
| A542 |  | CH₃ |  | CH₃ |  |
| A543 |  | H |  | H |  |
| A544 |  | CH₃ |  | H |  |
| A545 |  | H |  | CH₃ |  |
| A546 |  | CH₃ |  | CH₃ |  |

| A547 |  | H |  | H |  |
| --- | --- | --- | --- | --- | --- |
| A548 |  | CH₃ |  | H |  |
| A549 |  | H |  | CH₃ |  |
| A550 |  | CH₃ |  | CH₃ |  |
| A551 |  | H |  | H |  |
| A552 |  | CH₃ |  | H |  |
| A553 |  | H |  | CH₃ |  |
| A554 |  | CH₃ |  | CH₃ |  |
| A555 |  | H |  | H |  |
| A556 |  | CH₃ |  | H |  |
| A557 |  | H |  | CH₃ |  |
| A558 |  | CH₃ |  | CH₃ |  |

FIG. 1AY

| | | | | | |
|---|---|---|---|---|---|
| A559 | 2-amino-pyridin-5-yloxy | H | -C(O)-N(H)-S(O)₂-CH₃ | H | -C(O)-N(H)-CH(phenyl) (S-config) |
| A560 | 2-amino-pyridin-5-yloxy | CH₃ | -C(O)-N(H)-S(O)₂-CH₃ | H | -C(O)-N(H)-CH(phenyl) (S-config) |
| A561 | 2-amino-pyridin-5-yloxy | H | -C(O)-N(H)-S(O)₂-CH₃ | CH₃ | -C(O)-N(H)-CH(phenyl) (S-config) |
| A562 | 2-amino-pyridin-5-yloxy | CH₃ | -C(O)-N(H)-S(O)₂-CH₃ | CH₃ | -C(O)-N(H)-CH(phenyl) (S-config) |
| A563 | 2-amino-pyridin-5-yloxy | H | tetrazol-5-yl | H | -C(O)-N(H)-CH(phenyl) (S-config) |
| A564 | 2-amino-pyridin-5-yloxy | CH₃ | tetrazol-5-yl | H | -C(O)-N(H)-CH(phenyl) (S-config) |
| A565 | 2-amino-pyridin-5-yloxy | H | tetrazol-5-yl | CH₃ | -C(O)-N(H)-CH(phenyl) (S-config) |
| A566 | 2-amino-pyridin-5-yloxy | CH₃ | tetrazol-5-yl | CH₃ | -C(O)-N(H)-CH(phenyl) (S-config) |

FIG. 1AZ

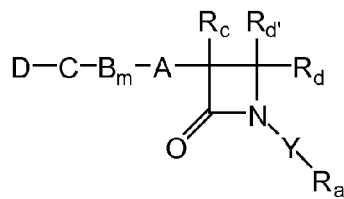

| Index | DCB$_m$A | R$_c$ | R$_d$ | R$_{d'}$ | Y-R$_a$ |
|---|---|---|---|---|---|
| A567 | H$_2$N-C$_6$H$_4$-O- | H | -C(O)OH | H | -C(O)NH-CH(CH$_3$)-Ph |
| A568 | H$_2$N-C$_6$H$_4$-O- | CH$_3$ | -C(O)OH | H | -C(O)NH-CH(CH$_3$)-Ph |
| A569 | H$_2$N-C$_6$H$_4$-O- | H | -C(O)OH | CH$_3$ | -C(O)NH-CH(CH$_3$)-Ph |
| A570 | H$_2$N-C$_6$H$_4$-O- | CH$_3$ | -C(O)OH | CH$_3$ | -C(O)NH-CH(CH$_3$)-Ph |
| A571 | H$_2$N-C$_6$H$_4$-O- | H | -C(O)OEt | H | -C(O)NH-CH(CH$_3$)-Ph |
| A572 | H$_2$N-C$_6$H$_4$-O- | CH$_3$ | -C(O)OEt | H | -C(O)NH-CH(CH$_3$)-Ph |
| A573 | H$_2$N-C$_6$H$_4$-O- | H | -C(O)OEt | CH$_3$ | -C(O)NH-CH(CH$_3$)-Ph |
| A574 | H$_2$N-C$_6$H$_4$-O- | CH$_3$ | -C(O)OEt | CH$_3$ | -C(O)NH-CH(CH$_3$)-Ph |
| A575 | H$_2$N-C$_6$H$_4$-O- | H | -C(O)OCH$_2$C(CH$_3$)$_3$ | H | -C(O)NH-CH(CH$_3$)-Ph |
| A576 | H$_2$N-C$_6$H$_4$-O- | CH$_3$ | -C(O)OCH$_2$C(CH$_3$)$_3$ | H | -C(O)NH-CH(CH$_3$)-Ph |

FIG. 1BA

| A577 | H₂N-phenyl-O- | H | -C(O)O-CH₂C(CH₃)₃ | CH₃ | -C(O)NH-CH(CH₃)-phenyl |
|---|---|---|---|---|---|
| A578 | H₂N-phenyl-O- | CH₃ | -C(O)O-CH₂C(CH₃)₃ | CH₃ | -C(O)NH-CH(CH₃)-phenyl |
| A579 | H₂N-phenyl-O- | H | -C(O)O-cyclopentyl | H | -C(O)NH-CH(CH₃)-phenyl |
| A580 | H₂N-phenyl-O- | CH₃ | -C(O)O-cyclopentyl | H | -C(O)NH-CH(CH₃)-phenyl |
| A581 | H₂N-phenyl-O- | H | -C(O)O-cyclopentyl | CH₃ | -C(O)NH-CH(CH₃)-phenyl |
| A582 | H₂N-phenyl-O- | CH₃ | -C(O)O-cyclopentyl | CH₃ | -C(O)NH-CH(CH₃)-phenyl |
| A583 | H₂N-phenyl-O- | H | -C(O)O-cyclobutyl | H | -C(O)NH-CH(CH₃)-phenyl |
| A584 | H₂N-phenyl-O- | CH₃ | -C(O)O-cyclobutyl | H | -C(O)NH-CH(CH₃)-phenyl |
| A585 | H₂N-phenyl-O- | H | -C(O)O-cyclobutyl | CH₃ | -C(O)NH-CH(CH₃)-phenyl |
| A586 | H₂N-phenyl-O- | CH₃ | -C(O)O-cyclobutyl | CH₃ | -C(O)NH-CH(CH₃)-phenyl |
| A587 | H₂N-phenyl-O- | H | -C(O)O-CH(CH₃)₂ | H | -C(O)NH-CH(CH₃)-phenyl |
| A588 | H₂N-phenyl-O- | CH₃ | -C(O)O-CH(CH₃)₂ | H | -C(O)NH-CH(CH₃)-phenyl |

FIG. 1BB

| | | | | | |
|---|---|---|---|---|---|
| A589 | H₂N–⌬–O–⌇ | H | ⌇–O–CH(CH₃)–C(=O) (isopropyl carbonate) | CH₃ | ⌇–C(=O)–NH–CH(CH₃)–Ph |
| A590 | H₂N–⌬–O–⌇ | CH₃ | ⌇–O–CH(CH₃)–C(=O) | CH₃ | ⌇–C(=O)–NH–CH(CH₃)–Ph |
| A591 | H₂N–⌬–O–⌇ | H | ⌇–CH₂–O–CH₂–Ph | H | ⌇–C(=O)–NH–CH(CH₃)–Ph |
| A592 | H₂N–⌬–O–⌇ | CH₃ | ⌇–CH₂–O–CH₂–Ph | H | ⌇–C(=O)–NH–CH(CH₃)–Ph |
| A593 | H₂N–⌬–O–⌇ | H | ⌇–CH₂–O–CH₂–Ph | CH₃ | ⌇–C(=O)–NH–CH(CH₃)–Ph |
| A594 | H₂N–⌬–O–⌇ | CH₃ | ⌇–CH₂–O–CH₂–Ph | CH₃ | ⌇–C(=O)–NH–CH(CH₃)–Ph |
| A595 | H₂N–⌬–O–⌇ | H | ⌇–CH₂–O–S(=O)₂–CH₃ | H | ⌇–C(=O)–NH–CH(CH₃)–Ph |
| A596 | H₂N–⌬–O–⌇ | CH₃ | ⌇–CH₂–O–S(=O)₂–CH₃ | H | ⌇–C(=O)–NH–CH(CH₃)–Ph |
| A597 | H₂N–⌬–O–⌇ | H | ⌇–CH₂–O–S(=O)₂–CH₃ | CH₃ | ⌇–C(=O)–NH–CH(CH₃)–Ph |
| A598 | H₂N–⌬–O–⌇ | CH₃ | ⌇–CH₂–O–S(=O)₂–CH₃ | CH₃ | ⌇–C(=O)–NH–CH(CH₃)–Ph |

FIG. 1BC

| | | | | | |
|---|---|---|---|---|---|
| A599 | H2N-phenyl-O- | H | -CH2-NH-S(=O)2-CH3 | H | -C(=O)-NH-CH(CH3)-phenyl |
| A600 | H2N-phenyl-O- | CH3 | -CH2-NH-S(=O)2-CH3 | H | -C(=O)-NH-CH(CH3)-phenyl |
| A601 | H2N-phenyl-O- | H | -CH2-NH-S(=O)2-CH3 | CH3 | -C(=O)-NH-CH(CH3)-phenyl |
| A602 | H2N-phenyl-O- | CH3 | -CH2-NH-S(=O)2-CH3 | CH3 | -C(=O)-NH-CH(CH3)-phenyl |
| A603 | H2N-phenyl-O- | H | -C(=O)-N(cyclopropyl) | H | -C(=O)-NH-CH(CH3)-phenyl |
| A604 | H2N-phenyl-O- | CH3 | -C(=O)-N(cyclopropyl) | H | -C(=O)-NH-CH(CH3)-phenyl |
| A605 | H2N-phenyl-O- | H | -C(=O)-N(cyclopropyl) | CH3 | -C(=O)-NH-CH(CH3)-phenyl |
| A606 | H2N-phenyl-O- | CH3 | -C(=O)-N(cyclopropyl) | CH3 | -C(=O)-NH-CH(CH3)-phenyl |
| A607 | H2N-phenyl-O- | H | -C(=O)-N(pyrrolidinyl) | H | -C(=O)-NH-CH(CH3)-phenyl |
| A608 | H2N-phenyl-O- | CH3 | -C(=O)-N(pyrrolidinyl) | H | -C(=O)-NH-CH(CH3)-phenyl |
| A609 | H2N-phenyl-O- | H | -C(=O)-N(pyrrolidinyl) | CH3 | -C(=O)-NH-CH(CH3)-phenyl |
| A610 | H2N-phenyl-O- | CH3 | -C(=O)-N(pyrrolidinyl) | CH3 | -C(=O)-NH-CH(CH3)-phenyl |

FIG. 1BD

| | | | | | |
|---|---|---|---|---|---|
| A611 | H2N-C6H4-O- | H | morpholine-C(O)- | H | -C(O)-NH-CH(CH3)-Ph |
| A612 | H2N-C6H4-O- | CH3 | morpholine-C(O)- | H | -C(O)-NH-CH(CH3)-Ph |
| A613 | H2N-C6H4-O- | H | morpholine-C(O)- | CH3 | -C(O)-NH-CH(CH3)-Ph |
| A614 | H2N-C6H4-O- | CH3 | morpholine-C(O)- | CH3 | -C(O)-NH-CH(CH3)-Ph |
| A615 | H2N-C6H4-O- | H | 3-pyridyl-NH-C(O)- | H | -C(O)-NH-CH(CH3)-Ph |
| A616 | H2N-C6H4-O- | CH3 | 3-pyridyl-NH-C(O)- | H | -C(O)-NH-CH(CH3)-Ph |
| A617 | H2N-C6H4-O- | H | 3-pyridyl-NH-C(O)- | CH3 | -C(O)-NH-CH(CH3)-Ph |
| A618 | H2N-C6H4-O- | CH3 | 3-pyridyl-NH-C(O)- | CH3 | -C(O)-NH-CH(CH3)-Ph |
| A619 | H2N-C6H4-O- | H | -CH2-C(O)-OH | H | -C(O)-NH-CH(CH3)-Ph |
| A620 | H2N-C6H4-O- | CH3 | -CH2-C(O)-OH | H | -C(O)-NH-CH(CH3)-Ph |
| A621 | H2N-C6H4-O- | H | -CH2-C(O)-OH | CH3 | -C(O)-NH-CH(CH3)-Ph |
| A622 | H2N-C6H4-O- | CH3 | -CH2-C(O)-OH | CH3 | -C(O)-NH-CH(CH3)-Ph |

| A623 |  | H |  | H |  |
| --- | --- | --- | --- | --- | --- |
| A624 |  | CH₃ |  | H |  |
| A625 |  | H |  | CH₃ |  |
| A626 |  | CH₃ |  | CH₃ |  |
| A627 |  | H |  | H |  |
| A628 |  | CH₃ |  | H |  |
| A629 |  | H |  | CH₃ |  |
| A630 |  | CH₃ |  | CH₃ |  |
| A631 |  | H |  | H |  |
| A632 |  | CH₃ |  | H |  |
| A633 |  | H |  | CH₃ |  |
| A634 |  | CH₃ |  | CH₃ |  |

| | | | | | |
|---|---|---|---|---|---|
| A635 |  | H |  | H |  |
| A636 |  | CH₃ |  | H |  |
| A637 |  | H |  | CH₃ |  |
| A638 |  | CH₃ |  | CH₃ |  |
| A639 |  | H |  | H |  |
| A640 |  | CH₃ |  | H |  |
| A641 |  | H |  | CH₃ |  |
| A642 |  | CH₃ |  | CH₃ |  |

FIG. 1BG

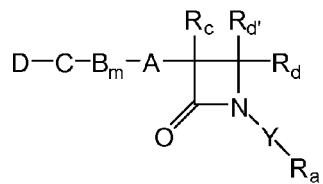

| Index | DCBmA | Rc | Rd | Rd' | Y-Ra |
|-------|-------|-----|-----|-----|------|
| A643 | H2N-pyridine-CH2-O- | H | -C(=O)OH | H | -C(=O)NH-CH(Ph) |
| A644 | H2N-pyridine-CH2-O- | CH3 | -C(=O)OH | H | -C(=O)NH-CH(Ph) |
| A645 | H2N-pyridine-CH2-O- | H | -C(=O)OH | CH3 | -C(=O)NH-CH(Ph) |
| A646 | H2N-pyridine-CH2-O- | CH3 | -C(=O)OH | CH3 | -C(=O)NH-CH(Ph) |
| A647 | H2N-pyridine-CH2-O- | H | -C(=O)OEt | H | -C(=O)NH-CH(Ph) |
| A648 | H2N-pyridine-CH2-O- | CH3 | -C(=O)OEt | H | -C(=O)NH-CH(Ph) |
| A649 | H2N-pyridine-CH2-O- | H | -C(=O)OEt | CH3 | -C(=O)NH-CH(Ph) |
| A650 | H2N-pyridine-CH2-O- | CH3 | -C(=O)OEt | CH3 | -C(=O)NH-CH(Ph) |
| A651 | H2N-pyridine-CH2-O- | H | -C(=O)OCH2C(CH3)3 | H | -C(=O)NH-CH(Ph) |
| A652 | H2N-pyridine-CH2-O- | CH3 | -C(=O)OCH2C(CH3)3 | H | -C(=O)NH-CH(Ph) |

| | | | | | |
|---|---|---|---|---|---|
| A653 |  | H |  | CH₃ |  |
| A654 |  | CH₃ |  | CH₃ |  |
| A655 |  | H |  | H |  |
| A656 |  | CH₃ |  | H |  |
| A657 |  | H |  | CH₃ |  |
| A658 |  | CH₃ |  | CH₃ |  |
| A659 |  | H |  | H |  |
| A660 |  | CH₃ |  | H |  |
| A661 |  | H |  | CH₃ |  |
| A662 |  | CH₃ |  | CH₃ |  |
| A663 |  | H |  | H |  |
| A664 |  | CH₃ |  | H |  |

| A665 |  | H |  | CH₃ |  |
| A666 |  | CH₃ |  | CH₃ |  |
| A667 |  | H |  | H |  |
| A668 |  | CH₃ |  | H |  |
| A669 |  | H |  | CH₃ |  |
| A670 |  | CH₃ |  | CH₃ |  |
| A671 |  | H |  | H |  |
| A672 |  | CH₃ |  | H |  |
| A673 |  | H |  | CH₃ |  |
| A674 |  | CH₃ |  | CH₃ |  |

FIG. 1BJ

| | | | | | |
|---|---|---|---|---|---|
| A675 | 6-aminopyridin-3-yl-CH₂-O- | H | -CH₂-NH-S(O)₂-CH₃ | H | -C(O)-NH-CH(CH₃)-Ph (S) |
| A676 | 6-aminopyridin-3-yl-CH₂-O- | CH₃ | -CH₂-NH-S(O)₂-CH₃ | H | -C(O)-NH-CH(CH₃)-Ph (S) |
| A677 | 6-aminopyridin-3-yl-CH₂-O- | H | -CH₂-NH-S(O)₂-CH₃ | CH₃ | -C(O)-NH-CH(CH₃)-Ph (S) |
| A678 | 6-aminopyridin-3-yl-CH₂-O- | CH₃ | -CH₂-NH-S(O)₂-CH₃ | CH₃ | -C(O)-NH-CH(CH₃)-Ph (S) |
| A679 | 6-aminopyridin-3-yl-CH₂-O- | H | -C(O)-NH-cyclopropyl | H | -C(O)-NH-CH(CH₃)-Ph (S) |
| A680 | 6-aminopyridin-3-yl-CH₂-O- | CH₃ | -C(O)-NH-cyclopropyl | H | -C(O)-NH-CH(CH₃)-Ph (S) |
| A681 | 6-aminopyridin-3-yl-CH₂-O- | H | -C(O)-NH-cyclopropyl | CH₃ | -C(O)-NH-CH(CH₃)-Ph (S) |
| A682 | 6-aminopyridin-3-yl-CH₂-O- | CH₃ | -C(O)-NH-cyclopropyl | CH₃ | -C(O)-NH-CH(CH₃)-Ph (S) |
| A683 | 6-aminopyridin-3-yl-CH₂-O- | H | -C(O)-pyrrolidin-1-yl | H | -C(O)-NH-CH(CH₃)-Ph (S) |
| A684 | 6-aminopyridin-3-yl-CH₂-O- | CH₃ | -C(O)-pyrrolidin-1-yl | H | -C(O)-NH-CH(CH₃)-Ph (S) |
| A685 | 6-aminopyridin-3-yl-CH₂-O- | H | -C(O)-pyrrolidin-1-yl | CH₃ | -C(O)-NH-CH(CH₃)-Ph (S) |
| A686 | 6-aminopyridin-3-yl-CH₂-O- | CH₃ | -C(O)-pyrrolidin-1-yl | CH₃ | -C(O)-NH-CH(CH₃)-Ph (S) |

| A687 |  | H |  | H |  |
| --- | --- | --- | --- | --- | --- |
| A688 |  | CH₃ |  | H |  |
| A689 |  | H |  | CH₃ |  |
| A690 |  | CH₃ |  | CH₃ |  |
| A691 |  | H |  | H |  |
| A692 |  | CH₃ |  | H |  |
| A693 |  | H |  | CH₃ |  |
| A694 |  | CH₃ |  | CH₃ |  |
| A695 |  | H |  | H |  |
| A696 |  | CH₃ |  | H |  |
| A697 |  | H |  | CH₃ |  |

| | | | | | |
|---|---|---|---|---|---|
| A698 |  | CH₃ |  | CH₃ |  |
| A699 |  | H |  | H |  |
| A700 |  | CH₃ |  | H |  |
| A701 |  | H |  | CH₃ |  |
| A702 |  | CH₃ |  | CH₃ |  |
| A703 |  | H |  | H |  |
| A704 |  | CH₃ |  | H |  |
| A705 |  | H |  | CH₃ |  |
| A706 |  | CH₃ |  | CH₃ |  |
| A707 |  | H |  | H |  |
| A708 |  | CH₃ |  | H |  |
| A709 |  | H |  | CH₃ |  |

| | | | | | |
|---|---|---|---|---|---|
| A710 |  | CH₃ |  | CH₃ |  |
| A711 |  | H |  | H |  |
| A712 |  | CH₃ |  | H |  |
| A713 |  | H |  | CH₃ |  |
| A714 |  | CH₃ |  | CH₃ |  |
| A715 |  | H |  | H |  |
| A716 |  | CH₃ |  | H |  |
| A717 |  | H |  | CH₃ |  |
| A718 |  | CH₃ |  | CH₃ |  |

FIG. 1BN

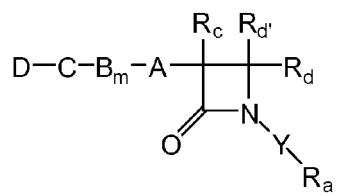

| Index | DCB$_m$A | R$_c$ | R$_d$ | R$_{d'}$ | Y-R$_a$ |
|---|---|---|---|---|---|
| A719 | H$_2$N-pyridine-CH$_2$-O- | H | -C(=O)OH | H | -C(=O)-NH-CH(CH$_3$)-Ph |
| A720 | H$_2$N-pyridine-CH$_2$-O- | CH$_3$ | -C(=O)OH | H | -C(=O)-NH-CH(CH$_3$)-Ph |
| A721 | H$_2$N-pyridine-CH$_2$-O- | H | -C(=O)OH | CH$_3$ | -C(=O)-NH-CH(CH$_3$)-Ph |
| A722 | H$_2$N-pyridine-CH$_2$-O- | CH$_3$ | -C(=O)OH | CH$_3$ | -C(=O)-NH-CH(CH$_3$)-Ph |
| A723 | H$_2$N-pyridine-CH$_2$-O- | H | -CH$_2$-C(=O)OH | H | -C(=O)-NH-CH(CH$_3$)-Ph |
| A724 | H$_2$N-pyridine-CH$_2$-O- | CH$_3$ | -CH$_2$-C(=O)OH | H | -C(=O)-NH-CH(CH$_3$)-Ph |
| A725 | H$_2$N-pyridine-CH$_2$-O- | H | -CH$_2$-C(=O)OH | CH$_3$ | -C(=O)-NH-CH(CH$_3$)-Ph |
| A726 | H$_2$N-pyridine-CH$_2$-O- | CH$_3$ | -CH$_2$-C(=O)OH | CH$_3$ | -C(=O)-NH-CH(CH$_3$)-Ph |
| A727 | H$_2$N-pyridine-CH$_2$-O- | H | -CH$_2$-C(=O)-N(Et)$_2$ | H | -C(=O)-NH-CH(CH$_3$)-Ph |
| A728 | H$_2$N-pyridine-CH$_2$-O- | CH$_3$ | -CH$_2$-C(=O)-N(Et)$_2$ | H | -C(=O)-NH-CH(CH$_3$)-Ph |

FIG. 1BO

| | | | | | |
|---|---|---|---|---|---|
| A729 | 2-amino-pyridin-4-yl-CH2-O- | H | -CH2-C(O)-N(Et)2 | CH3 | -C(O)-NH-CH(CH3)-Ph |
| A730 | 2-amino-pyridin-4-yl-CH2-O- | CH3 | -CH2-C(O)-N(Et)2 | CH3 | -C(O)-NH-CH(CH3)-Ph |
| A731 | 2-amino-pyridin-4-yl-CH2-O- | H | -CH2-C(O)-O-Et | H | -C(O)-NH-CH(CH3)-Ph |
| A732 | 2-amino-pyridin-4-yl-CH2-O- | CH3 | -CH2-C(O)-O-Et | H | -C(O)-NH-CH(CH3)-Ph |
| A733 | 2-amino-pyridin-4-yl-CH2-O- | H | -CH2-C(O)-O-Et | CH3 | -C(O)-NH-CH(CH3)-Ph |
| A734 | 2-amino-pyridin-4-yl-CH2-O- | CH3 | -CH2-C(O)-O-Et | CH3 | -C(O)-NH-CH(CH3)-Ph |
| A735 | 2-amino-pyrimidin-4-yl-CH2-O- | H | -CH2-COOH | H | -C(O)-NH-CH(CH3)-Ph |
| A736 | 2-amino-pyrimidin-4-yl-CH2-O- | CH3 | -CH2-COOH | H | -C(O)-NH-CH(CH3)-Ph |
| A737 | 2-amino-pyrimidin-4-yl-CH2-O- | H | -CH2-COOH | CH3 | -C(O)-NH-CH(CH3)-Ph |
| A738 | 2-amino-pyrimidin-4-yl-CH2-O- | CH3 | -CH2-COOH | CH3 | -C(O)-NH-CH(CH3)-Ph |
| A739 | 2-amino-pyrimidin-4-yl-CH2-O- | H | -CH2-CH2-COOH | H | -C(O)-NH-CH(CH3)-Ph |
| A740 | 2-amino-pyrimidin-4-yl-CH2-O- | CH3 | -CH2-CH2-COOH | H | -C(O)-NH-CH(CH3)-Ph |

| | | | | | |
|---|---|---|---|---|---|
| A752 | 2-amino-pyridin-4-ylmethyl | CH₃ | COOH | H | C(O)NH-CH(CH₃)-Ph |
| A753 | 2-amino-pyridin-4-ylmethyl | H | COOH | CH₃ | C(O)NH-CH(CH₃)-Ph |
| A754 | 2-amino-pyridin-4-ylmethyl | CH₃ | COOH | CH₃ | C(O)NH-CH(CH₃)-Ph |
| A755 | 2-amino-pyridin-4-ylmethyl | H | CH₂COOH | H | C(O)NH-CH(CH₃)-Ph |
| A756 | 2-amino-pyridin-4-ylmethyl | CH₃ | CH₂COOH | H | C(O)NH-CH(CH₃)-Ph |
| A757 | 2-amino-pyridin-4-ylmethyl | H | CH₂COOH | CH₃ | C(O)NH-CH(CH₃)-Ph |
| A758 | 2-amino-pyridin-4-ylmethyl | CH₃ | CH₂COOH | CH₃ | C(O)NH-CH(CH₃)-Ph |
| A759 | 2-amino-pyridin-4-ylmethyl | H | CH₂C(O)N(Et)₂ | H | C(O)NH-CH(CH₃)-Ph |
| A760 | 2-amino-pyridin-4-ylmethyl | CH₃ | CH₂C(O)N(Et)₂ | H | C(O)NH-CH(CH₃)-Ph |
| A761 | 2-amino-pyridin-4-ylmethyl | H | CH₂C(O)N(Et)₂ | CH₃ | C(O)NH-CH(CH₃)-Ph |
| A762 | 2-amino-pyridin-4-ylmethyl | CH₃ | CH₂C(O)N(Et)₂ | CH₃ | C(O)NH-CH(CH₃)-Ph |
| A763 | 2-amino-pyridin-4-ylmethyl | H | CH₂C(O)OEt | H | C(O)NH-CH(CH₃)-Ph |

| | | | | | |
|---|---|---|---|---|---|
| A764 |  | CH₃ |  | H |  |
| A765 |  | H |  | CH₃ |  |
| A766 |  | CH₃ |  | CH₃ |  |
| A767 |  | H |  | H |  |
| A768 |  | CH₃ |  | H |  |
| A769 |  | H |  | CH₃ |  |
| A770 |  | CH₃ |  | CH₃ |  |
| A771 |  | H |  | H |  |
| A772 |  | CH₃ |  | H |  |
| A773 |  | H |  | CH₃ |  |
| A774 |  | CH₃ |  | CH₃ |  |
| A775 |  | H |  | H |  |

| A776 |  | CH₃ |  | H |  |
| --- | --- | --- | --- | --- | --- |
| A777 |  | H |  | CH₃ |  |
| A778 |  | CH₃ |  | CH₃ |  |
| A779 |  | H |  | H |  |
| A780 |  | CH₃ |  | H |  |
| A781 |  | H |  | CH₃ |  |
| A782 |  | CH₃ |  | CH₃ |  |

FIG. 1BT

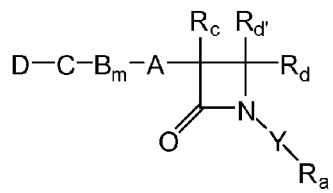

| Index | DCB<sub>m</sub>A | R<sub>c</sub> | R<sub>d</sub> | R<sub>d'</sub> | Y-R<sub>a</sub> |
|---|---|---|---|---|---|
| A783 | H₂N-C(=NH)-NH-CH=CH- | H | -COOH | H | -C(=O)-NH-CH(Ph) |
| A784 | H₂N-C(=NH)-NH-CH=CH- | H | -C(=O)OMe | H | -C(=O)-NH-CH(Ph) |
| A785 | H₂N-C(=NH)-NH-CH=CH- | H | -C(=O)OEt | H | -C(=O)-NH-CH(Ph) |
| A786 | H₂N-C(=NH)-NH-CH=CH- | H | -C(=O)OiPr | H | -C(=O)-NH-CH(Ph) |
| A787 | H₂N-C(=NH)-NH-CH=CH- | H | -C(=O)O-CH₂-tBu | H | -C(=O)-NH-CH(Ph) |
| A788 | H₂N-C(=NH)-NH-CH=CH- | H | -C(=O)O-cyclopropyl | H | -C(=O)-NH-CH(Ph) |
| A789 | H₂N-C(=NH)-NH-CH=CH- | H | -C(=O)O-cyclobutyl | H | -C(=O)-NH-CH(Ph) |
| A790 | H₂N-C(=NH)-NH-CH=CH- | H | -C(=O)O-cyclopentyl | H | -C(=O)-NH-CH(Ph) |
| A791 | H₂N-C(=NH)-NH-CH=CH- | H | -C(=O)O-cyclohexyl | H | -C(=O)-NH-CH(Ph) |
| A792 | H₂N-C(=NH)-NH-CH=CH- | H | -C(=O)N(Me)₂ | H | -C(=O)-NH-CH(Ph) |

| | | | | | |
|---|---|---|---|---|---|
| A793 |  | H |  | H |  |
| A794 |  | H |  | H |  |
| A795 |  | H |  | H |  |
| A796 |  | H |  | H |  |
| A797 |  | H |  | H |  |
| A798 |  | $CH_3$ |  | H |  |
| A799 |  | $CH_3$ |  | H |  |
| A800 |  | $CH_3$ |  | H |  |
| A801 |  | $CH_3$ |  | H |  |
| A802 |  | $CH_3$ |  | H |  |
| A803 |  | $CH_3$ |  | H |  |
| A804 |  | $CH_3$ |  | H |  |

| | | | | | | |
|---|---|---|---|---|---|---|
| A805 |  | CH₃ |  | H |  |
| A806 |  | CH₃ |  | H |  |
| A807 |  | CH₃ |  | H |  |
| A808 |  | CH₃ |  | H |  |
| A809 |  | CH₃ |  | H |  |
| A810 |  | CH₃ |  | H |  |
| A811 |  | CH₃ |  | H |  |
| A812 |  | H |  | H |  |
| A813 |  | H |  | H |  |
| A814 |  | H |  | H |  |
| A815 |  | H |  | H |  |
| A816 |  | H |  | H |  |

FIG. 1BW

| | | | | | |
|---|---|---|---|---|---|
| A817 | methylguanidine-N'-methylidene | H | cyclopropyl ester | H | (R)-phenylethyl amide |
| A818 | methylguanidine-N'-methylidene | H | cyclobutyl ester | H | (R)-phenylethyl amide |
| A819 | methylguanidine-N'-methylidene | H | cyclopentyl ester | H | (R)-phenylethyl amide |
| A820 | methylguanidine-N'-methylidene | H | cyclohexyl ester | H | (R)-phenylethyl amide |
| A821 | methylguanidine-N'-methylidene | H | N,N-dimethyl amide | H | (R)-phenylethyl amide |
| A822 | methylguanidine-N'-methylidene | H | N-methyl-N-ethyl amide | H | (R)-phenylethyl amide |
| A823 | methylguanidine-N'-methylidene | H | N,N-diethyl amide | H | (R)-phenylethyl amide |
| A824 | methylguanidine-N'-methylidene | H | pyrrolidinyl amide | H | (R)-phenylethyl amide |
| A825 | methylguanidine-N'-methylidene | H | piperidinyl amide | H | (R)-phenylethyl amide |
| A826 | N-methyl guanidine-N'-methylidene | H | carboxylic acid | H | (R)-phenylethyl amide |
| A827 | N-methyl guanidine-N'-methylidene | H | methyl ester | H | (R)-phenylethyl amide |
| A828 | N-methyl guanidine-N'-methylidene | H | ethyl ester | H | (R)-phenylethyl amide |

| A829 |  | H |  | H |  |
| A830 |  | H |  | H |  |
| A831 |  | H |  | H |  |
| A832 |  | H |  | H |  |
| A833 |  | H |  | H |  |
| A834 |  | H |  | H |  |
| A835 |  | H |  | H |  |
| A836 |  | H |  | H |  |
| A837 |  | H |  | H |  |
| A838 |  | H |  | H |  |
| A839 |  | H |  | H |  |
| A840 |  | H |  | H |  |

| | | | | | |
|---|---|---|---|---|---|
| A841 |  | H |  | H |  |
| A842 |  | H |  | H |  |
| A843 |  | H |  | H |  |
| A844 |  | H |  | H |  |
| A845 |  | H |  | H |  |
| A846 |  | H |  | H |  |
| A847 |  | H |  | H |  |
| A848 |  | H |  | H |  |
| A849 |  | H |  | H |  |
| A850 |  | H |  | H |  |
| A851 |  | H |  | H |  |
| A852 |  | H |  | H |  |

FIG. 1BZ

| A853 | (N-methyl, N'-methyl guanidine hydrazone CH=) | H | piperidine-C(O)-S | H | Ph-CH(CH₃)-NH-C(O)-S |
|---|---|---|---|---|---|
| A854 | H₂N-C(=NH)-NH-N=CH-S | H | HO-C(O)-S | CH₃ | Ph-CH(CH₃)-NH-C(O)-S |
| A855 | H₂N-C(=NH)-NH-N=CH-S | H | CH₃O-C(O)-S | CH₃ | Ph-CH(CH₃)-NH-C(O)-S |
| A856 | H₂N-C(=NH)-NH-N=CH-S | H | EtO-C(O)-S | CH₃ | Ph-CH(CH₃)-NH-C(O)-S |
| A857 | H₂N-C(=NH)-NH-N=CH-S | H | nPrO-C(O)-S | CH₃ | Ph-CH(CH₃)-NH-C(O)-S |
| A858 | H₂N-C(=NH)-NH-N=CH-S | H | iPrO-C(O)-S | CH₃ | Ph-CH(CH₃)-NH-C(O)-S |
| A859 | H₂N-C(=NH)-NH-N=CH-S | H | cyclopropyl-O-C(O)-S | CH₃ | Ph-CH(CH₃)-NH-C(O)-S |
| A860 | H₂N-C(=NH)-NH-N=CH-S | H | cyclobutyl-O-C(O)-S | CH₃ | Ph-CH(CH₃)-NH-C(O)-S |
| A861 | H₂N-C(=NH)-NH-N=CH-S | H | cyclopentyl-O-C(O)-S | CH₃ | Ph-CH(CH₃)-NH-C(O)-S |
| A862 | H₂N-C(=NH)-NH-N=CH-S | H | cyclohexyl-O-C(O)-S | CH₃ | Ph-CH(CH₃)-NH-C(O)-S |
| A863 | H₂N-C(=NH)-NH-N=CH-S | H | (CH₃)₂N-C(O)-S | CH₃ | Ph-CH(CH₃)-NH-C(O)-S |
| A864 | H₂N-C(=NH)-NH-N=CH-S | H | CH₃(Et)N-C(O)-S | CH₃ | Ph-CH(CH₃)-NH-C(O)-S |

FIG. 1CA

| | | | | | |
|---|---|---|---|---|---|
| A865 | H2N-C(=NH)-NH-N=CH- | H | -C(=O)N(Et)2 | CH3 | -C(=O)NH-CH(CH3)-Ph |
| A866 | H2N-C(=NH)-NH-N=CH- | H | -C(=O)-N(pyrrolidine) | CH3 | -C(=O)NH-CH(CH3)-Ph |
| A867 | H2N-C(=NH)-NH-N=CH- | H | -C(=O)-N(piperidine) | CH3 | -C(=O)NH-CH(CH3)-Ph |
| A868 | H2N-C(=NH)-NH-N=CH- | H | -C(=O)-N(piperidine) | CH3 | -C(=O)NH-CH(CH3)-(4-F-C6H4) |
| A869 | H2N-C(=NH)-NH-N=CH- | H | -C(=O)OCH3 | H | -C(=O)NH-CH(Ph)2 |
| A870 | H2N-C(=NH)-NH-N=CH- | H | -C(=O)OCH3 | H | -C(=O)NH-CH2-Ph |
| A871 | H2N-C(=NH)-NH-N=CH- | H | -C(=O)OCH3 | H | -C(=O)N(CH3)-CH2-Ph |
| A872 | H2N-C(=NH)-NH-N=CH- | H | -C(=O)OCH3 | H | -C(=O)NH-(1-naphthyl) |
| A873 | H2N-C(=NH)-NH-N=CH- | H | -C(=O)OCH3 | H | -C(=O)NH-CH2-(1-naphthyl) |
| A874 | H2N-C(=NH)-NH-N=CH- | H | -C(=O)O-cyclobutyl | H | -C(=O)NH-CH(Et)-Ph |

| | | | | | |
|---|---|---|---|---|---|
| A875 |  | H |  | H |  |
| A876 |  | H |  | H |  |
| A877 |  | H |  | H |  |
| A878 |  | H |  | H |  |
| A879 |  | H |  | H |  |
| A880 |  | H |  | H |  |
| A881 |  | H |  | H |  |
| A882 |  | H |  | H |  |
| A883 |  | H |  | H |  |
| A884 |  | H |  | H |  |

FIG. 1CC

| | | | | | |
|---|---|---|---|---|---|
| A885 | H₂N-C(=NH)-NH-CH=S | H | -C(=O)-N(Et)(Et) | H | -C(=O)-NH-CH₂-(1-naphthyl) |
| A886 | H₂N-C(=NH)-NH-CH=S | H | -C(=O)-N(Me)(Et) | H | -C(=O)-NH-CH(Et)(Ph) |
| A887 | H₂N-C(=NH)-NH-CH=S | H | -C(=O)-N(Me)(Et) | H | -C(=O)-NH-CH(Ph)(Ph) |
| A888 | H₂N-C(=NH)-NH-CH=S | H | -C(=O)-N(Me)(Et) | H | -C(=O)-NH-CH₂-Ph |
| A889 | H₂N-C(=NH)-NH-CH=S | H | -C(=O)-N(Me)(Et) | H | -C(=O)-N(H)-Ph |
| A890 | H₂N-C(=NH)-NH-CH=S | H | -C(=O)-N(Me)(Et) | H | -C(=O)-NH-(1-naphthyl) |
| A891 | H₂N-C(=NH)-NH-CH=S | H | -C(=O)-N(Me)(Et) | H | -C(=O)-NH-CH₂-(1-naphthyl) |
| A892 | H₂N-C(=NH)-NH-CH=S | H | -C(=O)-N(Et)(Et) | H | -C(=O)-NH-CH(Et)(Ph) |
| A893 | H₂N-C(=NH)-NH-CH=S | H | -C(=O)-N(Et)(Et) | H | -C(=O)-NH-CH(Ph)(Ph) |
| A894 | H₂N-C(=NH)-NH-CH=S | CH₃ | -C(=O)-N(Et)(Et) | H | -C(=O)-NH-CH₂-Ph |

FIG. 1CD

| | | | | | |
|---|---|---|---|---|---|
| A895 | H₂N-C(=NH)-NH-N=CH-S | CH₃ | S-C(=O)-N(Et)(Et) | H | S-C(=O)-NH-Ph |
| A896 | H₂N-C(=NH)-NH-N=CH-S | CH₃ | S-C(=O)-N(Et)(Et) | H | S-C(=O)-NH-(1-naphthyl) |
| A897 | H₂N-C(=NH)-NH-N=CH-S | CH₃ | S-C(=O)-N(Et)(Et) | H | S-C(=O)-NH-CH₂-(1-naphthyl) |
| A898 | H₂N-C(=NH)-NH-N=CH-S | CH₃ | S-C(=O)-N(Me)(Et) | H | S-C(=O)-NH-CH(Et)(Ph) |
| A899 | H₂N-C(=NH)-NH-N=CH-S | CH₃ | S-C(=O)-N(Me)(Et) | H | S-C(=O)-NH-CH(Ph)(Ph) |
| A900 | H₂N-C(=NH)-NH-N=CH-S | CH₃ | S-C(=O)-N(Me)(Et) | H | S-C(=O)-NH-CH₂-Ph |
| A901 | H₂N-C(=NH)-NH-N=CH-S | CH₃ | S-C(=O)-N(Me)(Et) | H | S-C(=O)-NH-Ph |
| A902 | H₂N-C(=NH)-NH-N=CH-S | CH₃ | S-C(=O)-N(Me)(Et) | H | S-C(=O)-NH-(1-naphthyl) |
| A903 | H₂N-C(=NH)-NH-N=CH-S | CH₃ | S-C(=O)-N(Me)(Et) | H | S-C(=O)-NH-CH₂-(1-naphthyl) |

FIG. 1CE

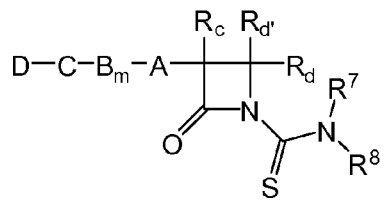

| Index | DCB$_m$A | R$_c$ | R$_d$ | R$_{d'}$ | R$^7$ | R$^8$ |
|---|---|---|---|---|---|---|
| A904 | H$_2$N-C(=NH)-NH-CH(R$^5$)-C(=O)- | H | -COOH | H | -C(=O)-NH-CH(Ph)- | H |
| A905 | H$_2$N-C(=NH)-NH-CH(R$^5$)-C(=O)- | CH$_3$ | -COOH | H | -C(=O)-NH-CH(Ph)- | H |
| A906 | H$_2$N-C(=NH)-NH-CH(R$^5$)-C(=O)- | H | -COOH | CH$_3$ | -C(=O)-NH-CH(Ph)- | H |
| A907 | H$_2$N-C(=NH)-NH-CH(R$^5$)-C(=O)- | H | -COOH | H | -C(=O)-NH-CH(Ph)- | H |
| A908 | H$_2$N-C(=NH)-NH-CH(R$^5$)-C(=O)- | CH$_3$ | -COOH | H | -C(=O)-NH-CH(Ph)- | H |
| A909 | H$_2$N-C(=NH)-NH-CH(R$^5$)-C(=O)- | H | -COOH | CH$_3$ | -C(=O)-NH-CH(Ph)- | H |
| A910 | H$_2$N-C(=NH)-NH-CH(R$^5$)-C(=O)- | H | -COOH | H | -C(=O)-NH-CH(Ph)- | H |
| A911 | H$_2$N-C(=NH)-NH-CH(R$^5$)-C(=O)- | CH$_3$ | -COOH | H | -C(=O)-NH-CH(Ph)- | H |
| A912 | H$_2$N-C(=NH)-NH-CH(R$^5$)-C(=O)- | H | -COOH | CH$_3$ | -C(=O)-NH-CH(Ph)- | H |

FIG. 1CF

| | | | | | | |
|---|---|---|---|---|---|---|
| A913 | H₂N-C(=NH)-NH-C(=O)-CH(R⁵)- | H | -C(=O)OH | H | -C(=O)-NH-CH(Ph)- | H |
| A914 | H₂N-C(=NH)-NH-C(=O)-CH(R⁵)- | CH₃ | -C(=O)OH | H | -C(=O)-NH-CH(Ph)- | H |
| A915 | H₂N-C(=NH)-NH-C(=O)-CH(R⁵)- | H | -C(=O)OH | CH₃ | -C(=O)-NH-CH(Ph)- | H |
| A916 | H₂N-C(=NH)-NH-C(=O)-CH(R⁵)- | H | -C(=O)OH | H | -C(=O)-NH-CH(Ph)- | |
| A917 | H₂N-C(=NH)-NH-C(=O)-CH(R⁵)- | CH₃ | -C(=O)OH | H | -C(=O)-NH-CH(Ph)- | |
| A918 | H₂N-C(=NH)-NH-C(=O)-CH(R⁵)- | H | -C(=O)OH | CH₃ | -C(=O)-NH-CH(Ph)- | |
| A919 | H₂N-C(=NH)-NH-C(=O)-CH(R⁵)- | H | -C(=O)OH | H | -C(=O)-NH-CH(Ph)- | |
| A920 | H₂N-C(=NH)-NH-C(=O)-CH(R⁵)- | CH₃ | -C(=O)OH | H | -C(=O)-NH-CH(Ph)- | |
| A921 | H₂N-C(=NH)-NH-C(=O)-CH(R⁵)- | H | -C(=O)OH | CH₃ | -C(=O)-NH-CH(Ph)- | |
| A922 | H₂N-C(=NH)-NH-C(=O)-CH(R⁵)- | H | -C(=O)OH | H | -C(=O)-NH-CH(Ph)- | |
| A923 | H₂N-C(=NH)-NH-C(=O)-CH(R⁵)- | CH₃ | -C(=O)OH | H | -C(=O)-NH-CH(Ph)- | |

FIG. 1CG

| | | | | | |
|---|---|---|---|---|---|
| A924 | H2N-C(=NH)-NH-C(=O)-CH(R5)- | H | -COOH | CH3 | -C(=O)-NH-CH(phenyl) |
| A925 | H2N-C(=NH)-NH-C(=O)-CH(R5)- | H | -COOH | H | -C(=O)-NH-CH(phenyl) |
| A926 | H2N-C(=NH)-NH-C(=O)-CH(R5)- | CH3 | -COOH | H | -C(=O)-NH-CH(phenyl) |
| A927 | H2N-C(=NH)-NH-C(=O)-CH(R5)- | H | -COOH | CH3 | -C(=O)-NH-CH(phenyl) |
| A928 | H2N-C(=NH)-NH-C(=O)-CH(R5)- | H | -COOH | H | -C(=O)-NH-CH(phenyl) |
| A929 | H2N-C(=NH)-NH-C(=O)-CH(R5)- | CH3 | -COOH | H | -C(=O)-NH-CH(phenyl) |
| A930 | H2N-C(=NH)-NH-C(=O)-CH(R5)- | H | -COOH | CH3 | -C(=O)-NH-CH(phenyl) |
| A931 | H2N-C(=NH)-NH-C(=O)-CH(R5)- | H | -COOH | H | -C(=O)-NH-CH(phenyl) |
| A932 | H2N-C(=NH)-NH-C(=O)-CH(R5)- | CH3 | -COOH | H | -C(=O)-NH-CH(phenyl) |
| A933 | H2N-C(=NH)-NH-C(=O)-CH(R5)- | H | -COOH | CH3 | -C(=O)-NH-CH(phenyl) |

| A934 |  | H |  | H |  | H |
|---|---|---|---|---|---|---|
| A935 |  | CH₃ |  | H |  | H |
| A936 |  | H |  | CH₃ |  | H |
| A937 |  | H |  | H |  | H |
| A938 |  | CH₃ |  | H |  | H |
| A939 |  | H |  | CH₃ |  | H |
| A940 |  | H |  | H |  | H |
| A941 |  | CH₃ |  | H |  | H |
| A942 |  | H |  | CH₃ |  | H |
| A943 |  | H |  | H |  | H |
| A944 |  | CH₃ |  | H |  | H |

FIG. 1CI

| | | | | | |
|---|---|---|---|---|---|
| A945 | H2N-C(=NH)-NH-C(=O)-CH(R5)- | H | -C(=O)OH | CH3 | -C(=O)-NH-CH(Ph)- |
| A946 | H2N-C(=NH)-NH-C(=O)-CH(R5)- | H | -C(=O)OH | H | -C(=O)-NH-CH(Ph)- |
| A947 | H2N-C(=NH)-NH-C(=O)-CH(R5)- | CH3 | -C(=O)OH | H | -C(=O)-NH-CH(Ph)- |
| A948 | H2N-C(=NH)-NH-C(=O)-CH(R5)- | H | -C(=O)OH | CH3 | -C(=O)-NH-CH(Ph)- |
| A949 | H2N-C(=NH)-NH-C(=O)-CH(R5)- | H | -C(=O)OH | H | -C(=O)-NH-CH(Ph)- |
| A950 | H2N-C(=NH)-NH-C(=O)-CH(R5)- | CH3 | -C(=O)OH | H | -C(=O)-NH-CH(Ph)- |
| A951 | H2N-C(=NH)-NH-C(=O)-CH(R5)- | H | -C(=O)OH | CH3 | -C(=O)-NH-CH(Ph)- |
| A952 | H2N-C(=NH)-NH-C(=O)-CH(R5)- | H | -C(=O)OH | H | -C(=O)-NH-CH(Ph)- |
| A953 | H2N-C(=NH)-NH-C(=O)-CH(R5)- | CH3 | -C(=O)OH | H | -C(=O)-NH-CH(Ph)- |
| A954 | H2N-C(=NH)-NH-C(=O)-CH(R5)- | H | -C(=O)OH | CH3 | -C(=O)-NH-CH(Ph)- |
| A955 | H2N-C(=NH)-NH-C(=O)-CH(R5)- | H | -C(=O)OH | H | -C(=O)-NH-CH(Ph)- |

FIG. 1CJ

| | | | | | | |
|---|---|---|---|---|---|---|
| A956 | H₂N-C(=NH)-NH-C(=O)-CH(R⁵)-(S) | CH₃ | (S)-COOH | H | (S)-C(=O)-NH-CH(▲)-Ph | |
| A957 | H₂N-C(=NH)-NH-C(=O)-CH(R⁵)-(S) | H | (S)-COOH | CH₃ | (S)-C(=O)-NH-CH(▲)-Ph | |
| A958 | H₂N-C(=NH)-NH-C(=O)-CH(R⁵)-(S) | H | (S)-COOH | H | (S)-C(=O)-NH-CH(▲)-Ph | |
| A959 | H₂N-C(=NH)-NH-C(=O)-CH(R⁵)-(S) | CH₃ | (S)-COOH | H | (S)-C(=O)-NH-CH(▲)-Ph | |
| A960 | H₂N-C(=NH)-NH-C(=O)-CH(R⁵)-(S) | H | (S)-COOH | CH₃ | (S)-C(=O)-NH-CH(▲)-Ph | |
| A961 | H₂N-C(=NH)-NH-C(=O)-CH(R⁵)-(S) | H | (S)-COOH | H | (S)-C(=O)-NH-CH(▲)-Ph | H |
| A962 | H₂N-C(=NH)-NH-C(=O)-CH(R⁵)-(S) | CH₃ | (S)-COOH | H | (S)-C(=O)-NH-CH(▲)-Ph | H |
| A963 | H₂N-C(=NH)-NH-C(=O)-CH(R⁵)-(S) | H | (S)-COOH | CH₃ | (S)-C(=O)-NH-CH(▲)-Ph | H |
| A964 | H₂N-C(=NH)-NH-C(=O)-CH(R⁵)-(S) | H | (S)-COOH | H | (S)-C(=O)-NH-CH(▲)-Ph | H |
| A965 | H₂N-C(=NH)-NH-C(=O)-CH(R⁵)-(S) | CH₃ | (S)-COOH | H | (S)-C(=O)-NH-CH(▲)-Ph | H |
| A966 | H₂N-C(=NH)-NH-C(=O)-CH(R⁵)-(S) | H | (S)-COOH | CH₃ | (S)-C(=O)-NH-CH(▲)-Ph | H |

FIG. 1CK

| | | | | | | |
|---|---|---|---|---|---|---|
| A967 | H2N-C(=NH)-NH-C(=O)-CH(R5)- | H | -C(=O)OH | H | -C(=O)-NH-CH(CH3)-Ph | H |
| A968 | H2N-C(=NH)-NH-C(=O)-CH(R5)- | CH3 | -C(=O)OH | H | -C(=O)-NH-CH(CH3)-Ph | H |
| A969 | H2N-C(=NH)-NH-C(=O)-CH(R5)- | H | -C(=O)OH | CH3 | -C(=O)-NH-CH(CH3)-Ph | H |
| A970 | H2N-C(=NH)-NH-C(=O)-CH(R5)- | H | -C(=O)OH | H | -C(=O)-NH-CH(CH3)-Ph | |
| A971 | H2N-C(=NH)-NH-C(=O)-CH(R5)- | CH3 | -C(=O)OH | H | -C(=O)-NH-CH(CH3)-Ph | |
| A972 | H2N-C(=NH)-NH-C(=O)-CH(R5)- | H | -C(=O)OH | CH3 | -C(=O)-NH-CH(CH3)-Ph | |
| A973 | H2N-C(=NH)-NH-C(=O)-CH(R5)- | H | -C(=O)OH | H | -C(=O)-NH-CH(CH3)-Ph | |
| A974 | H2N-C(=NH)-NH-C(=O)-CH(R5)- | CH3 | -C(=O)OH | H | -C(=O)-NH-CH(CH3)-Ph | |
| A975 | H2N-C(=NH)-NH-C(=O)-CH(R5)- | H | -C(=O)OH | CH3 | -C(=O)-NH-CH(CH3)-Ph | |
| A976 | H2N-C(=NH)-NH-C(=O)-CH(R5)- | H | -C(=O)OH | H | -C(=O)-NH-CH(CH3)-Ph | |
| A977 | H2N-C(=NH)-NH-C(=O)-CH(R5)- | CH3 | -C(=O)OH | H | -C(=O)-NH-CH(CH3)-Ph | |

FIG. 1CL

| | | | | | |
|---|---|---|---|---|---|
| A978 | H₂N-C(=NH)-NH-C(=O)-CH(R⁵)- | H | -COOH | CH₃ | -C(=O)-NH-CH(phenyl) |
| A979 | H₂N-C(=NH)-NH-C(=O)-CH(R⁵)- | H | -COOH | H | -C(=O)-NH-CH(phenyl) |
| A980 | H₂N-C(=NH)-NH-C(=O)-CH(R⁵)- | CH₃ | -COOH | H | -C(=O)-NH-CH(phenyl) |
| A981 | H₂N-C(=NH)-NH-C(=O)-CH(R⁵)- | H | -COOH | CH₃ | -C(=O)-NH-CH(phenyl) |
| A982 | H₂N-C(=NH)-NH-C(=O)-CH(R⁵)- | H | -COOH | H | -C(=O)-NH-CH(phenyl) |
| A983 | H₂N-C(=NH)-NH-C(=O)-CH(R⁵)- | CH₃ | -COOH | H | -C(=O)-NH-CH(phenyl) |
| A984 | H₂N-C(=NH)-NH-C(=O)-CH(R⁵)- | H | -COOH | CH₃ | -C(=O)-NH-CH(phenyl) |
| A985 | H₂N-C(=NH)-NH-C(=O)-CH(R⁵)- | H | -COOH | H | -C(=O)-NH-CH(phenyl) |
| A986 | H₂N-C(=NH)-NH-C(=O)-CH(R⁵)- | CH₃ | -COOH | H | -C(=O)-NH-CH(phenyl) |
| A987 | H₂N-C(=NH)-NH-C(=O)-CH(R⁵)- | H | -COOH | CH₃ | -C(=O)-NH-CH(phenyl) |

FIG. 1CM

| | | | | | | | |
|---|---|---|---|---|---|---|---|
| A988 | H₂N-C(NH)-NH-C(O)-CH(R⁵)- | H | -C(O)OH | H | -C(O)-NH-CH(phenyl)- | H | |
| A989 | H₂N-C(NH)-NH-C(O)-CH(R⁵)- | CH₃ | -C(O)OH | H | -C(O)-NH-CH(phenyl)- | H | |
| A990 | H₂N-C(NH)-NH-C(O)-CH(R⁵)- | H | -C(O)OH | CH₃ | -C(O)-NH-CH(phenyl)- | H | |
| A991 | H₂N-C(NH)-NH-C(O)-CH(R⁵)- | H | -C(O)OH | H | -C(O)-NH-CH(phenyl)- | H | |
| A992 | H₂N-C(NH)-NH-C(O)-CH(R⁵)- | CH₃ | -C(O)OH | H | -C(O)-NH-CH(phenyl)- | H | |
| A993 | H₂N-C(NH)-NH-C(O)-CH(R⁵)- | H | -C(O)OH | CH₃ | -C(O)-NH-CH(phenyl)- | H | |
| A994 | H₂N-C(NH)-NH-C(O)-CH(R⁵)- | H | -C(O)OH | H | -C(O)-NH-CH(phenyl)- | H | |
| A995 | H₂N-C(NH)-NH-C(O)-CH(R⁵)- | CH₃ | -C(O)OH | H | -C(O)-NH-CH(phenyl)- | H | |
| A996 | H₂N-C(NH)-NH-C(O)-CH(R⁵)- | H | -C(O)OH | CH₃ | -C(O)-NH-CH(phenyl)- | H | |
| A997 | H₂N-C(NH)-NH-C(O)-CH(R⁵)- | H | -C(O)OH | H | -C(O)-NH-CH(phenyl)- | H | |
| A998 | H₂N-C(NH)-NH-C(O)-CH(R⁵)- | CH₃ | -C(O)OH | H | -C(O)-NH-CH(phenyl)- | H | |

FIG. 1CN

| | | | | | |
|---|---|---|---|---|---|
| A999 | H2N-C(=NH)-NH-C(R5)(O)-ss | H | ss-C(O)-OH | CH3 | ss-C(O)-N(H)-CH(phenyl) |
| A1000 | H2N-C(=NH)-NH-C(R5)(O)-ss | H | ss-C(O)-OH | H | ss-C(O)-N(H)-CH(phenyl) |
| A1001 | H2N-C(=NH)-NH-C(R5)(O)-ss | CH3 | ss-C(O)-OH | H | ss-C(O)-N(H)-CH(phenyl) |
| A1002 | H2N-C(=NH)-NH-C(R5)(O)-ss | H | ss-C(O)-OH | CH3 | ss-C(O)-N(H)-CH(phenyl) |
| A1003 | H2N-C(=NH)-NH-C(R5)(O)-ss | H | ss-C(O)-OH | H | ss-C(O)-N(H)-CH(phenyl) |
| A1004 | H2N-C(=NH)-NH-C(R5)(O)-ss | CH3 | ss-C(O)-OH | H | ss-C(O)-N(H)-CH(phenyl) |
| A1005 | H2N-C(=NH)-NH-C(R5)(O)-ss | H | ss-C(O)-OH | CH3 | ss-C(O)-N(H)-CH(phenyl) |
| A1006 | H2N-C(=NH)-NH-C(R5)(O)-ss | H | ss-C(O)-OH | H | ss-C(O)-N(H)-CH(phenyl) |
| A1007 | H2N-C(=NH)-NH-C(R5)(O)-ss | CH3 | ss-C(O)-OH | H | ss-C(O)-N(H)-CH(phenyl) |
| A1008 | H2N-C(=NH)-NH-C(R5)(O)-ss | H | ss-C(O)-OH | CH3 | ss-C(O)-N(H)-CH(phenyl) |
| A1009 | H2N-C(=NH)-NH-C(R5)(O)-ss | H | ss-C(O)-OH | H | ss-C(O)-N(H)-CH(phenyl) |

FIG. 1CO

| A1010 | H2N-C(NH)-NH-C(O)-CHR5- | CH3 | -C(O)OH | H | -C(O)-NH-CH(Ph)- (S) | |
|---|---|---|---|---|---|---|
| A1011 | H2N-C(NH)-NH-C(O)-CHR5- | H | -C(O)OH | CH3 | -C(O)-NH-CH(Ph)- (S) | |
| A1012 | H2N-C(NH)-NH-C(O)-CHR5- | H | -C(O)OH | H | -C(O)-NH-CH(Ph)- (S) | |
| A1013 | H2N-C(NH)-NH-C(O)-CHR5- | CH3 | -C(O)OH | H | -C(O)-NH-CH(Ph)- (S) | |
| A1014 | H2N-C(NH)-NH-C(O)-CHR5- | H | -C(O)OH | CH3 | -C(O)-NH-CH(Ph)- (S) | |
| A1015 | H2N-C(NH)-NH-C(O)-CHR5- | H | -C(O)OH | H | -C(O)-NH-CH(Ph)- (S) | H |
| A1016 | H2N-C(NH)-NH-C(O)-CHR5- | CH3 | -C(O)OH | H | -C(O)-NH-CH(Ph)- (S) | H |
| A1017 | H2N-C(NH)-NH-C(O)-CHR5- | H | -C(O)OH | CH3 | -C(O)-NH-CH(Ph)- (S) | H |
| A1018 | H2N-C(NH)-NH-C(O)-CHR5- | H | -C(O)OH | H | -C(O)-NH-CH(Ph)- (S) | H |
| A1019 | H2N-C(NH)-NH-C(O)-CHR5- | CH3 | -C(O)OH | H | -C(O)-NH-CH(Ph)- (S) | H |
| A1020 | H2N-C(NH)-NH-C(O)-CHR5- | H | -C(O)OH | CH3 | -C(O)-NH-CH(Ph)- (S) | H |

| | | | | | | |
|---|---|---|---|---|---|---|
| A1021 |  | H |  | H |  | H |
| A1022 |  | CH₃ |  | H |  | H |
| A1023 |  | H |  | CH₃ |  | H |
| A1024 |  | H |  | H |  | |
| A1025 |  | CH₃ |  | H |  | |
| A1026 |  | H |  | CH₃ |  | |
| A1027 |  | H |  | H |  | |
| A1028 |  | CH₃ |  | H |  | |
| A1029 |  | H |  | CH₃ |  | |
| A1030 |  | H |  | H |  | |
| A1031 |  | CH₃ |  | H |  | |

| A1032 |  | H |  | CH₃ |  |
| A1033 |  | H |  | H |  |
| A1034 |  | CH₃ |  | H |  |
| A1035 |  | H |  | CH₃ |  |
| A1036 |  | H |  | H |  |
| A1037 |  | CH₃ |  | H |  |
| A1038 |  | H |  | CH₃ |  |
| A1039 |  | H |  | H |  |
| A1040 |  | CH₃ |  | H |  |
| A1041 |  | H |  | CH₃ |  |

FIG. 1CR

| | | | | | | |
|---|---|---|---|---|---|---|
| A1042 | H₂N-C(=NH)-NH-C(=O)-CH(R⁵)- | H | -C(=O)OH | H | -C(=O)-NH-CH(CH₃)-Ph | H |
| A1043 | H₂N-C(=NH)-NH-C(=O)-CH(R⁵)- | CH₃ | -C(=O)OH | H | -C(=O)-NH-CH(CH₃)-Ph | H |
| A1044 | H₂N-C(=NH)-NH-C(=O)-CH(R⁵)- | H | -C(=O)OH | CH₃ | -C(=O)-NH-CH(CH₃)-Ph | H |
| A1045 | H₂N-C(=NH)-NH-C(=O)-CH(R⁵)- | H | -C(=O)OH | H | -C(=O)-NH-CH(CH₃)-Ph | H |
| A1046 | H₂N-C(=NH)-NH-C(=O)-CH(R⁵)- | CH₃ | -C(=O)OH | H | -C(=O)-NH-CH(CH₃)-Ph | H |
| A1047 | H₂N-C(=NH)-NH-C(=O)-CH(R⁵)- | H | -C(=O)OH | CH₃ | -C(=O)-NH-CH(CH₃)-Ph | H |
| A1048 | H₂N-C(=NH)-NH-C(=O)-CH(R⁵)- | H | -C(=O)OH | H | -C(=O)-NH-CH(CH₃)-Ph | H |
| A1049 | H₂N-C(=NH)-NH-C(=O)-CH(R⁵)- | CH₃ | -C(=O)OH | H | -C(=O)-NH-CH(CH₃)-Ph | H |
| A1050 | H₂N-C(=NH)-NH-C(=O)-CH(R⁵)- | H | -C(=O)OH | CH₃ | -C(=O)-NH-CH(CH₃)-Ph | H |
| A1051 | H₂N-C(=NH)-NH-C(=O)-CH(R⁵)- | H | -C(=O)OH | H | -C(=O)-NH-CH(CH₃)-Ph | H |
| A1052 | H₂N-C(=NH)-NH-C(=O)-CH(R⁵)- | CH₃ | -C(=O)OH | H | -C(=O)-NH-CH(CH₃)-Ph | H |

| | | | | | | | | |
|---|---|---|---|---|---|---|---|---|
| A1053 |  | | H |  | | CH₃ |  | |
| A1054 |  | | H |  | | H |  | |
| A1055 |  | | CH₃ |  | | H |  | |
| A1056 |  | | H |  | | CH₃ |  | |
| A1057 |  | | H |  | | H |  | |
| A1058 |  | | CH₃ |  | | H |  | |
| A1059 |  | | H |  | | CH₃ |  | |
| A1060 |  | | H |  | | H |  | |
| A1061 |  | | CH₃ |  | | H |  | |
| A1062 |  | | H |  | | CH₃ |  | |
| A1063 |  | | H |  | | H |  | |

FIG. 1CT

| | | | | | | |
|---|---|---|---|---|---|---|
| A1064 | H2N-C(=NH)-NH-C(=O)-CH(R5)- | CH3 | -C(=O)-OH | H | -C(=O)-NH-CH(Ph)- | |
| A1065 | H2N-C(=NH)-NH-C(=O)-CH(R5)- | H | -C(=O)-OH | CH3 | -C(=O)-NH-CH(Ph)- | |
| A1066 | H2N-C(=NH)-NH-C(=O)-CH(R5)- | H | -C(=O)-OH | H | -C(=O)-NH-CH(Ph)- | |
| A1067 | H2N-C(=NH)-NH-C(=O)-CH(R5)- | CH3 | -C(=O)-OH | H | -C(=O)-NH-CH(Ph)- | |
| A1068 | H2N-C(=NH)-NH-C(=O)-CH(R5)- | H | -C(=O)-OH | CH3 | -C(=O)-NH-CH(Ph)- | |
| A1069 | H2N-C(=NH)-NH-C(=O)-CH(R5)- | H | -C(=O)-OH | H | -C(=O)-NH-CH(Ph)- | H |
| A1070 | H2N-C(=NH)-NH-C(=O)-CH(R5)- | CH3 | -C(=O)-OH | H | -C(=O)-NH-CH(Ph)- | H |
| A1071 | H2N-C(=NH)-NH-C(=O)-CH(R5)- | H | -C(=O)-OH | CH3 | -C(=O)-NH-CH(Ph)- | H |
| A1072 | H2N-C(=NH)-NH-C(=O)-CH(R5)- | H | -C(=O)-OH | H | -C(=O)-NH-CH(Ph)- | H |
| A1073 | H2N-C(=NH)-NH-C(=O)-CH(R5)- | CH3 | -C(=O)-OH | H | -C(=O)-NH-CH(Ph)- | H |
| A1074 | H2N-C(=NH)-NH-C(=O)-CH(R5)- | H | -C(=O)-OH | CH3 | -C(=O)-NH-CH(Ph)- | H |

FIG. 1CU

| | | | | | | |
|---|---|---|---|---|---|---|
| A1075 | H2N-C(NH)-NH-C(O)-CH(R5)-ss | H | ss-C(O)-OH | H | ss-C(O)-NH-CH(phenyl) | H |
| A1076 | H2N-C(NH)-NH-C(O)-CH(R5)-ss | CH3 | ss-C(O)-OH | H | ss-C(O)-NH-CH(phenyl) | H |
| A1077 | H2N-C(NH)-NH-C(O)-CH(R5)-ss | H | ss-C(O)-OH | CH3 | ss-C(O)-NH-CH(phenyl) | H |
| A1078 | H2N-C(NH)-NH-C(O)-CH(R5)-ss | H | ss-C(O)-OH | H | ss-C(O)-NH-CH(phenyl) | H |
| A1079 | H2N-C(NH)-NH-C(O)-CH(R5)-ss | CH3 | ss-C(O)-OH | H | ss-C(O)-NH-CH(phenyl) | H |
| A1080 | H2N-C(NH)-NH-C(O)-CH(R5)-ss | H | ss-C(O)-OH | CH3 | ss-C(O)-NH-CH(phenyl) | H |
| A1081 | H2N-C(NH)-NH-C(O)-CH(R5)-ss | H | ss-C(O)-OH | H | ss-C(O)-NH-CH(phenyl) | H |
| A1082 | H2N-C(NH)-NH-C(O)-CH(R5)-ss | CH3 | ss-C(O)-OH | H | ss-C(O)-NH-CH(phenyl) | H |
| A1083 | H2N-C(NH)-NH-C(O)-CH(R5)-ss | H | ss-C(O)-OH | CH3 | ss-C(O)-NH-CH(phenyl) | H |
| A1084 | H2N-C(NH)-NH-C(O)-CH(R5)-ss | H | ss-C(O)-OH | H | ss-C(O)-NH-CH(phenyl) | H |
| A1085 | H2N-C(NH)-NH-C(O)-CH(R5)-ss | CH3 | ss-C(O)-OH | H | ss-C(O)-NH-CH(phenyl) | H |

FIG. 1CV

| | | | | | |
|---|---|---|---|---|---|
| A1086 | H2N-C(NH)-NH-CH(R5)-C(O)- (guanidinyl group with R5) | H | -C(O)OH | CH3 | -C(O)-NH-CH-phenyl |
| A1087 | H2N-C(NH)-NH-CH(R5)-C(O)- | H | -C(O)OH | H | -C(O)-NH-CH-phenyl |
| A1088 | H2N-C(NH)-NH-CH(R5)-C(O)- | CH3 | -C(O)OH | H | -C(O)-NH-CH-phenyl |
| A1089 | H2N-C(NH)-NH-CH(R5)-C(O)- | H | -C(O)OH | CH3 | -C(O)-NH-CH-phenyl |
| A1090 | H2N-C(NH)-NH-CH(R5)-C(O)- | H | -C(O)OH | H | -C(O)-NH-CH-phenyl |
| A1091 | H2N-C(NH)-NH-CH(R5)-C(O)- | CH3 | -C(O)OH | H | -C(O)-NH-CH-phenyl |
| A1092 | H2N-C(NH)-NH-CH(R5)-C(O)- | H | -C(O)OH | CH3 | -C(O)-NH-CH-phenyl |
| A1093 | H2N-C(NH)-NH-CH(R5)-C(O)- | H | -C(O)OH | H | -C(O)-NH-CH-phenyl |
| A1094 | H2N-C(NH)-NH-CH(R5)-C(O)- | CH3 | -C(O)OH | H | -C(O)-NH-CH-phenyl |
| A1095 | H2N-C(NH)-NH-CH(R5)-C(O)- | H | -C(O)OH | CH3 | -C(O)-NH-CH-phenyl |

FIG. 1CW

| | | | | | | | |
|---|---|---|---|---|---|---|---|
| A1096 | H₂N-C(=NH)-NH-C(=O)-CH(R⁵)-ss | H | ss-C(=O)-OH | H | ss-C(=O)-NH-CH(▲)-Ph | H |
| A1097 | H₂N-C(=NH)-NH-C(=O)-CH(R⁵)-ss | CH₃ | ss-C(=O)-OH | H | ss-C(=O)-NH-CH(▲)-Ph | H |
| A1098 | H₂N-C(=NH)-NH-C(=O)-CH(R⁵)-ss | H | ss-C(=O)-OH | CH₃ | ss-C(=O)-NH-CH(▲)-Ph | H |
| A1099 | H₂N-C(=NH)-NH-C(=O)-CH(R⁵)-ss | H | ss-C(=O)-OH | H | ss-C(=O)-NH-CH(▲)-Ph | H |
| A1100 | H₂N-C(=NH)-NH-C(=O)-CH(R⁵)-ss | CH₃ | ss-C(=O)-OH | H | ss-C(=O)-NH-CH(▲)-Ph | H |
| A1101 | H₂N-C(=NH)-NH-C(=O)-CH(R⁵)-ss | H | ss-C(=O)-OH | CH₃ | ss-C(=O)-NH-CH(▲)-Ph | H |
| A1102 | H₂N-C(=NH)-NH-C(=O)-CH(R⁵)-ss | H | ss-C(=O)-OH | H | ss-C(=O)-NH-CH(▲)-Ph | H |
| A1103 | H₂N-C(=NH)-NH-C(=O)-CH(R⁵)-ss | CH₃ | ss-C(=O)-OH | H | ss-C(=O)-NH-CH(▲)-Ph | H |
| A1104 | H₂N-C(=NH)-NH-C(=O)-CH(R⁵)-ss | H | ss-C(=O)-OH | CH₃ | ss-C(=O)-NH-CH(▲)-Ph | H |
| A1105 | H₂N-C(=NH)-NH-C(=O)-CH(R⁵)-ss | H | ss-C(=O)-OH | H | ss-C(=O)-NH-CH(▲)-Ph | H |
| A1106 | H₂N-C(=NH)-NH-C(=O)-CH(R⁵)-ss | CH₃ | ss-C(=O)-OH | H | ss-C(=O)-NH-CH(▲)-Ph | H |

FIG. 1CX

| ID | Col1 | R5 | Col3 | Col4 | Col5 |
|---|---|---|---|---|---|
| A1107 | H₂N-C(=NH)-NH-C(=O)-CH(R⁵)- | H | -C(=O)-OH | CH₃ | -C(=O)-NH-CH(Ph)- |
| A1108 | H₂N-C(=NH)-NH-C(=O)-CH(R⁵)- | H | -C(=O)-OH | H | -C(=O)-NH-CH(Ph)- |
| A1109 | H₂N-C(=NH)-NH-C(=O)-CH(R⁵)- | CH₃ | -C(=O)-OH | H | -C(=O)-NH-CH(Ph)- |
| A1110 | H₂N-C(=NH)-NH-C(=O)-CH(R⁵)- | H | -C(=O)-OH | CH₃ | -C(=O)-NH-CH(Ph)- |
| A1111 | H₂N-C(=NH)-NH-C(=O)-CH(R⁵)- | H | -C(=O)-OH | H | -C(=O)-NH-CH(Ph)- |
| A1112 | H₂N-C(=NH)-NH-C(=O)-CH(R⁵)- | CH₃ | -C(=O)-OH | H | -C(=O)-NH-CH(Ph)- |
| A1113 | H₂N-C(=NH)-NH-C(=O)-CH(R⁵)- | H | -C(=O)-OH | CH₃ | -C(=O)-NH-CH(Ph)- |
| A1114 | H₂N-C(=NH)-NH-C(=O)-CH(R⁵)- | H | -C(=O)-OH | H | -C(=O)-NH-CH(Ph)- |
| A1115 | H₂N-C(=NH)-NH-C(=O)-CH(R⁵)- | CH₃ | -C(=O)-OH | H | -C(=O)-NH-CH(Ph)- |
| A1116 | H₂N-C(=NH)-NH-C(=O)-CH(R⁵)- | H | -C(=O)-OH | CH₃ | -C(=O)-NH-CH(Ph)- |
| A1117 | H₂N-C(=NH)-NH-C(=O)-CH(R⁵)- | H | -C(=O)-OH | H | -C(=O)-NH-CH(Ph)- |

FIG. 1CY

| A1118 | H2N-C(NH)-NH-C(O)-CH(R5)- (CH3) | CH3 | -COOH | H | -C(O)-NH-CH(phenyl) | |
|---|---|---|---|---|---|---|
| A1119 | H2N-C(NH)-NH-C(O)-CH(R5)- | H | -COOH | CH3 | -C(O)-NH-CH(phenyl) | |
| A1120 | H2N-C(NH)-NH-C(O)-CH(R5)- | H | -COOH | H | -C(O)-NH-CH(phenyl) | |
| A1121 | H2N-C(NH)-NH-C(O)-CH(R5)- | CH3 | -COOH | H | -C(O)-NH-CH(phenyl) | |
| A1122 | H2N-C(NH)-NH-C(O)-CH(R5)- | H | -COOH | CH3 | -C(O)-NH-CH(phenyl) | |
| A1123 | H2N-C(NH)-NH-C(O)-CH(R5)- | H | -COOH | H | -C(O)-NH-CH(phenyl) | H |
| A1124 | H2N-C(NH)-NH-C(O)-CH(R5)- | CH3 | -COOH | H | -C(O)-NH-CH(phenyl) | H |
| A1125 | H2N-C(NH)-NH-C(O)-CH(R5)- | H | -COOH | CH3 | -C(O)-NH-CH(phenyl) | H |
| A1126 | H2N-C(NH)-NH-C(O)-CH(R5)- | H | -COOH | H | -C(O)-NH-CH(phenyl) | H |
| A1127 | H2N-C(NH)-NH-C(O)-CH(R5)- | CH3 | -COOH | H | -C(O)-NH-CH(phenyl) | H |
| A1128 | H2N-C(NH)-NH-C(O)-CH(R5)- | H | -COOH | CH3 | -C(O)-NH-CH(phenyl) | H |

FIG. 1CZ

| | | | | | | |
|---|---|---|---|---|---|---|
| A1129 | H₂N-C(=NH)-NH-C(=O)-CH(R⁵)- | H | -C(=O)-OH | H | -C(=O)-NH-CH(Ph)- (S) | H |
| A1130 | H₂N-C(=NH)-NH-C(=O)-CH(R⁵)- | CH₃ | -C(=O)-OH | H | -C(=O)-NH-CH(Ph)- (S) | H |
| A1131 | H₂N-C(=NH)-NH-C(=O)-CH(R⁵)- | H | -C(=O)-OH | CH₃ | -C(=O)-NH-CH(Ph)- (S) | H |
| A1132 | H₂N-C(=NH)-NH-C(=O)-CH(R⁵)- | H | -C(=O)-OH | H | -C(=O)-NH-CH(Ph)- (R) | |
| A1133 | H₂N-C(=NH)-NH-C(=O)-CH(R⁵)- | CH₃ | -C(=O)-OH | H | -C(=O)-NH-CH(Ph)- (R) | |
| A1134 | H₂N-C(=NH)-NH-C(=O)-CH(R⁵)- | H | -C(=O)-OH | CH₃ | -C(=O)-NH-CH(Ph)- (R) | |
| A1135 | H₂N-C(=NH)-NH-C(=O)-CH(R⁵)- | H | -C(=O)-OH | H | -C(=O)-NH-CH(Ph)- (R) | |
| A1136 | H₂N-C(=NH)-NH-C(=O)-CH(R⁵)- | CH₃ | -C(=O)-OH | H | -C(=O)-NH-CH(Ph)- (R) | |
| A1137 | H₂N-C(=NH)-NH-C(=O)-CH(R⁵)- | H | -C(=O)-OH | CH₃ | -C(=O)-NH-CH(Ph)- (R) | |
| A1138 | H₂N-C(=NH)-NH-C(=O)-CH(R⁵)- | H | -C(=O)-OH | H | -C(=O)-NH-CH(Ph)- (R) | |
| A1139 | H₂N-C(=NH)-NH-C(=O)-CH(R⁵)- | CH₃ | -C(=O)-OH | H | -C(=O)-NH-CH(Ph)- (R) | |

FIG. 1DA

| | | | | | |
|---|---|---|---|---|---|
| A1140 | H₂N-C(=NH)-NH-C(=O)-CH(R⁵)-ss | H | ss-C(=O)-OH | CH₃ | ss-C(=O)-N-CH(phenyl) (S) |
| A1141 | H₂N-C(=NH)-NH-C(=O)-CH(R⁵)-ss | H | ss-C(=O)-OH | H | ss-C(=O)-N-CH(phenyl) (S) |
| A1142 | H₂N-C(=NH)-NH-C(=O)-CH(R⁵)-ss | CH₃ | ss-C(=O)-OH | H | ss-C(=O)-N-CH(phenyl) (S) |
| A1143 | H₂N-C(=NH)-NH-C(=O)-CH(R⁵)-ss | H | ss-C(=O)-OH | CH₃ | ss-C(=O)-N-CH(phenyl) (S) |
| A1144 | H₂N-C(=NH)-NH-C(=O)-CH(R⁵)-ss | H | ss-C(=O)-OH | H | ss-C(=O)-N-CH(phenyl) (R) |
| A1145 | H₂N-C(=NH)-NH-C(=O)-CH(R⁵)-ss | CH₃ | ss-C(=O)-OH | H | ss-C(=O)-N-CH(phenyl) (R) |
| A1146 | H₂N-C(=NH)-NH-C(=O)-CH(R⁵)-ss | H | ss-C(=O)-OH | CH₃ | ss-C(=O)-N-CH(phenyl) (R) |
| A1147 | H₂N-C(=NH)-NH-C(=O)-CH(R⁵)-ss | H | ss-C(=O)-OH | H | ss-C(=O)-N-CH(phenyl) (R) |
| A1148 | H₂N-C(=NH)-NH-C(=O)-CH(R⁵)-ss | CH₃ | ss-C(=O)-OH | H | ss-C(=O)-N-CH(phenyl) (R) |
| A1149 | H₂N-C(=NH)-NH-C(=O)-CH(R⁵)-ss | H | ss-C(=O)-OH | CH₃ | ss-C(=O)-N-CH(phenyl) (R) |

FIG. 1DB

| ID | | | | | | |
|---|---|---|---|---|---|---|
| A1150 | H₂N-C(NH)-NH-C(O)-CH(R⁵)- | H | -C(O)OH | H | -C(O)-NH-CH(Ph)- | H |
| A1151 | H₂N-C(NH)-NH-C(O)-CH(R⁵)- | CH₃ | -C(O)OH | H | -C(O)-NH-CH(Ph)- | H |
| A1152 | H₂N-C(NH)-NH-C(O)-CH(R⁵)- | H | -C(O)OH | CH₃ | -C(O)-NH-CH(Ph)- | H |
| A1153 | H₂N-C(NH)-NH-C(O)-CH(R⁵)- | H | -C(O)OH | H | -C(O)-NH-CH(Ph)- | H |
| A1154 | H₂N-C(NH)-NH-C(O)-CH(R⁵)- | CH₃ | -C(O)OH | H | -C(O)-NH-CH(Ph)- | H |
| A1155 | H₂N-C(NH)-NH-C(O)-CH(R⁵)- | H | -C(O)OH | CH₃ | -C(O)-NH-CH(Ph)- | H |
| A1156 | H₂N-C(NH)-NH-C(O)-CH(R⁵)- | H | -C(O)OH | H | -C(O)-NH-CH(Ph)- | H |
| A1157 | H₂N-C(NH)-NH-C(O)-CH(R⁵)- | CH₃ | -C(O)OH | H | -C(O)-NH-CH(Ph)- | H |
| A1158 | H₂N-C(NH)-NH-C(O)-CH(R⁵)- | H | -C(O)OH | CH₃ | -C(O)-NH-CH(Ph)- | H |
| A1159 | H₂N-C(NH)-NH-C(O)-CH(R⁵)- | H | -C(O)OH | H | -C(O)-NH-CH(Ph)- | H |
| A1160 | H₂N-C(NH)-NH-C(O)-CH(R⁵)- | CH₃ | -C(O)OH | H | -C(O)-NH-CH(Ph)- | H |

FIG. 1DC

| | | | | | |
|---|---|---|---|---|---|
| A1161 | guanidine-acyl with R⁵ | H | COOH | CH₃ | benzyl amide (S) |
| A1162 | guanidine-acyl with R⁵ | H | COOH | H | benzyl amide (S) |
| A1163 | guanidine-acyl with R⁵ | CH₃ | COOH | H | benzyl amide (S) |
| A1164 | guanidine-acyl with R⁵ | H | COOH | CH₃ | benzyl amide (R) |
| A1165 | guanidine-acyl with R⁵ | H | COOH | H | benzyl amide (R) |
| A1166 | guanidine-acyl with R⁵ | CH₃ | COOH | H | benzyl amide (R) |
| A1167 | guanidine-acyl with R⁵ | H | COOH | CH₃ | benzyl amide (S) |
| A1168 | guanidine-acyl with R⁵ | H | COOH | H | benzyl amide (S) |
| A1169 | guanidine-acyl with R⁵ | CH₃ | COOH | H | benzyl amide (S) |
| A1170 | guanidine-acyl with R⁵ | H | COOH | CH₃ | benzyl amide (R) |
| A1171 | guanidine-acyl with R⁵ | H | COOH | H | benzyl amide (R) |

| | | | | | |
|---|---|---|---|---|---|
| A1172 |  | CH₃ |  | H |  |
| A1173 |  | H |  | CH₃ |  |
| A1174 |  | H |  | H |  |
| A1175 |  | CH₃ |  | H |  |
| A1176 |  | H |  | CH₃ |  |
| A1177 |  | H |  | H |  |
| A1178 |  | CH₃ |  | H |  |
| A1179 |  | H |  | CH₃ |  |
| A1180 |  | H |  | H |  |
| A1181 |  | CH₃ |  | H |  |

FIG. 1DE

| | | | | | |
|---|---|---|---|---|---|
| A1182 | H₂N-C(NH)-NH-C(O)-CH(R⁵)- | H | -COOH | CH₃ | -C(O)-NH-CH(phenyl)- |
| A1183 | H₂N-C(NH)-NH-C(O)-CH(R⁵)- | H | -COOH | H | -C(O)-NH-CH(phenyl)- |
| A1184 | H₂N-C(NH)-NH-C(O)-CH(R⁵)- | CH₃ | -COOH | H | -C(O)-NH-CH(phenyl)- |
| A1185 | H₂N-C(NH)-NH-C(O)-CH(R⁵)- | H | -COOH | CH₃ | -C(O)-NH-CH(phenyl)- |
| A1186 | H₂N-C(NH)-NH-C(O)-CH(R⁵)- | H | -COOH | H | -C(O)-NH-CH(phenyl)- |
| A1187 | H₂N-C(NH)-NH-C(O)-CH(R⁵)- | CH₃ | -COOH | H | -C(O)-NH-CH(phenyl)- |
| A1188 | H₂N-C(NH)-NH-C(O)-CH(R⁵)- | H | -COOH | CH₃ | -C(O)-NH-CH(phenyl)- |
| A1189 | H₂N-C(NH)-NH-C(O)-CH(R⁵)- | H | -COOH | H | -C(O)-NH-CH(phenyl)- |
| A1190 | H₂N-C(NH)-NH-C(O)-CH(R⁵)- | CH₃ | -COOH | H | -C(O)-NH-CH(phenyl)- |
| A1191 | H₂N-C(NH)-NH-C(O)-CH(R⁵)- | H | -COOH | CH₃ | -C(O)-NH-CH(phenyl)- |
| A1192 | H₂N-C(NH)-NH-C(O)-CH(R⁵)- | H | -COOH | H | -C(O)-NH-CH(phenyl)- |

| | | R5 | | | |
|---|---|---|---|---|---|
| A1193 |  | CH₃ |  | H |  |
| A1194 |  | H |  | CH₃ |  |
| A1195 |  | H |  | H |  |
| A1196 |  | CH₃ |  | H |  |
| A1197 |  | H |  | CH₃ |  |
| A1198 |  | H |  | H |  |
| A1199 |  | CH₃ |  | H |  |
| A1200 |  | H |  | CH₃ |  |
| A1201 |  | H |  | H |  |
| A1202 |  | CH₃ |  | H |  |

FIG. 1DG

| | | | | | |
|---|---|---|---|---|---|
| A1203 | H₂N-C(NH)-NH-C(O)-CH(R⁵)-ss | H | ss-C(O)OH | CH₃ | ss-C(O)-NH-CH(Ph)- |
| A1204 | H₂N-C(NH)-NH-C(O)-CH(R⁵)-ss | H | ss-C(O)OH | H | ss-C(O)-NH-CH(Ph)- |
| A1205 | H₂N-C(NH)-NH-C(O)-CH(R⁵)-ss | CH₃ | ss-C(O)OH | H | ss-C(O)-NH-CH(Ph)- |
| A1206 | H₂N-C(NH)-NH-C(O)-CH(R⁵)-ss | H | ss-C(O)OH | CH₃ | ss-C(O)-NH-CH(Ph)- |
| A1207 | H₂N-C(NH)-NH-C(O)-CH(R⁵)-ss | H | ss-C(O)OH | H | ss-C(O)-NH-CH(Ph)- |
| A1208 | H₂N-C(NH)-NH-C(O)-CH(R⁵)-ss | CH₃ | ss-C(O)OH | H | ss-C(O)-NH-CH(Ph)- |
| A1209 | H₂N-C(NH)-NH-C(O)-CH(R⁵)-ss | H | ss-C(O)OH | CH₃ | ss-C(O)-NH-CH(Ph)- |
| A1210 | H₂N-C(NH)-NH-C(O)-CH(R⁵)-ss | H | ss-C(O)OH | H | ss-C(O)-NH-CH(Ph)- |
| A1211 | H₂N-C(NH)-NH-C(O)-CH(R⁵)-ss | CH₃ | ss-C(O)OH | H | ss-C(O)-NH-CH(Ph)- |
| A1212 | H₂N-C(NH)-NH-C(O)-CH(R⁵)-ss | H | ss-C(O)OH | CH₃ | ss-C(O)-NH-CH(Ph)- |
| A1213 | H₂N-C(NH)-NH-C(O)-CH(R⁵)-ss | H | ss-C(O)OH | H | ss-C(O)-NH-CH(Ph)- |

FIG. 1DH

| | | | | | |
|---|---|---|---|---|---|
| A1214 | H₂N-C(=NH)-NH-CH(R⁵)-C(=O)-NH-CH- | CH₃ | -C(=O)-OH | H | -C(=O)-NH-CH(phenyl)- |
| A1215 | H₂N-C(=NH)-NH-CH(R⁵)-C(=O)-NH-CH- | H | -C(=O)-OH | CH₃ | -C(=O)-NH-CH(phenyl)- |
| A1216 | H₂N-C(=NH)-NH-CH(R⁵)-C(=O)-NH-CH- | H | -C(=O)-OH | H | -C(=O)-NH-CH(phenyl)- |
| A1217 | H₂N-C(=NH)-NH-CH(R⁵)-C(=O)-NH-CH- | CH₃ | -C(=O)-OH | H | -C(=O)-NH-CH(phenyl)- |
| A1218 | H₂N-C(=NH)-NH-CH(R⁵)-C(=O)-NH-CH- | H | -C(=O)-OH | CH₃ | -C(=O)-NH-CH(phenyl)- |
| A1219 | H₂N-C(=NH)-NH-CH(R⁵)-C(=O)-NH-CH- | H | -C(=O)-OH | H | -C(=O)-NH-CH(phenyl)- |
| A1220 | H₂N-C(=NH)-NH-CH(R⁵)-C(=O)-NH-CH- | CH₃ | -C(=O)-OH | H | -C(=O)-NH-CH(phenyl)- |
| A1221 | H₂N-C(=NH)-NH-CH(R⁵)-C(=O)-NH-CH- | H | -C(=O)-OH | CH₃ | -C(=O)-NH-CH(phenyl)- |
| A1222 | H₂N-C(=NH)-NH-CH(R⁵)-C(=O)-NH-CH- | H | -C(=O)-OH | H | -C(=O)-NH-CH(phenyl)- |
| A1223 | H₂N-C(=NH)-NH-CH(R⁵)-C(=O)-NH-CH- | CH₃ | -C(=O)-OH | H | -C(=O)-NH-CH(phenyl)- |
| A1224 | H₂N-C(=NH)-NH-CH(R⁵)-C(=O)-NH-CH- | H | -C(=O)-OH | CH₃ | -C(=O)-NH-CH(phenyl)- |

FIG. 1DI

| A1225 | H₂N-C(NH)-NH-CH(R⁵)-C(O)- | H | -COOH | H | -C(O)-NH-CH(CH₃)-Ph |
|---|---|---|---|---|---|
| A1226 | H₂N-C(NH)-NH-CH(R⁵)-C(O)- | CH₃ | -COOH | H | -C(O)-NH-CH(CH₃)-Ph |
| A1227 | H₂N-C(NH)-NH-CH(R⁵)-C(O)- | H | -COOH | CH₃ | -C(O)-NH-CH(CH₃)-Ph |
| A1228 | H₂N-C(NH)-NH-CH(R⁵)-C(O)- | H | -CH₂-COOH | H | -C(O)-NH-CH(CH₃)-Ph |
| A1229 | H₂N-C(NH)-NH-CH(R⁵)-C(O)- | CH₃ | -CH₂-COOH | H | -C(O)-NH-CH(CH₃)-Ph |
| A1230 | H₂N-C(NH)-NH-CH(R⁵)-C(O)- | H | -CH₂-COOH | CH₃ | -C(O)-NH-CH(CH₃)-Ph |
| A1231 | H₂N-C(NH)-NH-CH(R⁵)-C(O)- | H | -COOH | H | -C(O)-NH-CH(CH₃)-Ph |
| A1232 | H₂N-C(NH)-NH-CH(R⁵)-C(O)- | CH₃ | -COOH | H | -C(O)-NH-CH(CH₃)-Ph |
| A1233 | H₂N-C(NH)-NH-CH(R⁵)-C(O)- | H | -COOH | CH₃ | -C(O)-NH-CH(CH₃)-Ph |
| A1234 | H₂N-C(NH)-NH-CH(R⁵)-C(O)- | H | -CH₂-COOH | H | -C(O)-NH-CH(CH₃)-Ph |

| | | | | | |
|---|---|---|---|---|---|
| A1235 |  | CH₃ |  | H |  |
| A1236 |  | H |  | CH₃ |  |
| A1237 |  | H |  | H |  |
| A1238 |  | CH₃ |  | H |  |
| A1239 |  | H |  | CH₃ |  |
| A1240 |  | H |  | H |  |
| A1241 |  | CH₃ |  | H |  |
| A1242 |  | H |  | CH₃ |  |
| A1243 |  | H |  | H |  |
| A1244 |  | CH₃ |  | H |  |
| A1245 |  | H |  | CH₃ |  |

FIG. 1DK

| | | | | | |
|---|---|---|---|---|---|
| A1246 | H2N-C(NH)-NH-CH(R5)-C(O)- [ss] | H | [ss]-C(O)-OH | H | [ss]-C(O)-NH-CH(CH3)-Ph |
| A1247 | H2N-C(NH)-NH-CH(R5)-C(O)- [ss] | CH3 | [ss]-C(O)-OH | H | [ss]-C(O)-NH-CH(CH3)-Ph |
| A1248 | H2N-C(NH)-NH-CH(R5)-C(O)- [ss] | H | [ss]-C(O)-OH | CH3 | [ss]-C(O)-NH-CH(CH3)-Ph |
| A1249 | H2N-C(NH)-NH-CH(R5)-C(O)- [ss] | H | [ss]-C(O)-OH | H | [ss]-C(O)-NH-CH(CH3)-Ph |
| A1250 | H2N-C(NH)-NH-CH(R5)-C(O)- [ss] | CH3 | [ss]-C(O)-OH | H | [ss]-C(O)-NH-CH(CH3)-Ph |
| A1251 | H2N-C(NH)-NH-CH(R5)-C(O)- [ss] | H | [ss]-C(O)-OH | CH3 | [ss]-C(O)-NH-CH(CH3)-Ph |
| A1252 | H2N-C(NH)-NH-CH(R5)-C(O)- [ss] | H | [ss]-C(O)-OH | H | [ss]-C(O)-NH-CH(CH3)-Ph |
| A1253 | H2N-C(NH)-NH-CH(R5)-C(O)- [ss] | CH3 | [ss]-C(O)-OH | H | [ss]-C(O)-NH-CH(CH3)-Ph |
| A1254 | H2N-C(NH)-NH-CH(R5)-C(O)- [ss] | H | [ss]-C(O)-OH | CH3 | [ss]-C(O)-NH-CH(CH3)-Ph |
| A1255 | H2N-C(NH)-NH-CH(R5)-C(O)- [ss] | H | [ss]-C(O)-OH | H | [ss]-C(O)-NH-CH(CH3)-Ph |
| A1256 | H2N-C(NH)-NH-CH(R5)-C(O)- [ss] | CH3 | [ss]-C(O)-OH | H | [ss]-C(O)-NH-CH(CH3)-Ph |

FIG. 1DL

| | | | | | |
|---|---|---|---|---|---|
| A1257 | H₂N-C(=NH)(NH)-NH-C(=O)-CH(R⁵)- | H | -CH₂-C(=O)-OH | CH₃ | -C(=O)-NH-CH(CH₃)-Ph (S) |
| A1258 | H₂N-C(=NH)(NH)-NH-C(=O)-CH(R⁵)- | H | -CH₂-C(=O)-OH | H | -C(=O)-NH-CH(CH₃)-Ph (S) |
| A1259 | H₂N-C(=NH)(NH)-NH-C(=O)-CH(R⁵)- | CH₃ | -CH₂-C(=O)-OH | H | -C(=O)-NH-CH(CH₃)-Ph (S) |
| A1260 | H₂N-C(=NH)(NH)-NH-C(=O)-CH(R⁵)- | H | -CH₂-C(=O)-OH | CH₃ | -C(=O)-NH-CH(CH₃)-Ph (S) |
| A1261 | H₂N-C(=NH)(NH)-NH-C(=O)-CH(R⁵)- | H | -CH₂-C(=O)-OH | H | -C(=O)-NH-CH(CH₃)-Ph (S) |
| A1262 | H₂N-C(=NH)(NH)-NH-C(=O)-CH(R⁵)- | CH₃ | -CH₂-C(=O)-OH | H | -C(=O)-NH-CH(CH₃)-Ph (S) |
| A1263 | H₂N-C(=NH)(NH)-NH-C(=O)-CH(R⁵)- | H | -CH₂-C(=O)-OH | CH₃ | -C(=O)-NH-CH(CH₃)-Ph (S) |
| A1264 | H₂N-C(=NH)(NH)-NH-C(=O)-CH(R⁵)- | H | -CH₂-C(=O)-OH | H | -C(=O)-NH-CH(CH₃)-Ph (S) |
| A1265 | H₂N-C(=NH)(NH)-NH-C(=O)-CH(R⁵)- | CH₃ | -CH₂-C(=O)-OH | H | -C(=O)-NH-CH(CH₃)-Ph (S) |
| A1266 | H₂N-C(=NH)(NH)-NH-C(=O)-CH(R⁵)- | H | -CH₂-C(=O)-OH | CH₃ | -C(=O)-NH-CH(CH₃)-Ph (S) |
| A1267 | H₂N-C(=NH)(NH)-NH-C(=O)-CH(R⁵)- | H | -CH₂-C(=O)-OH | H | -C(=O)-NH-CH(CH₃)-Ph (R) |

| | | | | | |
|---|---|---|---|---|---|
| A1268 |  | CH₃ |  | H |  |
| A1269 |  | H |  | CH₃ |  |
| A1270 |  | H |  | H |  |
| A1271 |  | CH₃ |  | H |  |
| A1272 |  | H |  | CH₃ |  |
| A1273 |  | H |  | H |  |
| A1274 |  | CH₃ |  | H |  |
| A1275 |  | H |  | CH₃ |  |
| A1276 |  | H |  | H |  |
| A1277 |  | CH₃ |  | H |  |
| A1278 |  | H |  | CH₃ |  |

| | | | | | |
|---|---|---|---|---|---|
| A1279 |  | H |  | H |  |
| A1280 |  | CH₃ |  | H |  |
| A1281 |  | H |  | CH₃ |  |
| A1282 |  | H |  | H |  |
| A1283 |  | CH₃ |  | H |  |
| A1284 |  | H |  | CH₃ |  |
| A1285 |  | H |  | H |  |
| A1286 |  | CH₃ |  | H |  |
| A1287 |  | H |  | CH₃ |  |
| A1288 |  | H |  | H |  |

FIG. 1DO

| | | | | | |
|---|---|---|---|---|---|
| A1289 | H₂N−C(=NH)−NH−C(=O)−CH(R⁵)−ss | CH₃ | ss−C(=O)−OH | H | ss−C(=O)−NH−CH(▲)−phenyl |
| A1290 | H₂N−C(=NH)−NH−C(=O)−CH(R⁵)−ss | H | ss−C(=O)−OH | CH₃ | ss−C(=O)−NH−CH(▲)−phenyl |
| A1291 | H₂N−C(=NH)−NH−C(=O)−CH(R⁵)−ss | H | ss−C(=O)−OH | H | ss−C(=O)−NH−CH(▲)−phenyl |
| A1292 | H₂N−C(=NH)−NH−C(=O)−CH(R⁵)−ss | CH₃ | ss−C(=O)−OH | H | ss−C(=O)−NH−CH(▲)−phenyl |
| A1293 | H₂N−C(=NH)−NH−C(=O)−CH(R⁵)−ss | H | ss−C(=O)−OH | CH₃ | ss−C(=O)−NH−CH(▲)−phenyl |
| A1294 | H₂N−C(=NH)−NH−C(=O)−CH(R⁵)−ss | H | ss−C(=O)−OH | H | ss−C(=O)−NH−CH(▲)−phenyl |
| A1295 | H₂N−C(=NH)−NH−C(=O)−CH(R⁵)−ss | CH₃ | ss−C(=O)−OH | H | ss−C(=O)−NH−CH(▲)−phenyl |
| A1296 | H₂N−C(=NH)−NH−C(=O)−CH(R⁵)−ss | H | ss−C(=O)−OH | CH₃ | ss−C(=O)−NH−CH(▲)−phenyl |
| A1297 | H₂N−C(=NH)−NH−C(=O)−CH(R⁵)−ss | H | ss−C(=O)−OH | H | ss−C(=O)−NH−CH(▲)−phenyl |
| A1298 | H₂N−C(=NH)−NH−C(=O)−CH(R⁵)−ss | CH₃ | ss−C(=O)−OH | H | ss−C(=O)−NH−CH(▲)−phenyl |
| A1299 | H₂N−C(=NH)−NH−C(=O)−CH(R⁵)−ss | H | ss−C(=O)−OH | CH₃ | ss−C(=O)−NH−CH(▲)−phenyl |

FIG. 1DP

| | | | | | |
|---|---|---|---|---|---|
| A1300 | H₂N-C(=NH)-NH-C(=O)-CH(R⁵)- | H | -C(=O)OH | H | -C(=O)-NH-CH(phenyl)- |
| A1301 | H₂N-C(=NH)-NH-C(=O)-CH(R⁵)- | CH₃ | -C(=O)OH | H | -C(=O)-NH-CH(phenyl)- |
| A1302 | H₂N-C(=NH)-NH-C(=O)-CH(R⁵)- | H | -C(=O)OH | CH₃ | -C(=O)-NH-CH(phenyl)- |
| A1303 | H₂N-C(=NH)-NH-C(=O)-CH(R⁵)- | H | -C(=O)OH | H | -C(=O)-NH-CH(phenyl)- |
| A1304 | H₂N-C(=NH)-NH-C(=O)-CH(R⁵)- | CH₃ | -C(=O)OH | H | -C(=O)-NH-CH(phenyl)- |
| A1305 | H₂N-C(=NH)-NH-C(=O)-CH(R⁵)- | H | -C(=O)OH | CH₃ | -C(=O)-NH-CH(phenyl)- |
| A1306 | H₂N-C(=NH)-NH-C(=O)-CH(R⁵)- | H | -C(=O)OH | H | -C(=O)-NH-CH(phenyl)- |
| A1307 | H₂N-C(=NH)-NH-C(=O)-CH(R⁵)- | CH₃ | -C(=O)OH | H | -C(=O)-NH-CH(phenyl)- |
| A1308 | H₂N-C(=NH)-NH-C(=O)-CH(R⁵)- | H | -C(=O)OH | CH₃ | -C(=O)-NH-CH(phenyl)- |
| A1309 | H₂N-C(=NH)-NH-C(=O)-CH(R⁵)- | H | -C(=O)OH | H | -C(=O)-NH-CH(phenyl)- |
| A1310 | H₂N-C(=NH)-NH-C(=O)-CH(R⁵)- | CH₃ | -C(=O)OH | H | -C(=O)-NH-CH(phenyl)- |

FIG. 1DQ

| | | | | | |
|---|---|---|---|---|---|
| A1311 | H₂N-C(=NH)-NH-C(=O)-CHR⁵- | H | -COOH | CH₃ | -C(=O)-NH-CH(CH₃)-Ph |
| A1312 | H₂N-C(=NH)-NH-C(=O)-CHR⁵- | H | -COOH | H | -C(=O)-NH-CH(CH₃)-Ph |
| A1313 | H₂N-C(=NH)-NH-C(=O)-CHR⁵- | CH₃ | -COOH | H | -C(=O)-NH-CH(CH₃)-Ph |
| A1314 | H₂N-C(=NH)-NH-C(=O)-CHR⁵- | H | -COOH | CH₃ | -C(=O)-NH-CH(CH₃)-Ph |
| A1315 | H₂N-C(=NH)-NH-C(=O)-CHR⁵- | H | -COOH | H | -C(=O)-NH-CH(CH₃)-Ph |
| A1316 | H₂N-C(=NH)-NH-C(=O)-CHR⁵- | CH₃ | -COOH | H | -C(=O)-NH-CH(CH₃)-Ph |
| A1317 | H₂N-C(=NH)-NH-C(=O)-CHR⁵- | H | -COOH | CH₃ | -C(=O)-NH-CH(CH₃)-Ph |
| A1318 | H₂N-C(=NH)-NH-C(=O)-CHR⁵- | H | -COOH | H | -C(=O)-NH-CH(CH₃)-Ph |
| A1319 | H₂N-C(=NH)-NH-C(=O)-CHR⁵- | CH₃ | -COOH | H | -C(=O)-NH-CH(CH₃)-Ph |
| A1320 | H₂N-C(=NH)-NH-C(=O)-CHR⁵- | H | -COOH | CH₃ | -C(=O)-NH-CH(CH₃)-Ph |
| A1321 | H₂N-C(=NH)-NH-C(=O)-CHR⁵- | H | -COOH | H | -C(=O)-NH-CH(CH₃)-Ph |

FIG. 1DR

| | | | | | |
|---|---|---|---|---|---|
| A1322 | H₂N−C(=NH)−NH−C(=O)−CH(R⁵)− | CH₃ | −COOH | H | −C(=O)−NH−CH(phenyl)− |
| A1323 | H₂N−C(=NH)−NH−C(=O)−CH(R⁵)− | H | −COOH | CH₃ | −C(=O)−NH−CH(phenyl)− |
| A1324 | H₂N−C(=NH)−NH−C(=O)−CH(R⁵)− | H | −COOH | H | −C(=O)−NH−CH(phenyl)− |
| A1325 | H₂N−C(=NH)−NH−C(=O)−CH(R⁵)− | CH₃ | −COOH | H | −C(=O)−NH−CH(phenyl)− |
| A1326 | H₂N−C(=NH)−NH−C(=O)−CH(R⁵)− | H | −COOH | CH₃ | −C(=O)−NH−CH(phenyl)− |
| A1327 | H₂N−C(=NH)−NH−C(=O)−CH(R⁵)− | H | −COOH | H | −C(=O)−NH−CH(phenyl)− |
| A1328 | H₂N−C(=NH)−NH−C(=O)−CH(R⁵)− | CH₃ | −COOH | H | −C(=O)−NH−CH(phenyl)− |
| A1329 | H₂N−C(=NH)−NH−C(=O)−CH(R⁵)− | H | −COOH | CH₃ | −C(=O)−NH−CH(phenyl)− |
| A1330 | H₂N−C(=NH)−NH−C(=O)−CH(R⁵)− | H | −COOH | H | −C(=O)−NH−CH(phenyl)− |
| A1331 | H₂N−C(=NH)−NH−C(=O)−CH(R⁵)− | CH₃ | −COOH | H | −C(=O)−NH−CH(phenyl)− |
| A1332 | H₂N−C(=NH)−NH−C(=O)−CH(R⁵)− | H | −COOH | CH₃ | −C(=O)−NH−CH(phenyl)− |

| A1333 |  | H |  | H |  |
| --- | --- | --- | --- | --- | --- |
| A1334 |  | CH$_3$ |  | H |  |
| A1335 |  | H |  | CH$_3$ |  |
| A1336 |  | H |  | H |  |
| A1337 |  | CH$_3$ |  | H |  |
| A1338 |  | H |  | CH$_3$ |  |

FIGURE 2A

| Compound No. | Compound Name | FXa IC50 | Tryptase IC50 |
|---|---|---|---|
| 155 | (2S,3R)-3-(3-guanidinopropyl)-1-((R)-1-(naphthalen-1-yl)ethylcarbamoyl)-4-oxoazetidine-2-carboxylic acid | (+++) | |
| 160 | (2S,3R)-3-(3-guanidinopropyl)-4-oxo-1-((R)-1-phenylethylcarbamoyl)azetidine-2-carboxylic acid | (+++) | |
| 64 | (2S,3R)-cyclobutyl 3-((E)-2-(2-carbamimidoylhydrazono)ethyl)-4-oxo-1-((R)-1-phenylethylcarbamoyl)azetidine-2-carboxylate | (+++) | (+++) |
| 65 | (2S,3R)-methyl 3-((E)-2-(2-carbamimidoylhydrazono)ethyl)-4-oxo-1-((R)-1-phenylethylcarbamoyl)azetidine-2-carboxylate | (+++) | |
| 63 | (2S,3R)-3-((E)-2-(2-carbamimidoylhydrazono)ethyl)-4-oxo-1-((R)-1-phenylpropylcarbamoyl)azetidine-2-carboxylic acid | (+++) | (+++) |
| 93 | (2S,3R)-3-((2-aminopyridin-4-yl)methyl)-4-oxo-1-((R)-1-phenylethylcarbamoyl)azetidine-2-carboxylic acid | (+++) | (+++) |
| 90 | (2S,3R)-ethyl 3-((2-aminopyridin-4-yl)methyl)-4-oxo-1-((R)-1-phenylethylcarbamothioyl)azetidine-2-carboxylate | (+++) | (+++) |
| 9 | (2S,3R)-3-(3-aminobenzyl)-1-((2S)-2-(benzyloxy)cyclopentylcarbamoyl)-4-oxoazetidine-2-carboxylic acid | (+++) | (+++) |
| 66 | (2S,3R)-3-((E)-2-(2-carbamimidoylhydrazono)ethyl)-N2,N2-diethyl-4-oxo-N1-((R)-1-phenylethyl)azetidine-1,2-dicarboxamide | (+++) | |
| 29 | (2S,3R)-3-((2-aminopyridin-4-yl)methyl)-N2,N2-diethyl-4-oxo-N1-((R)-1-phenylethyl)azetidine-1,2-dicarboxamide | (+++) | (+++) |

FIGURE 2B

| | | | |
|---|---|---|---|
| 25 | (2S,3R)-ethyl 3-((2-aminopyridin-4-yl)methyl)-1-((R)-1-(naphthalen-1-yl)ethylcarbamoyl)-4-oxoazetidine-2-carboxylate | (+++) | (+++) |
| 152 | (2S,3R)-ethyl 3-(3-guanidinopropyl)-4-oxo-1-(phenylcarbamoyl)azetidine-2-carboxylate | (+++) | |
| 96 | (2S,3R)-3-((2-aminopyridin-4-yl)methyl)-N2-(methylsulfonyl)-4-oxo-N1-((R)-1-phenylethyl)azetidine-1,2-dicarboxamide | (+++) | (+++) |
| 101 | (2S,3R)-3-((2-aminopyridin-4-yl)methyl)-N2-(4-fluorophenylsulfonyl)-N2-methyl-4-oxo-N1-((R)-1-phenylethyl)azetidine-1,2-dicarboxamide | (+++) | (+++) |
| 24 | (2S,3R)-3-((2-aminopyridin-4-yl)methyl)-1-((R)-1-(naphthalen-1-yl)ethylcarbamoyl)-4-oxoazetidine-2-carboxylic acid | (+++) | |
| 30 | (2S,3R)-3-((2-aminopyridin-4-yl)methyl)-N2-ethyl-N2-methyl-4-oxo-N1-((R)-1-phenylethyl)azetidine-1,2-dicarboxamide | (+++) | (+++) |
| 28 | (2S,3R)-ethyl 3-((2-aminopyridin-4-yl)methyl)-4-oxo-1-((R)-1-phenylethylcarbamoyl)azetidine-2-carboxylate | (+++) | (+++) |
| 8 | (2S,3R)-3-((2-aminopyridin-4-yl)methyl)-1-(benzhydrylcarbamoyl)-4-oxoazetidine-2-carboxylic acid | (+++) | (+++) |
| 159 | (2S,3R)-1-(4-ethylphenylcarbamoyl)-3-(3-guanidinopropyl)-4-oxoazetidine-2-carboxylic acid | (+++) | |
| 10 | (2S,3R)-3-((2-aminopyridin-4-yl)methyl)-N1,N2-bis((1S,2S)-2-(benzyloxy)cyclopentyl)-4-oxoazetidine-1,2-dicarboxamide | (+++) | (+++) |
| 23 | (2S,3R)-3-((2-aminopyridin-4-yl)methyl)-4-oxo-1-((R)-1-phenylethylcarbamoyl)azetidine-2-carboxylic acid | (+++) | (+++) |

FIGURE 2C

| | | | |
|---|---|---|---|
| 22 | (2S,3R)-3-((2-aminopyridin-4-yl)methyl)-4-oxo-1-(phenylcarbamoyl)azetidine-2-carboxylic acid | (+++) | (+++) |
| 67 | (2S,3R,E)-1-(biphenyl-4-ylcarbamoyl)-3-(2-(2-carbamimidoylhydrazono)ethyl)-4-oxoazetidine-2-carboxylic acid | (+++) | (+++) |
| 15 | (2S,3R)-methyl 3-((2-aminopyridin-4-yl)methyl)-1-(2-benzylphenylcarbamoyl)-4-oxoazetidine-2-carboxylate | (+++) | (+++) |
| 68 | (2S,3R,E)-methyl 3-(2-(2-carbamimidoylhydrazono)ethyl)-4-oxo-1-(phenylcarbamoyl)azetidine-2-carboxylate | (+++) | (+++) |
| 69 | (2S,3R)-3-((E)-2-(2-carbamimidoylhydrazono)ethyl)-4-oxo-1-((R)-1-phenylethylcarbamoyl)azetidine-2-carboxylic acid | (+++) | (+++) |
| 151 | (2S,3R)-3-(3-guanidinopropyl)-4-oxo-1-(phenylcarbamoyl)azetidine-2-carboxylic acid | (+++) | |
| 31 | (2S,3R)-3-((2-aminopyridin-4-yl)methyl)-2-(morpholine-4-carbonyl)-4-oxo-N-((R)-1-phenylethyl)azetidine-1-carboxamide | (+++) | (+++) |
| 154 | (2S,3R)-3-(3-guanidinopropyl)-1-(4-methoxyphenethylcarbamoyl)-4-oxoazetidine-2-carboxylic acid | (+++) | |
| 157 | (2S,3R)-3-(3-guanidinopropyl)-4-oxo-1-((S)-1-phenylethylcarbamoyl)azetidine-2-carboxylic acid | (+++) | |
| 153 | (2S,3R)-3-(3-guanidinopropyl)-1-(4-methoxybenzylcarbamoyl)-4-oxoazetidine-2-carboxylic acid | (-++) | |
| 158 | (2S,3R)-3-(3-guanidinopropyl)-1-((S)-1-(naphthalen-1-yl)ethylcarbamoyl)-4-oxoazetidine-2-carboxylic acid | (+++) | |

FIGURE 2D

| | | | |
|---|---|---|---|
| 156 | (2S,3R)-1-(3-ethylphenylcarbamoyl)-3-(3-guanidinopropyl)-4-oxoazetidine-2-carboxylic acid | (+++) | |
| 86 | (2R,3R)-ethyl 3-(3-aminophenylthio)-4-oxo-1-((R)-1-phenylethylcarbamoyl)azetidine-2-carboxylate | (+++) | (++) |
| 106 | ((2S,3R)-3-((2-aminopyridin-4-yl)methyl)-4-oxo-1-((R)-1-phenylethylcarbamoyl)azetidin-2-yl)methyl methanesulfonate | (+++) | (+++) |
| 72 | (2S,3R,E)-3-(2-(2-carbamimidoylhydrazono)ethyl)-4-oxo-1-(4-phenoxyphenylcarbamoyl)azetidine-2-carboxylic acid | (+++) | (+++) |
| 87 | (2R,3S)-ethyl 3-(3-aminophenylthio)-4-oxo-1-((R)-1-phenylethylcarbamoyl)azetidine-2-carboxylate | (+++) | (+++) |
| 70 | (2S,3R)-4-oxo-1-((R)-1-phenylethylcarbamoyl)-3-((E)-2-(2-(N-((R)-1-phenylethylcarbamoyl)carbamimidoyl)hydrazono)ethyl)azetidine-2-carboxylic acid | (+++) | |
| 73 | (2S,3R,E)-3-(2-(2-carbamimidoylhydrazono)ethyl)-4-oxo-1-(phenylcarbamoyl)azetidine-2-carboxylic acid | (+++) | (+++) |
| 74 | (2S,3R)-cyclobutyl 3-((E)-2-(2-(N-methylcarbamimidoyl)hydrazono)ethyl)-4-oxo-1-((R)-1-phenylethylcarbamoyl)azetidine-2-carboxylate | (+++) | (+++) |
| 16 | (2S,3R)-methyl 3-(3-aminobenzyl)-4-oxo-1-((1R,2S)-2-phenylcyclopropylcarbamoyl)azetidine-2-carboxylate | (+++) | (+++) |
| 75 | (2S,3R,E)-benzyl 1-(biphenyl-4-ylcarbamoyl)-3-(2-(2-carbamimidoylhydrazono)ethyl)-4-oxoazetidine-2-carboxylate | (+++) | (+++) |
| 39 | (2S,3R)-3-((2-aminopyridin-4-yl)methyl)-2-(hydroxymethyl)-N-((R)-1-(naphthalen-1-yl)ethyl)-4-oxoazetidine-1-carboxamide | (+++) | (++) |

FIGURE 2E

| | | | |
|---|---|---|---|
| 17 | (2S,3R)-methyl 3-((2-aminopyridin-4-yl)methyl)-1-((1R,2R)-2-(benzyloxy)cyclopentylcarbamoyl)-4-oxoazetidine-2-carboxylate | (+++) | (+++) |
| 119 | ethyl 2-((2R,3R)-3-((2-aminopyridin-4-yl)methyl)-4-oxo-1-((R)-1-phenylethylcarbamoyl)azetidin-2-yl)acetate | (+++) | |
| 76 | (2S,3R)-ethyl 3-((E)-2-(2-(N-methylcarbamimidoyl)hydrazono)ethyl)-4-oxo-1-((R)-1-phenylethylcarbamoyl)azetidine-2-carboxylate | (+++) | |
| 32 | (2S,3R)-3-((2-aminopyridin-4-yl)methyl)-4-oxo-N1-((R)-1-phenylethyl)-N2-(pyridin-3-yl)azetidine-1,2-dicarboxamide | (+++) | (+++) |
| 77 | (2S,3R)-3-((E)-2-(2-(N-methylcarbamimidoyl)hydrazono)ethyl)-4-oxo-1-((R)-1-phenylpropylcarbamoyl)azetidine-2-carboxylic acid | (++) | |
| 11 | (2S,3R)-3-((2-aminopyridin-4-yl)methyl)-N1,N2-bis(3-benzylphenyl)-4-oxoazetidine-1,2-dicarboxamide | (++) | |
| 26 | (2S,3R)-ethyl 3-((2-aminopyridin-4-yl)methyl)-4-oxo-1-(phenylcarbamoyl)azetidine-2-carboxylate | (++) | |
| 27 | (2S,3R)-benzyl 3-((2-aminopyridin-4-yl)methyl)-4-oxo-1-(phenylcarbamoyl)azetidine-2-carboxylate | (++) | |
| 71 | (2S,3R)-4-oxo-3-((E)-2-(2-(N-((R)-1-phenylethylcarbamoyl)carbamimidoyl)hydrazono)ethyl)azetidine-2-carboxylic acid | (++) | |
| 45d | (2S,3R)-4-methoxybenzyl 3-((2-aminopyridin-4-yl)methyl)-1-(benzofuran-2-yl)-4-oxoazetidine-2-carboxylate | (++) | |
| 78 | (2S,3R,E)-4-methoxybenzyl 3-(2-(2-carbamimidoylhydrazono)ethyl)-4-oxo-1-(phenylcarbamoyl)azetidine-2-carboxylate | (++) | |

FIGURE 2F

| | | | |
|---|---|---|---|
| 51 | (2S,3R)-methyl 3-((E)-2-(2-carbamimidoylhydrazono)ethyl)-3-methyl-4-oxo-1-((R)-1-phenylethylcarbamoyl)azetidine-2-carboxylate | (++) | (++) |
| B1 | [chemical structure] | (++) | |
| 12 | (2S,3R)-3-((2-aminopyridin-4-yl)methyl)-4-oxo-N1,N2-bis(3-phenoxyphenyl)azetidine-1,2-dicarboxamide | (++) | |
| B2 | 2-((2S,3R)-2-(methoxycarbonyl)-4-oxo-1-(phenylcarbamoyl)azetidin-3-yl)acetic acid | (++) | |
| 112 | (2R,3R)-ethyl 3-((2-aminopyridin-4-yl)methylthio)-4-oxo-1-((R)-1-phenylethylcarbamoyl)azetidine-2-carboxylate | (++) | |
| 79 | (2S,3R)-3-((E)-2-(2-(4,5-dihydro-1H-imidazol-2-yl)hydrazono)ethyl)-4-oxo-1-((R)-1-phenylpropylcarbamoyl)azetidine-2-carboxylic acid | (++) | |
| B3 | (2S,3R)-methyl 3-allyl-4-oxo-1-((R)-1-phenylethylcarbamoyl)azetidine-2-carboxylate | (++) | |
| B4 | (2S,3R)-isopropyl 3-(3-methoxybenzyl)-4-oxo-1-(phenylcarbamoyl)azetidine-2-carboxylate | (++) | |
| B5 | (2S,3R)-ethyl 4-oxo-1-((R)-1-phenylethylcarbamoyl)-3-(pyridin-3-yloxy)azetidine-2-carboxylate | (++) | |
| 41 | (2S,3R)-3-((2-aminopyridin-4-yl)methyl)-2-(hydroxymethyl)-4-oxo-N-((R)-1-phenylethyl)azetidine-1-carboxamide | (++) | (++) |
| 40 | ((2S,3R)-3-((2-aminopyridin-4-yl)methyl)-1-((R)-1-(naphthalen-1-yl)ethylcarbamoyl)-4-oxoazetidin-2-yl)methyl 1-(naphthalen-2-yl)ethylcarbamate | (++) | |

FIGURE 2G

| | | | |
|---|---|---|---|
| B6 | (R)-3-((2-aminopyridin-4-yl)methyl)-2,2-dimethyl-4-oxo-N-((R)-1-phenylethyl)azetidine-1-carboxamide | (++) | (++) |
| B7 | (2S,3R)-3-(benzo[d][1,3]dioxol-4-ylmethyl)-4-oxo-1-(phenylcarbamoyl)azetidine-2-carboxylic acid | (++) | |
| B8 | (2S,3R)-1-(2,4-dimethoxybenzyl)-3-(3-guanidinopropyl)-4-oxoazetidine-2-carboxylic acid | (++) | |
| B9 | (2S,3R)-3-(2-hydrazinylethyl)-4-oxo-1-((R)-1-phenylpropylcarbamoyl)azetidine-2-carboxylic acid | (++) | |
| 45a | (2S,3R)-3-((2-aminopyridin-4-yl)methyl)-1-(4-(4-fluorophenylcarbamoyl)phenyl)-4-oxoazetidine-2-carboxylic acid | (++) | |
| B10 | (2S,3R)-3-((2-aminopyridin-4-yl)methyl)-1-(4-(benzyloxy)-2-fluorophenyl)-4-oxoazetidine-2-carboxylic acid | (++) | |
| 114 | (2R,3S)-ethyl 3-((2-aminopyridin-4-yl)methylthio)-1-(4-methoxyphenyl)-4-oxoazetidine-2-carboxylate | (++) | |
| 46 | (2S,3R)-benzyl 3-((2-aminopyridin-4-yl)methyl)-1-(4-(benzyloxy)-2-fluorophenyl)-4-oxoazetidine-2-carboxylate | (++) | |
| B11 | (2S,3R)-3-(3-methoxybenzyl)-4-oxo-1-(phenylcarbamoyl)azetidine-2-carboxylic acid | (++) | |
| 129 | (2S,3R)-3-((3-aminobenzo[d]isoxazol-5-yl)methyl)-4-oxo-1-(phenylcarbamoyl)azetidine-2-carboxylic acid | (++) | |
| B12 | (2R,3S)-2-(2-(2-carbamimidoylhydrazinyl)ethyl)-4-ethoxy-4-oxo-3-(3-((S)-1-phenylethyl)ureido)butanoic acid | (++) | |

FIGURE 2H

| | | | |
|---|---|---|---|
| B13 | (2S,3R)-3-((E)-2-hydrazonoethyl)-4-oxo-1-((R)-1-phenylpropylcarbamoyl)azetidine-2-carboxylic acid | (++) | |
| 53 | (2S,3R)-ethyl 3-((2-aminopyridin-4-yl)methyl)-3-methyl-4-oxo-1-((R)-1-phenylethylcarbamoyl)azetidine-2-carboxylate | (++) | (++) |
| B14 | (2S,3R)-methyl 3-((E)-2-(3-methoxyphenylimino)ethyl)-4-oxo-1-((R)-1-phenylethylcarbamoyl)azetidine-2-carboxylate | (++) | |
| B15 | (2S,3R)-N-(3,4-dihydroxybenzyl)-1-(2,4-dimethoxybenzyl)-3-(3-guanidinopropyl)-4-oxoazetidine-2-carboxamide | (++) | |
| 130 | (2S,3R)-3-((3-amino-1H-indazol-5-yl)methyl)-4-oxo-1-(phenylcarbamoyl)azetidine-2-carboxylic acid | (++) | |
| 113 | (2R,3R)-ethyl 3-((2-aminopyridin-4-yl)methylthio)-1-(4-methoxyphenyl)-4-oxoazetidine-2-carboxylate | (++) | |
| B16 | (2S,3R)-methyl 3-((E)-2-(2-chlorophenylimino)ethyl)-4-oxo-1-((R)-1-phenylethylcarbamoyl)azetidine-2-carboxylate | (+) | |
| 45b | (2S,3R)-3-((2-aminopyridin-4-yl)methyl)-1-(3-(4-fluorophenylcarbamoyl)phenyl)-4-oxoazetidine-2-carboxylic acid | (+) | |
| B17 | 1-(3-((2S,3R)-1-(2,4-dimethoxybenzyl)-2-(hydroxymethyl)-4-oxoazetidin-3-yl)propyl)guanidine | (+) | |
| 37 | (2S,3R)-3-(3-chlorobenzyl)-4-oxo-1-(phenylcarbamoyl)azetidine-2-carboxylic acid | (+) | |
| 33 | (2S,3R)-benzyl 3-(2-(benzo[d][1,3]dioxol-5-yl)ethyl)-4-oxoazetidine-2-carboxylate | (+) | |

FIGURE 2I

| | | | |
|---|---|---|---|
| 35 | (2S,3R)-3-(2-(benzo[d][1,3]dioxol-5-yl)ethyl)-4-oxo-1-(phenylcarbamoyl)azetidine-2-carboxylic acid | (+) | |
| B18 | (2S,3R)-N-(3,4-dihydroxybenzyl)-1-(2,4-dimethoxybenzyl)-3-(3-guanidinopropyl)-4-oxoazetidine-2-carboxamide | (+) | |
| B19 | (2S,3R)-ethyl 3-((R)-3-(2-aminopyridin-4-yl)-1-oxo-1-(thiophen-2-yl)propan-2-yl)-4-oxoazetidine-2-carboxylate | (+) | |
| 137 | (2S,3R)-ethyl 3-((R)-3-(2-aminopyridin-4-yl)-1-oxo-1-((R)-1-phenylethylamino)propan-2-yl)-4-oxo-1-((R)-1-phenylethylcarbamoyl)azetidine-2-carboxylate | (+) | |
| 54 | (2S,3R)-3-((2-aminopyridin-4-yl)methyl)-3-methyl-4-oxo-1-((R)-1-phenylethylcarbamoyl)azetidine-2-carboxylic acid | (+) | (+) |
| 45c | (2S,3R)-3-((2-aminopyridin-4-yl)methyl)-1-(3-(benzyloxy)phenyl)-4-oxoazetidine-2-carboxylic acid | (+) | |
| 52 | (2S,3R)-3-((E)-2-(2-carbamimidoylhydrazono)ethyl)-3-methyl-4-oxo-1-((R)-1-phenylethylcarbamoyl)azetidine-2-carboxylic acid | (+) | |
| B20 | (2S,3R)-ethyl 3-((2-aminopyridin-4-yl)methylamino)-4-oxo-1-(thiophene-2-carbonyl)azetidine-2-carboxylate | (+) | |
| 34 | (2S,3R)-3-(benzofuran-5-ylmethyl)-4-oxo-1-(phenylcarbamoyl)azetidine-2-carboxylic acid | (+) | |
| 36 | (2S,3R)-3-(benzo[d][1,3]dioxol-5-ylmethyl)-4-oxo-1-(phenylcarbamoyl)azetidine-2-carboxylic acid | (+) | |
| B21 | (2S,3R)-methyl 3-((E)-2-(benzo[d][1,3]dioxol-5-ylimino)ethyl)-4-oxo-1-((R)-1-phenylethylcarbamoyl)azetidine-2-carboxylate | (+) | |

FIGURE 2J

| | | | |
|---|---|---|---|
| 83 | (2S,3R,E)-3-(2-(2-carbamimidoylhydrazono)ethyl)-4-oxo-1-(pyridin-2-yl)azetidine-2-carboxylic acid | (+) | |
| B22 | (2S,3R)-N-(benzo[d][1,3]dioxol-5-ylmethyl)-1-(2,4-dimethoxybenzyl)-3-(3-guanidinopropyl)-4-oxoazetidine-2-carboxamide | (+) | |
| B23 | (2S,3R)-ethyl 3-((2-aminopyridin-4-yl)methylamino)-4-oxoazetidine-2-carboxylate | >(+) | |
| B24 | (2S,3R)-methyl 3-(biphenyl-2-ylmethyl)-4-oxo-1-(phenylcarbamoyl)azetidine-2-carboxylate | >(+) | |
| B25 | (2S,3R,E)-4-methoxybenzyl 3-(2-(2-carbamimidoylhydrazono)ethyl)-4-oxoazetidine-2-carboxylate | >(+) | |
| 142 | (2S,3R)-methyl 3-allyl-4-oxo-1-(phenylcarbamoyl)azetidine-2-carboxylate | >(+) | |
| B26 | (S)-4-oxo-1-(phenylcarbamoyl)azetidine-2-carboxylic acid | >(+) | |
| B27 | (S)-benzyl 4-oxo-1-(phenylcarbamoyl)azetidine-2-carboxylate | >(+) | |
| B28 | (2S,3R)-benzyl 3-(2-(benzo[d][1,3]dioxol-5-yl)ethyl)-4-oxo-1-(phenylcarbamoyl)azetidine-2-carboxylate | >(+) | |
| B29 | (2S,3R)-4-methoxybenzyl 3-(3-chlorobenzyl)-4-oxo-1-(phenylcarbamoyl)azetidine-2-carboxylate | >(+) | |
| B30 | (2S,3R)-N2-isopropyl-3-(3-methoxybenzyl)-4-oxo-N1-phenylazetidine-1,2-dicarboxamide | >(+) | |

FIGURE 2K

| B31 | (2S,3R)-3-(biphenyl-2-ylmethyl)-4-oxo-1-(phenylcarbamoyl)azetidine-2-carboxylic acid | >(+) | |
|---|---|---|---|
| B32 | (S)-3,3-dibenzyl-4-oxo-1-(phenylcarbamoyl)azetidine-2-carboxylic acid | >(+) | |
| B33 | 1-(4-tert-butylphenylsulfonyl)-3-(3-chlorobenzyl)-4,4-dimethylazetidin-2-one | >(+) | |
| B34 | 1-(4-tert-butylbenzoyl)-3-(3-chlorobenzyl)-4,4-dimethylazetidin-2-one | >(+) | |
| B35 | (R)-3-(3-chlorobenzyl)-2,2-dimethyl-4-oxo-N-phenylazetidine-1-carboxamide | >(+) | |
| B36 | 1,3-bis(3-chlorobenzyl)-4,4-dimethylazetidin-2-one | >(+) | |
| B37 | 3-(3-chlorobenzyl)-4,4-dimethylazetidin-2-one | >(+) | |
| B38 | 1-(3-(2,2-dimethyl-4-oxoazetidin-3-yl)propyl)guanidine | >(+) | |
| B39 | (2S,3R)-benzyl 3-(benzofuran-5-ylmethyl)-4-oxo-1-(phenylcarbamoyl)azetidine-2-carboxylate | >(+) | |
| B40 | (S)-3,3-bis((3-aminobenzo[d]isoxazol-5-yl)methyl)-4-oxo-1-(phenylcarbamoyl)azetidine-2-carboxylic acid | >(+) | |
| B41 | (2S,3R)-methyl 3-((E)-2-(3-chlorophenylimino)ethyl)-4-oxo-1-((R)-1-phenylethylcarbamoyl)azetidine-2-carboxylate | >(+) | |

FIGURE 2L

| | | | |
|---|---|---|---|
| B42 | (2S,3R)-methyl 3-((E)-2-(4-chlorophenylimino)ethyl)-4-oxo-1-((R)-1-phenylethylcarbamoyl)azetidine-2-carboxylate | >(+) | |
| B43 | (2S)-methyl 3-(bis(2-aminoethyl)amino)-4-oxo-1-(phenylcarbamoyl)azetidine-2-carboxylate | >(+) | |
| B44 | (2S,3R)-methyl 3-(2-tert-butoxy-2-oxoethyl)-4-oxo-1-(phenylcarbamoyl)azetidine-2-carboxylate | >(+) | |
| B45 | (2S)-methyl 3-(1-((2-aminopyridin-4-yl)methyl)-3-phenylureido)-4-oxo-1-(phenylcarbamoyl)azetidine-2-carboxylate | >(+) | |
| B46 | (2S)-ethyl 3-(benzyloxy)-1-(4-methoxyphenyl)-4-oxoazetidine-2-carboxylate | >(+) | |
| B47 | (2S)-ethyl 3-(4-chlorophenoxy)-1-(4-methoxyphenyl)-4-oxoazetidine-2-carboxylate | >(+) | |
| B48 | (2S)-ethyl 3-hydroxy-1-(4-methoxyphenyl)-4-oxoazetidine-2-carboxylate | >(+) | |
| B49 | (2S)-ethyl 3-(tert-butyldimethylsilyloxy)-1-(4-methoxyphenyl)-4-oxoazetidine-2-carboxylate | >(+) | |
| B50 | [chemical structure] | >(+) | |
| B51 | (R)-3-((2-aminopyridin-4-yl)methylamino)-1-(benzo[d][1,3]dioxol-5-yl)azetidin-2-one | >(+) | |
| B52 | (R)-3-((2-aminopyridin-4-yl)methylamino)-2-oxo-N-((R)-1-phenylethyl)azetidine-1-carboxamide | >(+) | |

FIGURE 2M

| | | | |
|---|---|---|---|
| B53 | (2R,3S)-2-((2-aminopyridin-4-yl)methyl)-2-methyl-3-(3-((R)-1-phenylethyl)ureido)succinic acid | >(+) | |
| B54 | (2R,3R)-ethyl 3-mercapto-1-(4-methoxyphenyl)-4-oxoazetidine-2-carboxylate | >(+) | |
| B55 | (S)-2-(2-diazoacetyl)-4-oxo-N-((R)-1-phenylethyl)azetidine-1-carboxamide | >(+) | |
| B56 | ethyl 2-((S)-4-oxo-1-((R)-1-phenylethylcarbamoyl)azetidin-2-yl)acetate | >(+) | |
| B57 | (3R,4S)-1-(tert-butyldimethylsilyl)-4-(2-(diethylamino)acetyl)-3-(2-hydroxyethyl)azetidin-2-one | >(+) | |
| B58 | (2S,3R)-4-amino-3-((2-aminopyridin-4-yl)methyl)-2-(3-((S)-1-(naphthalen-1-yl)ethyl)ureido)-4-oxobutanoic acid | >(+) | |

SUBSTITUTED AZETIDINONES

CROSS-REFERENCES TO RELATED APPLICATIONS

The present application claims priority to U.S. Provisional Patent Application No. 60/668,325, filed Apr. 4, 2005 which is incorporated herein by reference in its entirety for all purposes.

BACKGROUND OF THE INVENTION

Bisacchi in U.S. Pat. No. 6,335,324 explicitly discloses 3-guanidinoalkyl-2-azetidinones which have one of the following two structures:

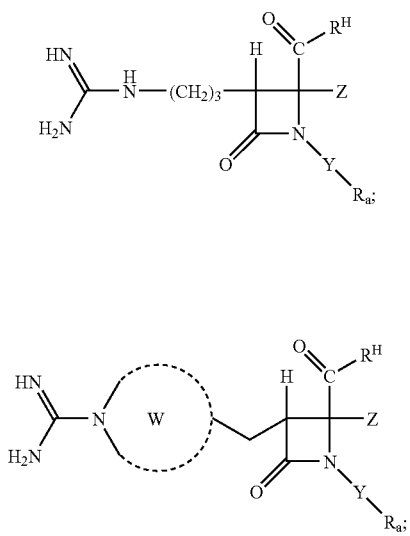

wherein W is an unsubstituted 4-8 membered cycloalkyl ring; Y is either C=O or $SO_2$; Z is either hydrogen or unsubstituted alkyl; $R^H$ can be any substitutent; and $R^2$ can be any substituent.

Bisacchi in U.S. Pat. Pub. No. 2004/0147502 A1 explicitly discloses 1-[piperazinecarbonyl]azetidinones of the formula:

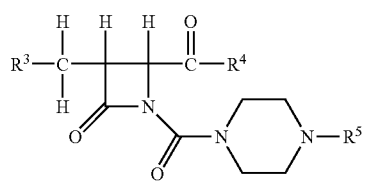

wherein $R^3$ is any substituent, $R^4$ is OH, $NH_2$, alkyl or heteroalkyl, and $R^5$ is any substituent.

Schumacher in U.S. Pat. Pub. No. 2004/0180855 A1 explicitly discloses methods of treating thrombosis in a mammal comprising administering a compound of the formula below that is selective for inhibition of Factor XIa.

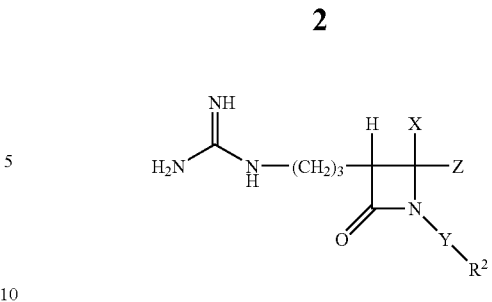

wherein X is COOH, COOR, CONR, unsubstituted alkyl and unsubstituted arylalkyl, Y is CO or $SO_2$, Z is H or unsubstituted alkyl, $R^2$ is substituted or unsubstituted alkyl, substituted or unsubstituted aryl, and substituted or unsubstituted heterocycloalkyl.

Thrombo-embolic disorders are the largest cause of mortality (myocardial infarction) and disability (stroke) in the industrialized world. Arterial thrombosis is initiated by atherosclerotic plaque rupture, exposure of tissue factor, and initiation of the coagulation vortex. A number of coagulation factors are present in the blood as precursors (e.g., Factors VII-XII), and when the coagulation system is triggered, these factors undergo a complicated, ordered series of reactions that ultimately lead to thrombin production. Thrombin is a proteolytic enzyme that occupies a central position in the coagulation process. Thrombin catalyzes the conversion of fibrinogen to fibrin, is a key effector enzyme for blood clotting, and is also pivotal for other functions. High concentrations of thrombin inhibit fibrinolysis by activating the Thrombin Activated Fibrinolysis Inhibitor (TAFI), which can also be activated by modest amounts of thrombin in the presence of soluble or membrane bound thrombomodulin. TAFIa removes the C-terminal lysine residues from fibrin, preventing the binding of t-PA and plasmin and thus, slowing fibrinolysis.

The complicated coagulation process is initiated by tissue factor (TF). Tissue factor binds and activates Factor VII (FVII), which is rapidly converted to activated Factor VIIa (FVIIa) to form a TF:FVIIa complex. The TF:FVIIa complex activates Factors IX and X. Factor Xa generates small amounts of thrombin. The small amounts of thrombin activate Factor V, Factor VIII and platelets, accelerating thrombin production by Factors IXa and Xa. Activation of Factor V and FVIII accelerates catalytic activity of FVIIIa:FIXa and FVa:FXa, resulting in dramatically increased thrombin production. Another wave of thrombin generation occurs as a result of thrombin activation of Factor XIa. Factor XI activates more Factor IX. As the concentration of thrombin increases, more thrombin is generated, which in turn activates TAFI to then inhibit fibrinolysis.

This coagulation process involves an intrinsic pathway and an extrinsic pathway. In the intrinsic pathway, Factor XII (aka Hageman Factor) is converted from its inactive form (zymogen) to an active form, i.e., Factor XIIa. Activated Factor XII enzymatically activates Factor XI to Factor XIa. Activated Factor XI activates Factor IXa. Factor IXa then converts Factor X to Factor Xa. FXa activates prothombin to thrombin. Thrombin cleaves fibrinogen to form insoluble fibrin (the clot). In the extrinsic pathway, addition of thromboplastin (i.e., tissue factor) to plasma activates Factor VII. This complex, in the presence of calcium ions and phospholipids, activates Factor X to Factor Xa. Once Factor Xa is generated, the remainder of the cascade is similar to the intrinsic pathway. As can be seen, Factor XIa is involved only in the intrinsic pathway.

In vitro, the degree to which FXIa contributes to thrombin generation, platelet activation, and fibrin formation depends on the concentration of tissue factor. For example, in the absence of FXI (i.e., in FXIa deficient plasma), plasma stimulated with low levels of tissue factor (clot formation>10 minutes) showed a delay in the time required to generate thrombin and form clots. A FXI deficiency also decreased the amount of thrombin generated and platelet aggregation in whole blood. However, in blood or plasma stimulated by higher concentration of tissue factor (clot formation<5 minutes), a FXI deficiency had no effect on the thrombin generation or clot formation. Thus, a FXI deficiency will generally prolong thrombin generation but not in situations where the plasma is stimulated with high concentrations of tissue factor.

FXIa, via expanded thrombin generation, also plays a role in resisting fibrinolysis. Resistance of plasma clots to tPA and uPA-induced fibrinolysis depends on thrombin concentration (generated endogenously or added exogenously) in the plasma. The time required for clot lysis is proportional to the plasma TAFIa concentrations. However, clot lysis can occur more rapidly, and the lysis made independent of plasma TAFI concentration, when blocking antibodies to FXIa are included in the assay.

Elevated levels of FXIa in the plasma and/or increased activation of FXIa is associated with various cardiovascular and other diseases. As an illustration, increased activation of FXIa occurs in patients with coronary artery disease and is related to the severity of the disease. Also, Factor IX activation peptide (a product of FXIa and TF:FVIIa cleavage of FIX) levels have been found to be significantly higher in patients with acute myocardial infarction and unstable angina compared with patients with stable angina. Concentrations of FXIa-$\alpha_1$AT (FXIa complexed to the serpin $\alpha$1-antitrypsin) were also elevated in patients with recent myocardial infarction or unstable angina. Patients with high levels of Factor XI are at risk for deep venous thrombosis.

Proteins or peptides that reportedly inhibit Factor XIa are disclosed in WO 01/27079 to Entremed, Inc. There are advantages in using small organic compounds, however, in preparing pharmaceuticals, e.g., small compounds generally have better oral bioavailability and compatibility in making formulations to aid in delivery of the drug as compared with large proteins or peptides. Small organic compounds have been disclosed that reportedly inhibit coagulation factors besides Factor XIa. For example, compounds effective in inhibiting Factor Xa are described in U.S. Pat. Nos. 6,344,450 and 6,297,233, and WO 00/47563. Compounds effective in inhibiting Factors VIIa, Xa, as well as tryptase and urokinase are described in U.S. Pat. No. 6,335,324. Factor Xa inhibitors are disclosed in WO 98/57937 to the duPont Merck Pharmaceutical Co., and Factor VIIa inhibitors are disclosed in U.S. Pat. No. 6,358,960 to Ono Pharmaceuticals Inc., ("Ono"), and in WO 01/44172 to Axys Pharm. Inc.

A possible adverse side effect associated with use of anti-thrombotic agents for treating cardiovascular diseases involves the risk of bleeding. For example, heparin is a known anti-thrombotic agent that has a highly-variable dose-related response, and its anticoagulant effects must be closely monitored to avoid a risk of serious bleeding. The erratic anticoagulant response of heparin is likely due to its propensity to bind non-specifically to plasma proteins. Aspirin also has been used as an anti-thrombotic agent but at high doses presents a risk of gastrointestinal bleeding. Thrombin inhibitors and their drawbacks are further discussed in WO 96/20689 to duPont Merck Pharmaceutical Co. Guanidine and beta lactam-containing compounds that are potent inhibitors of serine proteases including thrombin and tryptase are described in U.S. Pat. No. 6,335,324, the entire contents of which is incorporated herein by reference.

SUMMARY OF THE INVENTION

This invention is directed to the novel β-lactam compounds of formula I shown below and to a method for the use of such compounds as inhibitors of various in vivo enzyme systems including tryptase, thrombin, trypsin, Factor Xa, Factor VIIa, Factor XIa, and urokinase-type plasminogen activator and their use in treating and/or preventing asthma and/or allergic rhinitis and/or thrombotic disorders.

In a first aspect, the invention provides a compound according to the following structure:

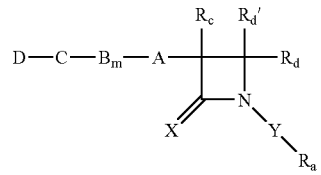

In this structure, A is a member selected from $CR^1R^2$, $NR^{1a}$, O, S and $SO_n$. The symbol n is an integer selected from 0 to 2. Each $R^{1a}$ is a member independently selected from a negative charge, a salt counterion, H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $C(O)R^5$, $NR^3R^4$, $OR^3$ and $SO_2R^5$. $R^3$ and $R^4$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $C(O)R^6$, and $SO_2R^6$. $R^6$ is a member selected from substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^5$ is a member selected from substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^3$ and $R^4$ can be optionally joined, together with the atoms to which they are attached, to form a 4-8 membered ring. $R^1$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $NR^7R^8$, $SO_nR^9$, halogen, $C(O)R^7$, $CO_2R^7$, $C(O)NR^7R^8$, and $OR^7$. Each $R^7$ and each $R^8$ is a member independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $C(O)R^{10}$, $C(O)OR^{10}$, $NR^{10}R^{10a}$, $OR^{10}$, $SO_2R^{10}$ and $S(O)R^{10}$ wherein $R^{10}$ and $R^{10a}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^9$ is a member selected from substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^7$ and $R^8$ can be optionally joined, together with the atoms to which they are attached, to form a 4-8 membered ring. $R^2$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl and halogen. $R^1$ and $R^2$ can together represent an acyl group. $R^1$ and $R^2$ can be optionally joined together in a 3-8 membered ring. B is a member independently selected from substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, carboxamido, $NR^{11}$, —S—, and —O—. $R^{11}$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $C(O)R^{10}$, $C(O)OR^{10}$, $NR^{10}R^{10a}$, $OR^{10}$, $SO_2R^{10}$ and $S(O)R^{10}$. The symbol m is an integer selected from 0 to 3. C is a member selected from a bond, C=O, $SO_2$, N=C, —O— and —O—$CR^5R^{10}$—. $R^5$ and $R^{10}$ can be optionally joined, together with the atoms to which they are attached, to form a 3-8 membered ring. D is a member selected from substituted or unsubstituted cycloalkyl, substituted or unsubstituted heterocycloalkyl, substituted or unsubstituted aryl, substituted or unsubstituted heteroaryl, substituted or unsubstituted amidine, substituted or unsubstituted amidinohydrazone, substituted or unsubstituted guanidine, and substituted or unsubstituted amine. A and B can be optionally joined, together with the atoms to which they are attached, to form a 3-8 membered ring. A and C can be optionally joined, together with the atoms to which they are attached, to form a 3-8 membered ring. A and D can be optionally joined, together with the atoms to which they are attached, to form a 3-8 membered ring. B and C can be optionally joined, together with the atoms to which they are attached, to form a 3-8 membered ring. B and D can be optionally joined, together with the atoms to which they are attached, to form a 3-8 membered ring. C and D can be optionally joined, together with the atoms to which they are attached, to form a 3-8 membered ring. If m is greater than 2, each independently selected B can be optionally joined to form a 3-8 membered ring. X is a member selected from S, O, and $NR^7$. Y is a member selected from a bond, C=Q, $CR^{12}R^{13}$, and $SO_n$. Q is a member selected from S, O, and $NR^7$. $R^{12}$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, halogen. $R^{13}$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl halogen. $R^{12}$ and $R^{13}$ can be optionally joined, together with the atoms to which they are attached, to form a 4-8 membered ring. $R_a$ is a member selected from $NR^7R^8$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^7$ and $R^8$ can be optionally joined, together with the atoms to which they are attached, to form a 4-8 membered ring. $R_c$ is a member selected from H, substituted or unsubstituted alkyl and halogen. $R_d$ is a member selected from $R^{16}$, $(CR^{14}R^{15})_pR^{16}$, $C(R^{14})$=$CR^{16}R^{23}$ and $CCR^{16}$. The symbol p is an integer selected from 0 to 3. $R^{14}$ and $R^{23}$ are members independently selected from H, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^{15}$ is a member selected from H, halogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{16}$ is a member selected from halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $C(O)R^{18}$, $OR^{19}$, —OC(=Q)$NR^{19}R^{21}$, —$NR^{19}C$(=Q)$NR^{19}R^{21}$, —$NR^{20}SO_2R^{19}$, $OSO_2R^{19}$, $SO_2R^{21}$, $S(O)R^{21}$, $SO_2NR^{19}R^{20}$, $NR^{19}R^{20}$ and CN. $R^{18}$ is a member selected from substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $OR^{21}$, $SR^{21}$, $NR^{19}R^{20}$, and —$NR^{19}SO_2R^{20}$. $R^{19}$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{20}$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $C(O)R^{22}$, $SO_2R^{22}$. $R^{22}$ is a member selected from substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^{21}$ is a member selected from a negative charge, a salt counterion, H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —$OR^{22}$ and —$SR^{22}$. $R^{14}$ and $R^{15}$ can be joined together in a 4-8 membered ring. $R^{19}$ and $R^{21}$ can be optionally joined, together with the atoms to which they are attached, to form a 4-8 membered ring. $R^{14}$ and $R^{23}$ can be optionally joined, together with the atoms to which they are attached, to form a 4-8 membered ring. $R^{19}$ and $R^{20}$ can be optionally joined, together with the atoms to which they are attached, to form a 4-8 membered ring. $R_d{}'$ is a member selected from H, substituted or unsubstituted alkyl and halogen. $R_c$ and $R_d$ can be optionally joined, together with the atoms to which they are attached, to form a 5-8 membered ring. $R_c$ and $R_d{}'$ can be optionally joined, together with the atoms to which they are attached, to form a 5-8 membered ring.

In an exemplary embodiment, the compound is subject to one or more of the following provisos. In an exemplary embodiment, the structure has the proviso that if a) Y is a member selected from C=O and $SO_2$;
   ABC, in combination, form unsubstituted alkyl; and
   D is substituted or unsubstituted guanidine; or b) Y is a member selected from C=O and SO$_2$;
AB, in combination, form unsubstituted alkyl; and
CD, in combination, form

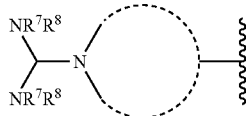

wherein the dotted line represents carbon atoms necessary for the formation of one ring having 4 to 8 atoms;

then R$_c$ cannot be a member selected from CH$_3$, CH$_2$CH$_3$, substituted alkyl, and unsubstituted alkyl; and R$_d$ and R$_d$' cannot be members selected from CH$_3$ and CH$_3$; CH$_2$CH$_3$ and CH$_2$CH$_3$; CH$_2$CH$_3$ and CH$_3$; CH$_3$ and CH$_2$CH$_3$; substituted or unsubstitued alkyl and substituted or unsubstitued alkyl; H and substituted or unsubstitued alkyl; substituted or unsubstitued alkyl and H; H and COOH; H and COOR$^{1a}$; H and CONR$^7$R$^8$; unsubstituted alkyl and COOH; unsubstituted alkyl and COOR$^{1a}$; H and unsubstituted phenylalkyl; unsubstituted alkyl and unsubstituted phenylalkyl.

In another exemplary embodiment, part (a) of this proviso is a) Y is a member selected from C=O and SO$_2$;
ABC, in combination, form substituted alkyl; and
D is substituted or unsubstituted guanidine.

In another exemplary embodiment, R$_c$ of this proviso cannot be substituted alkyl. In another exemplary embodiment, R$_c$ of this proviso cannot be unsubstitued alkyl.

In another exemplary embodiment, R$_d$ and R$_d$' of this proviso cannot be members selected from CH$_3$ and CH$_3$; CH$_2$CH$_3$ and CH$_2$CH$_3$; CH$_2$CH$_3$ and CH$_3$; CH$_3$ and CH$_2$CH$_3$; H and COOH; H and COOR$^{1a}$; H and CONR$^7$R$^8$; unsubstituted alkyl and COOH; unsubstituted alkyl and COOR$^{1a}$; H and unsubstituted phenylalkyl; unsubstituted alkyl and unsubstituted phenylalkyl.

In another exemplary embodiment, the structure has the following proviso: if the compound has the following structure:

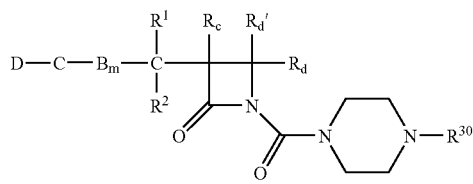

wherein R$^{30}$ is a member selected from H, SO$_2$—R$^{31}$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; wherein R$^{31}$ is unsubstituted alkyl, then at least one of R$_d$ and R$_d$' does not comprise a carbonyl group which is directly attached, or alpha, to the azetidinone ring. In another exemplary embodiment, at least one of R$_d$ and R$_d$' does not comprise a carbonyl group. In another exemplary embodiment, R$^{30}$ does not comprise a carbon atom.

In another exemplary embodiment, the structure has the following proviso: the compound cannot have the following structure:

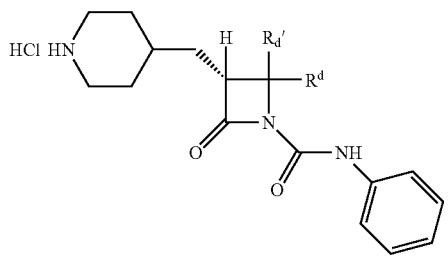

wherein at least one of R$_d$ and R$_d$' comprise a carbonyl group which is directly attached, or alpha, to the azetidinone ring. In another exemplary embodiment, the compound cannot have the following structure:

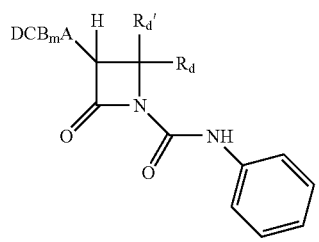

wherein DCB$_m$A comprises a piperidine ring or a salt thereof. In another exemplary embodiment, the compound cannot have the following structure:

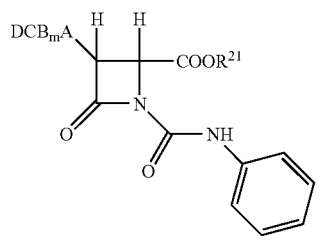

wherein DCB$_m$A comprises a piperidine ring or a salt thereof.

In another exemplary embodiment, the structure has the following proviso: the compound cannot have the following structure:

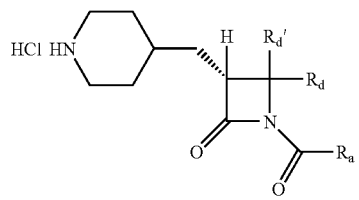

wherein R$_a$ is NHR$^8$, and R$^8$ includes a substituted or unsubstituted phenyl. In another exemplary embodiment, R$^8$ is unsubstituted phenyl. In yet another exemplary embodiment, R$_a$ is N(H)(unsubstituted phenyl). In another exemplary embodiment, the structure has the following proviso: the compound cannot have the following structure:

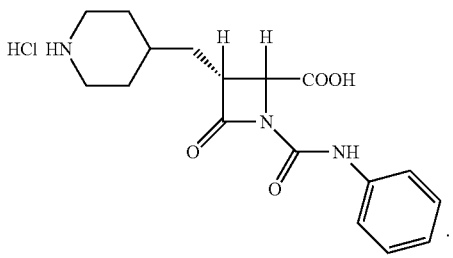

In another exemplary embodiment, the structure has the following proviso: the compound cannot be a chemical compound which is explicitly disclosed (ie does not contain any variables) in U.S. Pat. No. 6,335,324. In another exemplary embodiment, the structure has the following proviso: the compound cannot be a chemical compound which is explicitly disclosed (ie does not contain any variables) in U.S. Pat. Pub. No. 2004/0147502. In another exemplary embodiment, the structure has the following proviso: the compound cannot be a chemical compound which is explicitly disclosed (ie does not contain any variables) in U.S. Pat. Pub. No. 2004/0180855.

In an exemplary embodiment, D is arnidinohydrazone. In another exemplary embodiment, D is aminopyridine. In an exemplary embodiment, D is 2-aminopyridine. In an exemplary embodiment, D is 2-aminoaryl. In an exemplary embodiment, D is 2-aminophenyl. In an exemplary embodiment, A is S.

In an exemplary embodiment, at least one of said $R^1$, $R^{1a}$, $R^2$, $R^3$, $R^4$, $R^5$, $R^6$, $R^7$, $R^8$, $R^9$, $R^{10}$, $R^{10a}$, $R^{11}$, $R^{12}$, $R^{13}$, $R^{14}$, $R^{15}$, $R^{16}$, $R^{18}$, $R^{19}$, $R^{20}$, $R^{21}$, $R^{22}$ and $R^{23}$ is a member selected from substituted or unsubstituted arylalkyl and substituted or unsubstituted heteroarylakyl. In another exemplary embodiment, D is a member selected from substituted or unsubstituted guanidine, substituted or unsubstituted amidinohydrazone, substituted or unsubstituted pyridine, substituted or unsubstituted aminopyridine.

In a second aspect, the invention provides a compound according to the following structure:

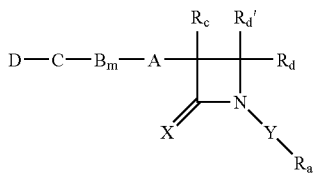

In this structure, $AB_mC$, in combination, is a member selected from substituted or unsubstituted alkyl and substituted or unsubstituted heteroalkyl. D is a member selected from substituted or unsubstituted guanidine, substituted or unsubstituted amidinohydrazone, substituted or unsubstituted pyridine, substituted or unsubstituted aminopyridine. $R_c$ is a member selected from H and substituted or unsubstituted alkyl. $R_d{}'$ is a member selected from H and substituted or unsubstituted alkyl. $R_d$ is a member selected from $R^{16}$, $(CR^{14}R^{15})_pR^{16}$, $C(R^{14})\!\!=\!\!CR^{16}R^{23}$ and $CCR^{16}$. The symbol p is an integer selected from 0 to 3. $R^{14}$ and $R^{23}$ are members independently selected from H, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^{15}$ is a member selected from H, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^{16}$ is a member selected from halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $C(O)R^{18}$, $OR^{19}$, $-\!OC(\!=\!Q)NR^{19}R^{21}$, $-\!NR^{19}C(\!=\!Q)NR^{19}R^{21}$, $-\!NR^{20}SO_2R^{19}$, $OSO_2R^{19}$, $SO_2R^{21}$, $SOR^{21}$, $SO_2NR^{19}R^{20}$, $NR^{19}R^{20}$, CN. $R^{18}$ is a member selected from substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $OR^{21}$, $NR^{19}R^{20}$, and $-\!NR^{19}SO_2R^{20}$. $R^{19}$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^{20}$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $C(O)R^{22}$, $SO_2R^{22}$. $R^{22}$ is a member selected from substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^{21}$ is a member selected from substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted aryl, substituted or unsubstituted heteroaryl, $-\!OR^{22}$. $R^{14}$ and $R^{15}$ can be optionally joined, together with the atoms to which they are attached, to form a 4-8 membered ring. $R^{19}$ and $R^{21}$ can be optionally joined, together with the atoms to which they are attached, to form a 4-8 membered ring. $R^{14}$ and $R^{23}$ can be optionally joined, together with the atoms to which they are attached, to form a 4-8 membered ring. $R^{19}$ and $R^{20}$ can be optionally joined, together with the atoms to which they are attached, to form a 4-8 membered ring. X is a member selected from S, O, and $NR^{35}$. $R^{35}$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $C(O)R^{36}$, $SO_2R^{36}$. $R^{36}$ is a member selected from substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. Y is a member selected from a bond, $C\!\!=\!\!Q$, $CR^{12}R^{13}$, and $SO_n$. The symbol n is a member selected from 0 to 2. Q is a member selected from S, O, and $NR^7$. $R^{12}$ is a member selected from H, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{13}$ is a member selected from H, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{12}$ and $R^{13}$ can be optionally joined, together with the atoms to which they are attached, to form a 4-8 membered ring. $R_a$ is a member selected from $NR^7R^8$, substituted or unsubstituted alkyl substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^7$ and $R^8$ can be optionally joined, together with the atoms to which they are attached, to form a 4-8 membered ring.

In an exemplary embodiment, the compounds of the second aspect are subject to one or more of the following provisos. In an exemplary embodiment, the structure has the proviso that when D is unsubstituted guanidine, $AB_mC$ cannot be unsubstituted alkyl. In an exemplary embodiment, the structure has the proviso that if the compound has the following structure:

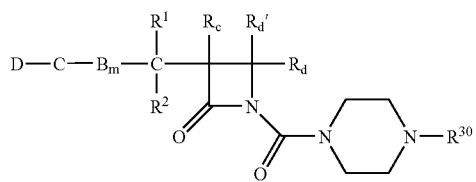

in which $R^{30}$ is a member selected from H, $SO_2$—$R^{31}$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{31}$ is unsubstituted alkyl, then at least one of $R_d$ and $R_d'$ does not comprise a carbonyl group which is directly attached, or alpha, to the azetidinone ring.

In an exemplary embodiment, the second aspect has the proviso that the compound cannot have the following structure:

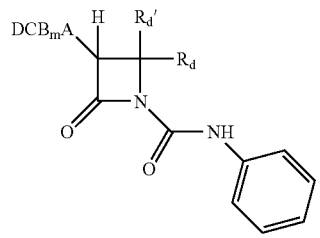

wherein $DCB_mA$ comprises a piperidine ring or a salt thereof.

In an exemplary embodiment of one of the aspects of the invention, at least one of said $R^{1a}$, $R^{12}$, $R^{13}$, $R^{14}$, $R^{15}$, $R^{16}$, $R^{18}$, $R^{19}$, $R^{20}$, $R^{21}$, $R^{22}$, $R^{23}$, $R^{35}$, $R^{36}$ and $R_a$ is a member selected from substituted or unsubstituted arylalkyl and substituted or unsubstituted heteroarylakyl.

In an exemplary embodiment of one of the aspects of the invention, D is a member selected from substituted or unsubstituted aryl, substituted or unsubstituted heteroaryl, substituted or unsubstituted amidine, substituted or unsubstituted amidinohydrazone, substituted or unsubstituted guanidine and substituted or unsubstituted amine.

In an exemplary embodiment of one of the aspects of the invention, D is substituted or unsubstituted guanidine, and $AB_mC$, in combination, form a member selected from D-N=CR-$Z^5$, D-O-$Z^5$, D-$SO_2Z^5$, —O-D, D-$SO_2Z^5$, substituted or unsubstituted alkylene, substituted or unsubstituted acylene, and substituted or unsubstituted heteroalkylene, and $Z^5$ is a member selected from substituted or unsubstituted alkylene and substituted or unsubstituted acylene.

In anexemplary embodiment of one of the aspects of the invention, D is a member selected from sustituted aryl and substituted or unsubstituted heteroaryl, and $AB_mC$, in combination, form a member selected from D-N=$CR^{1a}$-$Z^5$, D-O-$Z^5$, D-$SO_2N$, D-N=CR—, —O-D, —$SO_2$-D, substituted and substituted alkylene, substituted or unsubstituted acylene, and substituted or unsubstituted heteroalkylene, and $Z^5$ is a member selected from substituted or unsubstituted alkylene and substituted and unsubstituted acylene.

In an exemplary embodiment of one of the aspects of the invention, $AB_mCD$, in combination, form a member selected from

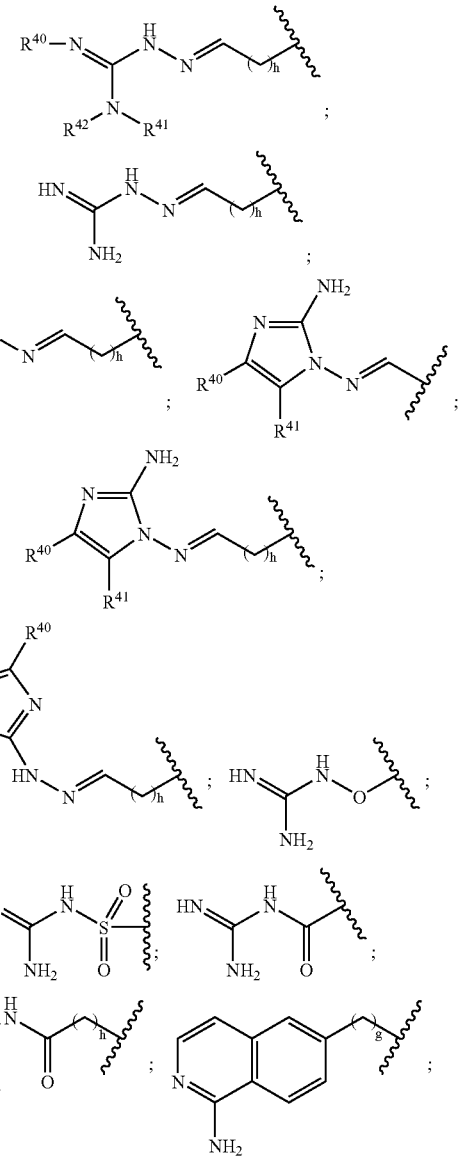

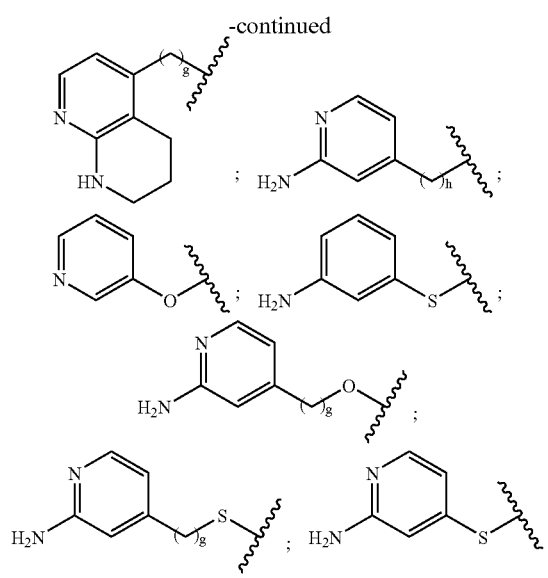

wherein the symbol g is an integer selected from 1 to 4. Each symbol h is an integer independently selected from 0 to 4. $R^{40}$, $R^{41}$ and $R^{42}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment of one of the aspects of the invention, $R_d$ is a member selected from

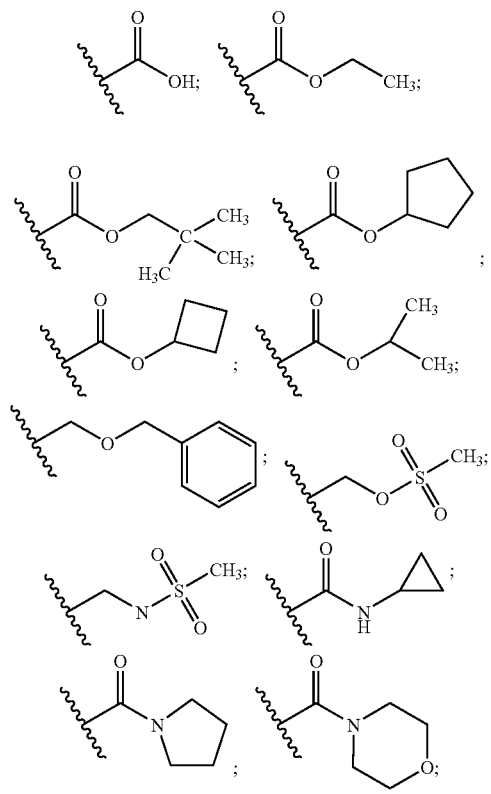

and $CF_3$.

In an exemplary embodiment of one of the aspects of the invention, —Y—$R_a$, in combination, form a member selected from

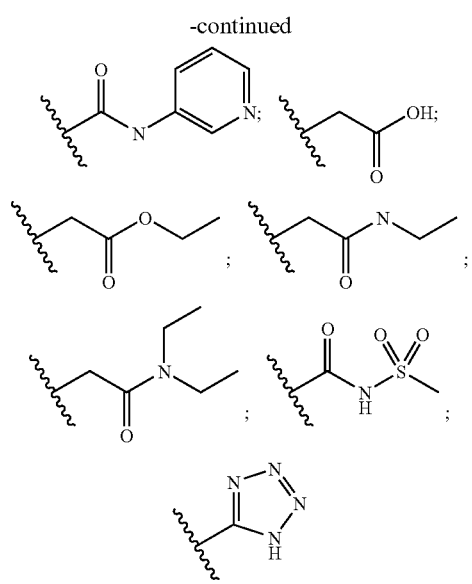

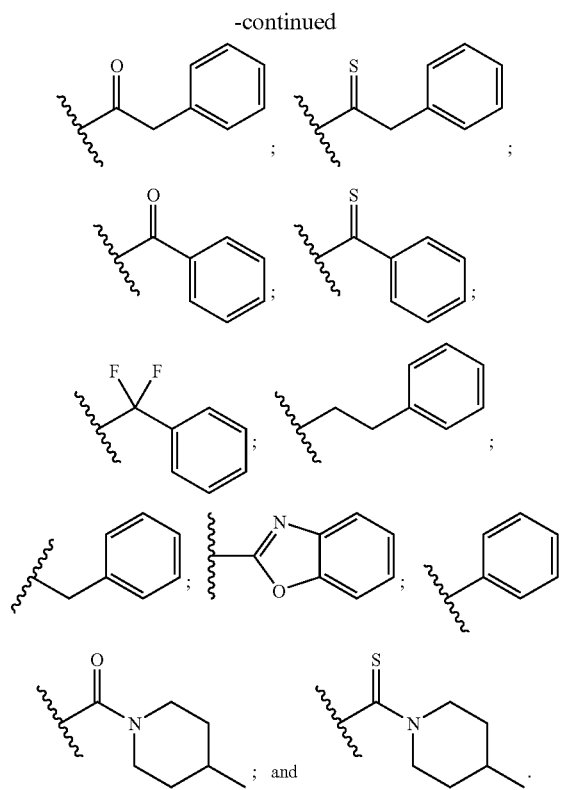

In an exemplary embodiment of one of the aspects of the invention, $R_c$ is a member selected from H, methyl and ethyl.

In an exemplary embodiment of one of the aspects of the invention, X is S. In an exemplary embodiment of one of the aspects of the invention, X is O.

In an exemplary embodiment of one of the aspects of the invention, $R_a$ is a member selected from

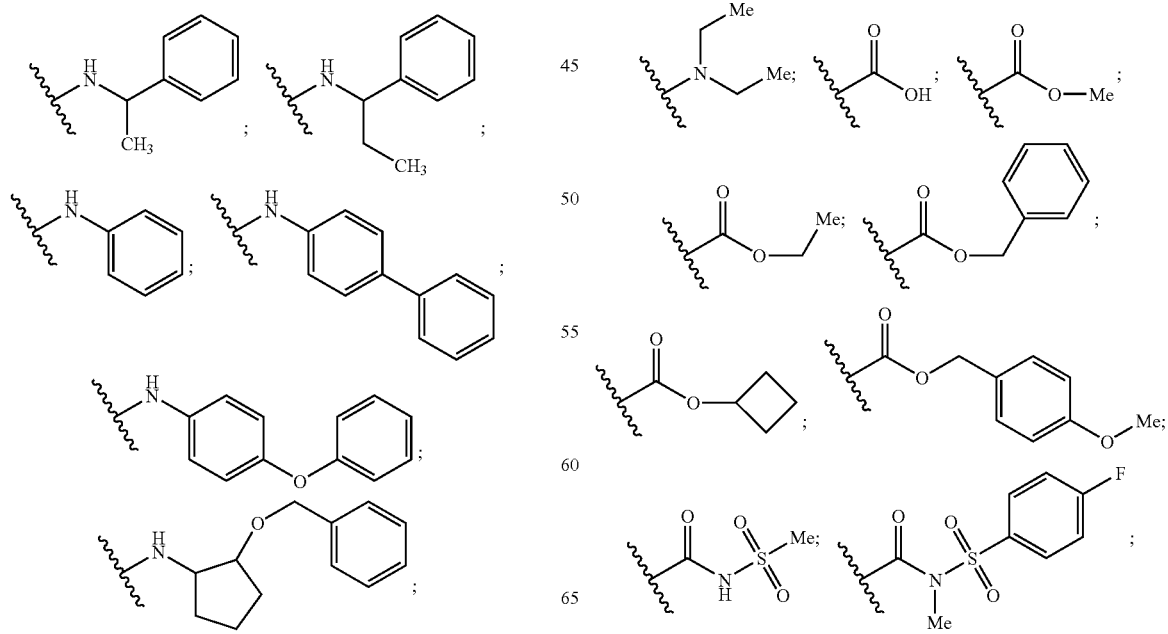

$R_d$ is a member selected from

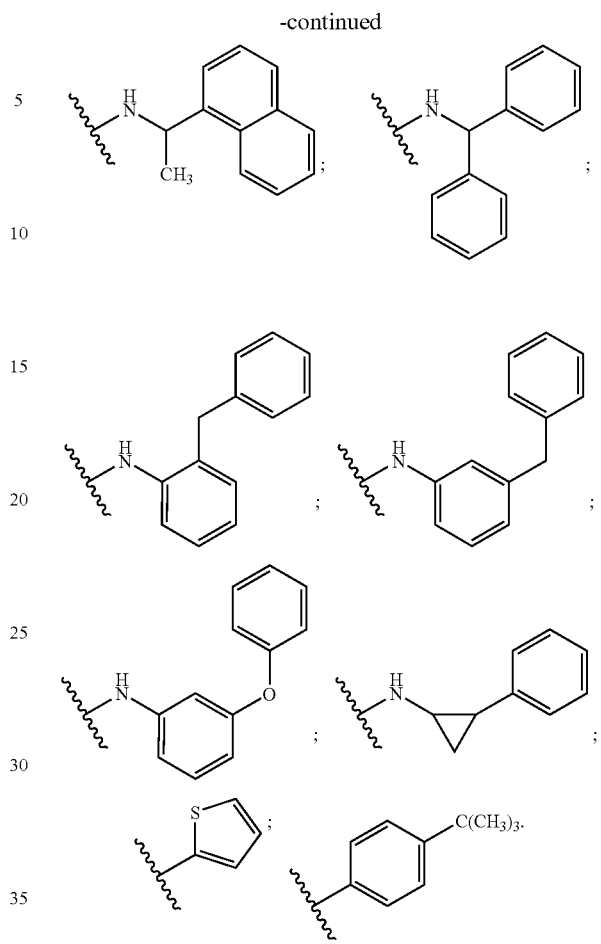

-continued

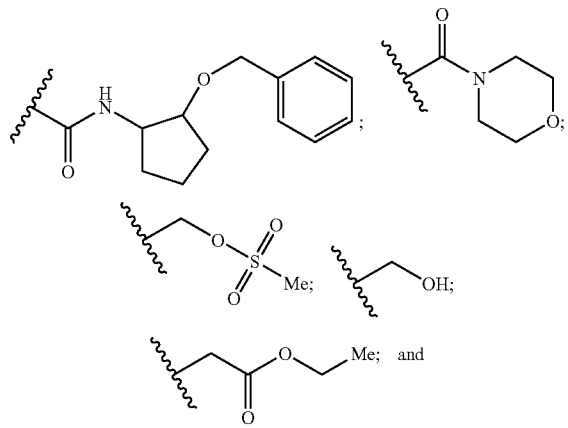

Y is a member selected from C(O) and S(O).

In another exemplary embodiment of one of the aspects of the invention, AB$_m$CD, in combination, form a member selected from

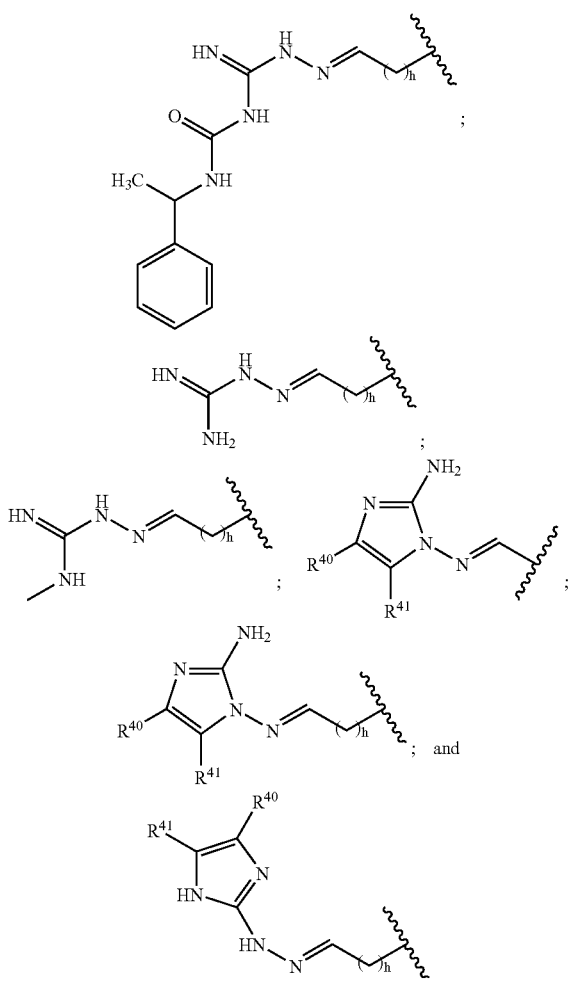

wherein h is an integer selected from 0 to 4.

In another aspect, the invention provides a compound according to the following structure:

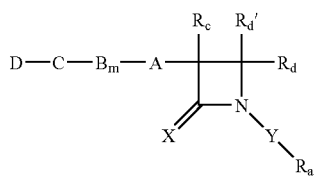

wherein
AB$_m$CD, in combination, is a member selected from:

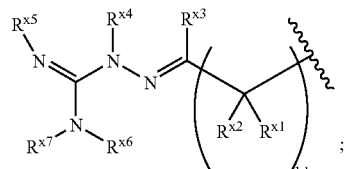

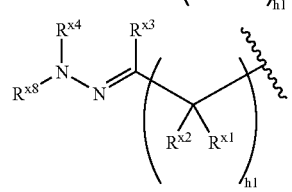

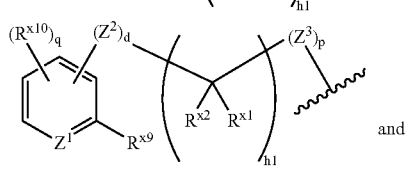

and

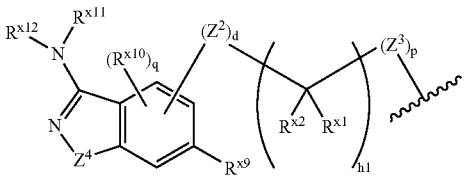

in which the symbol h1 is a member selected from 0 to 4. The symbol q is a member selected from 0 to 3. The symbol r is a member selected from 0 to 2. The symbols d and p are members independently selected from 0 and 1. The symbol $Z^1$ is member selected from $CR^{x13}$ and N. The symbol $Z^4$ is a member selected from $NR^7$ and S. $R^{x1, Rx2, Rx9}$, $R^{x10}$ and $R^{x13}$ are members independently selected from H, $OR^{y1}$, $S(O)_{n1}R^{y1}$, $NR^{y1}R^{y2}$, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{x3}$, $R^{x4}$, $R^{x5}$, $R^{x6}$, $R^{x7}$, $R^{x8}$, $R^{x11}$ and $R^{x12}$ are members independently selected from a positive charge, a salt counterion, H, $S(O)_{n1}R^{y1}$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The symbol n1 is a member selected from 0 to 2. $R^{y1}$ and $R^{y2}$ are members independently selected from a charge (positive or negative), a salt counterion, H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $Z^2$ and $Z^3$ are members selected from $S(O)_{n1}$, O, and $NR^7$. The symbol n1 is a member selected from 0 to 2. Each $R^7$ is a member selected from a positive charge, salt counterion, H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $C(O)R^{10}$, $C(O)OR^{10}$, $NR^{10}R^{10a}$, $OR^{10}$, $SO_2R^{10}$ and $S(O)R^{10}$. Each $R^{10}$ and each $R^{10a}$ is a member independently selected from a positive charge, salt counterion, H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The symbol X is a member selected from O and S. The symbol Y is a member selected from C=Q. Q is a member selected from S and O. $R_a$ is a member selected from $R^{x14}$ and $NR^{x15}R^{x16}$. $R^{x14}$ is a member selected from $OR^{y3}$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{x15}$ and $R^{x16}$ are members independently selected from H, $SO_2R^{y3}$, $NR^{y3}R^{y4}$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{y3}$ and $R^{y4}$ are members independently selected from a charge (either positive or negative), a salt counterion, H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R_c$ is a member selected from H, substituted or unsubstituted alkyl and halogen. $R_d$ is a member selected from

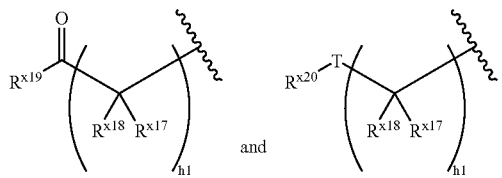

The symbol h1 is a member selected from 0 to 4. T is a member selected from $NR^{x23}$ and O. $R^{x19}$ is a member selected from $OR^{y5}$, $SR^{y5}$, $NR^{y5}R^{y6}$, $NR^{x23}SO_2R^{x22}$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{x22}$ is a member selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{x23}$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{x20}$ is a member selected from H, $C(O)R^{x24}$, $SO_2R^{x24}$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{x24}$ is a member selected from $OR^{x22}$, $NR^{x22}R^{x23}$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{x17}$ and $R^{x18}$ are members independently selected from H, $OR^{y5}$, $S(O)_{n1}R^{y5}$, $NR^{y5}R^{y6}$, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{y5}$ and $R^{y6}$ are members independently selected from a charge (positive or negative), a salt counterion, H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R_d'$ is a member selected from H, substituted or unsubstituted alkyl and halogen. $R_c$ and $R_d$ can be optionally joined, together with the atoms to which they are attached, to form a 5-8 membered ring. $R_c$ and $R_d'$ can be optionally joined, together with the atoms to which they are attached, to form a 5-8 membered ring. $R^{x1}$ and $R^{x2}$ can be optionally joined, together with the atoms to which they are attached, to form a 5-8 membered ring. $R^{x2}$ and $R^{x3}$ can be optionally joined, together with the atoms to which they are attached, to form a 5-8 membered ring. $R^{x3}$ and $R^{x4}$ can be optionally joined, together with the atoms to which they are attached, to form a 5-8 membered ring. $R^{x4}$ and $R^{x5}$ can be optionally joined, together with the atoms to which they are attached, to form a 5-8 membered ring. $R^{x4}$ and $R^{x6}$ can be optionally joined, together with the atoms to which they are attached, to form a 5-8 membered ring. $R^{x5}$ and $R^{x6}$ can be optionally joined, together with the atoms to which they are attached, to form a 5-8 membered ring. $R^{x6}$ and $R^{x7}$ can be optionally joined, together with the atoms to which they are attached, to form a 5-8 membered ring. $R^{x4}$ and $R^{x8}$ can be optionally joined, together with the atoms to which they are attached, to form a 5-8 membered ring. $R^{x2}$ and $R^{x9}$ can be optionally joined, together with the atoms to which they are attached, to form a 5-8 membered ring. two $R^{x10}$ can be optionally joined, together with the atoms to which they are attached, to form a 5-8 membered ring. $R^{x9}$ and $R^{x10}$ can be optionally joined, together with the atoms to which they are attached, to form a 5-8 membered ring. $R^{x12}$ and $R^{x11}$ can be optionally joined, together with the atoms to which they are attached, to form a 5-8 membered ring. $R^{x11}$ and $R^{x10}$ can be optionally joined, together with the atoms to which they are attached, to form a 5-8 membered ring. $R^{y1}$ and $R^{y2}$ can be optionally joined, together with the atoms to which they are attached, to form a 5-8 membered ring. $R^{y3}$ and $R^{y4}$ can be optionally joined, together with the atoms to which they are attached, to form a 5-8 membered ring. $R^{x15}$ and $R^{x16}$ can be optionally joined, together with the atoms to which they are attached, to form a 5-8 membered ring. $R^{22}$ and $R^{23}$ can be optionally joined, together with the atoms to which they are attached, to form a 5-8 membered ring.

In an exemplary embodiment, the compound is subject to one or more of the provisos which are described herein. In an exemplary embodiment, the compound has the proviso that if a) Y is C=O;

ABC, in combination, form unsubstituted alkyl; and

D is substituted or unsubstituted guanidine; or b) Y is C=O;
   AB, in combination, form unsubstituted alkyl; and
   CD, in combination, form

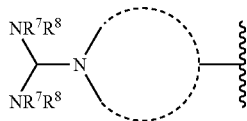

wherein
   the dotted line represents carbon atoms necessary for the formation of one ring having 4 to 8 atoms;

then $R_c$ cannot be a member selected from $CH_3$ and $CH_2CH_3$; and $R_d$ and $R_d'$ cannot be members selected from $CH_3$ and $CH_3$; $CH_2CH_3$ and $CH_2CH_3$; $CH_2CH_3$ and $CH_3$; $CH_3$ and $CH_2CH_3$; H and COOH; H and $COOR^{y5}$; H and $CONR^{10}R^{10a}$; unsubstituted alkyl and COOH; unsubstituted alkyl and $COOR^{y5}$; H and unsubstituted phenylalkyl; unsubstituted alkyl and unsubstituted phenylalkyl. In another exemplary embodiment, $R_c$ cannot be a member selected from $CH_3$, $CH_2CH_3$, substituted alkyl, and unsubstituted alkyl; and $R_d$ and $R_d'$ cannot be members selected from $CH_3$ and $CH_3$; $CH_2CH_3$ and $CH_2CH_3$; $CH_2CH_3$ and $CH_3$; $CH_3$ and $CH_2CH_3$; substituted or unsubstitued alkyl and substituted or unsubstitued alkyl; H and substituted or unsubstitued alkyl; substituted or unsubstitued alkyl and H; H and COOH; H and $COOR^{y5}$; H and $CONR^{10}R^{10a}$; unsubstituted alkyl and COOH; unsubstituted alkyl and $COOR^{y5}$; H and unsubstituted phenylalkyl; unsubstituted alkyl and unsubstituted phenylalkyl.

In another exemplary embodiment, part (a) of this proviso is
a) Y is a member selected from C=O and $SO_2$;
   ABC, in combination, form substituted alkyl; and
   D is substituted or unsubstituted guanidine.

In another exemplary embodiment, $R_c$ of this proviso cannot be substitued alkyl. In another exemplary embodiment, $R_c$ of this proviso cannot be unsubstitued alkyl.

In another exemplary embodiment, $R_d$ and $R_d'$ of this proviso cannot be members selected from $CH_3$ and $CH_3$; $CH_2CH_3$ and $CH_2CH_3$; $CH_2CH_3$ and $CH_3$; $CH_3$ and $CH_2CH_3$; H and COOH; H and $COOR^{y5}$; H and $CONR^{10}R^{10a}$; unsubstituted alkyl and COOH; unsubstituted alkyl and $COOR^{y5}$; H and unsubstituted phenylalkyl; unsubstituted alkyl and unsubstituted phenylalkyl.

In another exemplary embodiment, the structure has the following proviso: if the compound has the following structure:

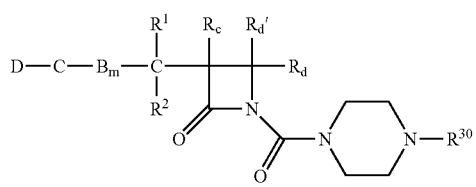

wherein $R^{30}$ is a member selected from H, $SO_2$—$R^{31}$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

wherein $R^{31}$ is unsubstituted alkyl, then at least one of $R_d$ and $R_d'$ does not comprise a carbonyl group which is directly attached, or alpha, to the azetidinone ring.

In another exemplary embodiment, the structure has the following proviso: the compound cannot have the following structure:

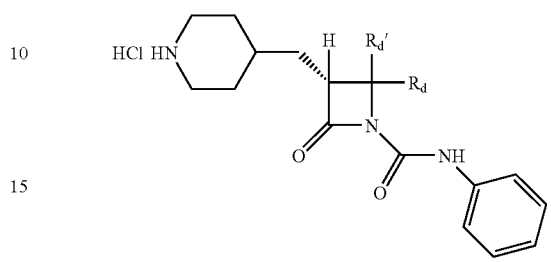

wherein at least one of $R_d$ and $R_d'$ comprise a carbonyl group which is directly attached, or alpha, to the azetidinone ring. In another exemplary embodiment, the compound cannot have the following structure:

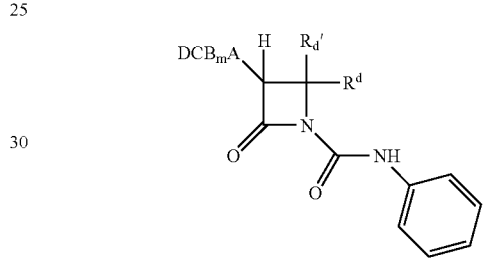

wherein $DCB_mA$ comprises a piperidine ring or a salt thereof. In another exemplary embodiment, the compound cannot have the following structure:

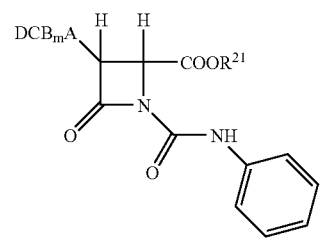

wherein $DCB_mA$ comprises a piperidine ring or a salt thereof.

In another exemplary embodiment, the structure has the following proviso: the compound cannot have the following structure:

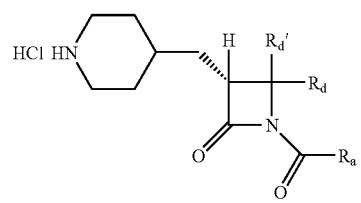

wherein $R_a$ is $NHR^8$, and $R^8$ includes a substituted or unsubstituted phenyl. In another exemplary embodiment, $R^8$ is unsubstituted phenyl. In yet another exemplary embodiment, $R_a$ is N(H)(unsubstituted phenyl). In another exemplary embodiment, the structure has the following proviso: the compound cannot have the following structure:

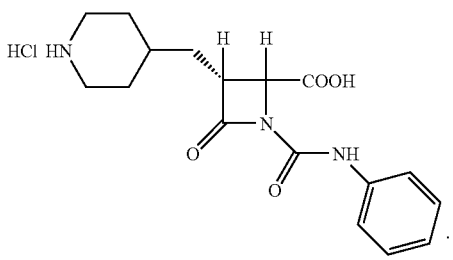

In another exemplary embodiment, the structure has the following proviso: the compound cannot be a chemical compound which is explicitly disclosed (ie does not contain any variables) in U.S. Pat. No. 6,335,324. In another exemplary embodiment, the structure has the following proviso: the compound cannot be a chemical compound which is explicitly disclosed (ie does not contain any variables) in U.S. Pat. Pub. No. 2004/0147502. In another exemplary embodiment, the structure has the following proviso: the compound cannot be a chemical compound which is explicitly disclosed (ie does not contain any variables) in U.S. Pat. Pub. No. 2004/0180855.

In another aspect, the invention provides a method of making one of the compounds of the invention. General and specific methods of synthesizing the compounds are provided herein.

In an exemplary embodiment, the invention provides a pharmaceutical composition comprising an effective amount of a compound of the invention including an inner salt or a pharmaceutically acceptable salt thereof, a hydrolysable ester thereof, or a solvate thereof and one or more pharmaceutically acceptable excipients. In an exemplary embodiment, the pharmaceutical composition is useful for enhancing thrombolyis or treating thrombosis, asthma, chronic asthma, or allergic rhinitis.

In an exemplary embodiment, the invention provides a pharmaceutical composition useful for treating asthma or allergic rhinitis comprising an effective amount of a compound of the invention including an inner salt or a pharmaceutically acceptable salt thereof, a hydrolysable ester thereof, or a solvate thereof and one or more pharmaceutically acceptable excipients.

In an exemplary embodiment, the invention provides a pharmaceutical composition useful for treating chronic asthma comprising an effective amount of a compound of the invention including an inner salt or a pharmaceutically acceptable salt thereof, a hydrolysable ester thereof, or a solvate thereof and one or more pharmaceutically acceptable excipients.

In an exemplary embodiment, the invention provides a method for treating asthma, chronic asthma or allergic rhinitis in a mammalian species comprising administering an effective amount of the composition of the invention.

In an exemplary embodiment, the invention provides a method for treating chronic asthma in a mammalian species comprising administering by inhalation to the bronchioles an effective amount of the composition of the invention.

In an exemplary embodiment, the invention provides a method of inhibiting tryptase in a mammal by administration of a compound according to the invention. In another exemplary embodiment, the invention provides a method of inhibiting factor XIa in a mammal by administration of a compound according to the invention. In yet another exemplary embodiment, the invention provides a method for enhancing thrombolysis or inhibiting or preventing thrombosis in a mammalian species comprising administering an effective amount of the composition of the invention.

In an exemplary embodiment, the invention provides a method of treating thrombosis in a mammal comprising administering to the mammal a pharmaceutical composition that inhibits thrombosis in the mammal, wherein the pharmaceutical composition contains a therapeutically effective amount of a compound according to the invention that is selective for inhibiting Factor XIa.

In an exemplary embodiment, the invention provides a method of treating thrombosis in a mammal comprising administration of a compound according to the invention to the mammal having sufficient selectivity and potency for inhibition of Factor XIa, wherein the administration of the small molecule inhibits thrombosis in the mammal with no substantial effect on bleeding times in the mammal.

In an exemplary embodiment, the invention provides a method of inhibiting Factor XIa in a mammal by administration of a compound according to the invention.

BRIEF DESCRIPTION OF THE DRAWINGS

FIGS. 2A to 2M show tables that include exemplary compounds of the invention and their IC50 data for Factor XIa (FXIa) and tryptase. In this figure, (+++) represents an IC50 value between 0.1 nM and 99.9 nM; (++) represents an IC50 value between 100 nM and 9.99 µM; (+) represents an IC50 value between 10 µM and 99.9 µM; and >(+) represents an IC50 value greater than 99.9 µM.

DETAILED DESCRIPTION OF THE INVENTION AND PREFERRED EMBODIMENTS

I. Definitions and Abbreviations

Figure 1A:
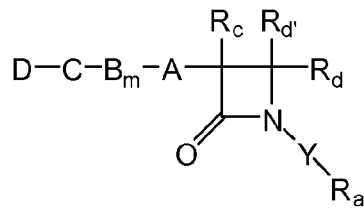
FIGS. 1A to 1DS show tables that include exemplary compounds of the invention.

AcN-acetonitrile; AcOH acetic acid; Allyl Br allyl bromide; $BH_3$ borane; t-Boc tert-butoxycarbonyl; $Boc_2O$ di-tert-butoxycarbonyl anhydride; BuLi butyl lithium; CAN ceric ammonium nitrate; $CCl_4$ carbon tetrachloride; CDI carbonyl diimimidazole; DCC dicyclohexyl carbodiimide; DCM dichloromethane; DIEA diisopropylethylamine; DMAP dimethylaminopyridine; DMF dimethylformamide; EDC 1-ethyl-3-(3'-dimethylaminopropyl)carbodiimide; ESI-MS electrospray ionization mass spectrometry; EtOAc ethyl acetate; EtOH ethyl alcohol; HCl hydrochloric-acid; HOBt 1-hydroxybenzotriazole; HPLC high pressure liquid chromatography; LC-MS liquid chromatography mass spectrometry; LDA lithium diisopropylamide; LiHMDS lithium hexamethyldisilazide; MeOH methyl alcohol; MS mass spectrometry; NBS N-bromo succinimide; NMR nuclear magnetic resonance; Pd/C palladium on carbon; TBAF tetrabutylarunonium fluoride; TBDMS tert-butyldimethylsilyl; TEA triethylamine; TFA trifluoroacetic acid; THF tetrahydrofuran; TIPS triisopropylsilyl; TLC thin layer chromatography; $TMSCHN_2$ trimethylsilyl diazomethane; TMSCl trimethylsilyl chloride.

"Reactive functional group," as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

"Non-covalent protein binding groups" are moieties that interact with an intact or denatured polypeptide in an associative manner. The interaction may be either reversible or irreversible in a biological milieu. The incorporation of a "non-covalent protein binding group" into a chelating agent or complex of the invention provides the agent or complex with the ability to interact with a polypeptide in a non-covalent manner. Exemplary non-covalent interactions include hydrophobic-hydrophobic and electrostatic interactions. Exemplary "non-covalent protein binding groups" include anionic groups, e.g., phosphate, thiophosphate, phosphonate, carboxylate, boronate, sulfate, sulfone, thiosulfate, and thiosulfonate.

As used herein, "linking member" refers to a covalent chemical bond that includes at least one heteroatom. Exemplary linking members include —C(O)NH—, —C(O)O—, —NH—, —S—, —O—, and the like.

The term "targeting group" is intended to mean a moiety that is: (1) able to actively direct the entity to which it is attached (e.g., contrast agent) to a target region, e.g., a tumor; or (2) is preferentially passively absorbed by or entrained within a target tissue, for example a tumor. The targeting group can be a small molecule, which is intended to include both non-peptides and peptides. The targeting group can also be a macromolecule, which includes, but is not limited to, saccharides, lectins, receptors, ligand for receptors, proteins such as BSA, antibodies, poly(ethers), dendrimers, poly (amino acids) and so forth.

The term "cleavable group" is intended to mean a moiety that allows for release of the chelate from the rest of the conjugate by cleaving a bond linking the chelate (or chelate linker arm construct) to the remainder of the conjugate. Such cleavage is either chemical in nature, or enzymatically mediated. Exemplary enzymatically cleavable groups include natural amino acids or peptide sequences that end with a natural amino acid.

In addition to enzymatically cleavable sites, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleaveable groups are known in the art. See, for example, Jung et al., *Biochem. Biophys. Acta,* 761: 152-162 (1983); Joshi et al., *J. Biol. Chem.,* 265: 14518-14525 (1990); Zarling et al., *J. Immunol.,* 124: 913-920 (1980); Bouizar et al., *Eur. J. Biochem.,* 155: 141-147 (1986); Park et al., *J. Biol. Chem.,* 261: 205-210 (1986); Browning et al., *J. Immunol.,* 143: 1859-1867 (1989). Moreover a broad range of cleavable, bifunctional (both homo- and hetero-bifunctional) spacer arms are commercially available from suppliers such as Pierce.

The symbol $\sim\!\!\sim$, whether utilized as a bond or displayed perpendicular to a bond indicates the point at which the displayed moiety is attached to the remainder of the molecule, solid support, etc.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose an appropriate method for a particular situation. See, generally, Furniss et al. (eds.),VOGEL'S ENCYCLOPEDIA OF PRACTICAL ORGANIC CHEMISTRY 5$^{TH}$ ED., Longman Scientific and Technical Ltd., Essex, 1991, pp. 809-816; and Heller, *Acc. Chem. Res.* 23: 128 (1990).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Where substituent groups are specified by their conventional chemical formulae, written from left to right, they equally encompass the chemically identical substituents, which would result from writing the structure from right to left, e.g., —CH$_2$O— is intended to also recite —OCH$_2$—; —NHS(O)$_2$— is also intended to represent —S(O)$_2$HN—; etc.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quatemized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to three heteroatoms may be consecutive, such as, for example, —$CH_2$—NH—$OCH_3$, —$CH_2$—O—$SO_2$—O—$CH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

In general, the term "acyl" is also selected from the group set forth above. As used herein, the term "acyl" refers to groups attached to, and fuilfilling the valence of a carbonyl carbon that is either directly or indirectly attached to the compounds of the present invention.

In general, the term "acylene" refers to an alkylene group which comprises an acyl group.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quatemized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted or unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R'', R''' and R'''' groups when more than one of these groups is present. When R' and R'' are attached to the same nitrogen atom, they can be combined with the nitrogen atom to form a 5-, 6-, or 7-membered ring. For example, —NR'R'' is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, the aryl substituents and heteroaryl substituents are generally referred to as "aryl substituents" and "heteroaryl substituents," respectively and are varied and selected from, for example: halogen, —OR', =O, =NR', =N—OR', —NR'R'', —SR', -halogen, —SiR'R''R''', —OC(O)R', —C(O)R', —CO$_2$R', —CONR'R'', —OC(O)NR'R'', —NR''C(O)R', —NR'—C(O)NR''R''', —NR''C(O)$_2$R', —NR—C(NR'R''R''')=NR'''', —NR—C(NR'R'')=NR''', —S(O)R', —S(O)$_2$R', —S(O)$_2$NR'R'', —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R'', R''' and R'''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R'', R''' and R'''' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR''R''')$_d$—, where s and d are independently integers of from 0 to 3, and X is —O—, —NR'—, —S—, —S(O)—, —S(O)$_2$—, or —S(O)$_2$NR'—. The substituents R, R', R'' and R''' are preferably independently selected from hydrogen or substituted or unsubstituted (C$_1$-C$_6$)alkyl.

As used herein, the term "heteroatom" is meant to include oxygen (O), nitrogen (N), sulfur (S), silicon (Si), phosphorus (P) and boron (B).

The symbol "R" is a general abbreviation that represents a substituent group that is selected from substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl groups.

The term "amidinohydrazone", as used herein, refers to a moiety according to the following structure:

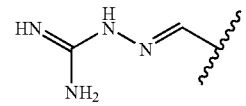

wherein one or more of the hydrogens in this structure can be replaced with an 'R' group.

"Protecting group," as used herein refers to a portion of a substrate that is substantially stable under a particular reaction condition, but which is cleaved from the substrate under a different reaction condition. A protecting group can also be selected such that it participates in the direct oxidation of the aromatic ring component of the compounds of the invention. For examples of useful protecting groups, see, for example, Greene et al., PROTECTIVE GROUPS IN ORGANIC SYNTHESIS, John Wiley & Sons, New York, 1991.

"Ring" as used herein means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 8-membered ring" means there are 5 to 8 atoms in the encircling arrangement. The ring optionally included a heteroatom. Thus, the term "5- to 8-membered ring" includes, for example pyridinyl and piperidinyl. The term "ring" further includes a ring system comprising more than one "ring", wherein each "ring" is independently defined as above.

The term, "phenylalkyl", as used herein, refers to a moiety in which the phenyl ring is connected to the rest of the molecule through an alkyl chain. Examples of phenylalkyl moieties include phenylmethyl

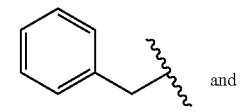

and phenylethyl

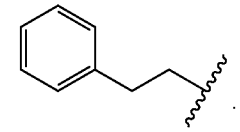

Other examples of substituted phenylalkyl is 3-chlorophenyl-propyl

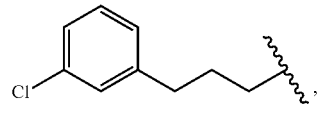

phenyl-2chloropropyl

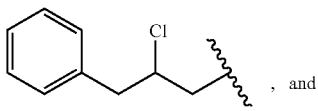, and 3-chlorophenyl-2chloropropyl

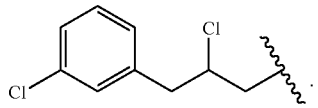.

The term "pharmaceutically acceptable salts" includes salts of the active compounds which are prepared with relatively nontoxic acids or bases, depending on the particular substituents found on the compounds described herein. When compounds of the present invention contain relatively acidic fuictionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, trifluoroacetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

III. Compounds

Figure 1E:
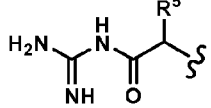
Figure 1E:
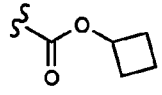
Figure 1E:
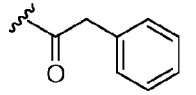
Figure 1E:
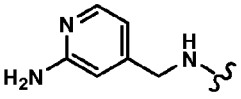
Figure 1E:
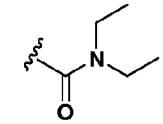
Figure 1E:
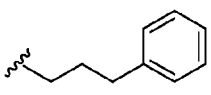
Figure 1E:
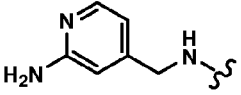
Figure 1E:
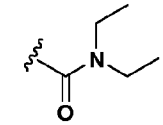
Figure 1E:
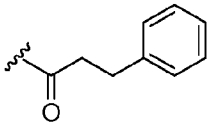
Figure 1E:
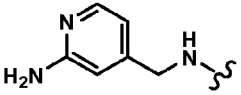
Figure 1E:
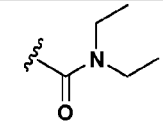
Figure 1E:
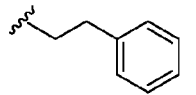
Figure 1E:
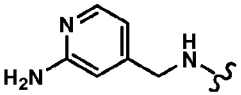
Figure 1E:
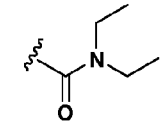
Figure 1E:
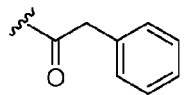
Figure 1E:
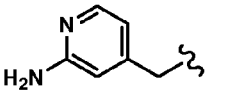
Figure 1E:
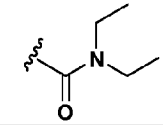
Figure 1E:
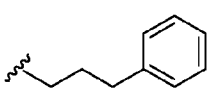
Figure 1E:
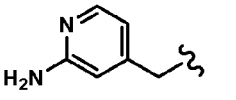
Figure 1E:
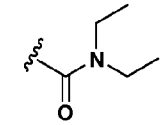
Figure 1E:
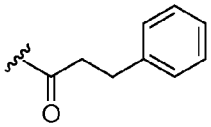
Figure 1E:
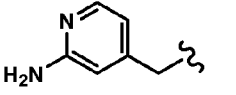
Figure 1E:
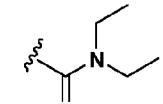
Figure 1E:
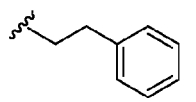
Figure 1E:
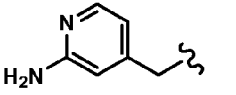
Figure 1E:
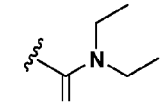
Figure 1E:
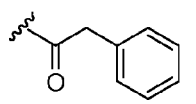
Figure 1E:
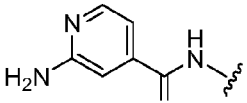
Figure 1E:
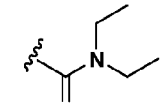
Figure 1E:
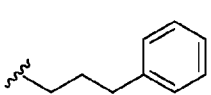
Figure 1E:
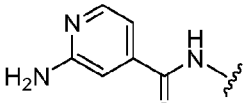
Figure 1E:
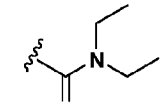
Figure 1E:
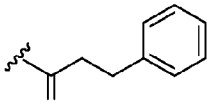
Figure 1E:
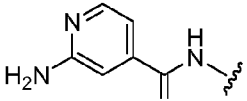
Figure 1E:
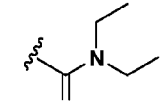
Figure 1E:
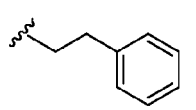
Figure 1H:
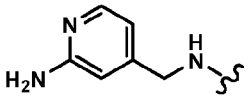
Figure 1H:
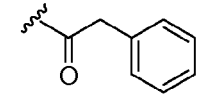
Figure 1H:
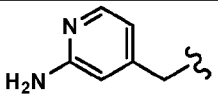
Figure 1H:
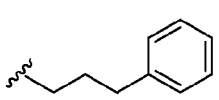
Figure 1H:
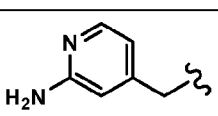
Figure 1H:
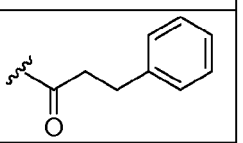
Figure 1H:

Figure 1H:

Figure 1H:

Figure 1H:

Figure 1H:
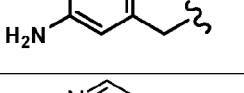
Figure 1H:
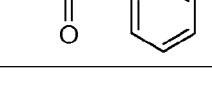
Figure 1H:
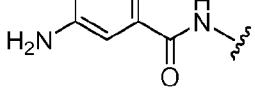
Figure 1H:
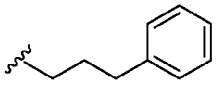
Figure 1H:
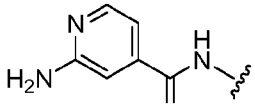
Figure 1H:
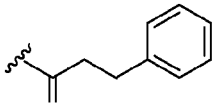
Figure 1H:
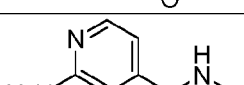
Figure 1H:
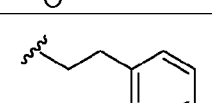
Figure 1H:
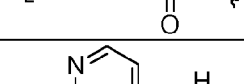
Figure 1H:
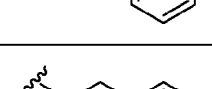
Figure 1H:
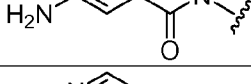
Figure 1H:
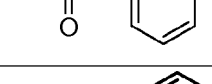
Figure 1H:
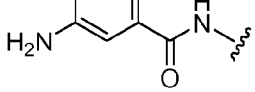
Figure 1H:
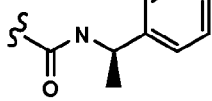
Figure 1M:
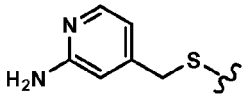
Figure 1M:
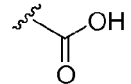
Figure 1M:
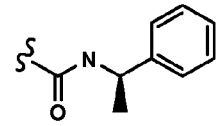
Figure 1M:
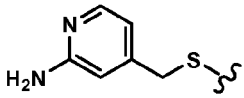
Figure 1M:
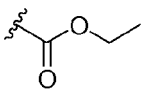
Figure 1M:
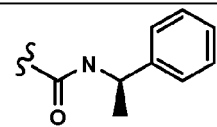
Figure 1M:
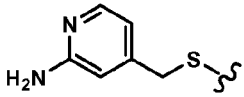
Figure 1M:
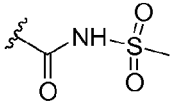
Figure 1M:
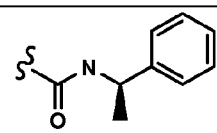
Figure 1M:
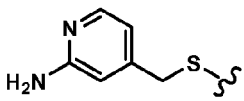
Figure 1M:
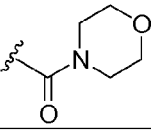
Figure 1M:
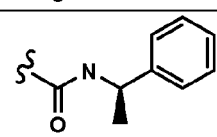
Figure 1M:
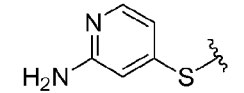
Figure 1M:
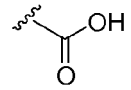
Figure 1M:
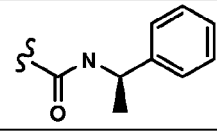
Figure 1M:
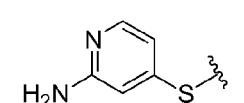
Figure 1M:
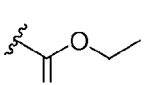
Figure 1M:
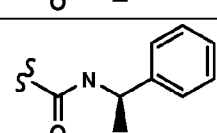
Figure 1M:
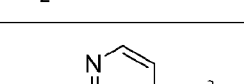
Figure 1M:
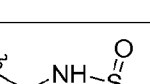
Figure 1M:
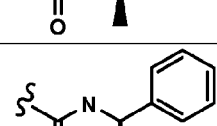
Figure 1M:
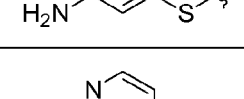
Figure 1M:
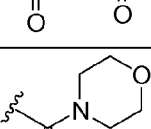
Figure 1M:
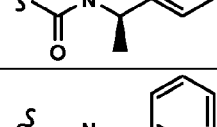
Figure 1M:
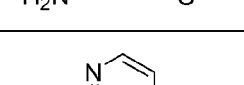
Figure 1M:
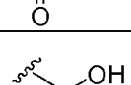
Figure 1M:
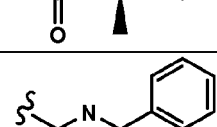
Figure 1M:
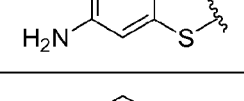
Figure 1M:
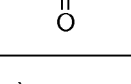
Figure 1M:
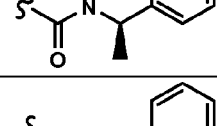
Figure 1M:
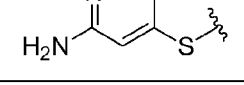
Figure 1M:
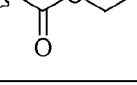
Figure 1M:
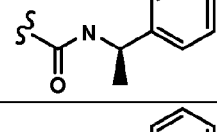
Figure 1M:
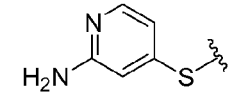
Figure 1M:
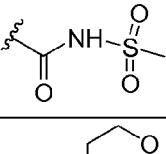
Figure 1M:
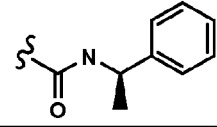
Figure 1N:
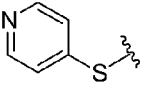
Figure 1N:
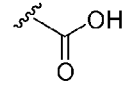
Figure 1N:
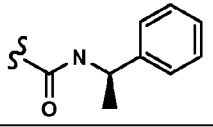
Figure 1N:
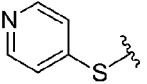
Figure 1N:
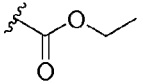
Figure 1N:
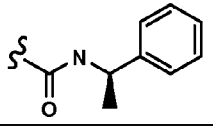
Figure 1N:
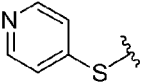
Figure 1N:
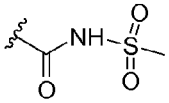
Figure 1N:
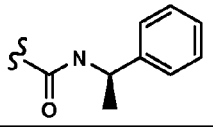
Figure 1N:
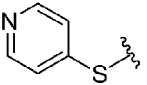
Figure 1N:
Figure 1N:
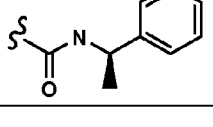
Figure 1O:
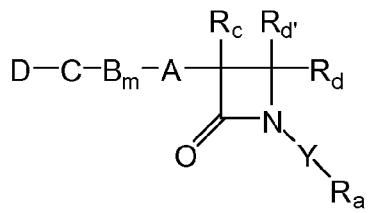
Figure 1P:
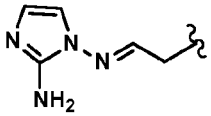
Figure 1P:
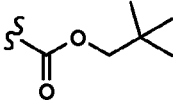
Figure 1P:
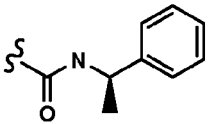
Figure 1P:
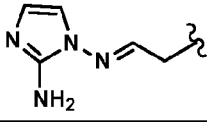
Figure 1P:
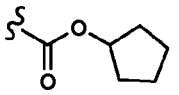
Figure 1P:
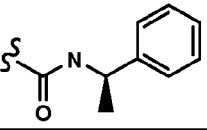
Figure 1P:
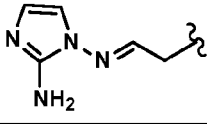
Figure 1P:
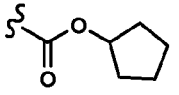
Figure 1P:
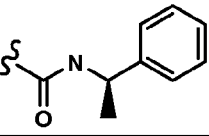
Figure 1P:
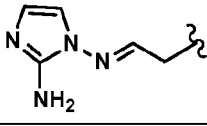
Figure 1P:
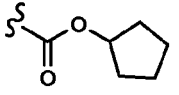
Figure 1P:
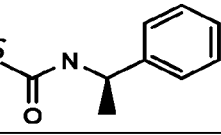
Figure 1P:
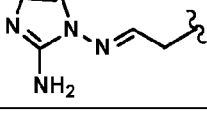
Figure 1P:
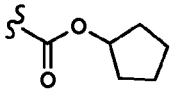
Figure 1P:
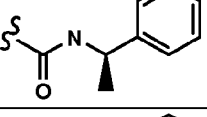
Figure 1P:
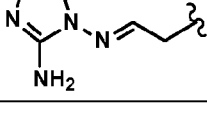
Figure 1P:
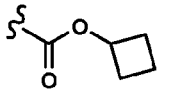
Figure 1P:
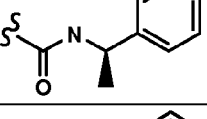
Figure 1P:
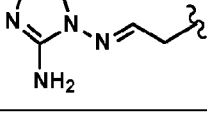
Figure 1P:
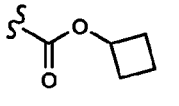
Figure 1P:
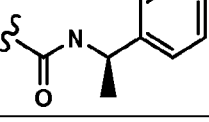
Figure 1P:
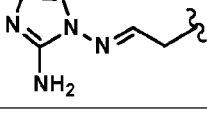
Figure 1P:
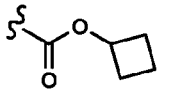
Figure 1P:
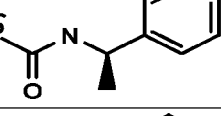
Figure 1P:
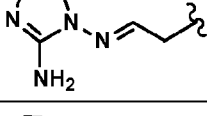
Figure 1P:
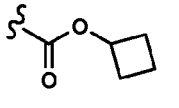
Figure 1P:
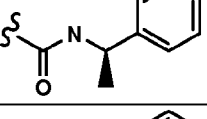
Figure 1P:
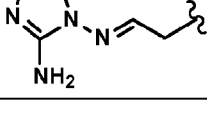
Figure 1P:
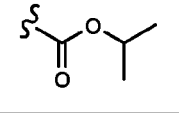
Figure 1P:
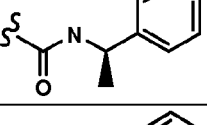
Figure 1P:
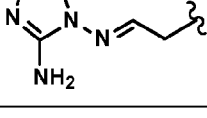
Figure 1P:
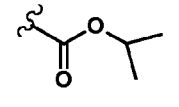
Figure 1P:
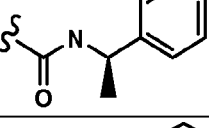
Figure 1P:
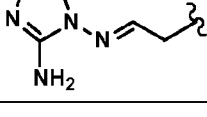
Figure 1P:
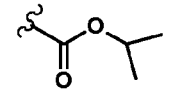
Figure 1P:
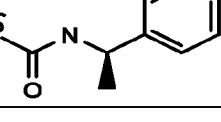
Figure 1Q:
Figure 1Q:
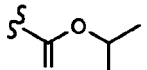
Figure 1Q:
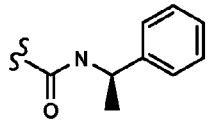
Figure 1Q:
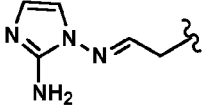
Figure 1Q:

Figure 1Q:

Figure 1Q:
Figure 1Q:

Figure 1Q:

Figure 1Q:
Figure 1Q:

Figure 1Q:

Figure 1Q:
Figure 1Q:

Figure 1Q:

Figure 1Q:
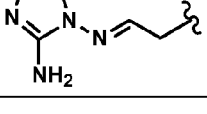
Figure 1Q:

Figure 1Q:

Figure 1Q:
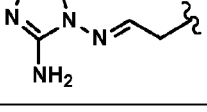
Figure 1Q:

Figure 1Q:

Figure 1Q:
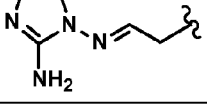
Figure 1Q:

Figure 1Q:

Figure 1Q:
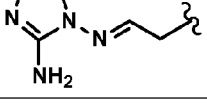
Figure 1Q:

Figure 1Q:

Figure 1Q:
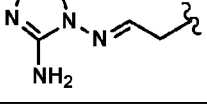
Figure 1Q:

Figure 1Q:

Figure 1Q:
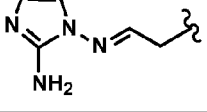
Figure 1Q:

Figure 1Q:

Figure 1S:
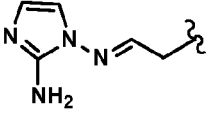
Figure 1X:
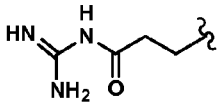
Figure 1X:
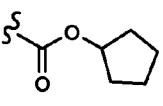
Figure 1X:
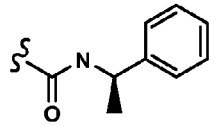
Figure 1X:
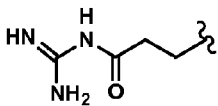
Figure 1X:
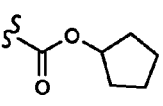
Figure 1X:
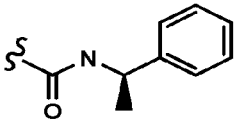
Figure 1X:
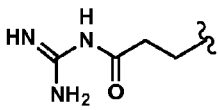
Figure 1X:
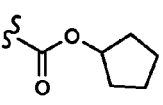
Figure 1X:
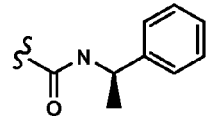
Figure 1X:
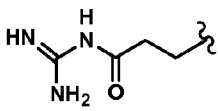
Figure 1X:
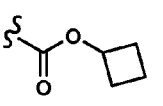
Figure 1X:
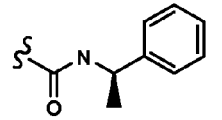
Figure 1X:
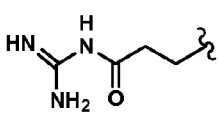
Figure 1X:
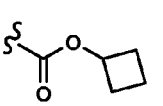
Figure 1X:
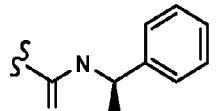
Figure 1X:
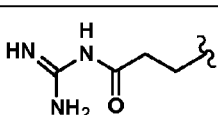
Figure 1X:
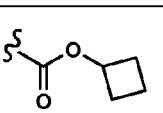
Figure 1X:
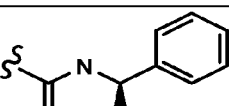
Figure 1X:
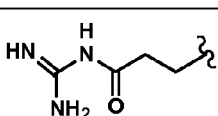
Figure 1X:
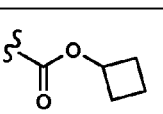
Figure 1X:
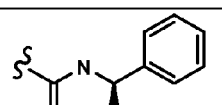
Figure 1X:
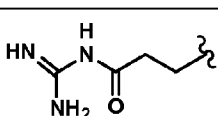
Figure 1X:
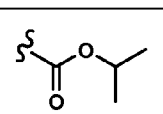
Figure 1X:
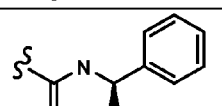
Figure 1X:
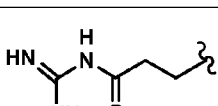
Figure 1X:
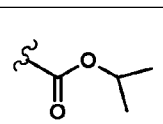
Figure 1X:
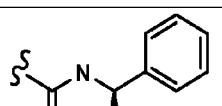
Figure 1X:
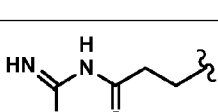
Figure 1X:
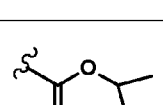
Figure 1X:
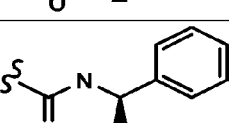
Figure 1X:
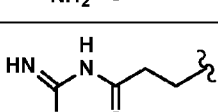
Figure 1X:
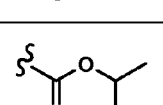
Figure 1X:
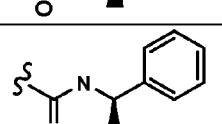
Figure 1X:
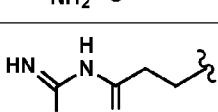
Figure 1X:
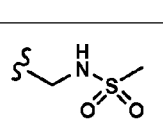
Figure 1X:
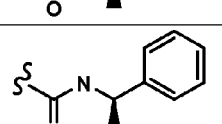
Figure 1Z:
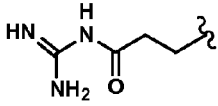
Figure 1Z:
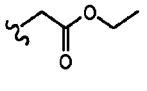
Figure 1Z:
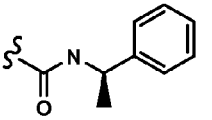
Figure 1Z:
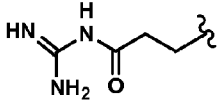
Figure 1Z:
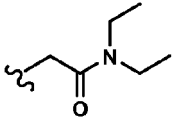
Figure 1Z:
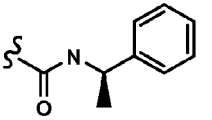
Figure 1Z:
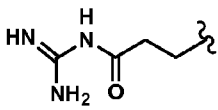
Figure 1Z:
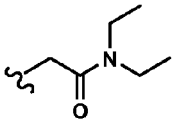
Figure 1Z:
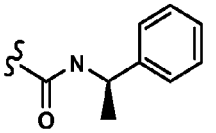
Figure 1Z:
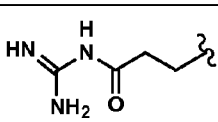
Figure 1Z:
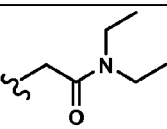
Figure 1Z:
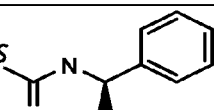
Figure 1Z:
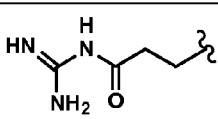
Figure 1Z:
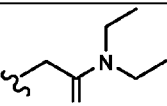
Figure 1Z:
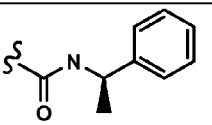
Figure 1Z:
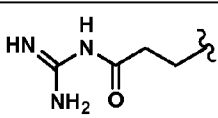
Figure 1Z:
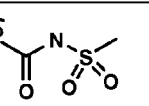
Figure 1Z:
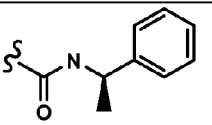
Figure 1Z:
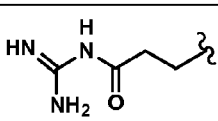
Figure 1Z:
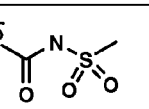
Figure 1Z:
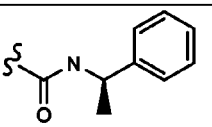
Figure 1Z:
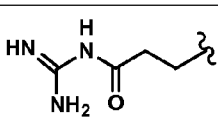
Figure 1Z:
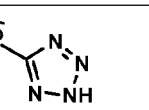
Figure 1Z:
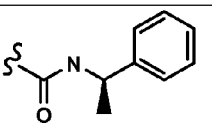
Figure 1Z:
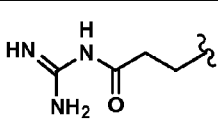
Figure 1Z:
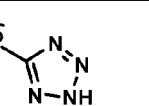
Figure 1Z:
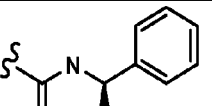
Figure 1Z:
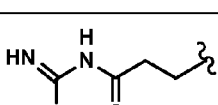
Figure 1Z:
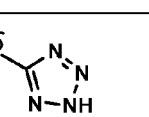
Figure 1Z:
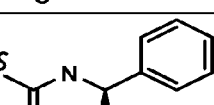
Figure 1Z:
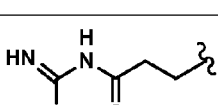
Figure 1Z:
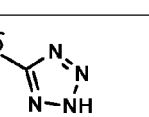
Figure 1Z:
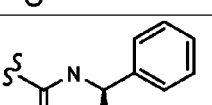
Figure 1Z:
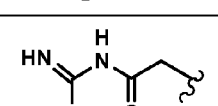
Figure 1Z:
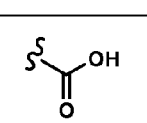
Figure 1Z:
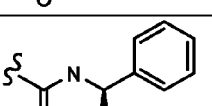
Figure 1A:
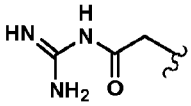
Figure 1A:
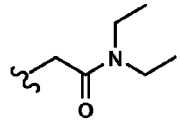
Figure 1A:
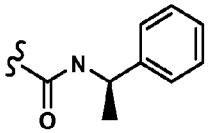
Figure 1A:
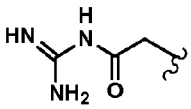
Figure 1A:
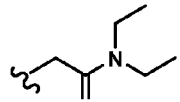
Figure 1A:
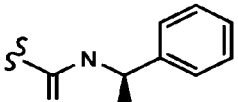
Figure 1A:
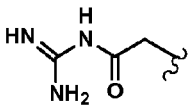
Figure 1A:
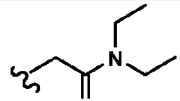
Figure 1A:
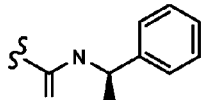
Figure 1A:
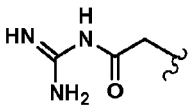
Figure 1A:
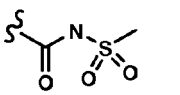
Figure 1A:
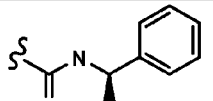
Figure 1A:
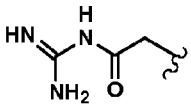
Figure 1A:
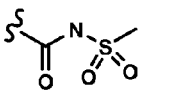
Figure 1A:
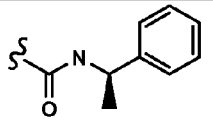
Figure 1A:
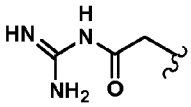
Figure 1A:
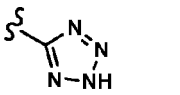
Figure 1A:
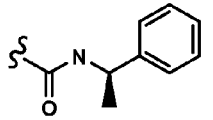
Figure 1A:
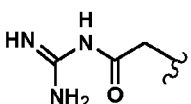
Figure 1A:
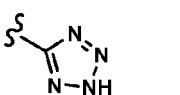
Figure 1A:
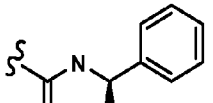
Figure 1A:
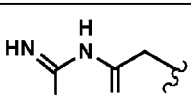
Figure 1A:
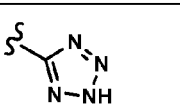
Figure 1A:
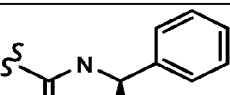
Figure 1A:
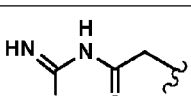
Figure 1A:
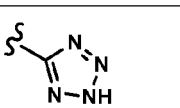
Figure 1A:
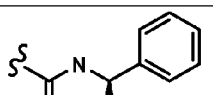
Figure 1A:
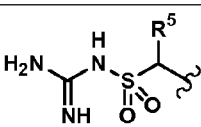
Figure 1A:
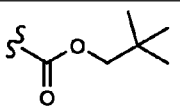
Figure 1A:
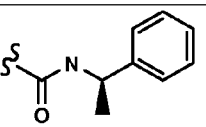
Figure 1A:
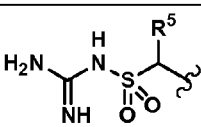
Figure 1A:
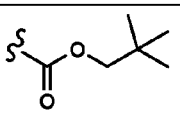
Figure 1A:
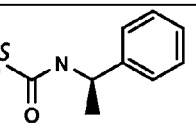
Figure 1A:
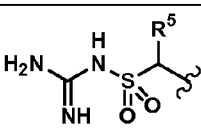
Figure 1A:
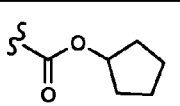
Figure 1A:
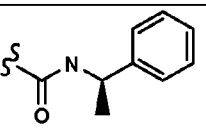
Figure 1A:
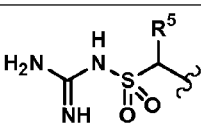
Figure 1A:
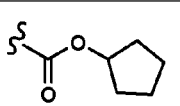
Figure 1A:
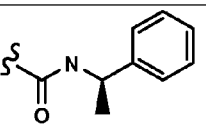
Figure 1A:
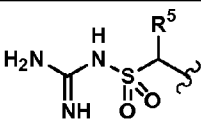
Figure 1A:
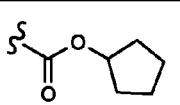
Figure 1A:
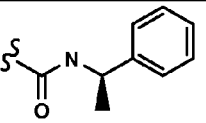
Figure 1A:
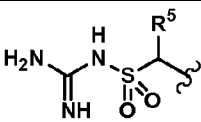
Figure 1A:
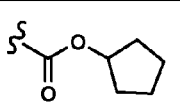
Figure 1A:
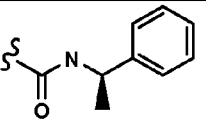
Figure 1A:
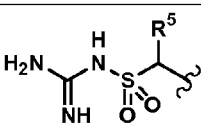
Figure 1A:
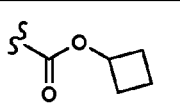
Figure 1A:
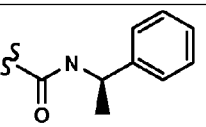
Figure 1A:
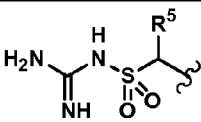
Figure 1A:
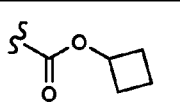
Figure 1A:
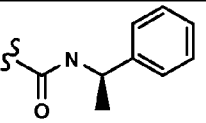
Figure 1A:
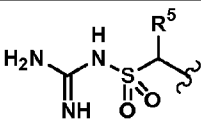
Figure 1A:
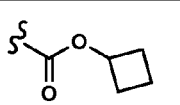
Figure 1A:
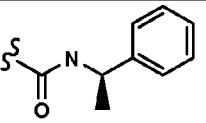
Figure 1A:
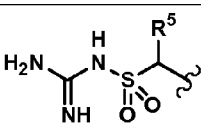
Figure 1A:
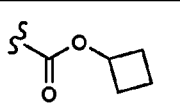
Figure 1A:
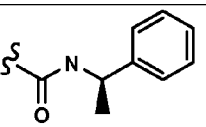
Figure 1A:
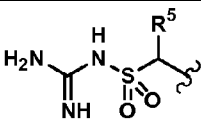
Figure 1A:
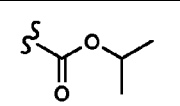
Figure 1A:
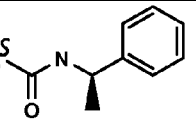
Figure 1A:
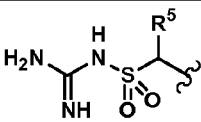
Figure 1A:
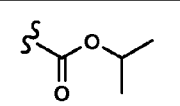
Figure 1A:
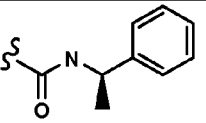
Figure 1A:
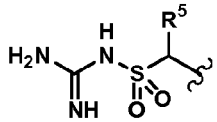
Figure 1A:
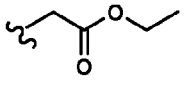
Figure 1A:
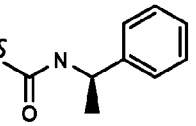
Figure 1A:
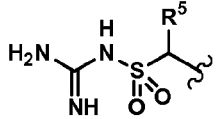
Figure 1A:
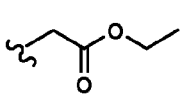
Figure 1A:
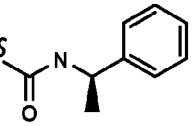
Figure 1A:
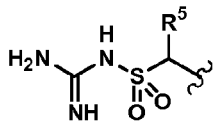
Figure 1A:
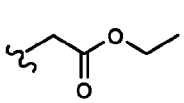
Figure 1A:
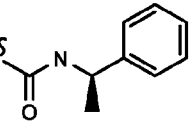
Figure 1A:
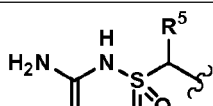
Figure 1A:
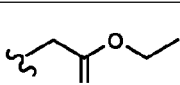
Figure 1A:
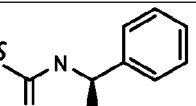
Figure 1A:
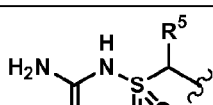
Figure 1A:
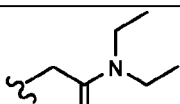
Figure 1A:
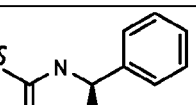
Figure 1A:
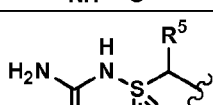
Figure 1A:
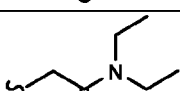
Figure 1A:
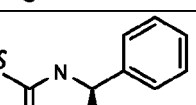
Figure 1A:
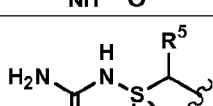
Figure 1A:
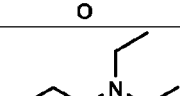
Figure 1A:
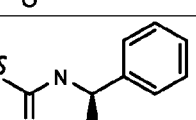
Figure 1A:
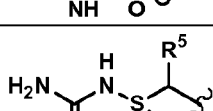
Figure 1A:
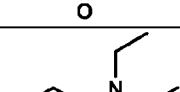
Figure 1A:
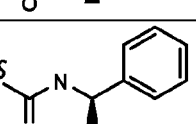
Figure 1A:
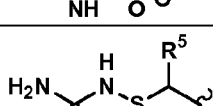
Figure 1A:
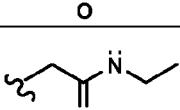
Figure 1A:
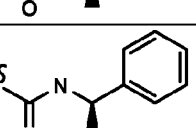
Figure 1A:
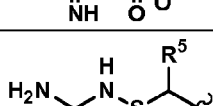
Figure 1A:
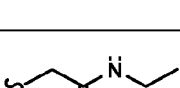
Figure 1A:
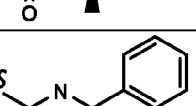
Figure 1A:
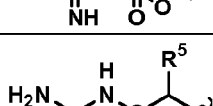
Figure 1A:
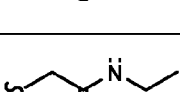
Figure 1A:
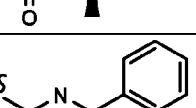
Figure 1A:
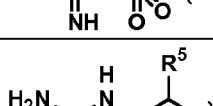
Figure 1A:
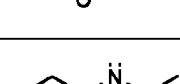
Figure 1A:
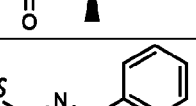
Figure 1A:
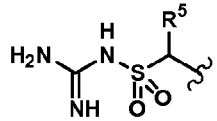
Figure 1A:
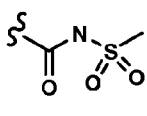
Figure 1A:
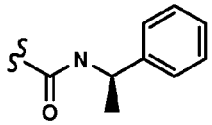
Figure 1A:
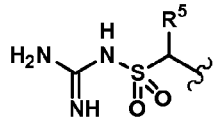
Figure 1A:
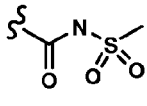
Figure 1A:
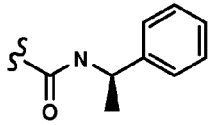
Figure 1A:
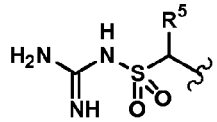
Figure 1A:
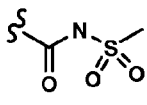
Figure 1A:
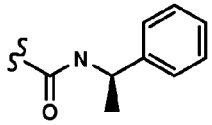
Figure 1A:
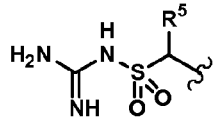
Figure 1A:
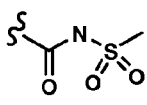
Figure 1A:
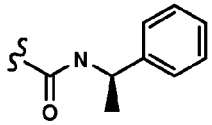
Figure 1A:
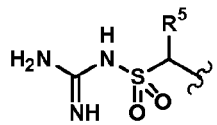
Figure 1A:
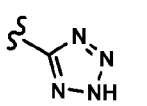
Figure 1A:
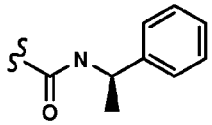
Figure 1A:
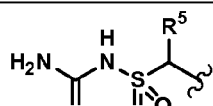
Figure 1A:
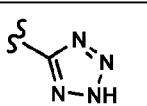
Figure 1A:
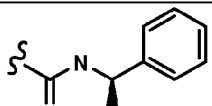
Figure 1A:
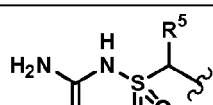
Figure 1A:
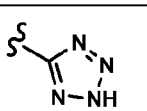
Figure 1A:
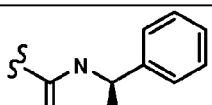
Figure 1A:
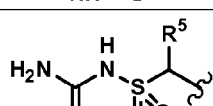
Figure 1A:
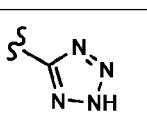
Figure 1A:
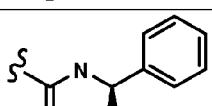
Figure 1A:
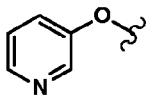
Figure 1A:
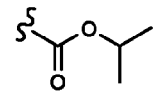
Figure 1A:
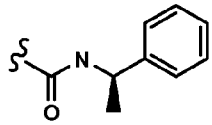
Figure 1A:
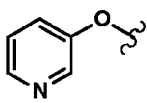
Figure 1A:
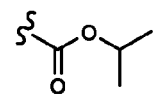
Figure 1A:
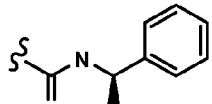
Figure 1A:
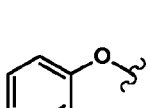
Figure 1A:
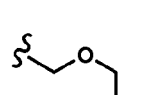
Figure 1A:
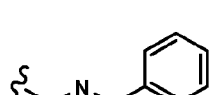
Figure 1A:
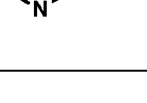
Figure 1A:
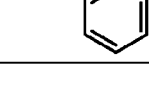
Figure 1A:
Figure 1A:
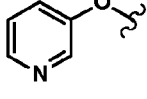
Figure 1A:
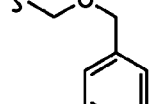
Figure 1A:
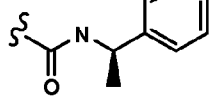
Figure 1A:
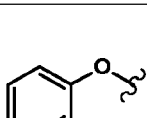
Figure 1A:
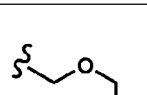
Figure 1A:
Figure 1A:
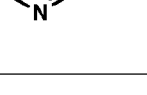
Figure 1A:
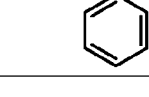
Figure 1A:
Figure 1A:
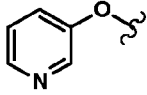
Figure 1A:
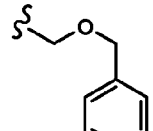
Figure 1A:
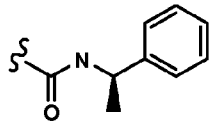
Figure 1A:
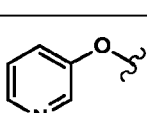
Figure 1A:
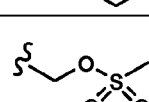
Figure 1A:
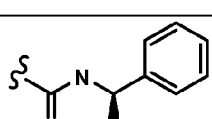
Figure 1A:
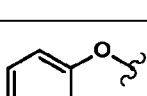
Figure 1A:
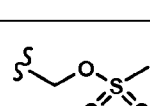
Figure 1A:
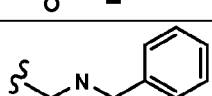
Figure 1A:
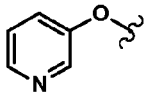
Figure 1A:
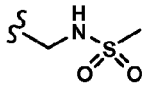
Figure 1A:
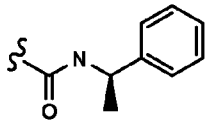
Figure 1A:
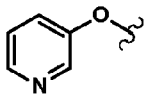
Figure 1A:
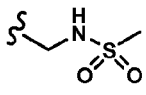
Figure 1A:
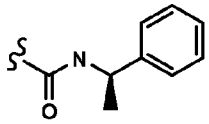
Figure 1A:
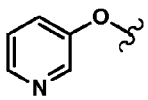
Figure 1A:
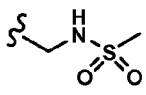
Figure 1A:
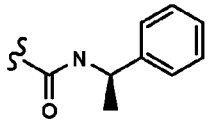
Figure 1A:
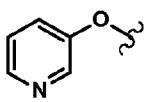
Figure 1A:
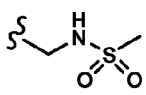
Figure 1A:
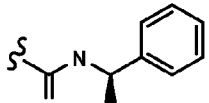
Figure 1A:
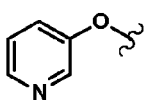
Figure 1A:
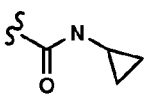
Figure 1A:
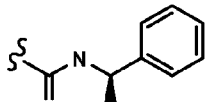
Figure 1A:
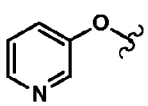
Figure 1A:
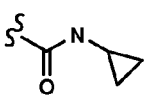
Figure 1A:
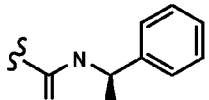
Figure 1A:
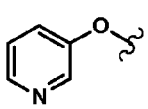
Figure 1A:
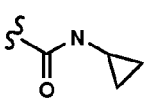
Figure 1A:
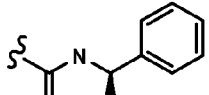
Figure 1A:
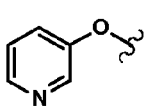
Figure 1A:
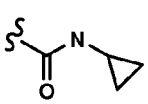
Figure 1A:
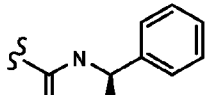
Figure 1A:
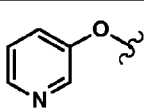
Figure 1A:
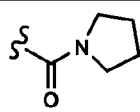
Figure 1A:
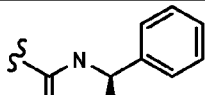
Figure 1A:
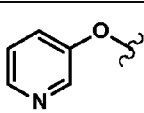
Figure 1A:
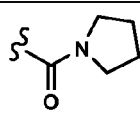
Figure 1A:
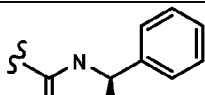
Figure 1A:
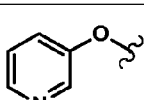
Figure 1A:
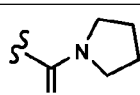
Figure 1A:
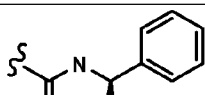
Figure 1A:
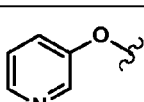
Figure 1A:
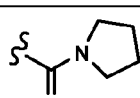
Figure 1A:
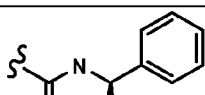
Figure 1A:
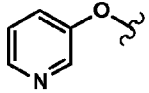
Figure 1A:
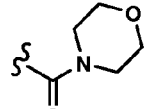
Figure 1A:
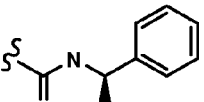
Figure 1A:
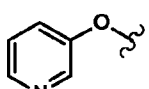
Figure 1A:
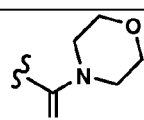
Figure 1A:
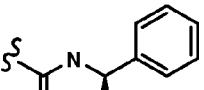
Figure 1A:
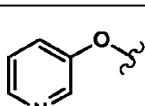
Figure 1A:
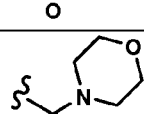
Figure 1A:
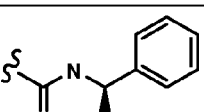
Figure 1A:
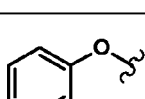
Figure 1A:
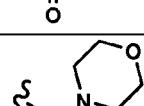
Figure 1A:
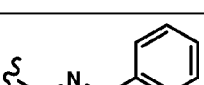
Figure 1A:
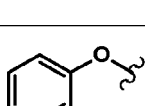
Figure 1A:
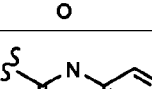
Figure 1A:
Figure 1A:
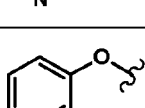
Figure 1A:
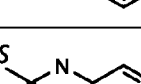
Figure 1A:
Figure 1A:
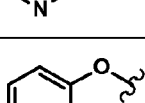
Figure 1A:
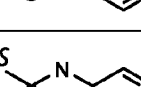
Figure 1A:
Figure 1A:
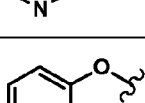
Figure 1A:
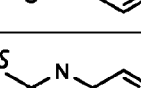
Figure 1A:
Figure 1A:
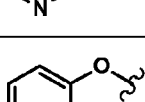
Figure 1A:
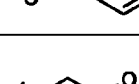
Figure 1A:
Figure 1A:
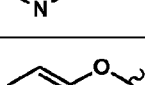
Figure 1A:
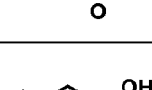
Figure 1A:
Figure 1A:
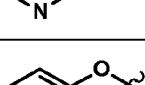
Figure 1A:
Figure 1A:
Figure 1A:
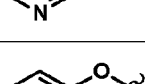
Figure 1A:
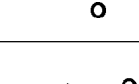
Figure 1A:
Figure 1A:
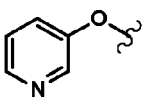
Figure 1A:
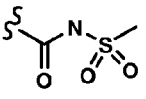
Figure 1A:
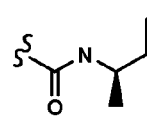
Figure 1A:
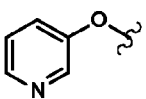
Figure 1A:
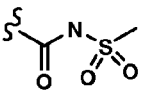
Figure 1A:
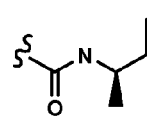
Figure 1A:
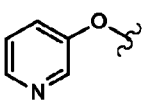
Figure 1A:
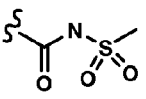
Figure 1A:
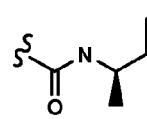
Figure 1A:
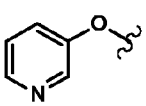
Figure 1A:
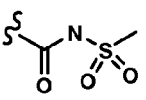
Figure 1A:
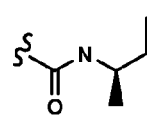
Figure 1A:
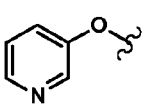
Figure 1A:
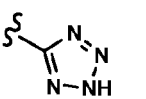
Figure 1A:
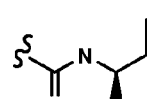
Figure 1A:
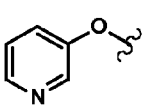
Figure 1A:
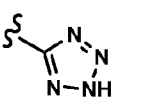
Figure 1A:
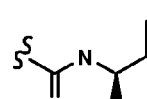
Figure 1A:
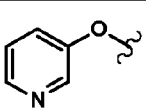
Figure 1A:
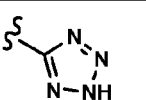
Figure 1A:
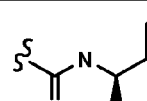
Figure 1A:
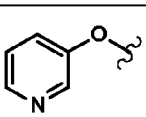
Figure 1A:
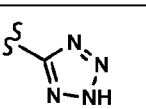
Figure 1A:
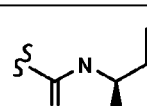
Figure 1A:
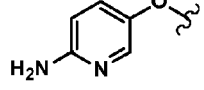
Figure 1A:
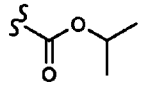
Figure 1A:
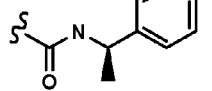
Figure 1A:
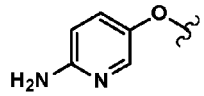
Figure 1A:
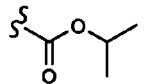
Figure 1A:
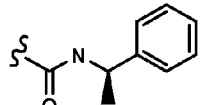
Figure 1A:
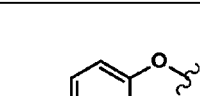
Figure 1A:
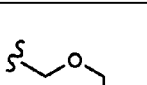
Figure 1A:
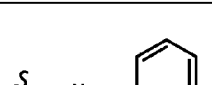
Figure 1A:
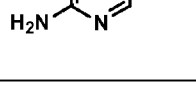
Figure 1A:
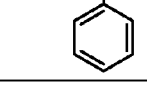
Figure 1A:
Figure 1A:
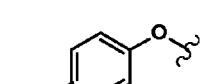
Figure 1A:
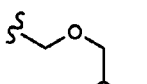
Figure 1A:
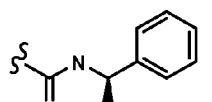
Figure 1A:
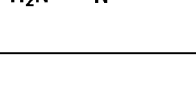
Figure 1A:
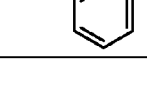
Figure 1A:
Figure 1A:
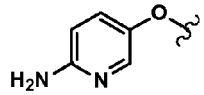
Figure 1A:
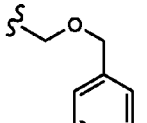
Figure 1A:
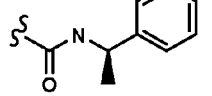
Figure 1A:
Figure 1A:
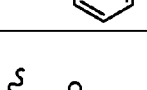
Figure 1A:
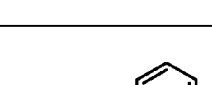
Figure 1A:
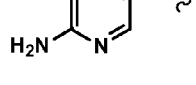
Figure 1A:
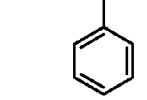
Figure 1A:
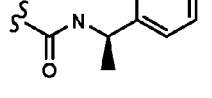
Figure 1A:
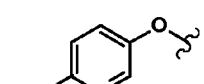
Figure 1A:
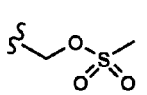
Figure 1A:
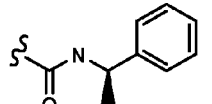
Figure 1A:
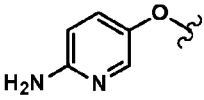
Figure 1A:
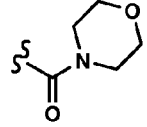
Figure 1A:
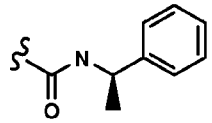
Figure 1A:
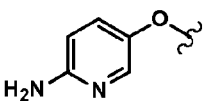
Figure 1A:
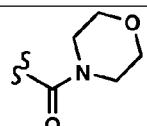
Figure 1A:
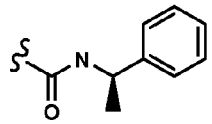
Figure 1A:
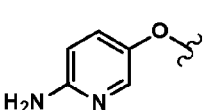
Figure 1A:
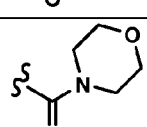
Figure 1A:
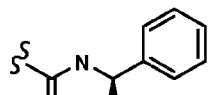
Figure 1A:
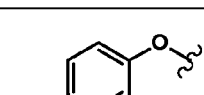
Figure 1A:
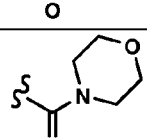
Figure 1A:
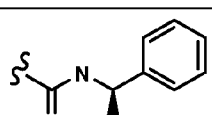
Figure 1A:
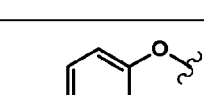
Figure 1A:
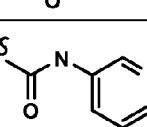
Figure 1A:
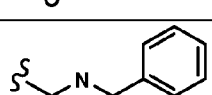
Figure 1A:
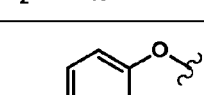
Figure 1A:
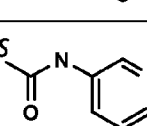
Figure 1A:
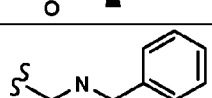
Figure 1A:
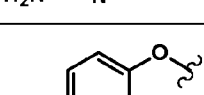
Figure 1A:
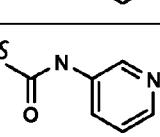
Figure 1A:
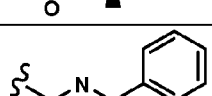
Figure 1A:
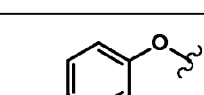
Figure 1A:
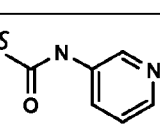
Figure 1A:
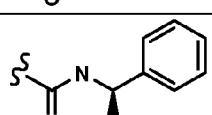
Figure 1A:
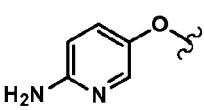
Figure 1A:
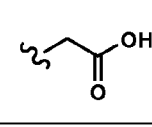
Figure 1A:
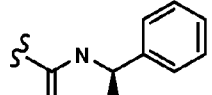
Figure 1A:
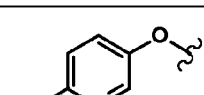
Figure 1A:
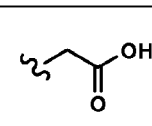
Figure 1A:
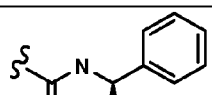
Figure 1A:
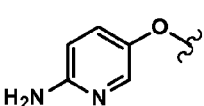
Figure 1A:
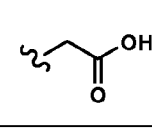
Figure 1A:
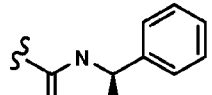
Figure 1A:
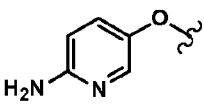
Figure 1A:
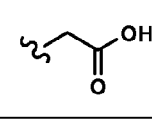
Figure 1A:
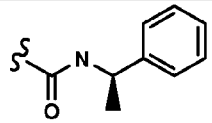
Figure 1A:
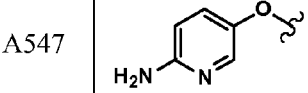
Figure 1A:
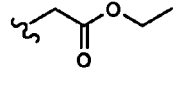
Figure 1A:
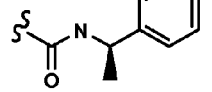
Figure 1A:
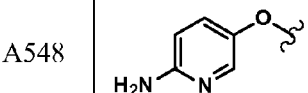
Figure 1A:
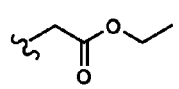
Figure 1A:
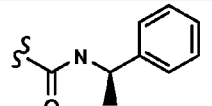
Figure 1A:
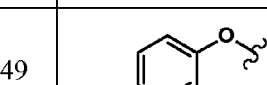
Figure 1A:
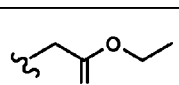
Figure 1A:
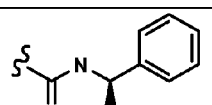
Figure 1A:
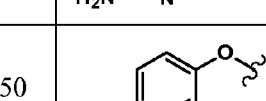
Figure 1A:
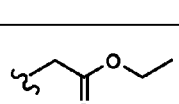
Figure 1A:
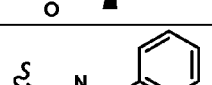
Figure 1A:
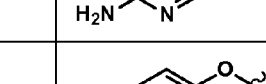
Figure 1A:
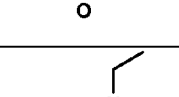
Figure 1A:
Figure 1A:
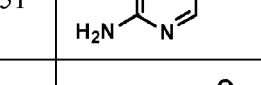
Figure 1A:
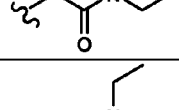
Figure 1A:
Figure 1A:
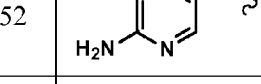
Figure 1A:
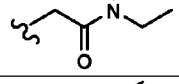
Figure 1A:
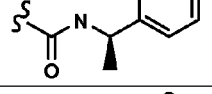
Figure 1A:
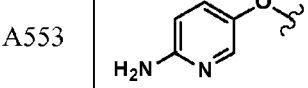
Figure 1A:
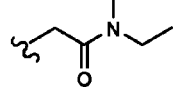
Figure 1A:
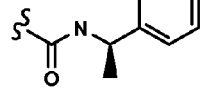
Figure 1A:
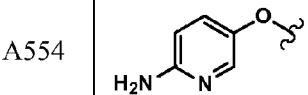
Figure 1A:
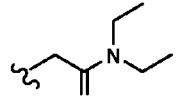
Figure 1A:
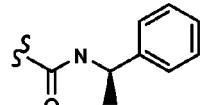
Figure 1A:
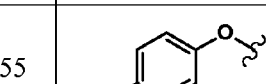
Figure 1A:
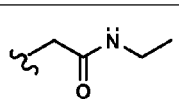
Figure 1A:
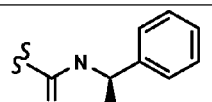
Figure 1A:
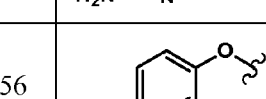
Figure 1A:
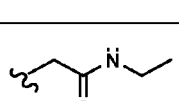
Figure 1A:
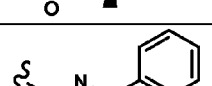
Figure 1A:
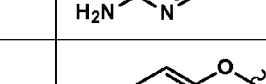
Figure 1A:
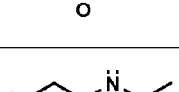
Figure 1A:
Figure 1B:
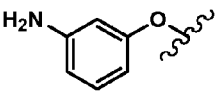
Figure 1B:
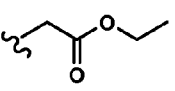
Figure 1B:
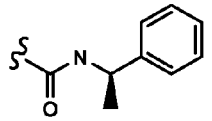
Figure 1B:
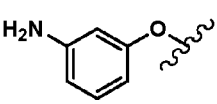
Figure 1B:
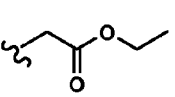
Figure 1B:
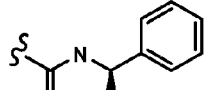
Figure 1B:
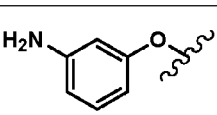
Figure 1B:
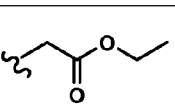
Figure 1B:
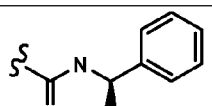
Figure 1B:
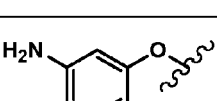
Figure 1B:
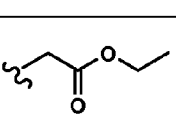
Figure 1B:
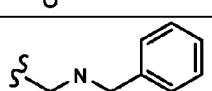
Figure 1B:
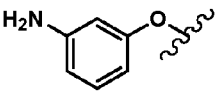
Figure 1B:
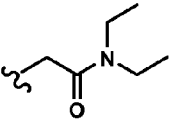
Figure 1B:
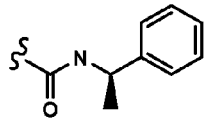
Figure 1B:
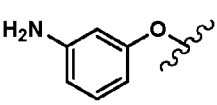
Figure 1B:
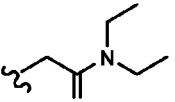
Figure 1B:
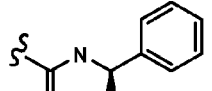
Figure 1B:
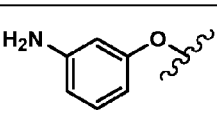
Figure 1B:
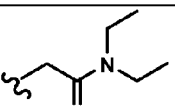
Figure 1B:
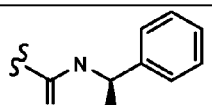
Figure 1B:
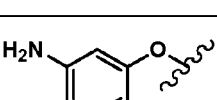
Figure 1B:
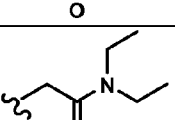
Figure 1B:
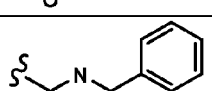
Figure 1B:
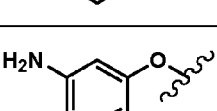
Figure 1B:
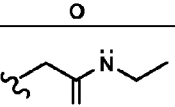
Figure 1B:
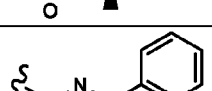
Figure 1B:
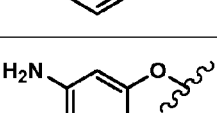
Figure 1B:
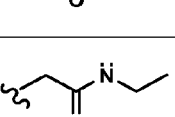
Figure 1B:
Figure 1B:
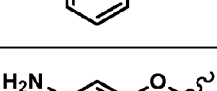
Figure 1B:
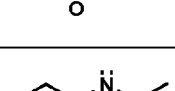
Figure 1B:
Figure 1B:
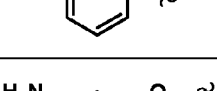
Figure 1B:
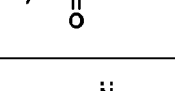
Figure 1B:
Figure 1B:
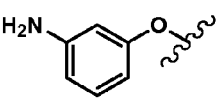
Figure 1B:
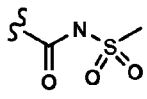
Figure 1B:
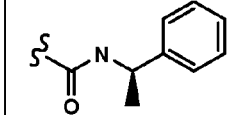
Figure 1B:
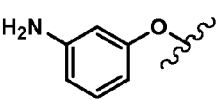
Figure 1B:
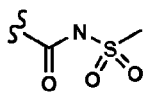
Figure 1B:
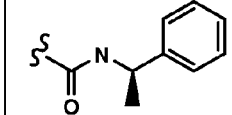
Figure 1B:
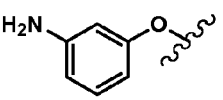
Figure 1B:
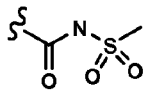
Figure 1B:
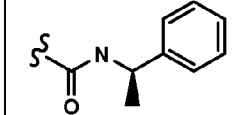
Figure 1B:
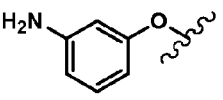
Figure 1B:
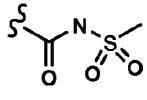
Figure 1B:
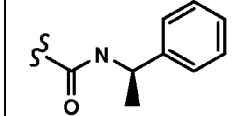
Figure 1B:
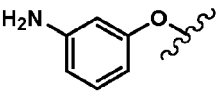
Figure 1B:
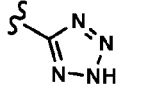
Figure 1B:
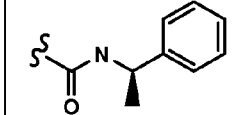
Figure 1B:
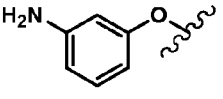
Figure 1B:
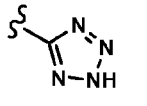
Figure 1B:
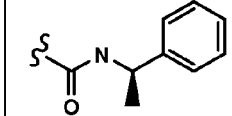
Figure 1B:
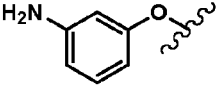
Figure 1B:
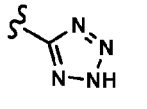
Figure 1B:
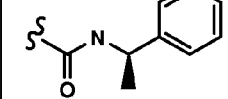
Figure 1B:
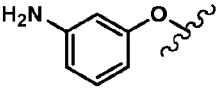
Figure 1B:
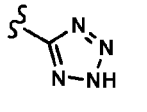
Figure 1B:
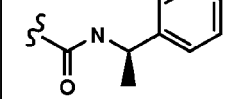
Figure 1B:
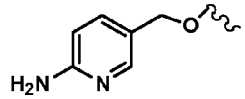
Figure 1B:
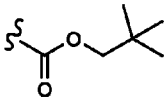
Figure 1B:
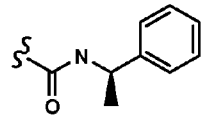
Figure 1B:
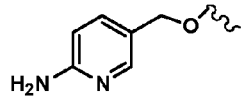
Figure 1B:
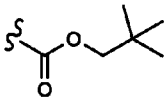
Figure 1B:
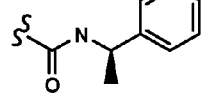
Figure 1B:
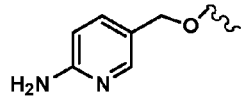
Figure 1B:
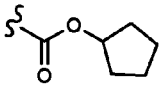
Figure 1B:
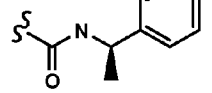
Figure 1B:
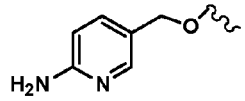
Figure 1B:
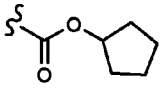
Figure 1B:
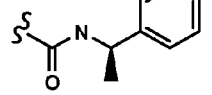
Figure 1B:
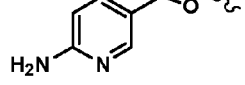
Figure 1B:
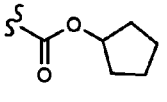
Figure 1B:
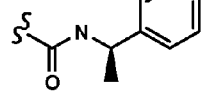
Figure 1B:
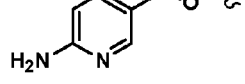
Figure 1B:
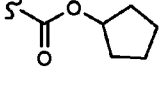
Figure 1B:
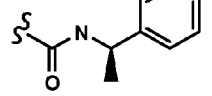
Figure 1B:
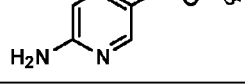
Figure 1B:
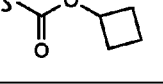
Figure 1B:
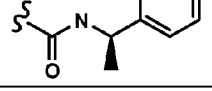
Figure 1B:
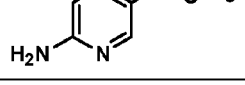
Figure 1B:
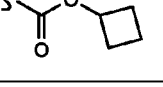
Figure 1B:
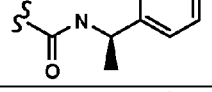
Figure 1B:
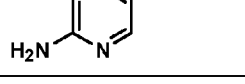
Figure 1B:
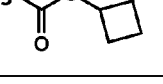
Figure 1B:
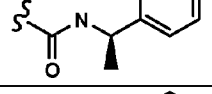
Figure 1B:
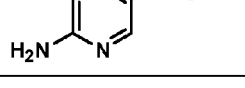
Figure 1B:
Figure 1B:
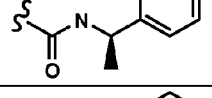
Figure 1B:
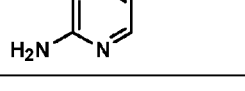
Figure 1B:
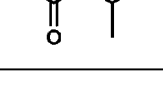
Figure 1B:
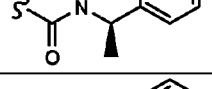
Figure 1B:
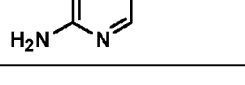
Figure 1B:
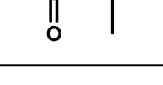
Figure 1B:
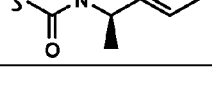
Figure 1B:
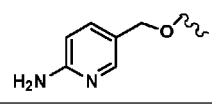
Figure 1B:
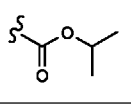
Figure 1B:
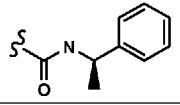
Figure 1B:
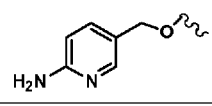
Figure 1B:
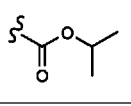
Figure 1B:
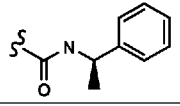
Figure 1B:
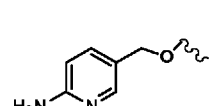
Figure 1B:
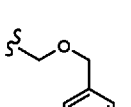
Figure 1B:
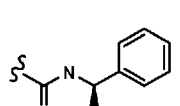
Figure 1B:
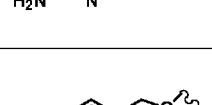
Figure 1B:
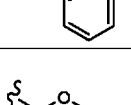
Figure 1B:
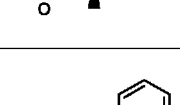
Figure 1B:
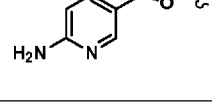
Figure 1B:
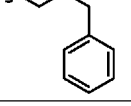
Figure 1B:
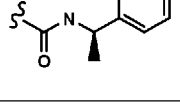
Figure 1B:
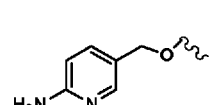
Figure 1B:
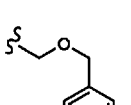
Figure 1B:
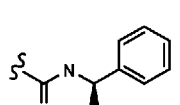
Figure 1B:
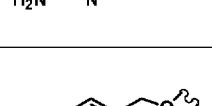
Figure 1B:
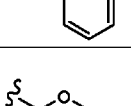
Figure 1B:
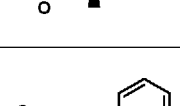
Figure 1B:
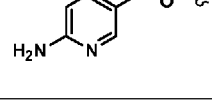
Figure 1B:
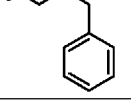
Figure 1B:
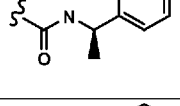
Figure 1B:
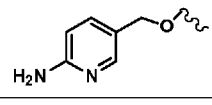
Figure 1B:
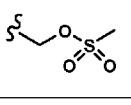
Figure 1B:
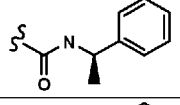
Figure 1B:
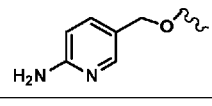
Figure 1B:
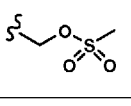
Figure 1B:
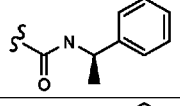
Figure 1B:
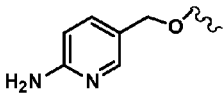
Figure 1B:
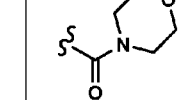
Figure 1B:
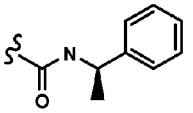
Figure 1B:
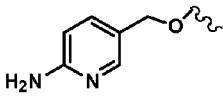
Figure 1B:
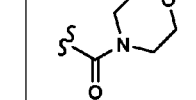
Figure 1B:
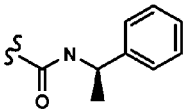
Figure 1B:
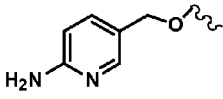
Figure 1B:
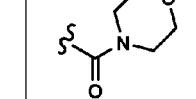
Figure 1B:
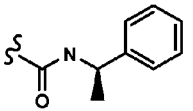
Figure 1B:
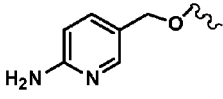
Figure 1B:
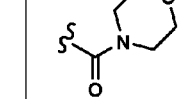
Figure 1B:
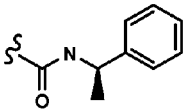
Figure 1B:
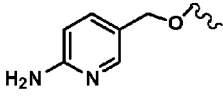
Figure 1B:
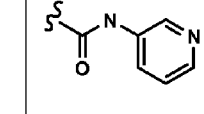
Figure 1B:
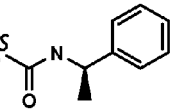
Figure 1B:
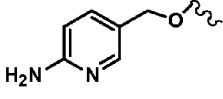
Figure 1B:
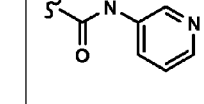
Figure 1B:
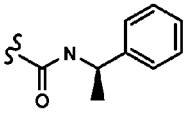
Figure 1B:
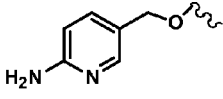
Figure 1B:
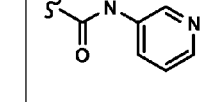
Figure 1B:
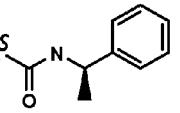
Figure 1B:
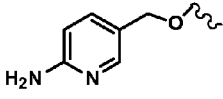
Figure 1B:
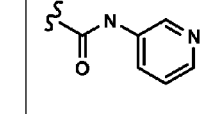
Figure 1B:
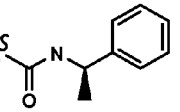
Figure 1B:
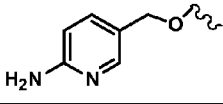
Figure 1B:
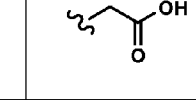
Figure 1B:
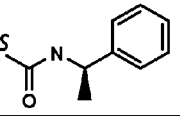
Figure 1B:
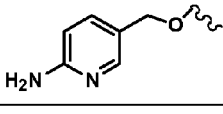
Figure 1B:
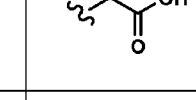
Figure 1B:
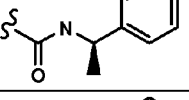
Figure 1B:
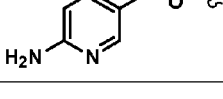
Figure 1B:
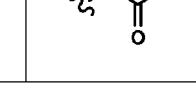
Figure 1B:
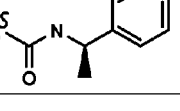
Figure 1B:
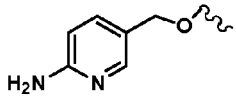
Figure 1B:
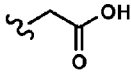
Figure 1B:
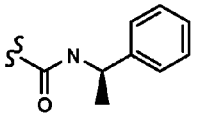
Figure 1B:
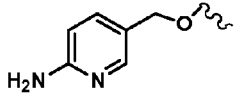
Figure 1B:
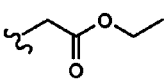
Figure 1B:
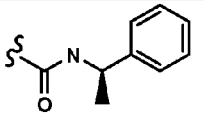
Figure 1B:
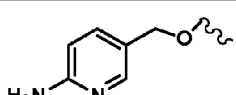
Figure 1B:
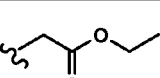
Figure 1B:
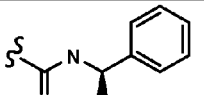
Figure 1B:
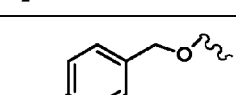
Figure 1B:
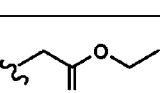
Figure 1B:
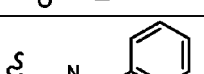
Figure 1B:
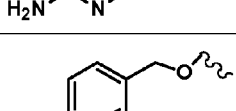
Figure 1B:
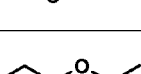
Figure 1B:
Figure 1B:
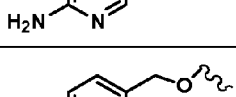
Figure 1B:
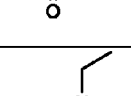
Figure 1B:
Figure 1B:
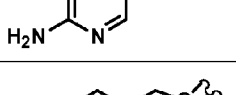
Figure 1B:
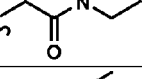
Figure 1B:
Figure 1B:
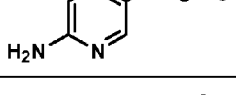
Figure 1B:
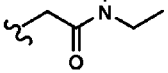
Figure 1B:
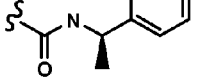
Figure 1B:
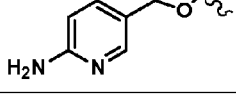
Figure 1B:
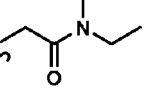
Figure 1B:
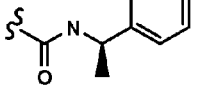
Figure 1B:
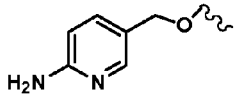
Figure 1B:
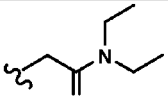
Figure 1B:
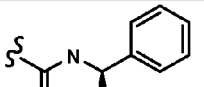
Figure 1B:
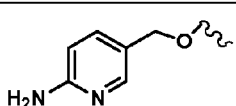
Figure 1B:
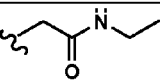
Figure 1B:
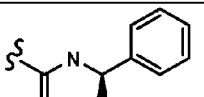
Figure 1B:
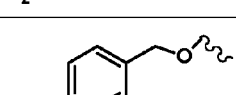
Figure 1B:
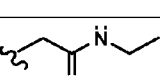
Figure 1B:
Figure 1B:
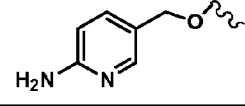
Figure 1B:
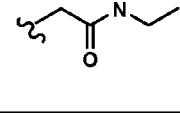
Figure 1B:
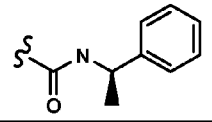
Figure 1B:
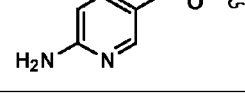
Figure 1B:
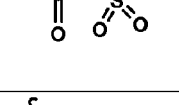
Figure 1B:
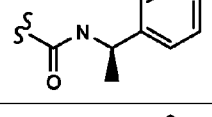
Figure 1B:
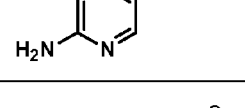
Figure 1B:
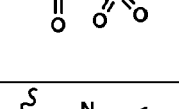
Figure 1B:
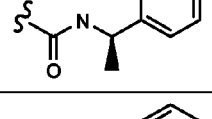
Figure 1B:
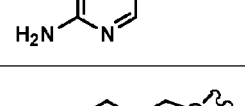
Figure 1B:
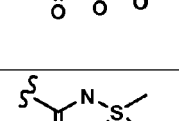
Figure 1B:
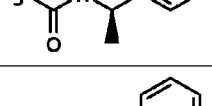
Figure 1B:
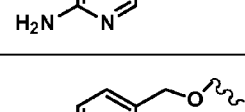
Figure 1B:
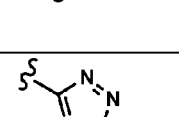
Figure 1B:
Figure 1B:
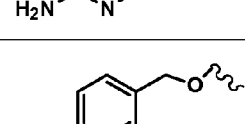
Figure 1B:
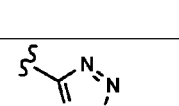
Figure 1B:
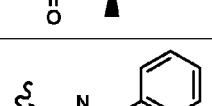
Figure 1B:
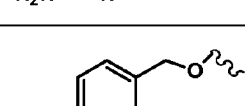
Figure 1B:
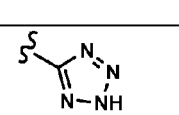
Figure 1B:
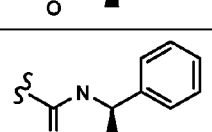
Figure 1B:
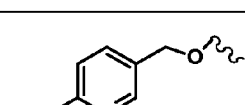
Figure 1B:
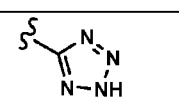
Figure 1B:
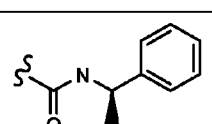
Figure 1B:
Figure 1B:
Figure 1B:
Figure 1B:
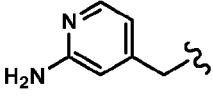
Figure 1B:
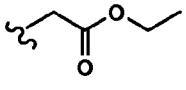
Figure 1B:
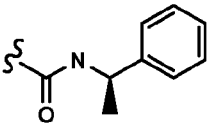
Figure 1B:
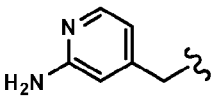
Figure 1B:
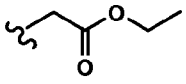
Figure 1B:
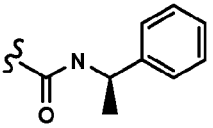
Figure 1B:
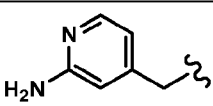
Figure 1B:
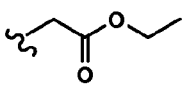
Figure 1B:
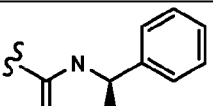
Figure 1B:
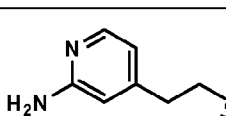
Figure 1B:
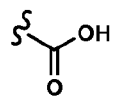
Figure 1B:
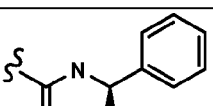
Figure 1B:
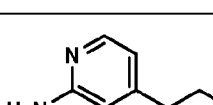
Figure 1B:
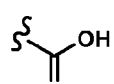
Figure 1B:
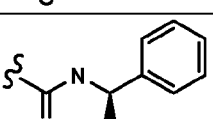
Figure 1B:
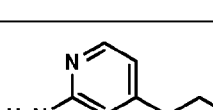
Figure 1B:
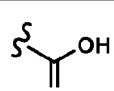
Figure 1B:
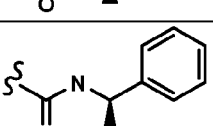
Figure 1B:
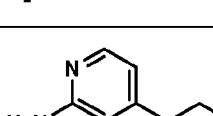
Figure 1B:
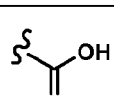
Figure 1B:
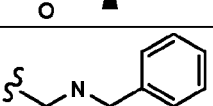
Figure 1B:
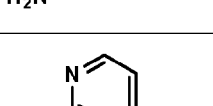
Figure 1B:
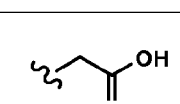
Figure 1B:
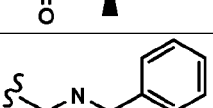
Figure 1B:
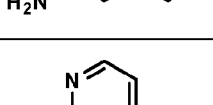
Figure 1B:
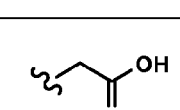
Figure 1B:
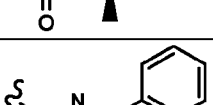
Figure 1B:
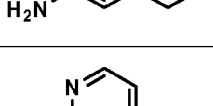
Figure 1B:
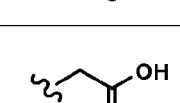
Figure 1B:
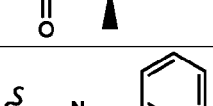
Figure 1B:
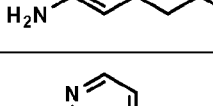
Figure 1B:
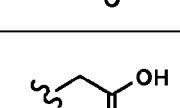
Figure 1B:
Figure 1B:
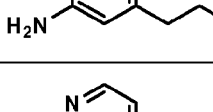
Figure 1B:
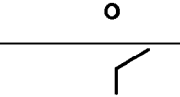
Figure 1B:
Figure 1B:
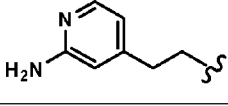
Figure 1B:
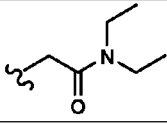
Figure 1B:
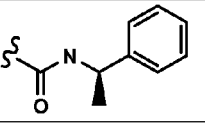
Figure 1B:
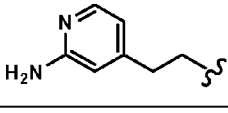
Figure 1B:
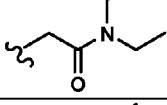
Figure 1B:
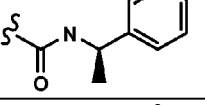
Figure 1B:
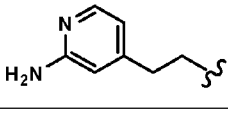
Figure 1B:
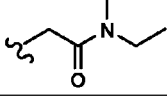
Figure 1B:
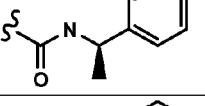
Figure 1B:
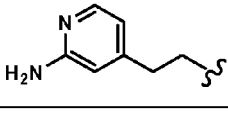
Figure 1B:
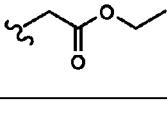
Figure 1B:
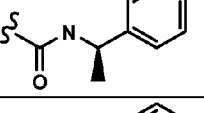
Figure 1B:
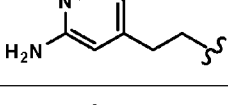
Figure 1B:
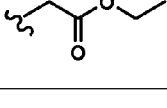
Figure 1B:
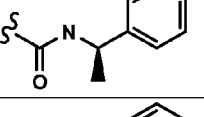
Figure 1B:
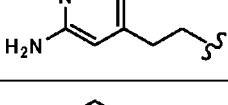
Figure 1B:
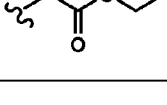
Figure 1B:
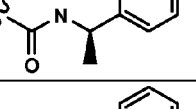
Figure 1B:
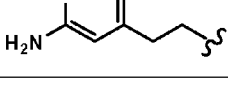
Figure 1B:
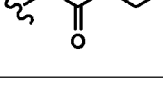
Figure 1B:
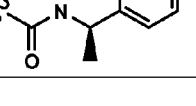
Figure 1B:
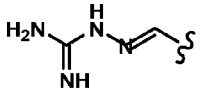
Figure 1B:
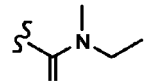
Figure 1B:
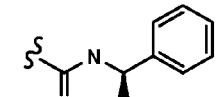
Figure 1B:
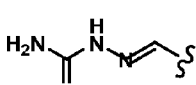
Figure 1B:
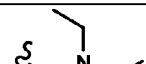
Figure 1B:
Figure 1B:
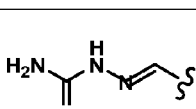
Figure 1B:
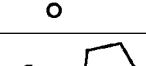
Figure 1B:
Figure 1B:
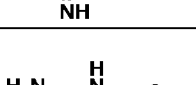
Figure 1B:
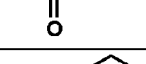
Figure 1B:
Figure 1B:
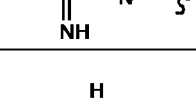
Figure 1B:
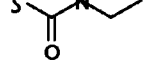
Figure 1B:
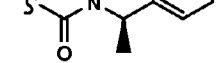
Figure 1B:
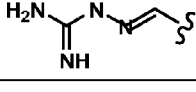
Figure 1B:
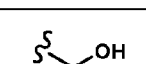
Figure 1B:
Figure 1B:
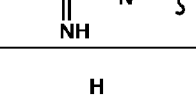
Figure 1B:
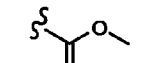
Figure 1B:
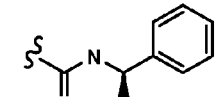
Figure 1B:
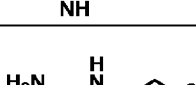
Figure 1B:
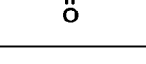
Figure 1B:
Figure 1B:
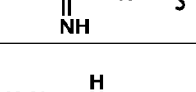
Figure 1B:
Figure 1B:
Figure 1B:
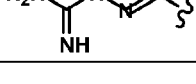
Figure 1B:
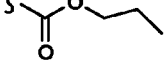
Figure 1B:
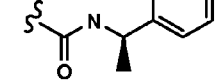
Figure 1B:
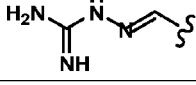
Figure 1B:
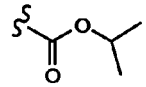
Figure 1B:
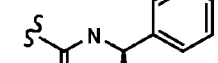
Figure 1B:
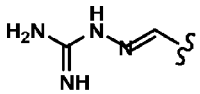
Figure 1B:
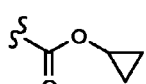
Figure 1B:
Figure 1B:
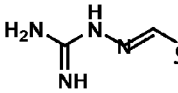
Figure 1B:
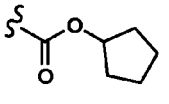
Figure 1B:
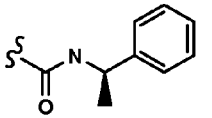
Figure 1B:
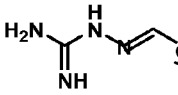
Figure 1B:
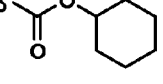
Figure 1B:
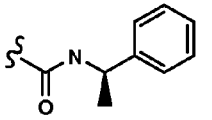
Figure 1B:
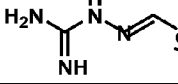
Figure 1B:
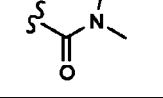
Figure 1B:
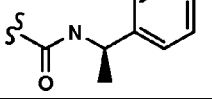
Figure 1B:
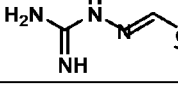
Figure 1B:
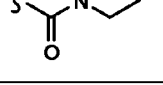
Figure 1B:
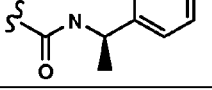
Figure 1B:
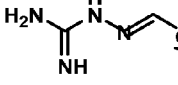
Figure 1B:
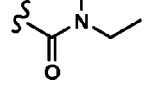
Figure 1B:
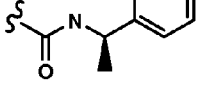
Figure 1B:
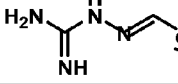
Figure 1B:
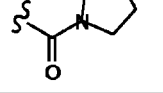
Figure 1B:
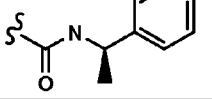
Figure 1B:
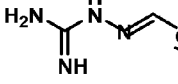
Figure 1B:
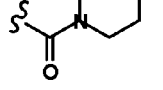
Figure 1B:
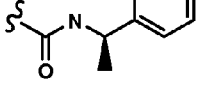
Figure 1B:
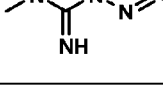
Figure 1B:
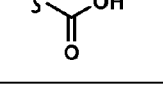
Figure 1B:
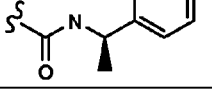
Figure 1B:
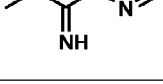
Figure 1B:
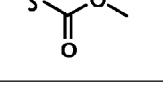
Figure 1B:
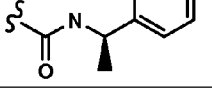
Figure 1B:
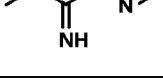
Figure 1B:
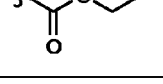
Figure 1B:
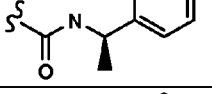
Figure 1B:
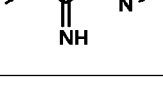
Figure 1B:
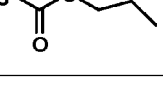
Figure 1B:
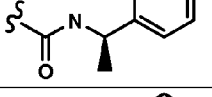
Figure 1B:
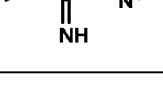
Figure 1B:
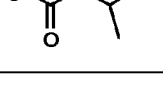
Figure 1B:
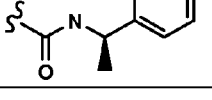
Figure 1B:
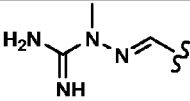
Figure 1B:
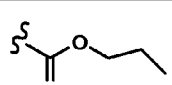
Figure 1B:
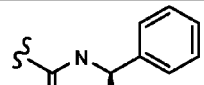
Figure 1B:
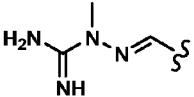
Figure 1B:
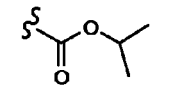
Figure 1B:
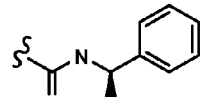
Figure 1B:
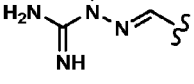
Figure 1B:
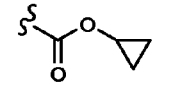
Figure 1B:
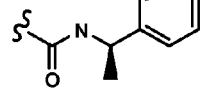
Figure 1B:
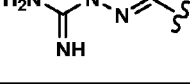
Figure 1B:
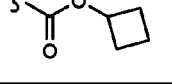
Figure 1B:
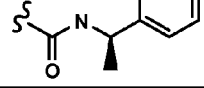
Figure 1B:
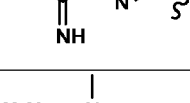
Figure 1B:
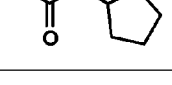
Figure 1B:
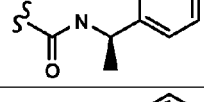
Figure 1B:
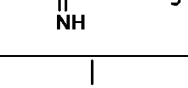
Figure 1B:
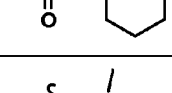
Figure 1B:
Figure 1B:
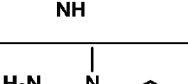
Figure 1B:
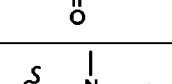
Figure 1B:
Figure 1B:
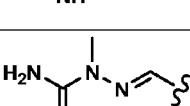
Figure 1B:
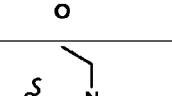
Figure 1B:
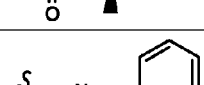
Figure 1B:
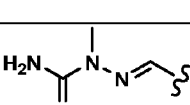
Figure 1B:
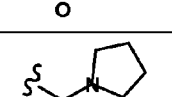
Figure 1B:
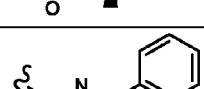
Figure 1B:
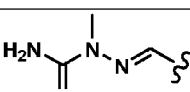
Figure 1B:
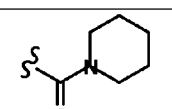
Figure 1B:
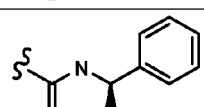
Figure 1B:
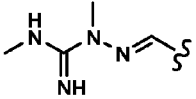
Figure 1B:
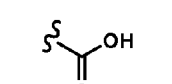
Figure 1B:
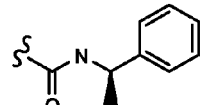
Figure 1B:
Figure 1B:
Figure 1B:
Figure 1B:
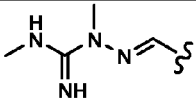
Figure 1B:
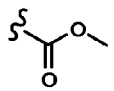
Figure 1B:
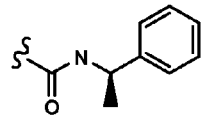
Figure 1B:
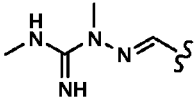
Figure 1B:
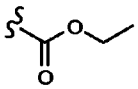
Figure 1B:
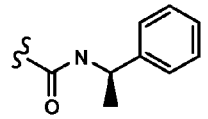
Figure 1B:
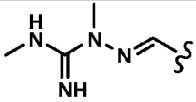
Figure 1B:
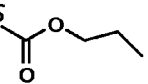
Figure 1B:
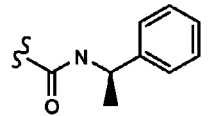
Figure 1B:
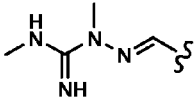
Figure 1B:
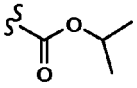
Figure 1B:
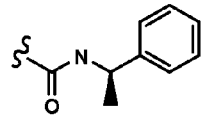
Figure 1B:
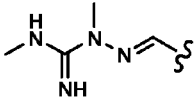
Figure 1B:
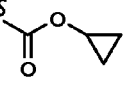
Figure 1B:
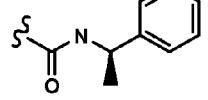
Figure 1B:
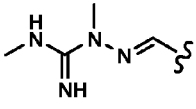
Figure 1B:
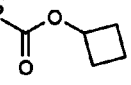
Figure 1B:
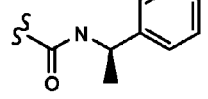
Figure 1B:
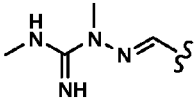
Figure 1B:
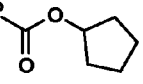
Figure 1B:
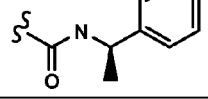
Figure 1B:
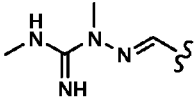
Figure 1B:
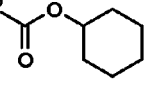
Figure 1B:
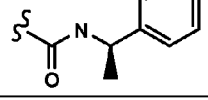
Figure 1B:
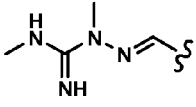
Figure 1B:
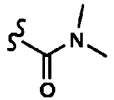
Figure 1B:
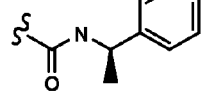
Figure 1B:
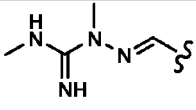
Figure 1B:
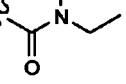
Figure 1B:
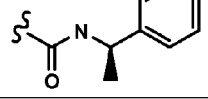
Figure 1B:
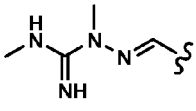
Figure 1B:
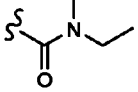
Figure 1B:
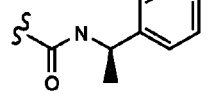
Figure 1B:
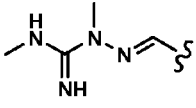
Figure 1B:
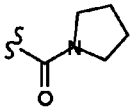
Figure 1B:
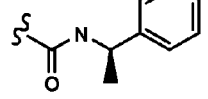
Figure 1C:
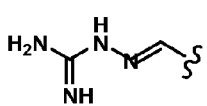
Figure 1C:
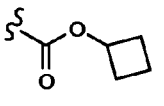
Figure 1C:
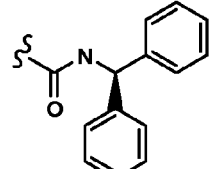
Figure 1C:
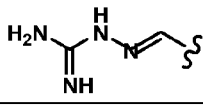
Figure 1C:
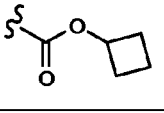
Figure 1C:
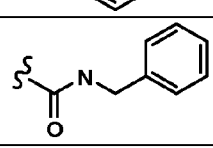
Figure 1C:
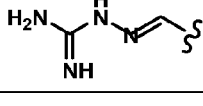
Figure 1C:
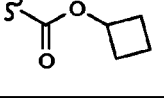
Figure 1C:
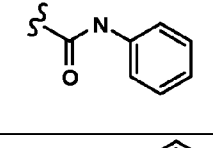
Figure 1C:
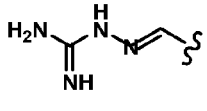
Figure 1C:
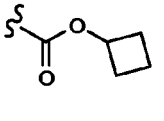
Figure 1C:
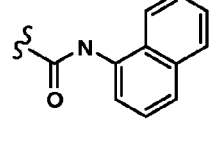
Figure 1C:
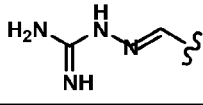
Figure 1C:
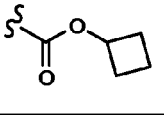
Figure 1C:
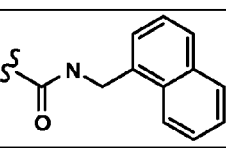
Figure 1C:
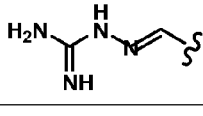
Figure 1C:
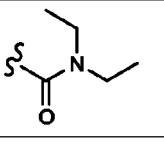
Figure 1C:
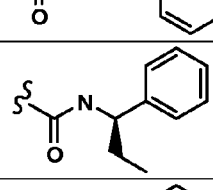
Figure 1C:
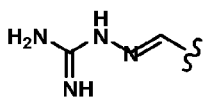
Figure 1C:
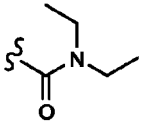
Figure 1C:
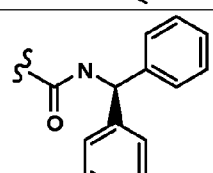
Figure 1C:
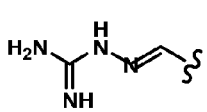
Figure 1C:
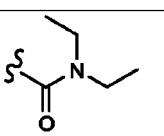
Figure 1C:
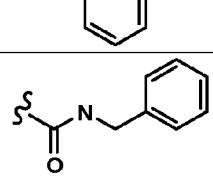
Figure 1C:
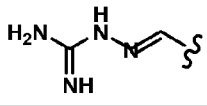
Figure 1C:
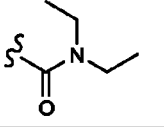
Figure 1C:
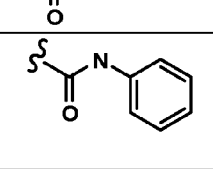
Figure 1C:
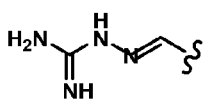
Figure 1C:
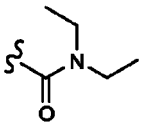
Figure 1C:
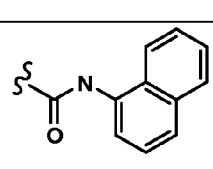
Figure 1C:
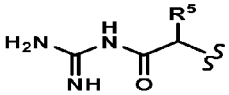
Figure 1C:
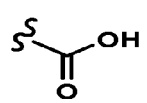
Figure 1C:
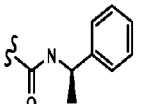
Figure 1C:
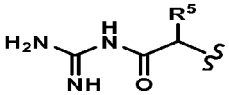
Figure 1C:
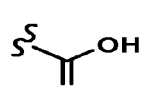
Figure 1C:
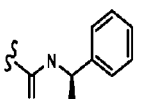
Figure 1C:
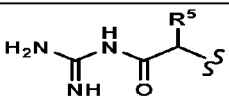
Figure 1C:
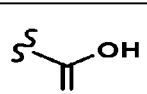
Figure 1C:
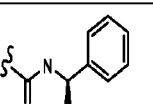
Figure 1C:
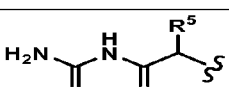
Figure 1C:
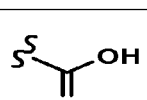
Figure 1C:
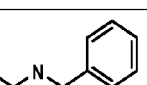
Figure 1C:
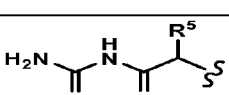
Figure 1C:
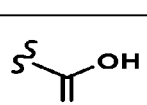
Figure 1C:
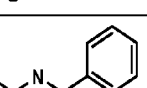
Figure 1C:
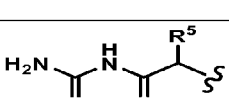
Figure 1C:
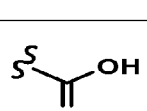
Figure 1C:
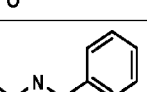
Figure 1C:
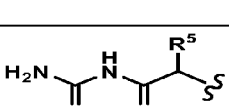
Figure 1C:
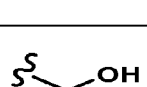
Figure 1C:
Figure 1C:
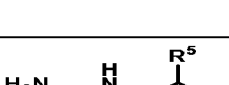
Figure 1C:
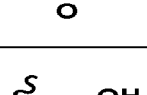
Figure 1C:
Figure 1C:
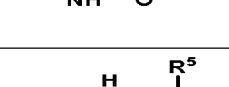
Figure 1C:
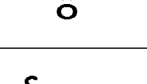
Figure 1C:
Figure 1C:
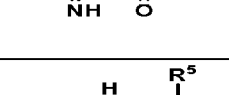
Figure 1C:
Figure 1C:
Figure 1C:
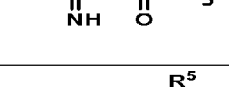
Figure 1C:
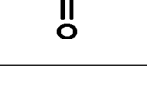
Figure 1C:
Figure 1C:
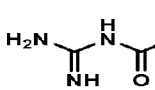
Figure 1C:
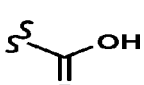
Figure 1C:
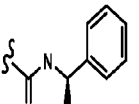
Figure 1C:
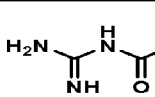
Figure 1C:
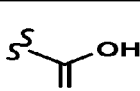
Figure 1C:
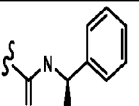
Figure 1C:
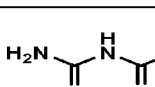
Figure 1C:
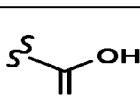
Figure 1C:
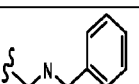
Figure 1C:
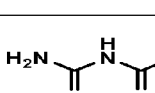
Figure 1C:
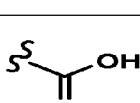
Figure 1C:
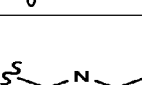
Figure 1C:
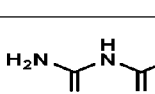
Figure 1C:
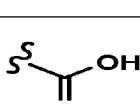
Figure 1C:
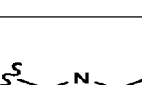
Figure 1C:
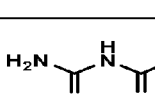
Figure 1C:
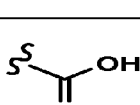
Figure 1C:
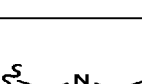
Figure 1C:
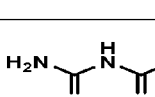
Figure 1C:
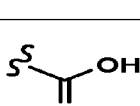
Figure 1C:
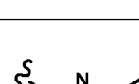
Figure 1C:
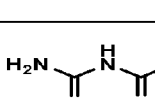
Figure 1C:
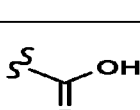
Figure 1C:
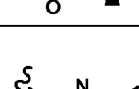
Figure 1C:
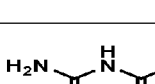
Figure 1C:
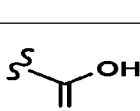
Figure 1C:
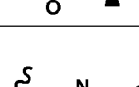
Figure 1C:
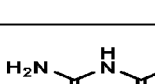
Figure 1C:
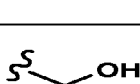
Figure 1C:
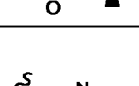
Figure 1C:
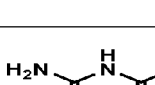
Figure 1C:
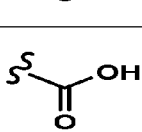
Figure 1C:
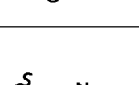
Figure 1C:
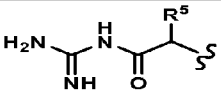
Figure 1C:
Figure 1C:
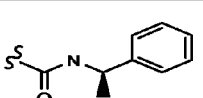
Figure 1C:
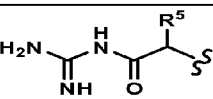
Figure 1C:
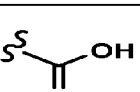
Figure 1C:
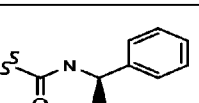
Figure 1C:
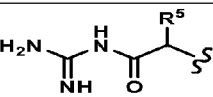
Figure 1C:
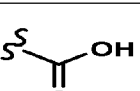
Figure 1C:
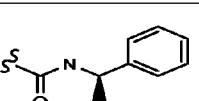
Figure 1C:
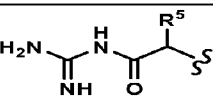
Figure 1C:
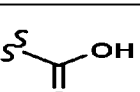
Figure 1C:
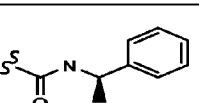
Figure 1C:
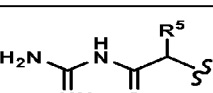
Figure 1C:
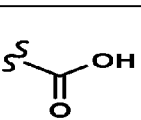
Figure 1C:
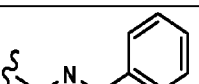
Figure 1C:
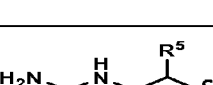
Figure 1C:
Figure 1C:
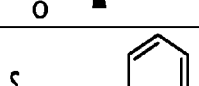
Figure 1C:
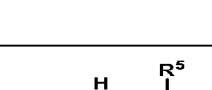
Figure 1C:
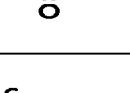
Figure 1C:
Figure 1C:
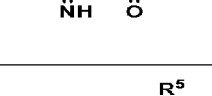
Figure 1C:
Figure 1C:
Figure 1C:
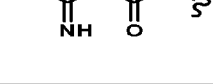
Figure 1C:
Figure 1C:
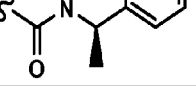
Figure 1C:
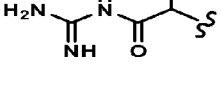
Figure 1C:
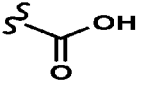
Figure 1C:
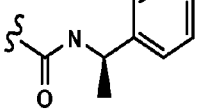
Figure 1C:
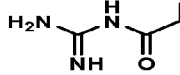
Figure 1C:
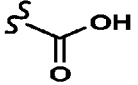
Figure 1C:
Figure 1C:
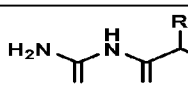
Figure 1C:
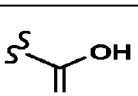
Figure 1C:
Figure 1C:
Figure 1C:
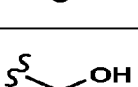
Figure 1C:
Figure 1C:
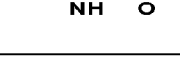
Figure 1C:
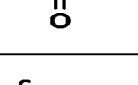
Figure 1C:
Figure 1C:
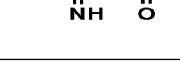
Figure 1C:
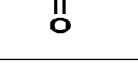
Figure 1C:
Figure 1C:
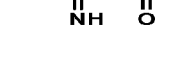
Figure 1C:
Figure 1C:
Figure 1C:
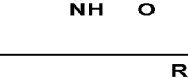
Figure 1C:
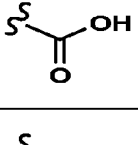
Figure 1C:
Figure 1C:
Figure 1C:
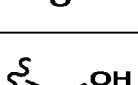
Figure 1C:
Figure 1C:
Figure 1C:
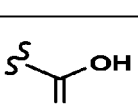
Figure 1C:
Figure 1C:
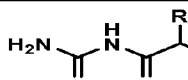
Figure 1C:
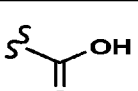
Figure 1C:
Figure 1C:
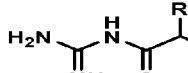
Figure 1C:
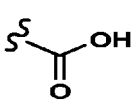
Figure 1C:
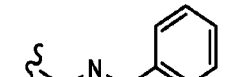
Figure 1D:
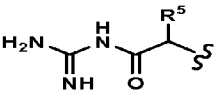
Figure 1D:
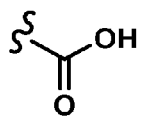
Figure 1D:
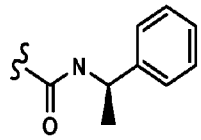
Figure 1D:
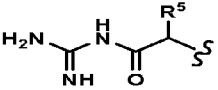
Figure 1D:
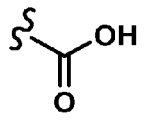
Figure 1D:
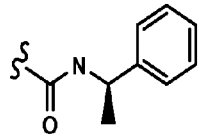
Figure 1D:
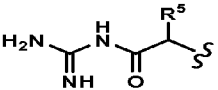
Figure 1D:
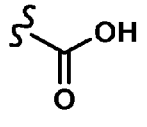
Figure 1D:
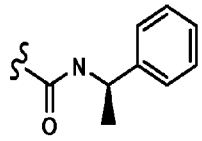
Figure 1D:
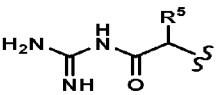
Figure 1D:
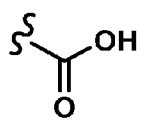
Figure 1D:
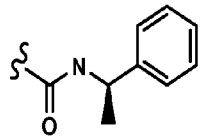
Figure 1D:
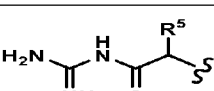
Figure 1D:
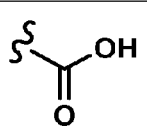
Figure 1D:
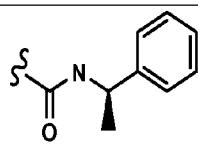
Figure 1D:
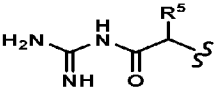
Figure 1D:
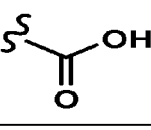
Figure 1D:
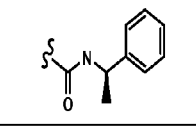
Figure 1D:
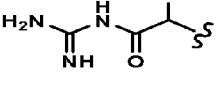
Figure 1D:
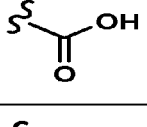
Figure 1D:
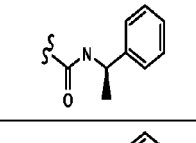
Figure 1D:
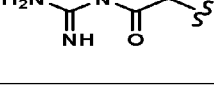
Figure 1D:
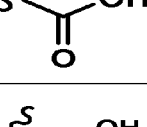
Figure 1D:
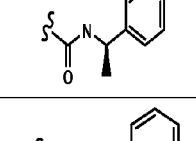
Figure 1D:
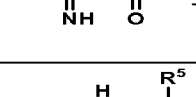
Figure 1D:
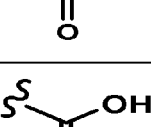
Figure 1D:
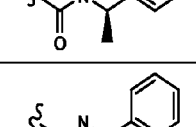
Figure 1D:
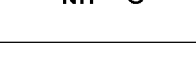
Figure 1D:
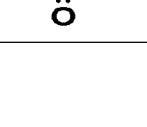
Figure 1D:
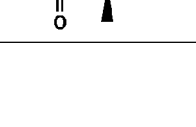
Figure 1D:
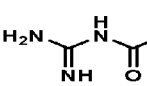
Figure 1D:
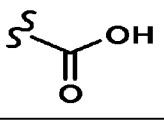
Figure 1D:
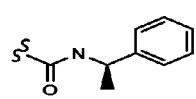
Figure 1D:
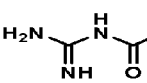
Figure 1D:
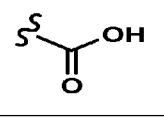
Figure 1D:
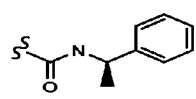
Figure 1D:
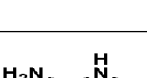
Figure 1D:
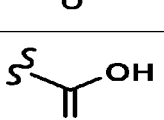
Figure 1D:
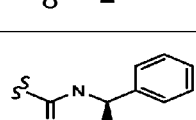
Figure 1D:
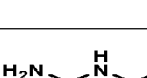
Figure 1D:
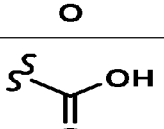
Figure 1D:
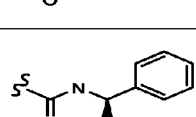
Figure 1D:
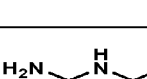
Figure 1D:
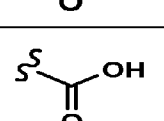
Figure 1D:
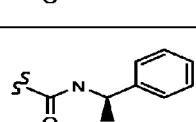
Figure 1D:
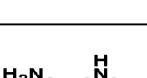
Figure 1D:
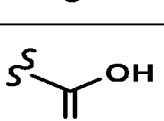
Figure 1D:
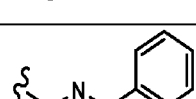
Figure 1D:
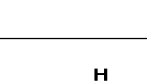
Figure 1D:
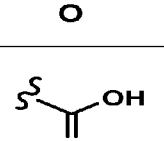
Figure 1D:
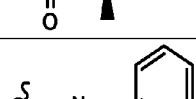
Figure 1D:
Figure 1D:
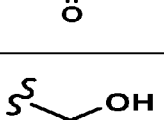
Figure 1D:
Figure 1D:
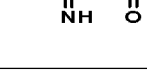
Figure 1D:
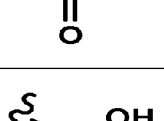
Figure 1D:
Figure 1D:
Figure 1D:
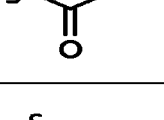
Figure 1D:
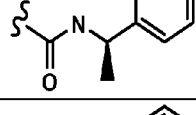
Figure 1D:
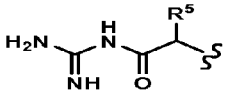
Figure 1D:
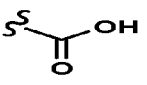
Figure 1D:
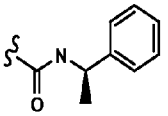
Figure 1D:
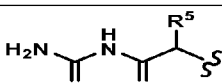
Figure 1D:
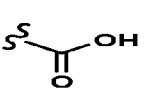
Figure 1D:
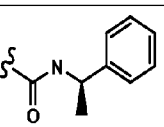
Figure 1D:
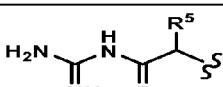
Figure 1D:
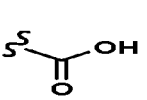
Figure 1D:
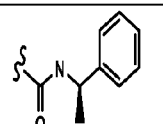
Figure 1D:
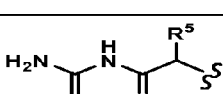
Figure 1D:
Figure 1D:
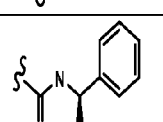
Figure 1D:
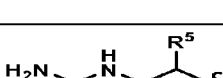
Figure 1D:
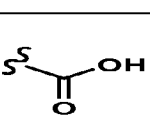
Figure 1D:
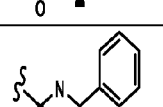
Figure 1D:
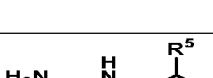
Figure 1D:
Figure 1D:
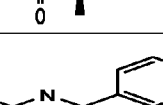
Figure 1D:
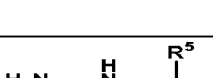
Figure 1D:
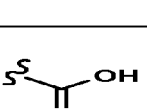
Figure 1D:
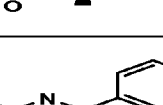
Figure 1D:
Figure 1D:
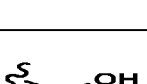
Figure 1D:
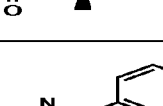
Figure 1D:
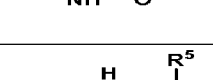
Figure 1D:
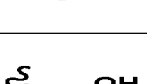
Figure 1D:
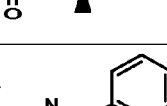
Figure 1D:
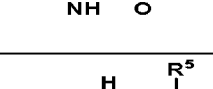
Figure 1D:
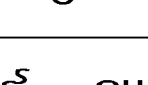
Figure 1D:
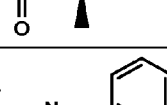
Figure 1D:
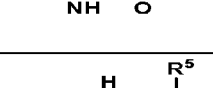
Figure 1D:
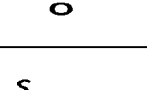
Figure 1D:
Figure 1D:
Figure 1D:
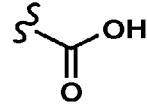
Figure 1D:
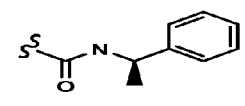
Figure 1D:
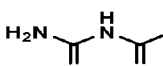
Figure 1D:
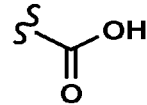
Figure 1D:
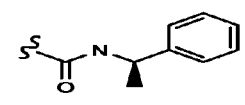
Figure 1D:
Figure 1D:
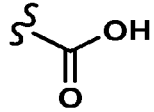
Figure 1D:
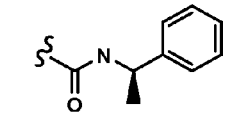
Figure 1D:
Figure 1D:
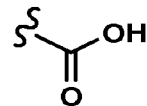
Figure 1D:
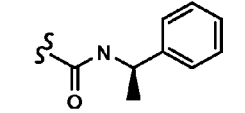
Figure 1D:
Figure 1D:
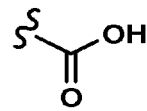
Figure 1D:
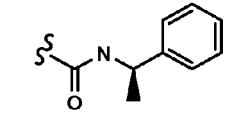
Figure 1D:
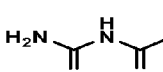
Figure 1D:
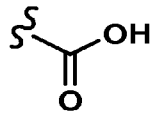
Figure 1D:
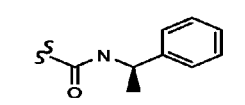
Figure 1D:
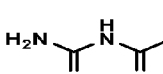
Figure 1D:
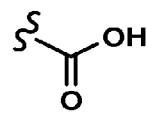
Figure 1D:
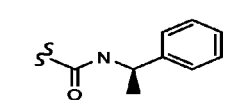
Figure 1D:
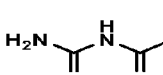
Figure 1D:
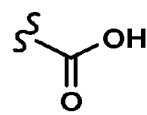
Figure 1D:
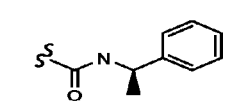
Figure 1D:
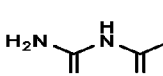
Figure 1D:
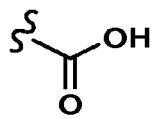
Figure 1D:
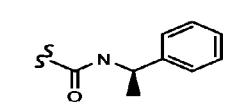
Figure 1D:
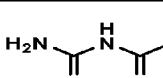
Figure 1D:
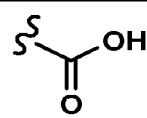
Figure 1D:
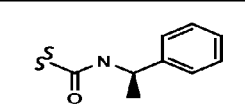
Figure 1D:
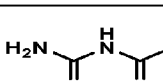
Figure 1D:
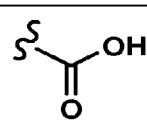
Figure 1D:
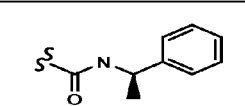
Figure 1D:
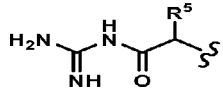
Figure 1D:
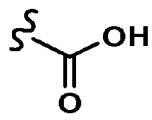
Figure 1D:
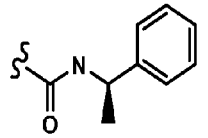
Figure 1D:
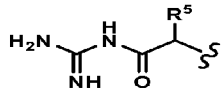
Figure 1D:
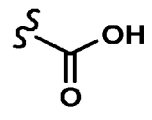
Figure 1D:
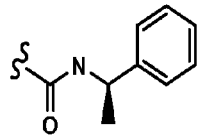
Figure 1D:
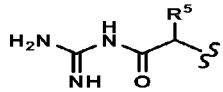
Figure 1D:
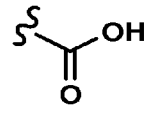
Figure 1D:
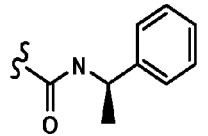
Figure 1D:
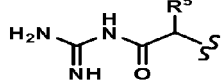
Figure 1D:
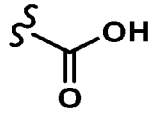
Figure 1D:
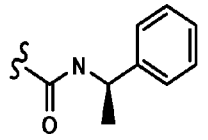
Figure 1D:
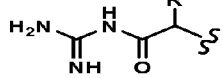
Figure 1D:
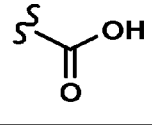
Figure 1D:
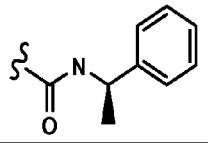
Figure 1D:
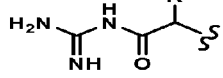
Figure 1D:
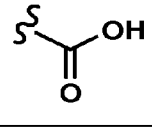
Figure 1D:
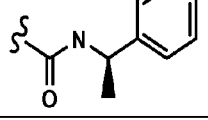
Figure 1D:
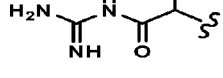
Figure 1D:
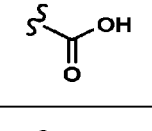
Figure 1D:
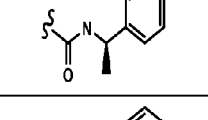
Figure 1D:
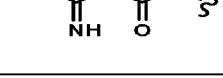
Figure 1D:
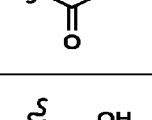
Figure 1D:
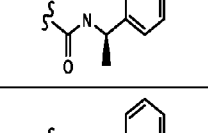
Figure 1D:
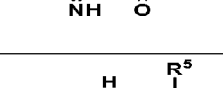
Figure 1D:
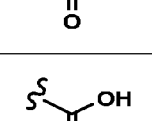
Figure 1D:
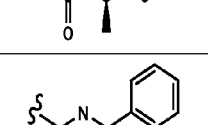
Figure 1D:
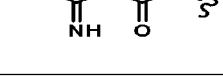
Figure 1D:
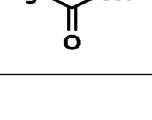
Figure 1D:
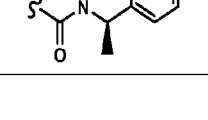
Figure 1D:
Figure 1D:
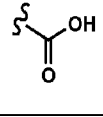
Figure 1D:
Figure 1D:
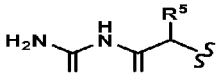
Figure 1D:
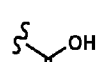
Figure 1D:
Figure 1D:
Figure 1D:
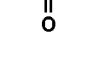
Figure 1D:
Figure 1D:
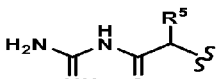
Figure 1D:
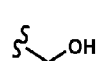
Figure 1D:
Figure 1D:
Figure 1D:
Figure 1D:
Figure 1D:
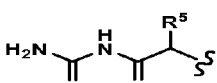
Figure 1D:
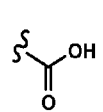
Figure 1D:
Figure 1R:
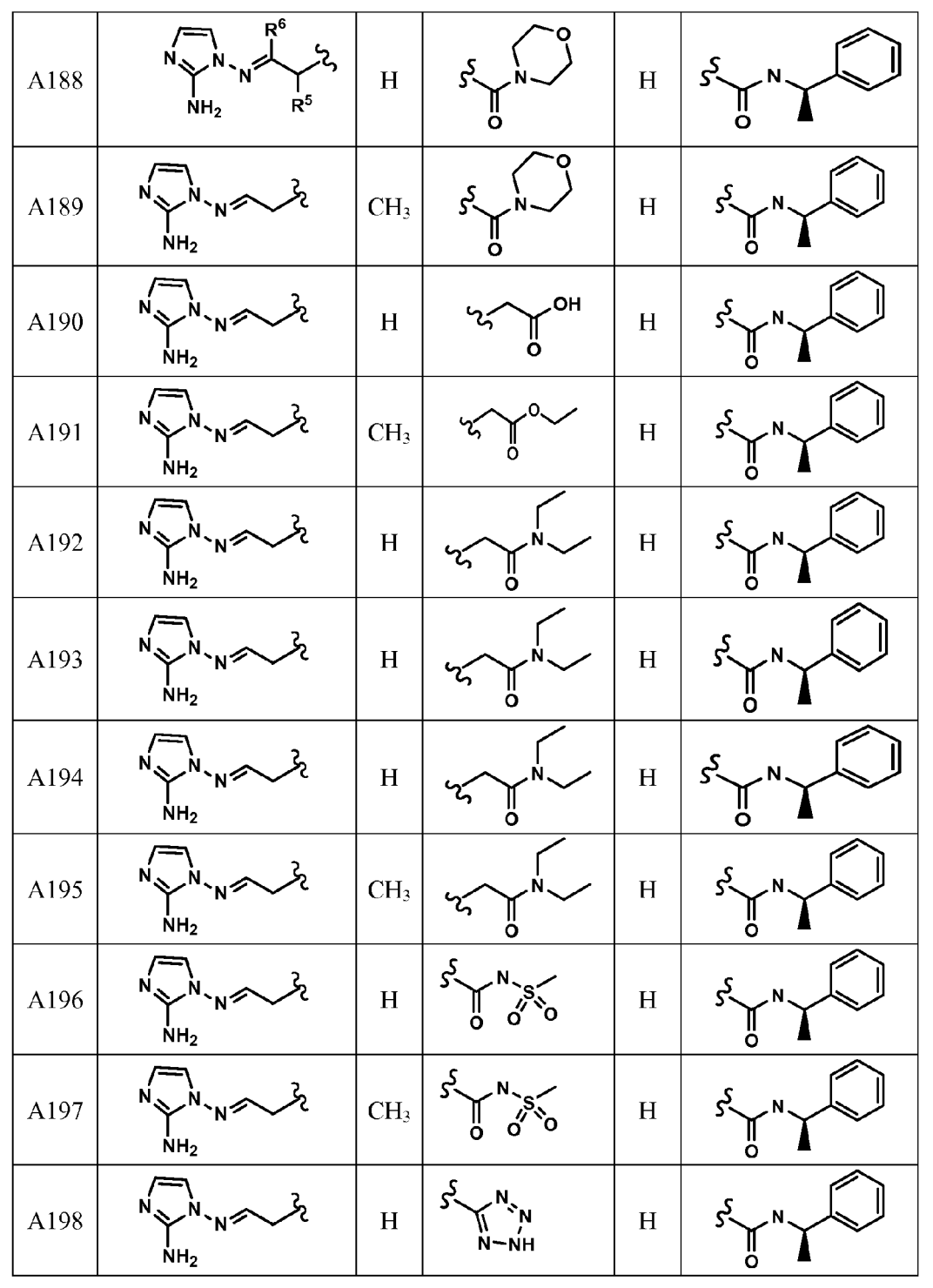
Figure 1U:
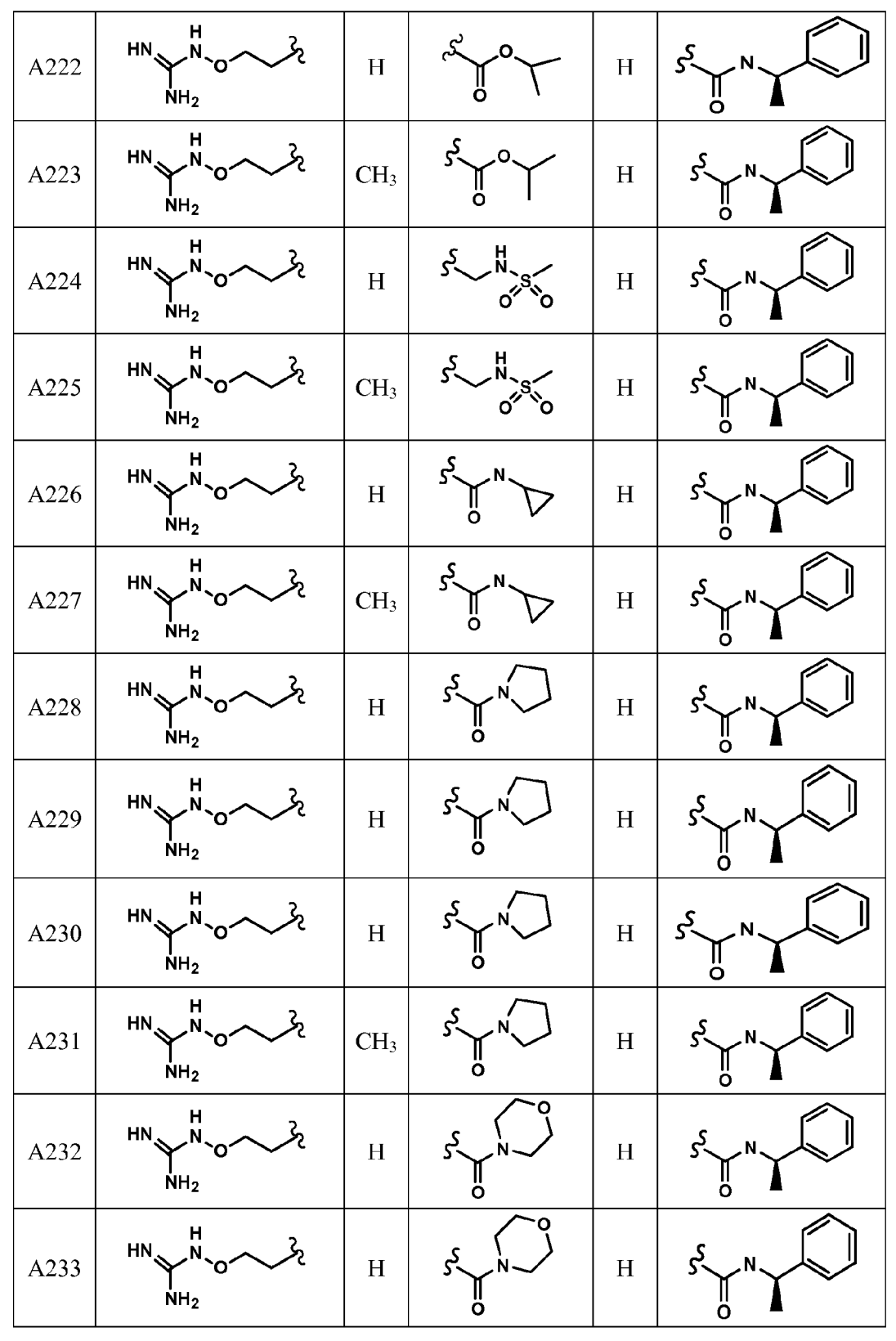

Representative compounds of the invention are provided in FIG. 1 and FIG. 2.

IV. Synthesis and Purification of the Compounds

The compounds of the invention are synthesized by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention, it is not intended to define the scope of reactions or reaction sequences that are useful in preparing the compounds of the present invention.

IV. a) 2-Guanidinyl 2-oxo ethylene

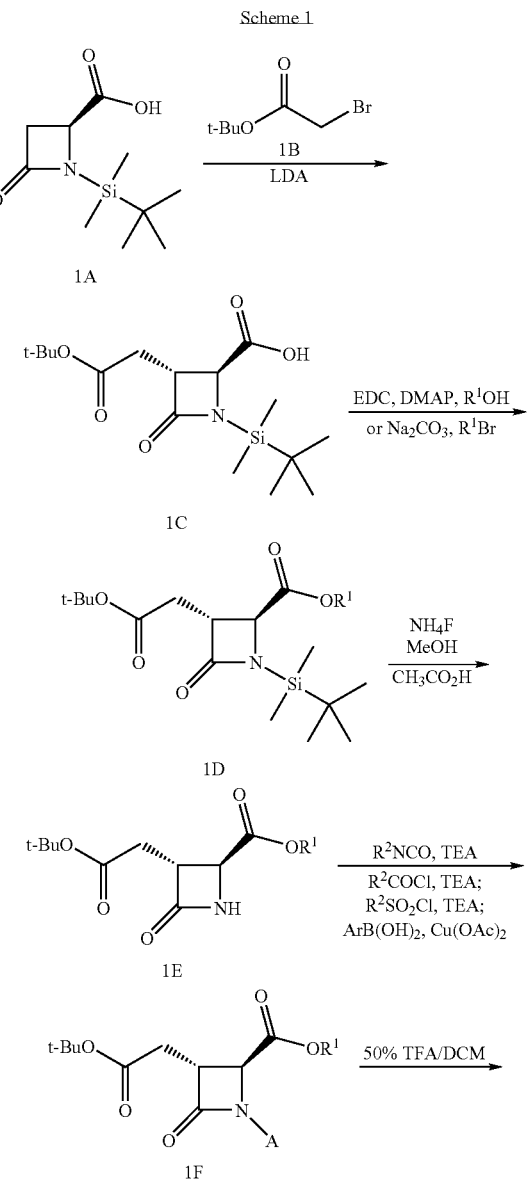

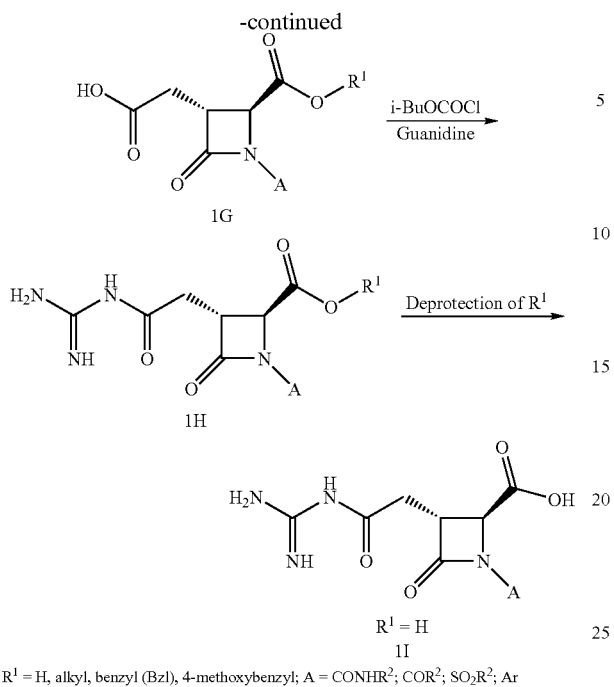

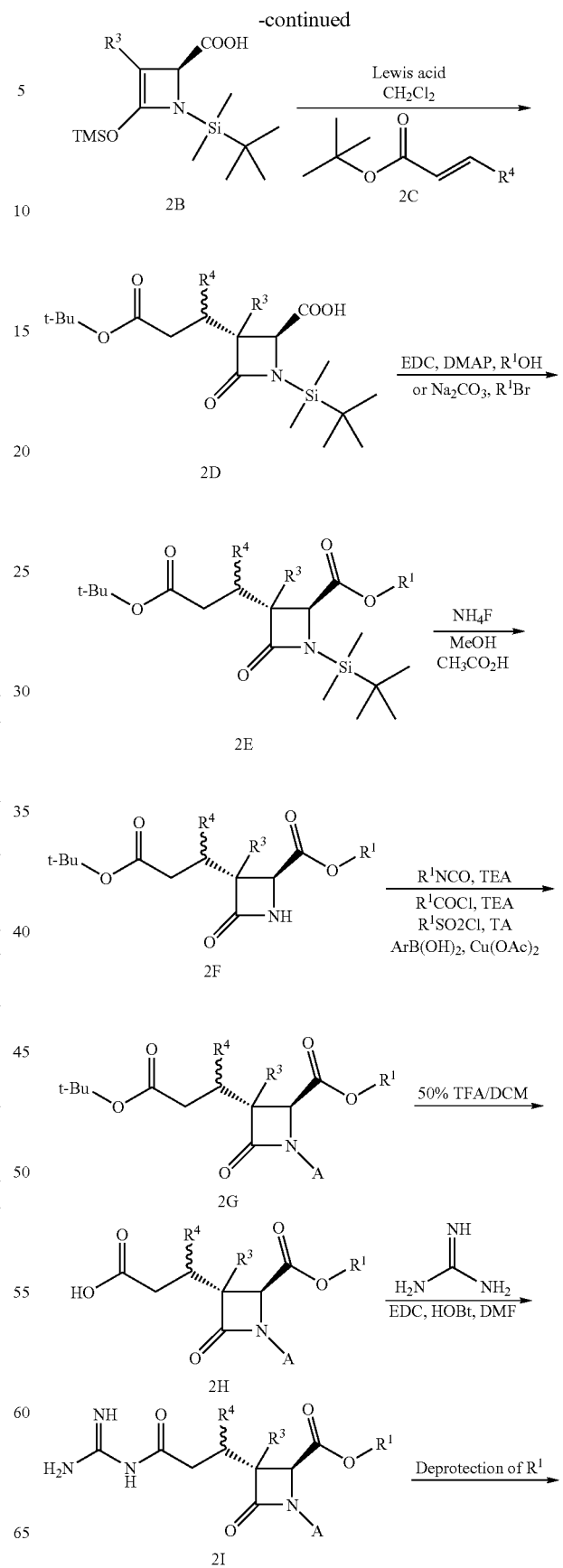

One method of synthesizing compounds of the invention with 2-guanidinyl-2-oxo-ethylene substituents is shown in Scheme 1. In this Scheme, 1A can be treated with bromomethyl t-butyl ester 1B and lithium diisopropyl amide ("LDA") in order to provide 1C. 1C then undergoes esterification with an alcohol ($R^1$—OH), EDC, DMAP in order to provide 1D. 1C can alternatively undergo esterification under alkylation conditions using a halogenated compound and sodium carbonate in order to provide 1D. 1D can be desilylated using a mixture of ammonium fluoride, methanol, and acetic acid in order to provide 1E. 1E can be treated with an isocyanate and TEA to produce 1F with an urea moiety. 1E can alternatively be treated with an acyl chloride and TEA to produce 1F with an amide moiety. 1E can alternatively be treated with a sulfonyl chloride and TEA to produce 1F with a sulfonamide moiety. 1E can alternatively be treated with an aryl boronic acid and Cu(OAc)$_2$ to produce 1F with an aryl moiety. 1F can be treated with TFA in order to remove the t-butyl group on 1F to produce 1G. 1G can be treated with guanidine and isobutylchloroformate in order to produce 1H. 1H can be converted to the acid 1I by treating with hydrogen and palladium on carbon in ethyl acetate when $R^1$=benzyl, or trifluoroacetic acid (TFA) when $R^1$=4-methoxybenzyl.

Scheme 2

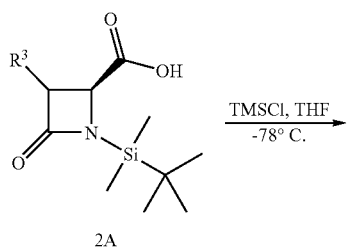

-continued

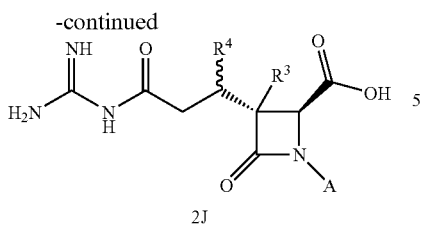

2J $R^1$ = H, alkyl, benzyl (Bzl), 4-methoxybenzyl; A = CONHR$^2$; COR$^2$; SO$_2$R$^2$; Ar, R$^3$ = H, Me; R$^4$ = Me, alkyl, aryl A second method of synthesizing compounds of the invention with 2-guanidinyl-2-oxo-ethylene substituents is shown in Scheme 2. In this Scheme, 2A can be treated with 5 trimethylsilylchloride in THF in order to provide 2B. 2B can then be treated with 2C and an appropriate metal catalyst in order to provide 2D. 2D can then be treated with an alcohol ($R^1$—OH), EDC, DMAP in order to provide 2E. 2D can alternatively undergo esterification via alkylation using a halogenated compound and sodium carbonate in order to provide 2E. 2E can be then treated with a mixture of ammonium fluoride, methanol, and acetic acid in order to provide 2F. 2F can be treated with an isocyanate and TEA to produce 2G with a urea moiety. 2F can alternatively be treated with an acyl chloride and TEA to produce 2G with an amide moiety. 2F can alternatively be treated with a sulfonyl chloride and TEA to produce 2G with a sulfonamide moiety. 2F can alternatively be treated with an aryl boronic acid and Cu(OAc)$_2$ to produce 2G with a substituted or unsubstitued aryl moiety. A substituted or unsubstitued heteroaryl moiety may be used in place of the aryl moiety. 2G can be treated with TFA in order to deprotect the t-butyl group on 2G and to produce 2H. 2H can then be treated with guanidine under peptide coupling conditions (e.g. ethyl diisopropyl carbodiimide (EDC) and hydroxybenzotriazole (HOBt) in order to product 2I. 2I can be converted to 2J by treating with hydrogen and palladium on carbon in ethyl acetate when $R^1$=benzyl, or trifluoroacetic acid (TFA) when $R^1$=4-methoxybenzyl.

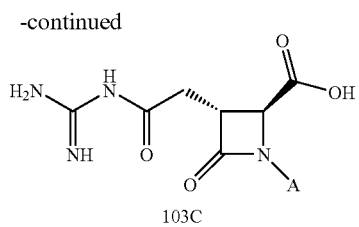

103C $R^1$ = H, alkl, benzyl (Bzl), 4-methoxybenzyl; A = CONHR$^2$; COR$^2$; SO$_2$R$^2$; aryl, heteroaryl A method of synthesizing azetedinones bearing R$_3$ substituents containing an acylguanidine moiety is described in scheme 103. The preparation of 103A is described in scheme 1. This compound may be coupled via an internediate mixed anhydride with guanidine to provide 103B. 103B can be converted to the acid 103C by treating with hydrogen and palladium on carbon in ethyl acetate when $R^1$=benzyl, or trifluoroacetic acid (TFA) when $R^1$=4-methoxybenzyl.

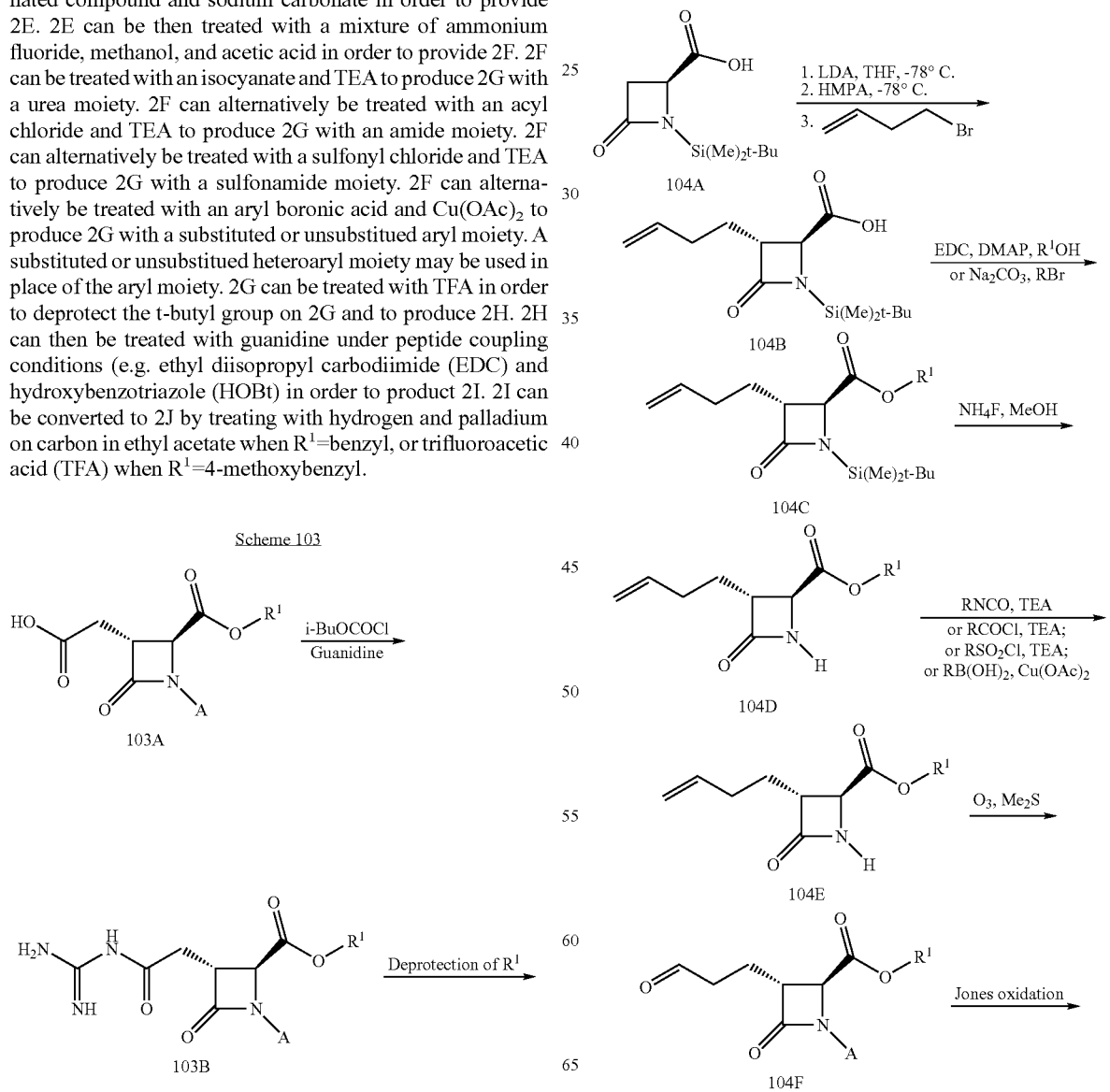

-continued

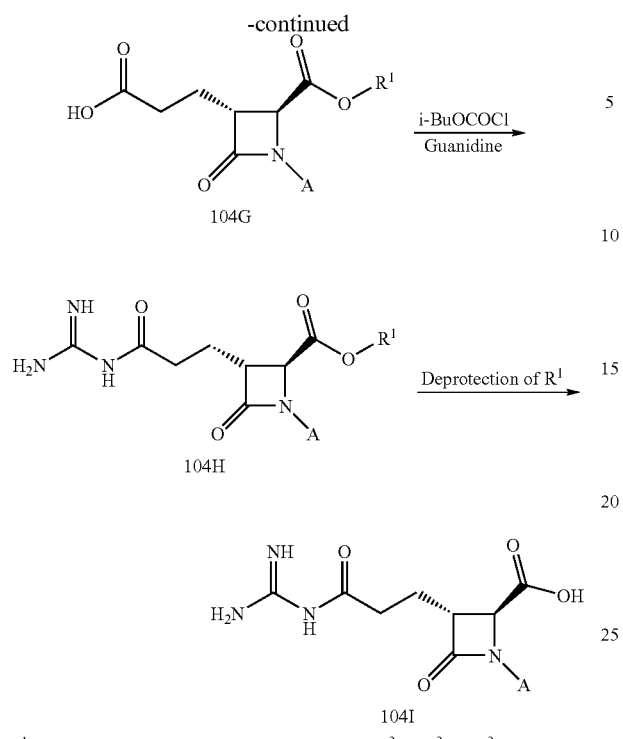

104I $R^1$ = H, alkl, benzyl (Bzl), 4-methoxybenzyl; A = $CONHR^2$; $COR^2$; $SO_2R^2$; aryl, heteroaryl A method of synthesizing azetedinones bearing $R_3$ substituents containing an acylguanidine moiety is described in scheme 104. Alylation of the dianion of acid 104A using homoallyl bromide provides 104B. Esterification can provide 104C. Desilylation affords 104D. 104D can then be treated with an isocyanate and TEA to produce 104E with a urea functionality. 104D can alternatively be treated with an acyl chloride and TEA to produce 104E with an amide functionality. 104D can alternatively be treated with a sulfonyl chloride and TEA to produce 104E with a sulfonamide functionality. 104D can alternatively be treated with an aryl boronic acid and $Cu(OAc)_2$ to produce 104E with an aryl functionality. Ozonolysis provides aldehyde 104F. Oxidation can provide 104G. Coupling with guanidine via an active ester provides 104H. 104H can be converted to the acid 104I by treating with hydrogen and palladium on carbon in ethyl acetate when $R^1$=benzyl, or trifluoroacetic acid (TFA) when $R^1$=4-methoxybenzyl.

IV. b) N-guanidinyl 2-iminyl ethylene

Scheme 3

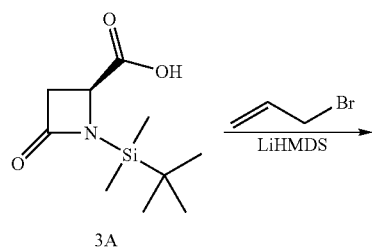

3A

-continued

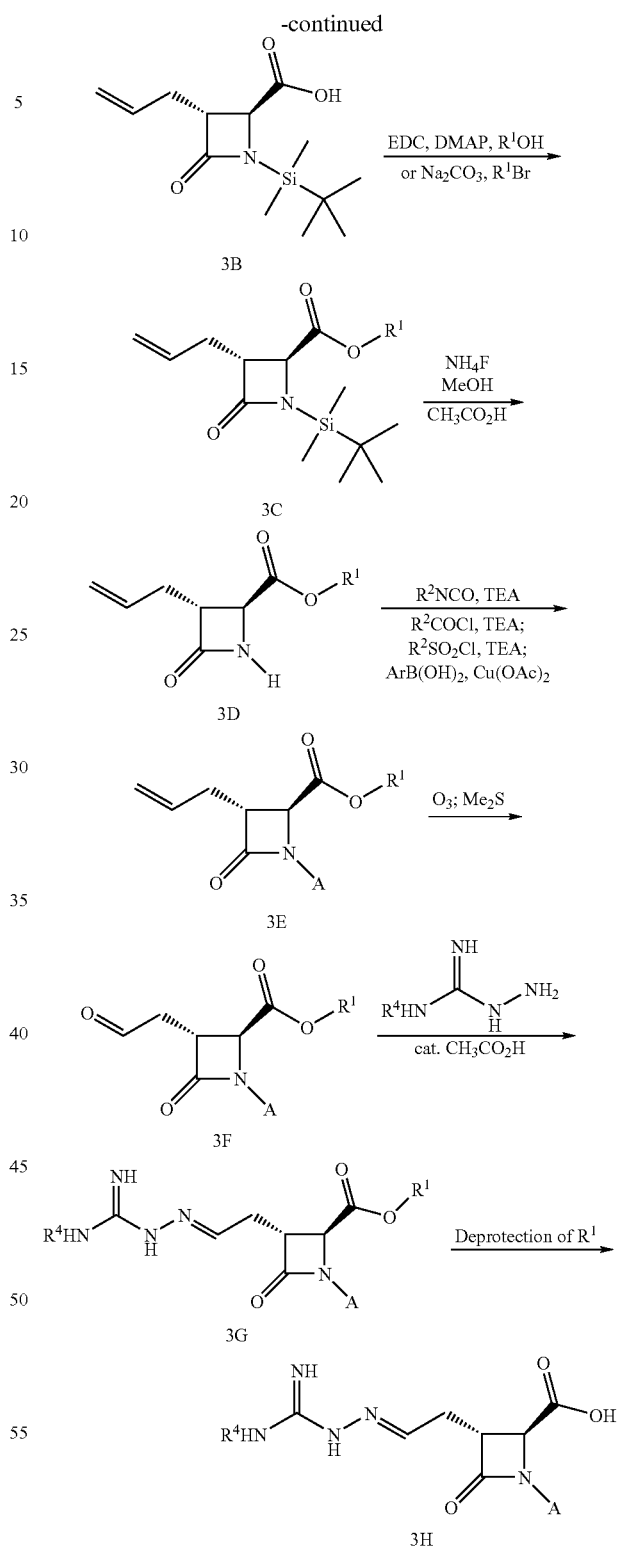

$R^1$ = H, alkyl, benzyl (Bzl), 4-methoxybenzyl; A = $CONHR^2$; $COR^2$; $SO_2R^2$; Ar
$R^4$ = H, alkyl, Bzl One method of synthesizing compounds of the invention with N-guanidinyl-2-iminyl-ethylene substituents is shown in Scheme 3. In this Scheme, 3A can be treated with lithium hexamethyldisilazide (LiHMDS) and 2-propenyl bromide to produce 3B. 3B can be treated with an alcohol ($R^1$—OH), EDC, DMAP in order to produce 3C. 3B can alternatively be treated with a halogenated compound and sodium carbonate in order to provide 3C. 3C can then be treated with a mixture of ammonium fluoride, methanol, and acetic acid in order to provide 3D. 3D can then be treated with an isocyanate and TEA to produce 3E with an urea moiety. 3D alternatively be treated with an acyl chloride and TEA to produce 3E with an amide moiety. 3D can alternatively be treated with a sulfonyl chloride and TEA to produce 3E with a sulfonamide moiety. 3D can alternatively be treated with an aryl boronic acid and $Cu(OAc)_2$ to produce 3E with a substituted or unsubstitued aryl moiety. A substituted or unsubstitued heteroaryl moiety may be used in place of the aryl moiety. 3E can be subjected to ozonolysis to produce 3F. 3F can be treated with substituted or unsubstituted aminoguanidine and a catalytic amount of an organic acid in order to produce 3G. Finally, 3G can be converted to 3H by treating with hydrogen and palladium on carbon in ethyl acetate when $R^1$=benzyl, or trifluoroacetic acid (TFA) when $R^1$=4-methoxybenzyl.

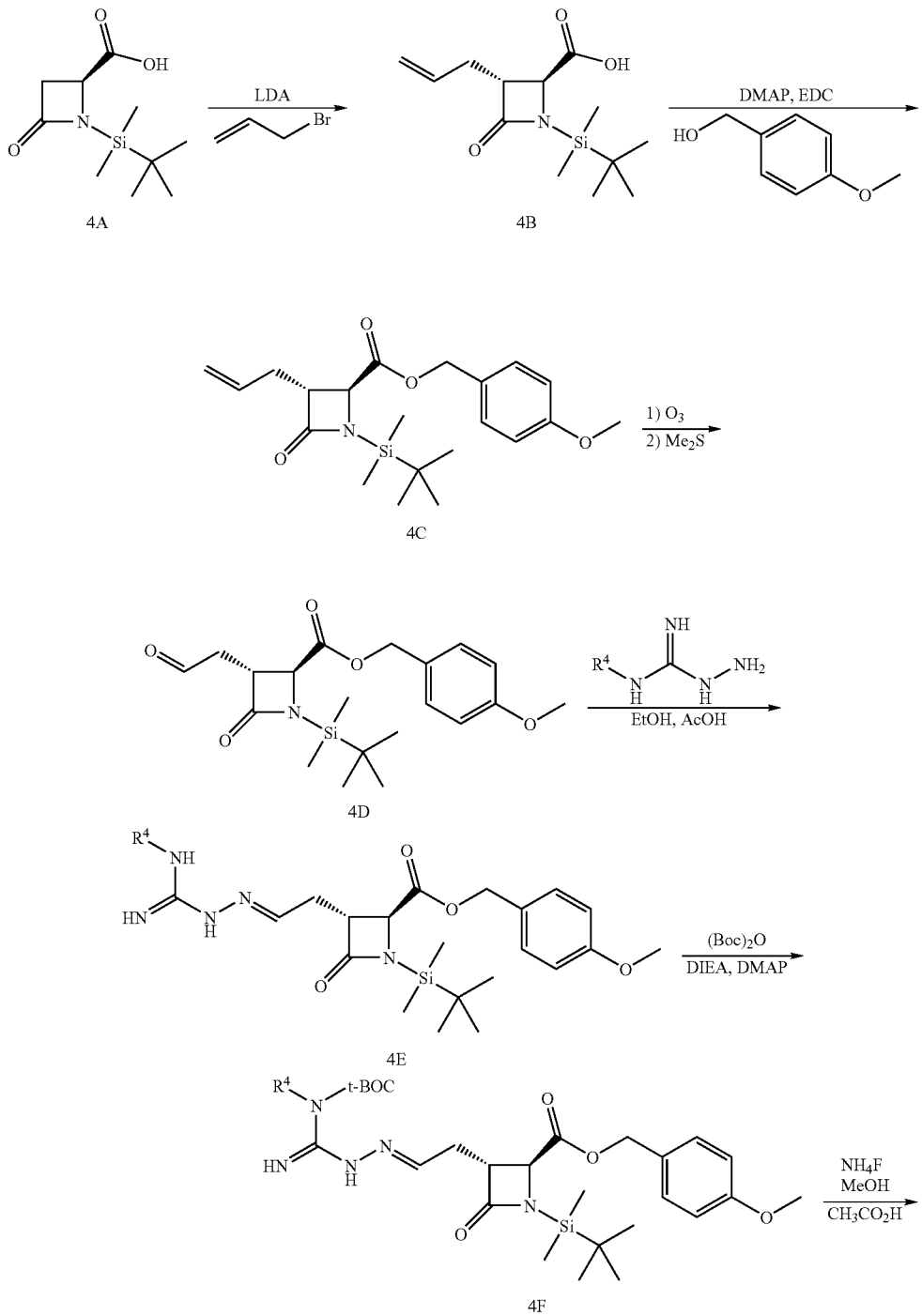

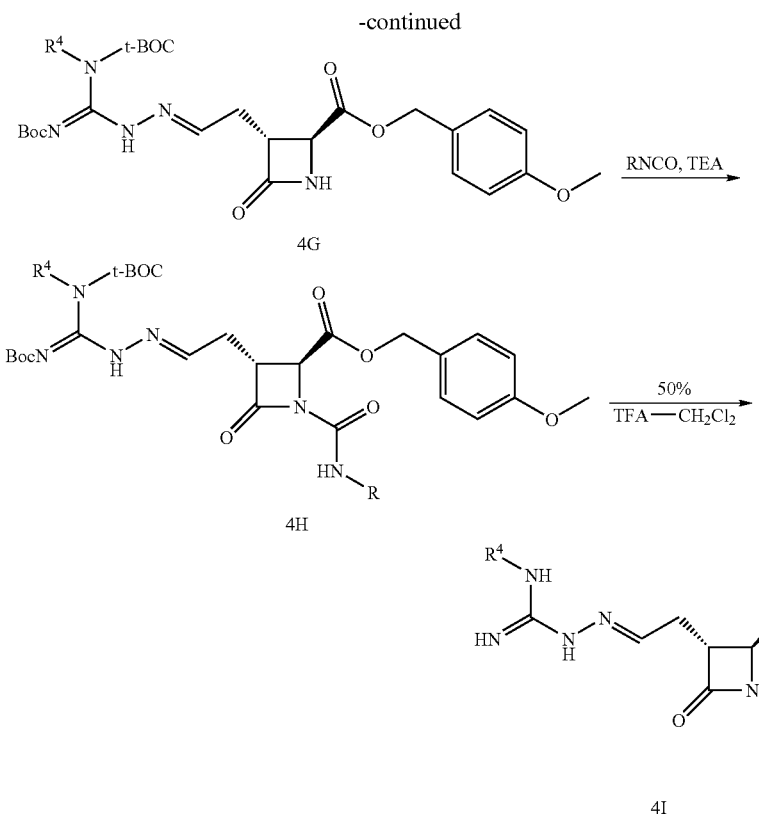

Another method of synthesizing compounds of the invention with N-guanidinyl-2-iminyl-ethylene substituents is shown in Scheme 4. In this Scheme, 4A can be treated with LDA and allyl bromide to produce 4B. 4B can be then treated with 4-methoxybenzyl alcohol, EDC and DMAP in order to produce 4C. 4C can be subjected to ozonolysis to produce 4D. 4D can be treated with substituted or unsubstituted aminoguanidine ($R^4$=H, alkyl) and a catalytic amount of an organic acid in order to produce 4E. 4E can then be treated with $(BOC)_2O$, DIEA and DMAP in order to produce 4F. 4F can then be treated with a mixture of ammonium fluoride, methanol, and acetic acid in order to provide 4G. 4G can then be treated with an isocyanate and TEA to produce 4H with an urea moiety. 4H can then be treated with TFA in order to produce 4I.

Scheme 5

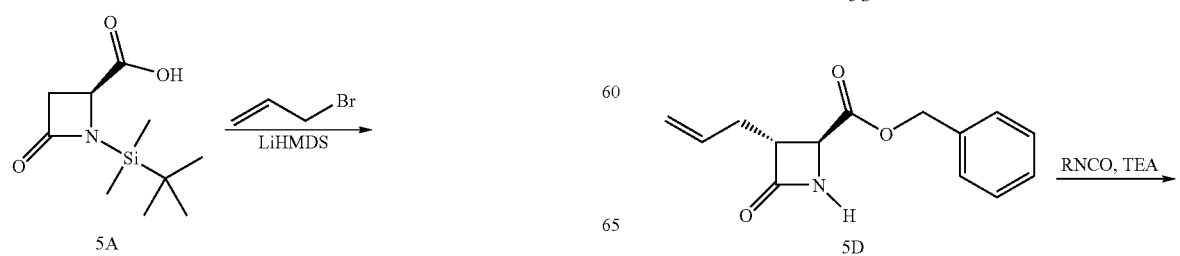

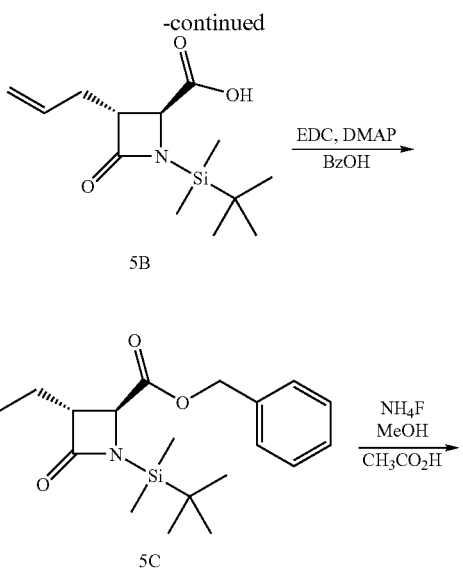

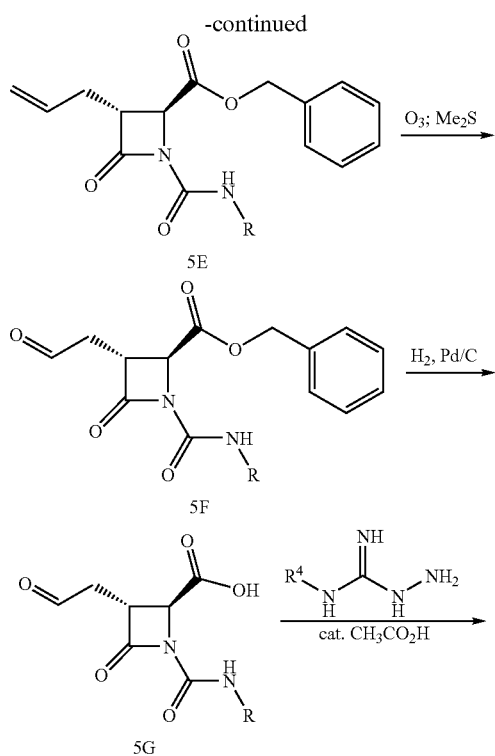
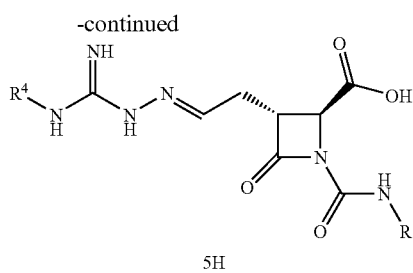

Another method of synthesizing compounds of the invention with N-guanidinyl-2-iminyl-ethylene substituents is shown in Scheme 5. In this Scheme, 5A can be treated with LiHMDS and 2-propenyl bromide to produce 5B. 5B can be treated with benzyl alcohol, EDC, DMAP in order to produce 5C. 5C can be treated with a mixture of ammonium fluoride and methanol in order to provide 5D. 5D can be treated with an isocyanate and TEA to produce 5E with an urea moiety. 5E can be subjected to ozonolysis to produce 5F. 5F can be subjected to hydrogenolysis in order to produce 5G. 5G can be treated with substituted or unsubstituted aminoguanidine and a catalytic amount of an organic acid in order to produce 5H.

Scheme 6

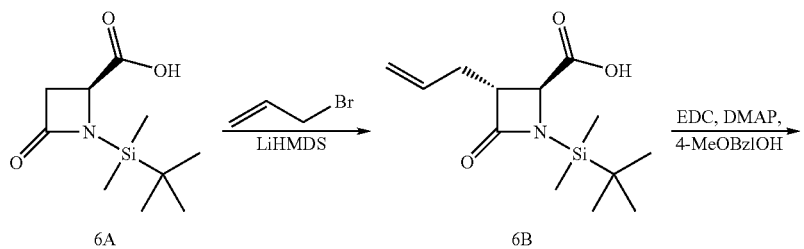

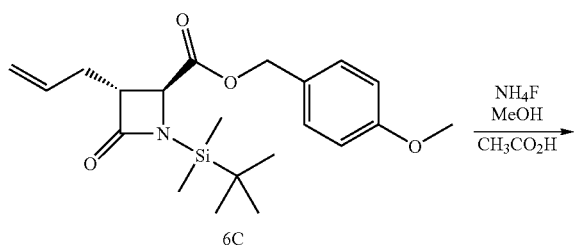

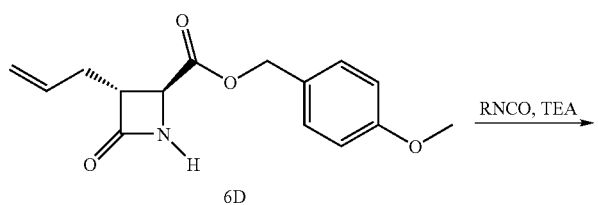

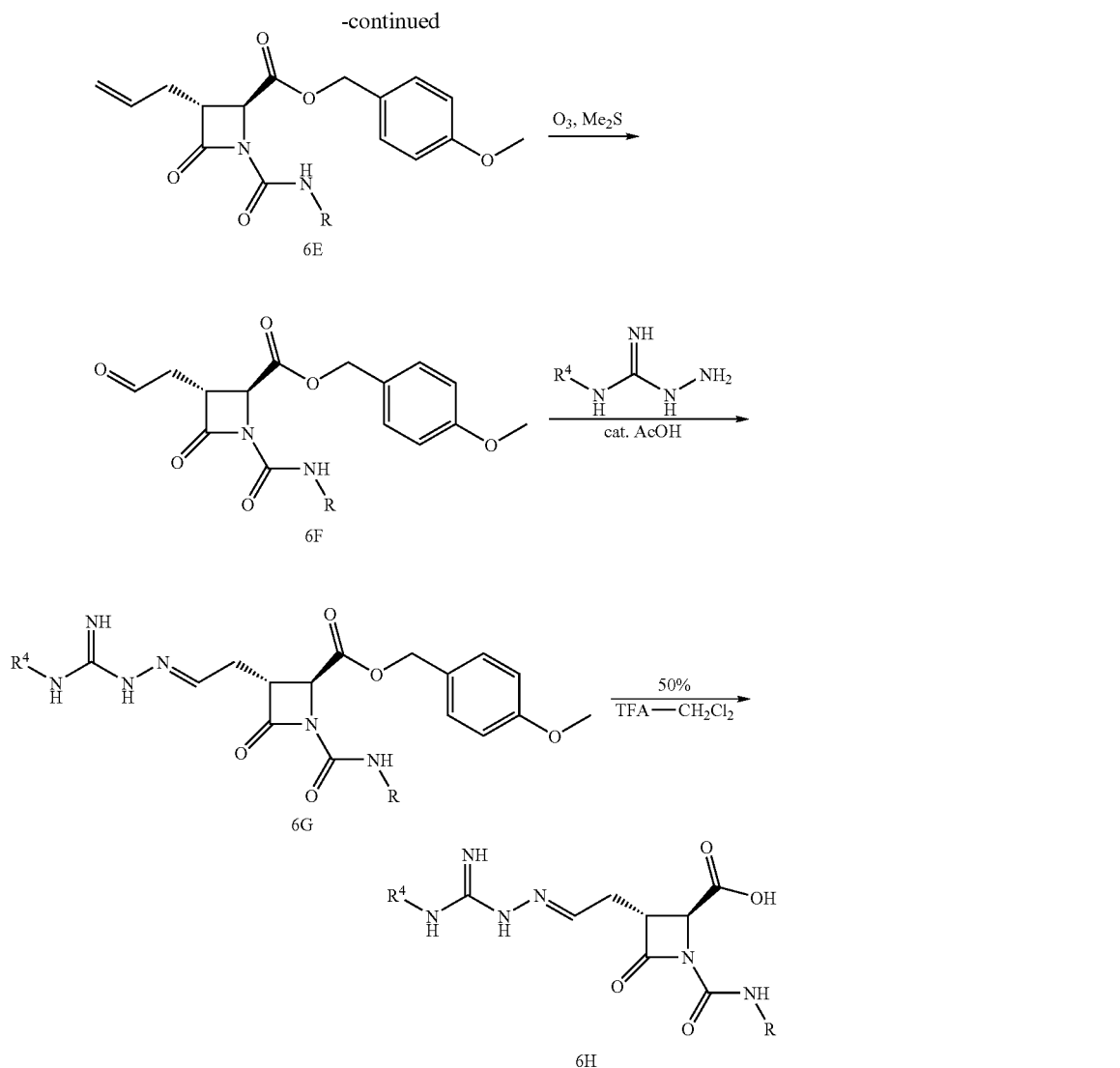

Another method of synthesizing compounds of the invention with N-guanidinyl-2-iminyl-ethylene substituents is shown in Scheme 6. In this Scheme, 6A can be treated with LiHMDS and 2-propenyl bromide to produce 6B. 6B can be treated with 4-methoxybenzyl alcohol, EDC, DMAP in order to produce 6C. 6C can be treated with a mixture of ammonium fluoride, methanol, and acetic acid in order to provide 6D. 6D can be treated with an isocyanate and TEA to produce 6E with an urea moiety. 6E can be subjected to ozonolysis to produce 6F. 6F can be treated with substituted or unsubstituted aminoguanidine and a catalytic amount of an organic acid in order to produce 6G. 6G can then be treated with TFA in order to produce 6H.

Scheme 7

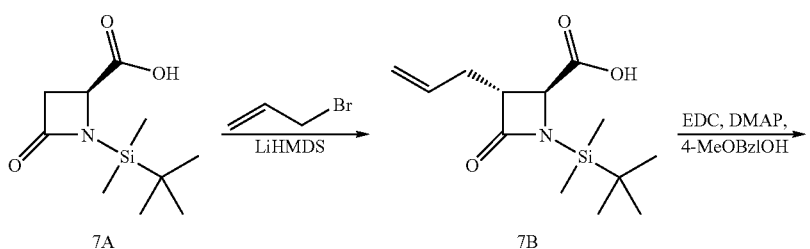

-continued
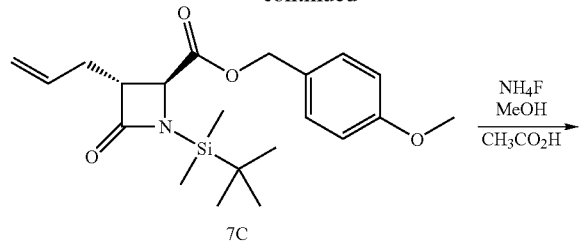
7C
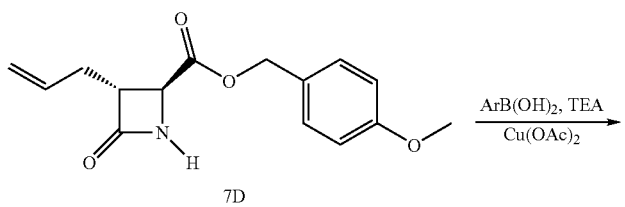
7D
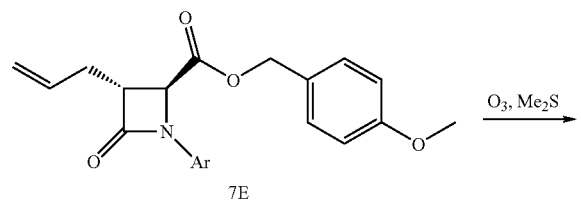
7E
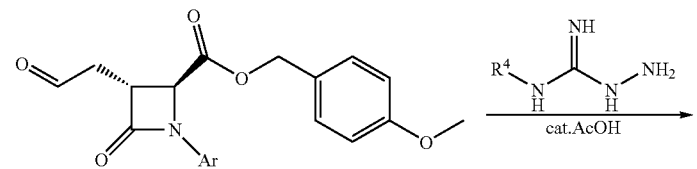
7F
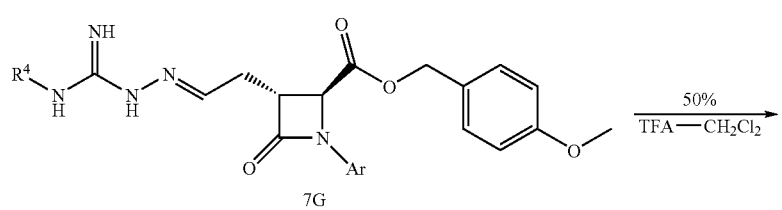
7G
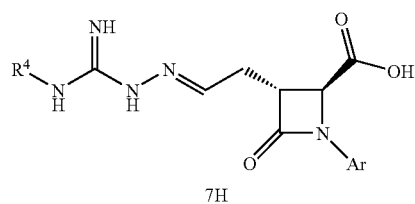
7H
Ar = aryl, substituted aryl, heteroaryl Another method of synthesizing compounds of the invention with N-guanidinyl-2-iminyl-ethylene substituents is shown in Scheme 7. In this Scheme, 7A can be treated with LiHMDS and 2-propenyl bromide to produce 7B. 7B can be treated with 4-methoxybenzyl alcohol, EDC, DMAP in order to produce 7C. 7C can be treated with ammonium fluoride, methanol, and acetic acid in order to provide 7D. 7D can be treated with an aryl boronic acid and Cu(OAc)$_2$ to produce 7E with a substituted or unsubstitued aryl moiety. A substituted or unsubstitued heteroaryl moiety may be used in place of the aryl moiety. 7E can be subjected to ozonolysis to produce 7F. 7F can be treated with substituted or unsubstituted guanidine and a catalytic amount of an organic acid in order to produce 7G. 7G can be treated with TFA in order to produce 7H.

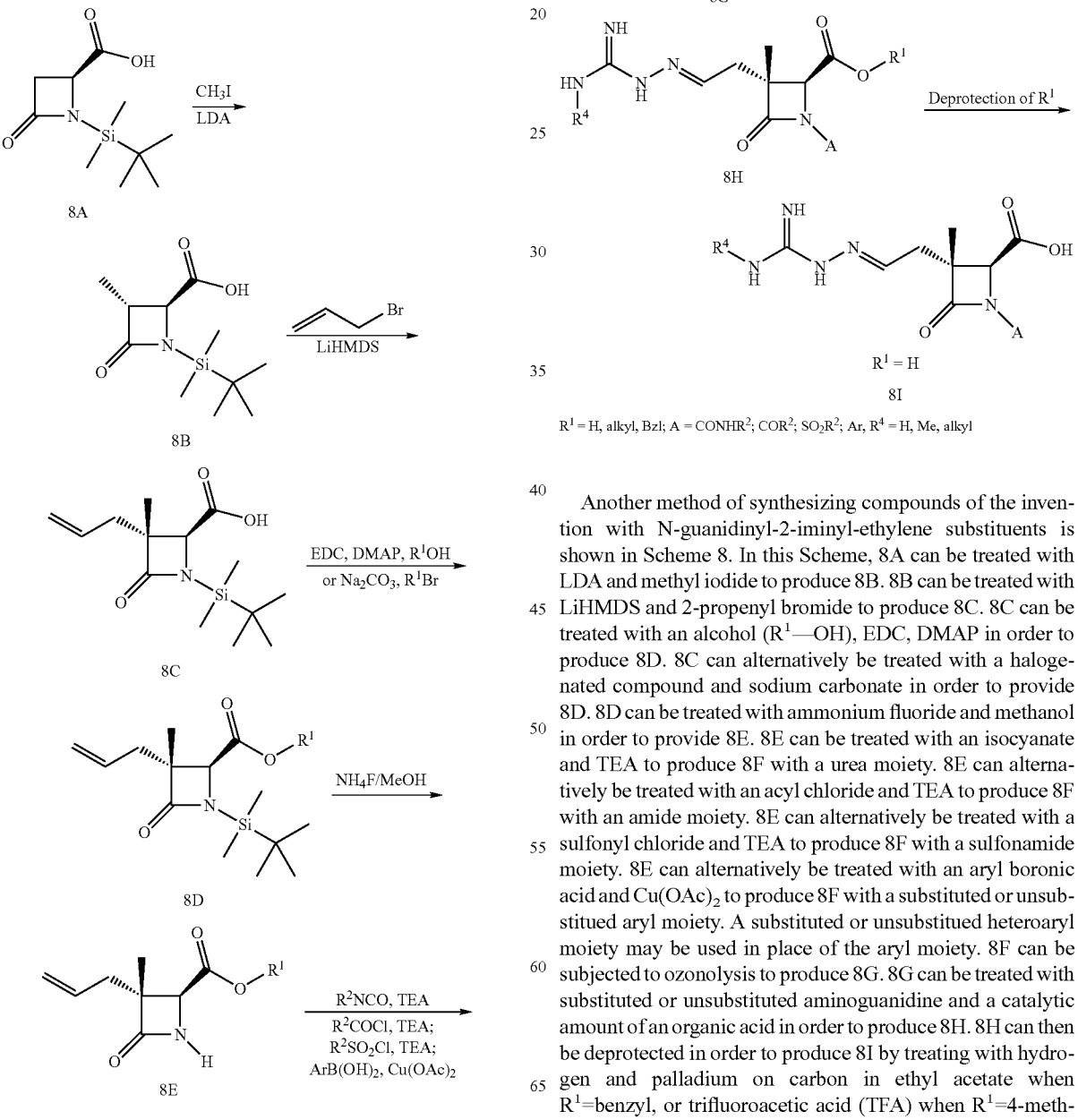

Scheme 8

$R^1$ = H, alkyl, Bzl; A = CONHR$^2$; COR$^2$; SO$_2$R$^2$; Ar, R$^4$ = H, Me, alkyl Another method of synthesizing compounds of the invention with N-guanidinyl-2-iminyl-ethylene substituents is shown in Scheme 8. In this Scheme, 8A can be treated with LDA and methyl iodide to produce 8B. 8B can be treated with LiHMDS and 2-propenyl bromide to produce 8C. 8C can be treated with an alcohol (R$^1$—OH), EDC, DMAP in order to produce 8D. 8C can alternatively be treated with a halogenated compound and sodium carbonate in order to provide 8D. 8D can be treated with ammonium fluoride and methanol in order to provide 8E. 8E can be treated with an isocyanate and TEA to produce 8F with a urea moiety. 8E can alternatively be treated with an acyl chloride and TEA to produce 8F with an amide moiety. 8E can alternatively be treated with a sulfonyl chloride and TEA to produce 8F with a sulfonamide moiety. 8E can alternatively be treated with an aryl boronic acid and Cu(OAc)$_2$ to produce 8F with a substituted or unsubstitued aryl moiety. A substituted or unsubstitued heteroaryl moiety may be used in place of the aryl moiety. 8F can be subjected to ozonolysis to produce 8G. 8G can be treated with substituted or unsubstituted aminoguanidine and a catalytic amount of an organic acid in order to produce 8H. 8H can then be deprotected in order to produce 8I by treating with hydrogen and palladium on carbon in ethyl acetate when R$^1$=benzyl, or trifluoroacetic acid (TFA) when R$^1$=4-methoxybenzyl.

IV. c) N1-ethylidene-1H-imidazole-1,2-diamine

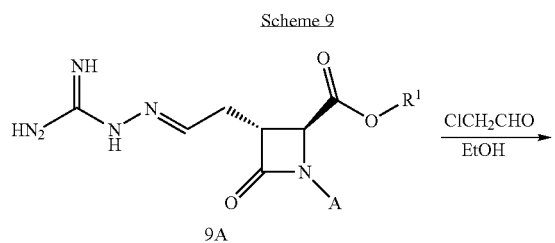

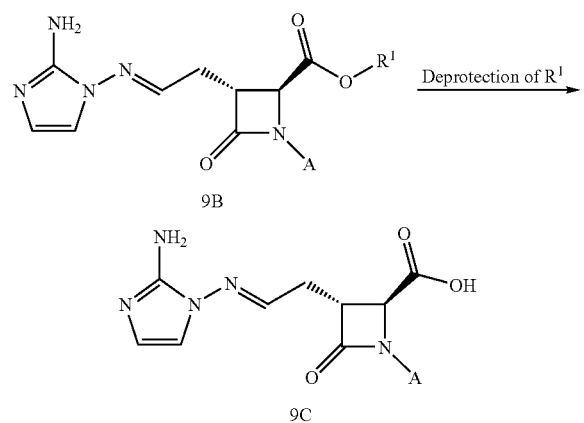

$R^1$ = H, alkyl, Bzl, 4-methoxybenzyl; A = $CONHR^2$; $COR^2$; $SO_2R^2$; aryl, substituted aryl, heteroaryl One method of synthesizing compounds of the invention with N-[2-amino-pyrazinyl] 2-iminyl ethylene substituents is shown in Scheme 9. 9A is a compound that can be produced by the methods described in Schemes 3-8. 9A can be treated with $ClCH_2CHO$ in ethanol in order to produce 9B. 9B can be used to produce 9C by treating with hydrogen and palladium on carbon in ethyl acetate when $R^1$=benzyl, or trifluoroacetic acid (TFA) when $R^1$=4-methoxybenzyl.

IV. d) 1-(4,5-dihydro-1H-imidazol-2-yl)-2-propylidenehydrazine

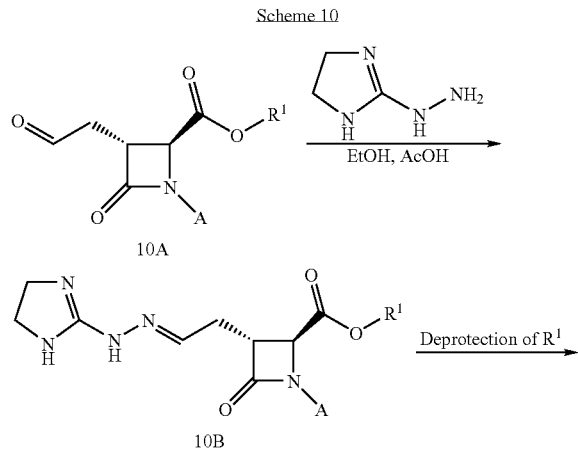

-continued

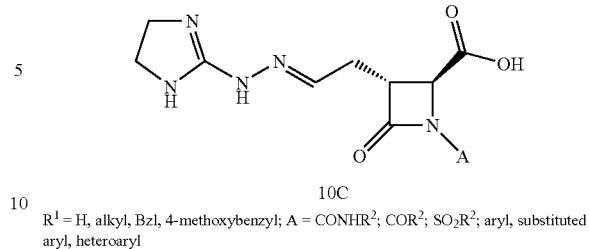

$R^1$ = H, alkyl, Bzl, 4-methoxybenzyl; A = $CONHR^2$; $COR^2$; $SO_2R^2$; aryl, substituted aryl, heteroaryl One method of synthesizing compounds of the invention with N-[dihydroimidazyl] 2-hydrazinylimino ethylene substituents is shown in Scheme 10. 10A is a compound that can be produced by the methods described in Schemes 3-8 (See 3F, 5F, 6F, 7F, 8G). 10A can be treated with 1-(4,5-dihydro-1H-imidazol-2-yl)hydrazine

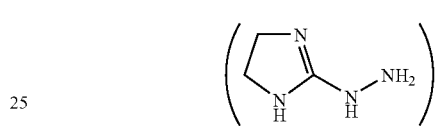

in ethanol and acetic acid in order to produce 10B. 10B can be converted to 10C by treating with hydrogen and palladium on carbon in ethyl acetate when $R^1$=benzyl, or trifluoroacetic acid (TFA) when $R^1$=4-methoxybenzyl.

IV. e) Heteroarylmethyl

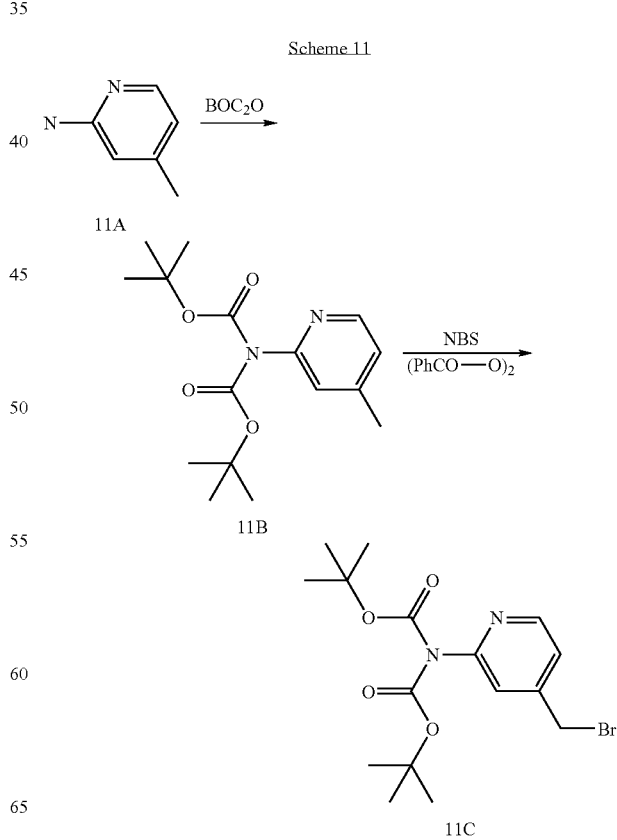

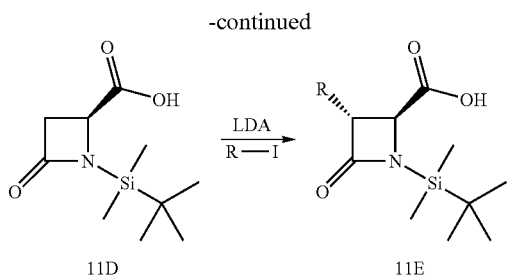

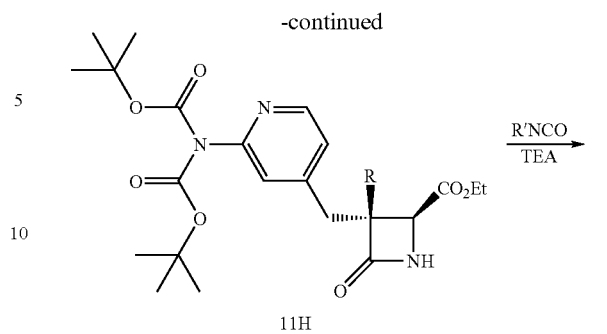

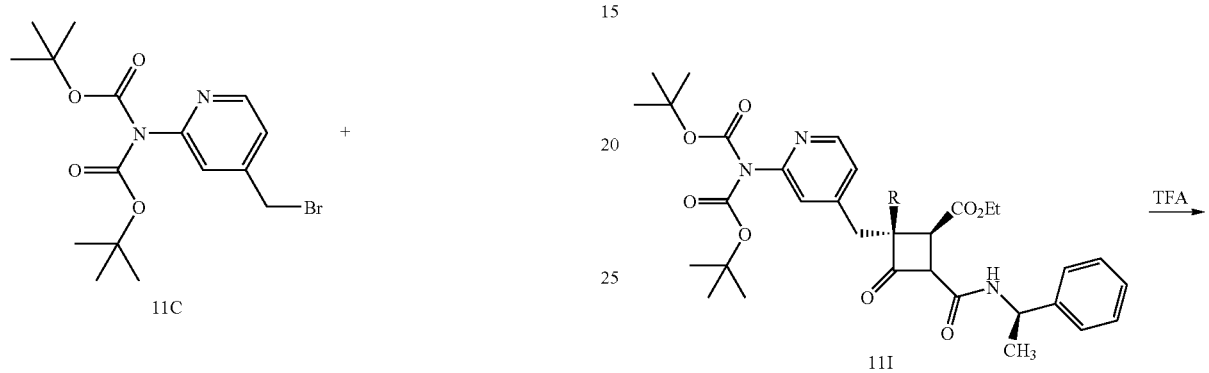

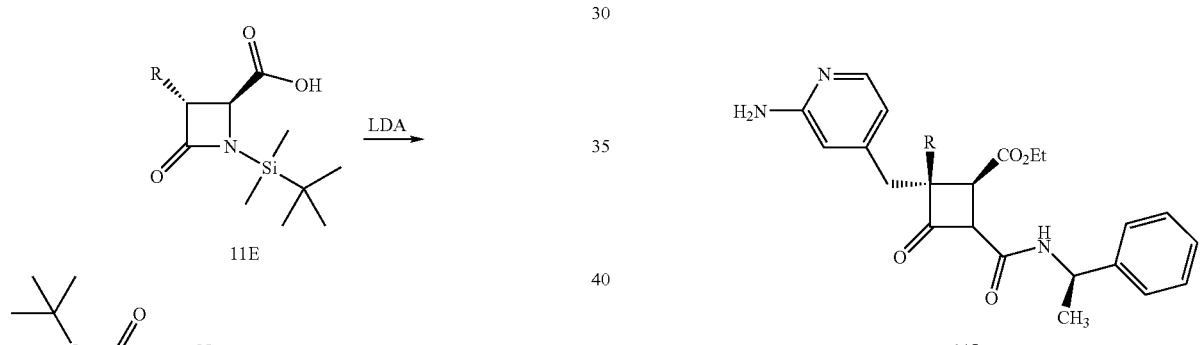

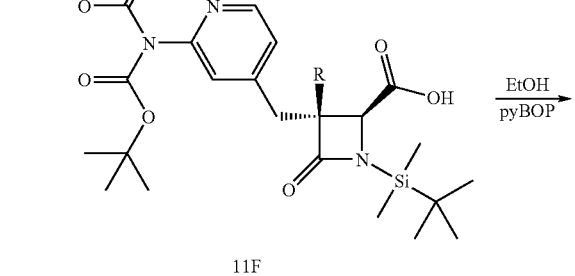

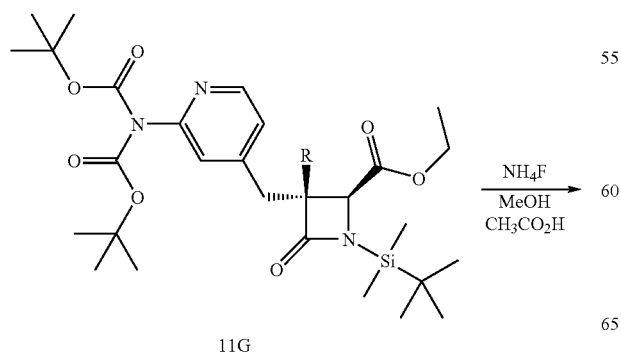

An alternative method of synthesizing heteroarylmethyl substituents is shown in Scheme 11. Bis-BOC protection of 11A and bromination provides 11C. 11C can be used in the LDA-mediated alkylation of 11E. 11E can in turn prepared from 11D by LDA-mediated alkylation with iodomethane, where R=Me. The alkylated product 11F can be converted to 11G using ethanol and a peptide coupling agent such as pyBOP. 11G can be desilylated to 11H using ammonium fluoride, converted to urea 11I using and an appropriate isocyanate and triethylamine, and deprotected with TFA to provide 11J.

Scheme 12

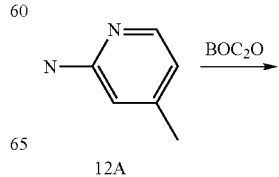

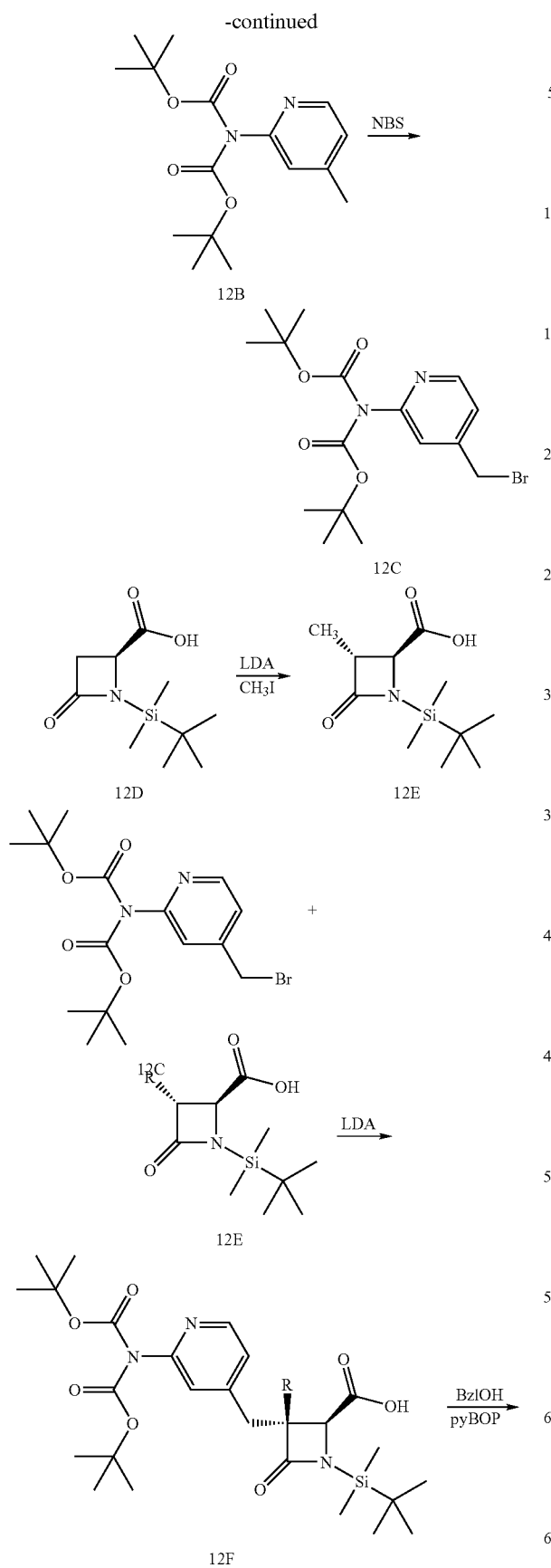
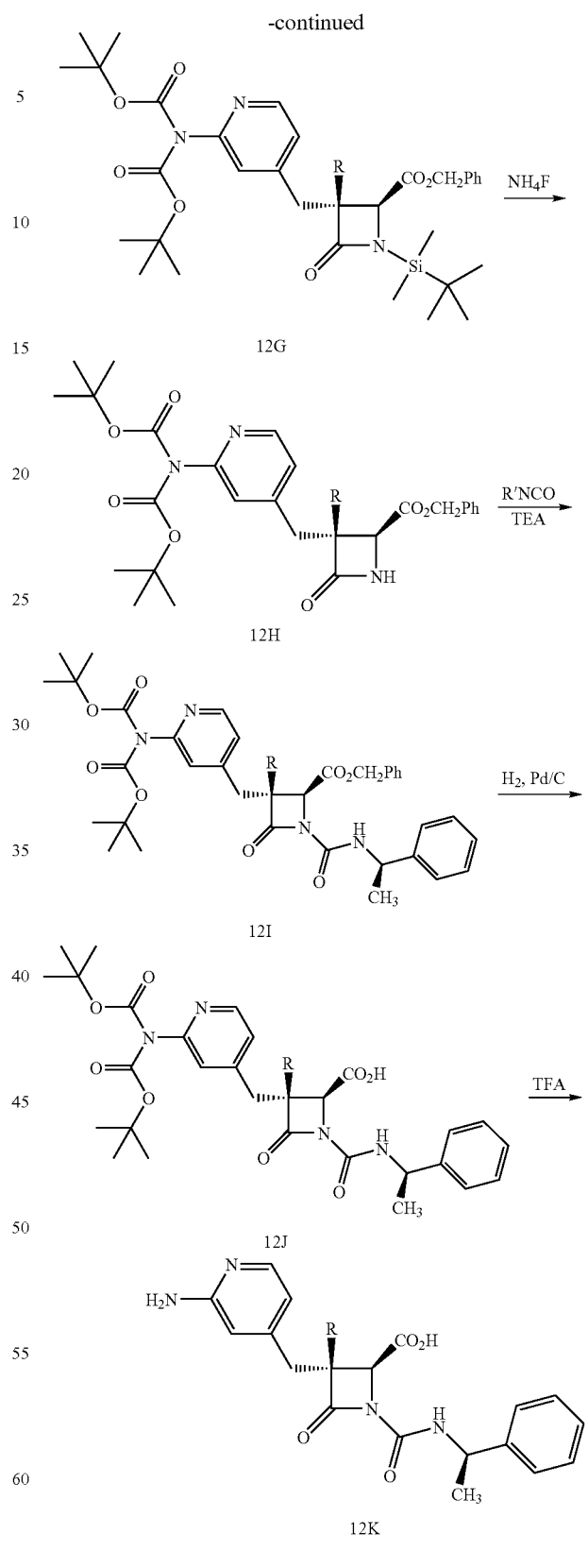
An alternative method of synthesizing heteroarylmethyl substituents is shown in Scheme 12. Compound 12F was described in scheme 11 (compound 11F with R=H). A benzyl ester 12G can be prepared from 12F using benzyl alcohol and a peptide coupling agent such as pyBOP. 12G can be desilylated with ammonium fluoride to provide 12H. Treatment with an appropriate isocyanate can provide 12I. Hydrogenolysis can provide 12J, and BOC removal using TFA can provide 12K.

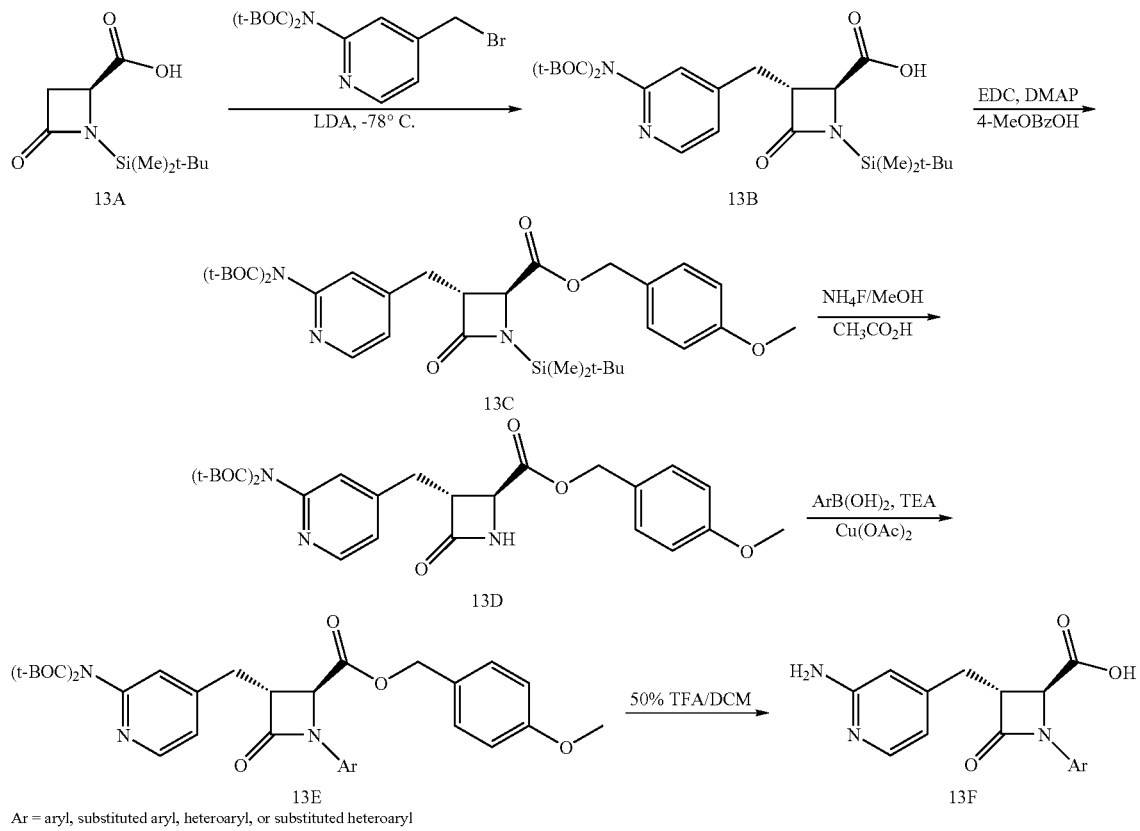

An alternative method of synthesizing heteroarylmethyl substituents is shown in Scheme 13. 13D is prepared an analogous fashion to 12G (with R=H) in scheme 12. 13D can be treated with an aryl boronic acid to provide 13E, and the aryl moiety may be substituted aryl, aryl, or heteroaryl. 13B can treated with TFA to give acid 13F.

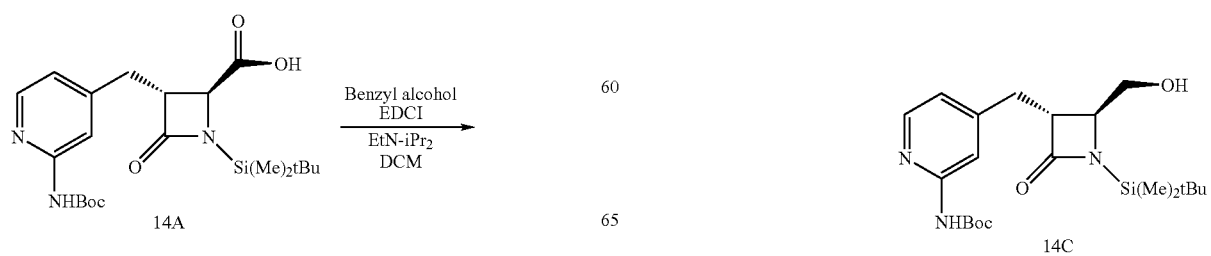

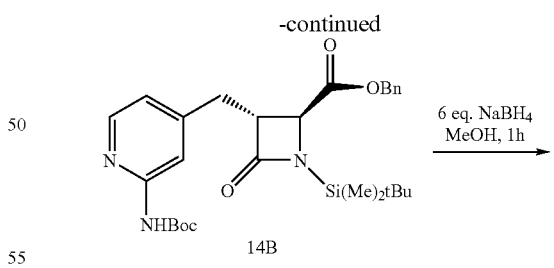

-continued

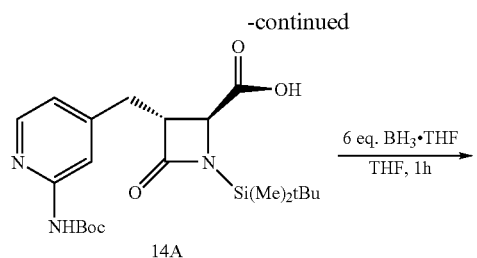
14A

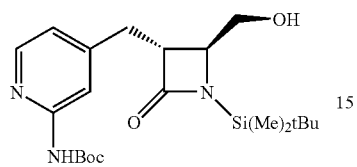
14C

A precursor for the synthesis of many heteroarylmethyl variants can be prepared according to Scheme 14. 14A can be treated with a mixture of benzyl alcohol, EDC, and di-isopropylethylamine in DCM to produce 14B. 14B can be treated with excess sodium borohydride in order to produce 14C. 14A can alternatively be directed converted to 14C through reduction with $BH_3$ in THF.

Scheme 15

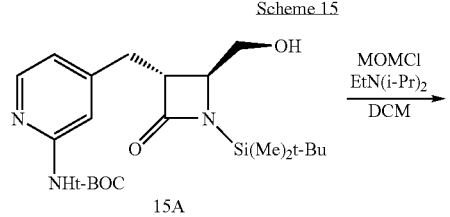
15A

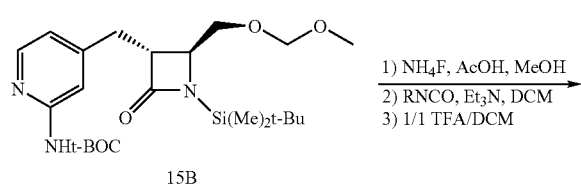
15B

15C

RNCO = any isocyanate

Compound 15A from Scheme 14 can be used to produce 15B by alkylation with chloromethyl methyl ether. 15B can be readily converted to 15C as shown in scheme 15, by ammonium fluoride mediated desilylation, isocyanate acylation, and TFA-mediated BOC deprotection.

Scheme 16

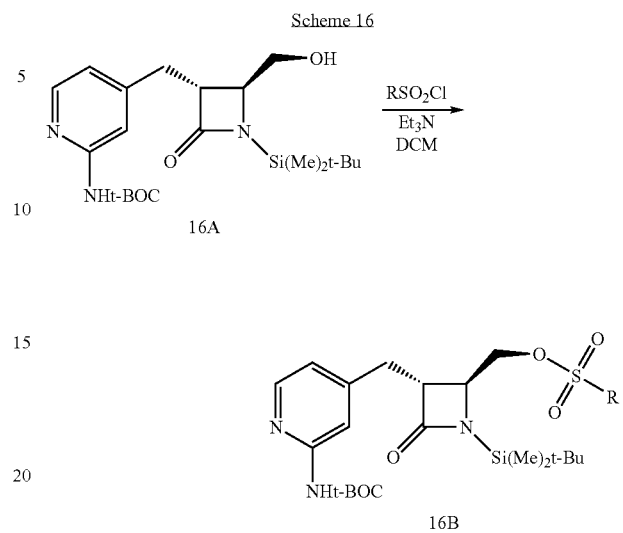
16A

16B

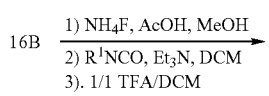

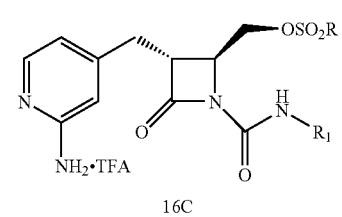
16C

R = alkyl or aryl, substituted aryl, heteroaryl
$R_1$NCO = any isocyanate 16A from scheme 14 can be used to produce 16B by base-mediated sulfonylation. 16B can be readily converted to 16C by 3 steps that include ammonium fluoride mediated desilylation, isocyanate acylation, and BOC deprotection with TFA.

Scheme 17

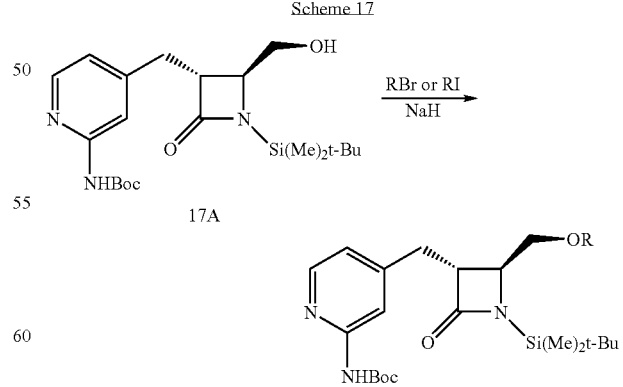
17A

17B

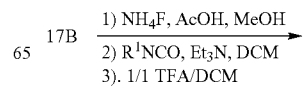

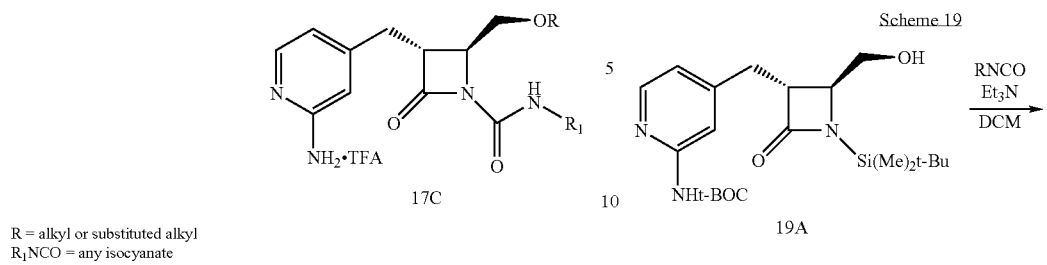

17C

R = alkyl or substituted alkyl
R₁NCO = any isocyanate

The precursor from Scheme 14 (17A) can be used to produce 17B by base-mediated alkylation. 17B can be readily converted to 17C by 3 steps that include ammonium fluoride mediated desilylation, isocyanate acylation, and BOC deprotection with TFA.

Scheme 18

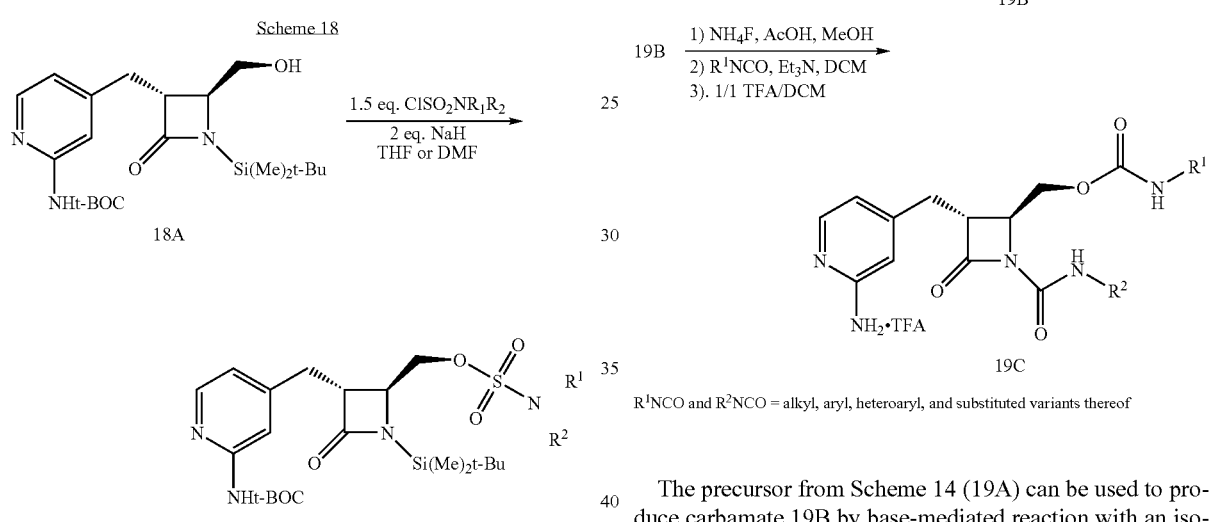

18A

18B

R = alkyl or substituted alkyl
R₁NCO = any isocyanate 18B  1) NH₄F, AcOH, MeOH
      2) R¹NCO, Et₃N, DCM
      3). 1/1 TFA/DCM

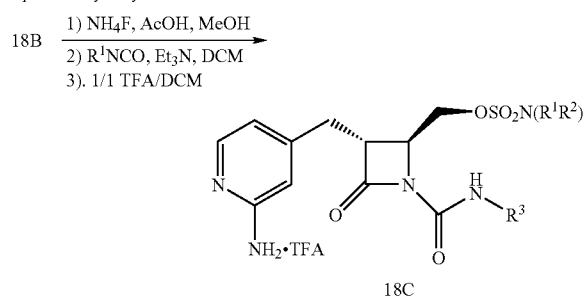

18C

R¹ and R² can be together or independently alkyl or aryl, optionally substituted with everything and/or together forming a ring
R³NCO = any isocyanate The precursor from Scheme 14 (18A) can be used to produce 18B by base-mediated reaction with a sulfamoyl chloride. 18B can be readily converted to 18C by 3 steps that include ammonium fluoride mediated desilylation, isocyanate acylation, and BOC deprotection with TFA.

Scheme 19

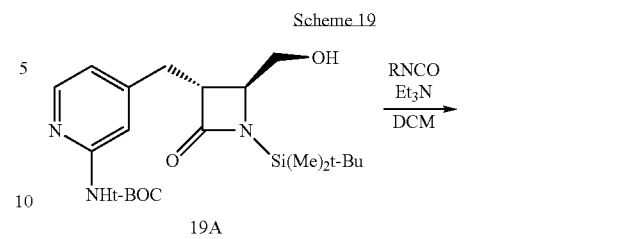

19A

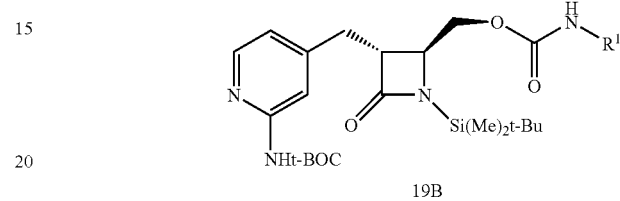

19B 19B  1) NH₄F, AcOH, MeOH
      2) R¹NCO, Et₃N, DCM
      3). 1/1 TFA/DCM

19C

R¹NCO and R²NCO = alkyl, aryl, heteroaryl, and substituted variants thereof

The precursor from Scheme 14 (19A) can be used to produce carbamate 19B by base-mediated reaction with an isocyanate. 19B can be readily converted to 19C by 3 steps that include ammonium fluoride mediated desilylation, isocyanate acylation, and BOC deprotection with TFA.

Scheme 20

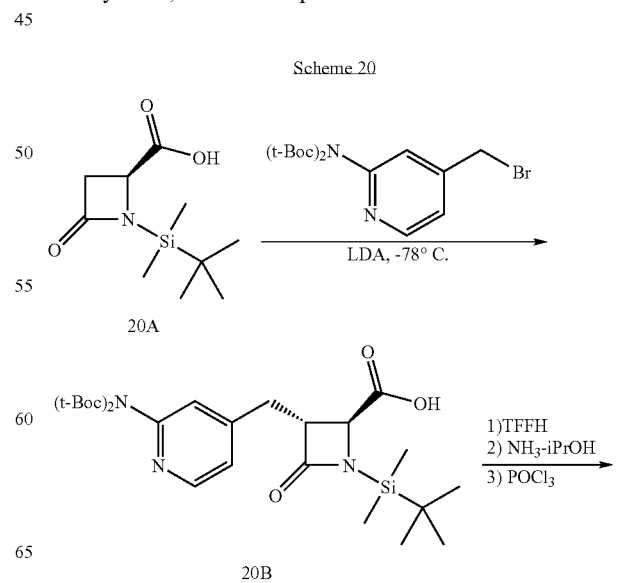

20A

20B

1) TFFH
2) NH₃-iPrOH
3) POCl₃

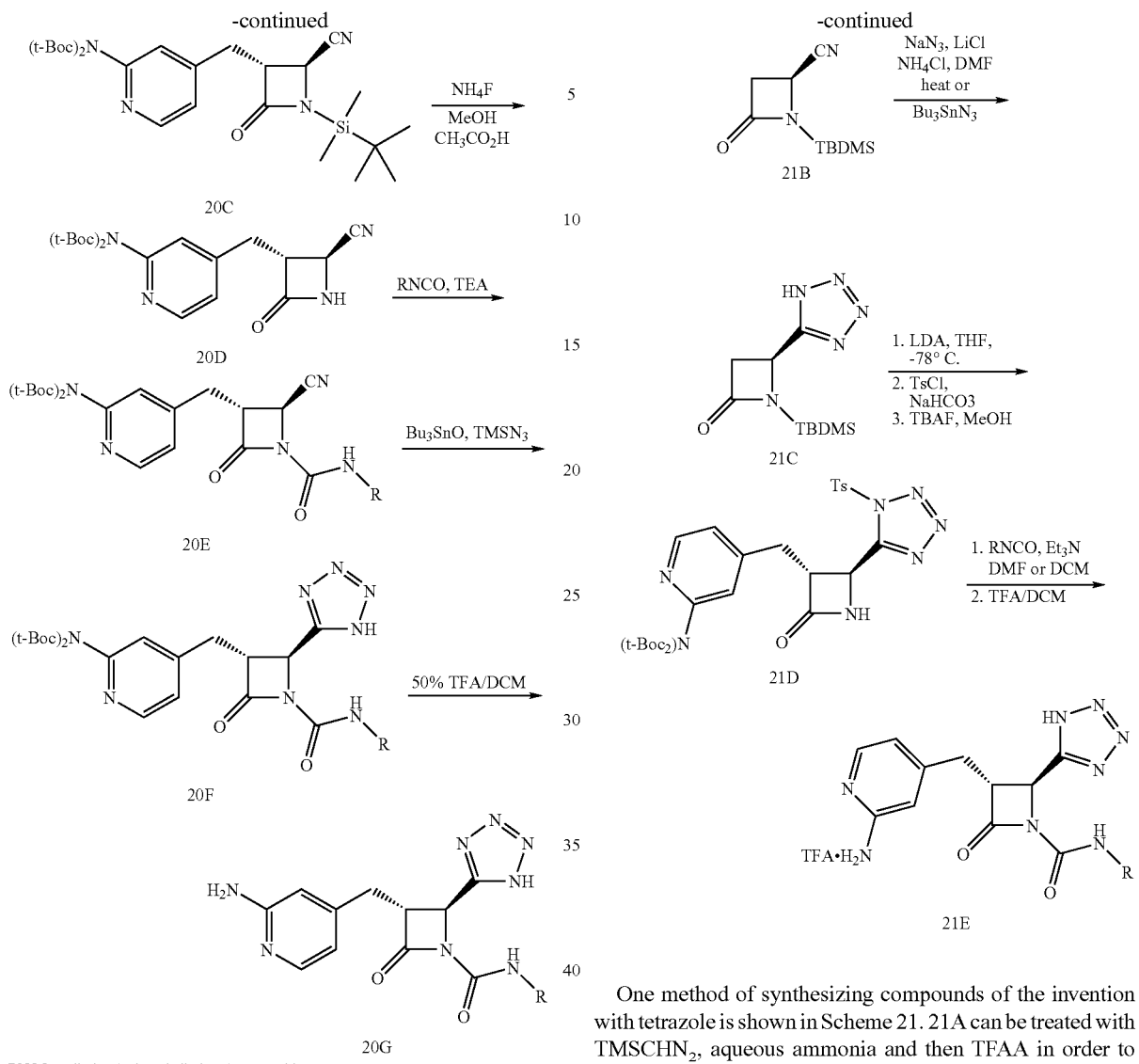

RNCO = alkyl, substituted alkyl, or heteroaryl isocyanate

One method of synthesizing compounds of the invention with tetrazole is shown in Scheme 20. LDA-mediated alkylation of 20A can provide acid 20B. 20B can be converted to the nitrile 20C by coupling via an acyl halide, reaction with ammonia to form a primary amide, and finally dehydration. 20C can be desilylated with ammonium fluoride to form 20D. Treatment of 20D with an isocyanate provides urea 20E. The nitrile can be used to form tetrazole 20F using TMS azide and a tin oxide reagent. TFA-mediated BOC deprotection provides urea 20G.

One method of synthesizing compounds of the invention with tetrazole is shown in Scheme 21. 21A can be treated with TMSCHN$_2$, aqueous ammonia and then TFAA in order to produce 21B. 21B can be treated with sodium azide in the presence of LiCl, NH$_4$Cl and DMF in order to produce 21C. 21C can also obtained by reacting 21B with azidotributylstannane. 21C can then be alkylated with LDA and the Boc-protected bromo-aminopyridine, protected with tosyl chloride and finally subjected to TBDMS removal under TBAF conditions to produce 21D. 21D can then be acylated with an isocyanate and all protecting groups removed with TFA to produce desired tetazoles 21E.

Scheme 22

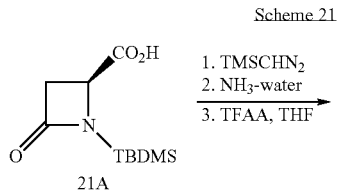

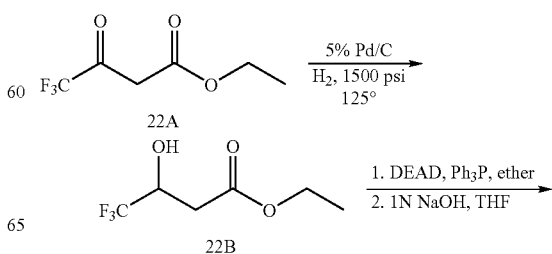

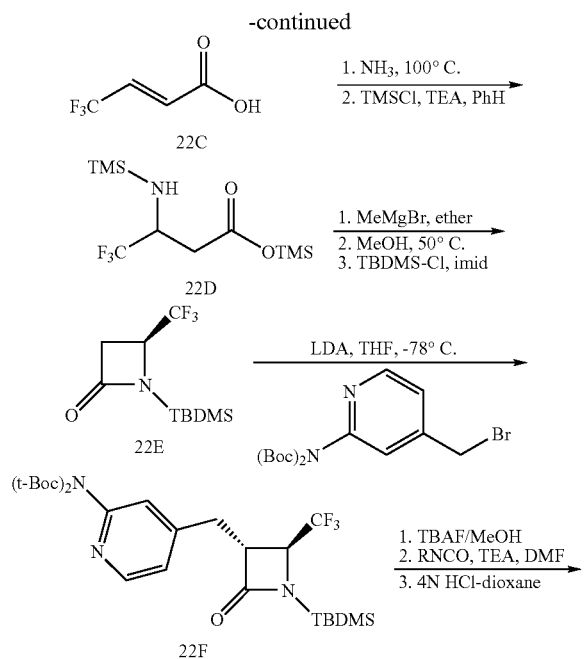
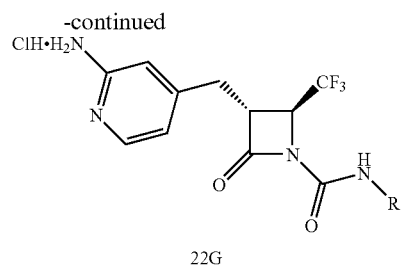

One method of synthesizing compounds of the invention with trifluoromethyl is shown in Scheme 22. 22A can be hydrogenated to provide ketone 22B. Ketone 22B can then be subjected to Mitsunobu conditions followed by elimination to form 22C. 22C can be transformed by Michael addition of ammonia and protection of the amine to give 22D. Treatment of 22D with methylmagnesium bromide to cyclize to the β-lactam followed by methanolysis and TBDMS protection to give 22E. 22E can then be alkylated to give 22F. 22F can be treated with TBAF to remove the TBDMS group, acylated and then all protecting groups removed with TFA to produce desired $CF_3$ compounds of the invention 22G.

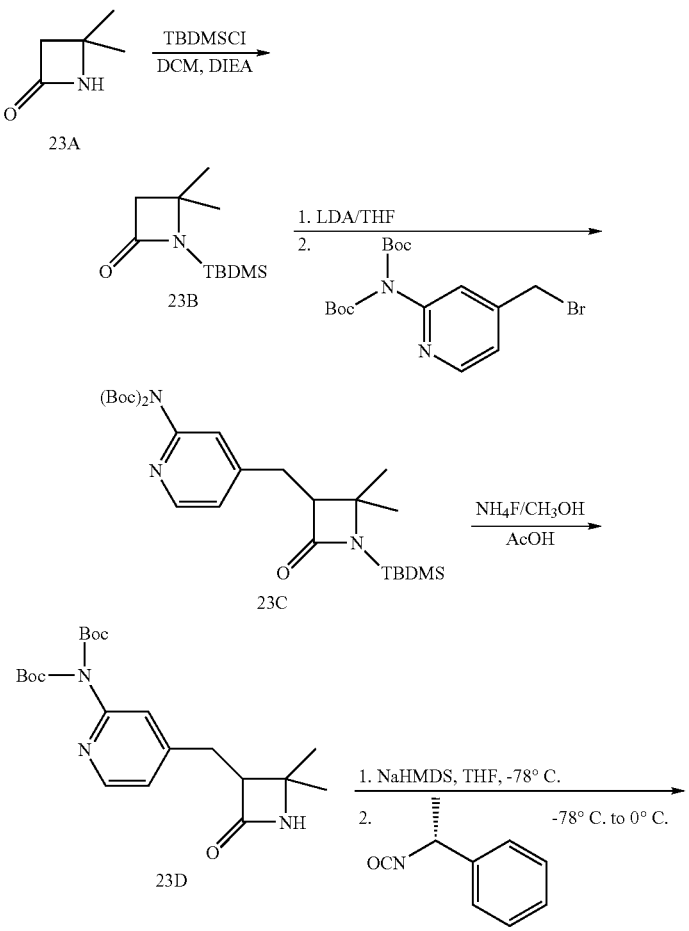

Scheme 23

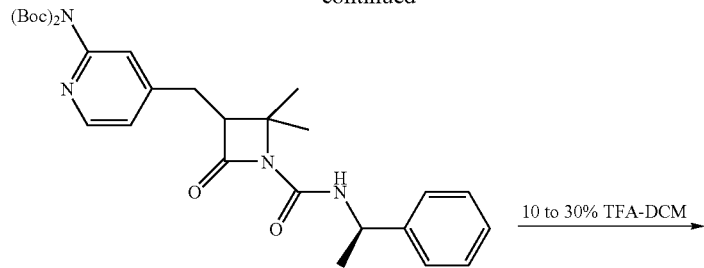

23E

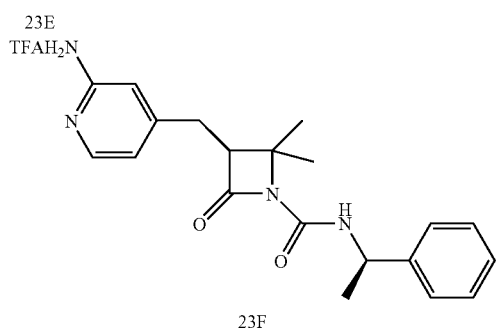

23F

One method of synthesizing compounds of the invention with geminally substituted methyl groups is shown in Scheme 23. 23A can be treated with TBDMSCl and TEA to produce 23B. 23B can be treated with LDA and then Bis-BOC protected 4-(bromomethyl)pyridin-2-amine in order to produce 23C. 23C can be treated with ammonium fluoride in methanol in order to produce 23D. 23D can be treated with NaHMDS and then an isocyanate in order to produce 23E. 23E can be treated with TFA in dichloromethane in order to produce 23F.

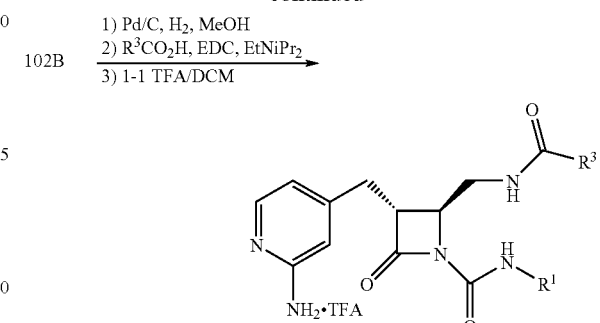

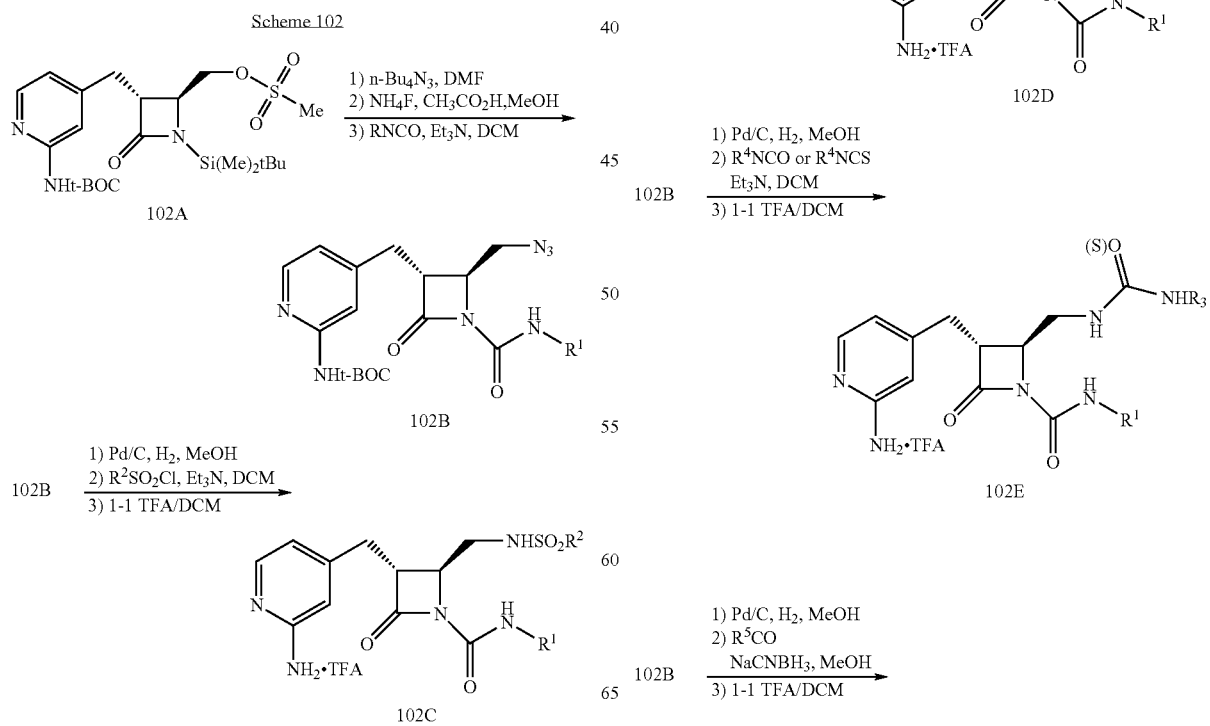

-continued

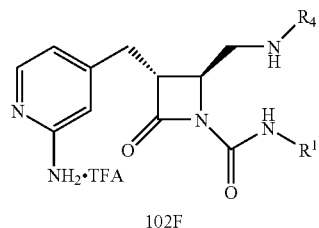

102F

R¹NCO: any isocyanate
R₂SO₂Cl any sulfonyl chloride
R₃CO₂H: any carboxylic acid
R⁴NCO, R⁴NCS: any isocyanate or thioisocyanate
R⁵CHO: any aldehyde A method of synthesizing azetedinones bearing $R_4$ substituents containing sulfonamide, amides, urea, thiourea, and amino groups is shown in Scheme 102. Compound 102A is described in scheme 16. 102A can be converted to 102B by a three step sequence including displacement of the mesylate with azide, desilylation, and acylation with an appropriate isocyanate. 102B can be converted to sulfonamide 102C by a sequence involving reduction, sulfonylation, and BOC deprotection with TFA. Additionally, 102B can be converted to amide 102D by a sequence involving reduction, coupling with a carboxylic acid, and BOC deprotection with TFA. Additionally, 102B can be converted to urea 102E by a sequence involving reduction, acylation with an isocyanate, and BOC deprotection with TFA. Additionally, 102B can be converted to amine 102F by a sequence involving reduction, reductive amination with an aldehyde, and BOC deprotection with TFA.

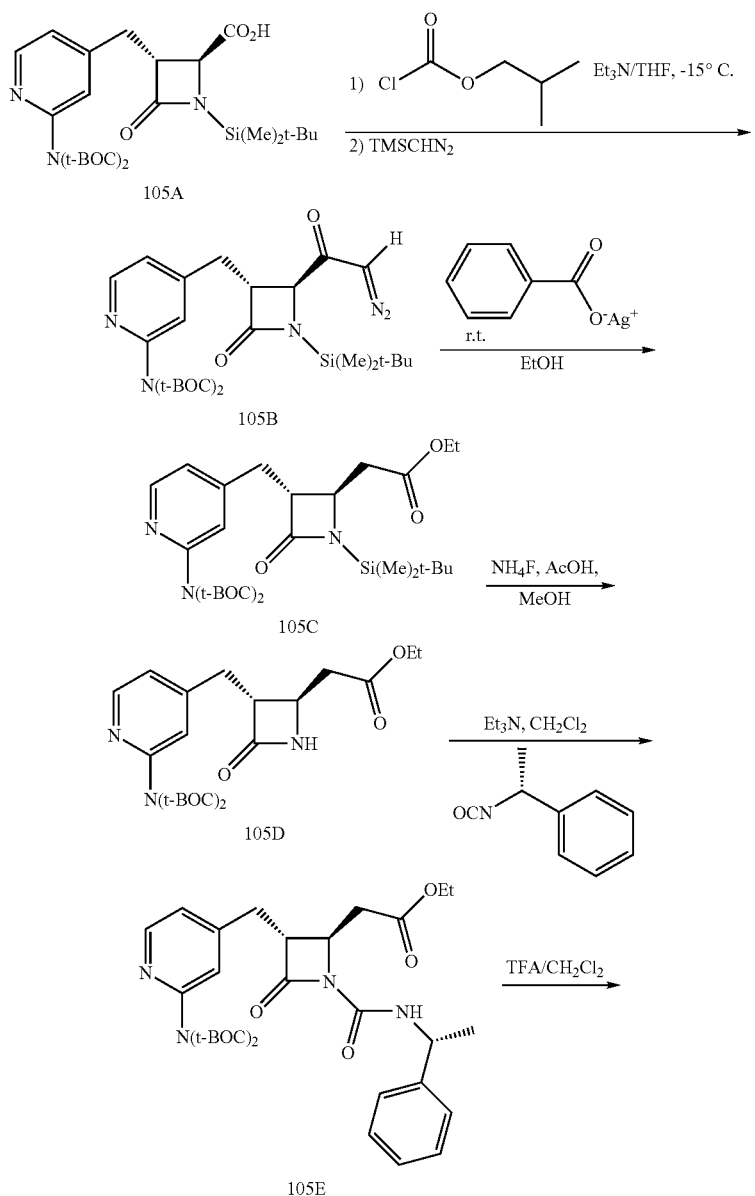

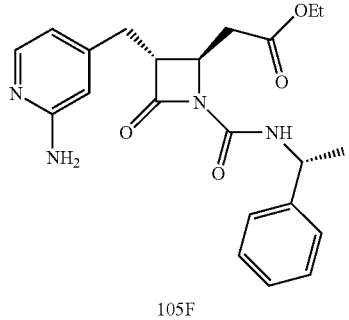

105F

A method of synthesizing azetedinones bearing R₄ substituents bearing a methylene (CH2) group attached to the azetidinone is shown in scheme 105. Acid 105A (scheme 11) can be coverted to diazoketone 105B via the reaction of its mixed anhydride with TMS diazomethane. Silver promoted rearrangement provides 105C. Desilylation can provides 105D. Acylation with an appropriate isocyanate can provide 105E. TFA deprotection can provide 105F.

Scheme 106

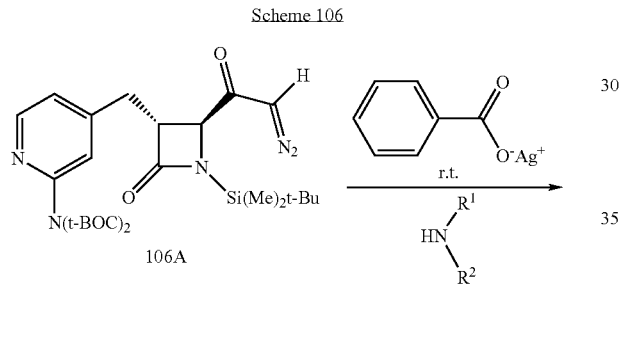

106A

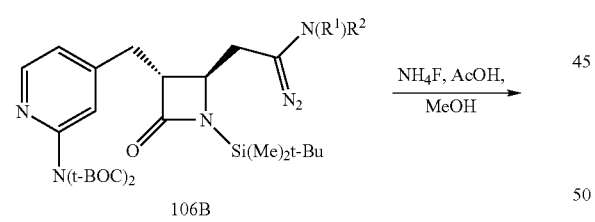

106B

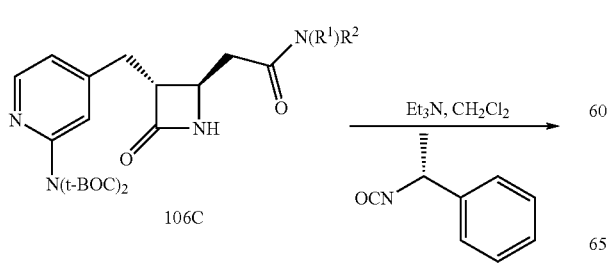

106C

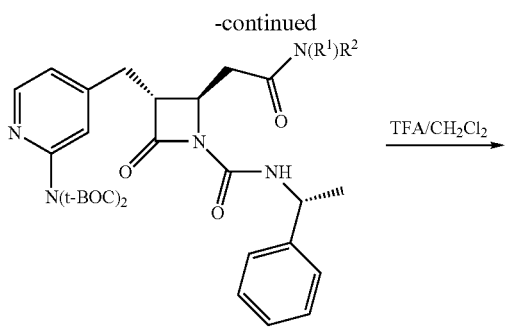

106D

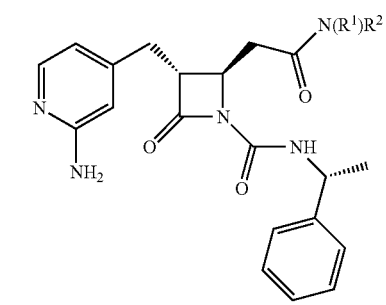

106F

A method of synthesizing azetedinones bearing R₄ substituents bearing a methylene (CH₂) group attached to the azetidinone is shown in scheme 106. Diazoketone 106A (scheme 105) can undergo silver promoted rearrangement in the presence of an amine to provide 106B. Desilylation can provides 106C. Acylation with an appropriate isocyanate can provide 106D. TFA deprotection can provide 106E.

IV. f) Aryloxy

Scheme 24

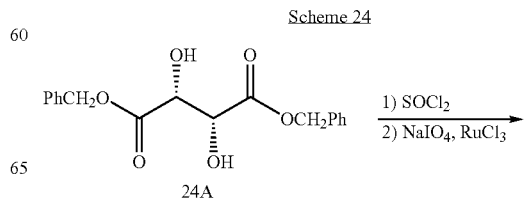

24A

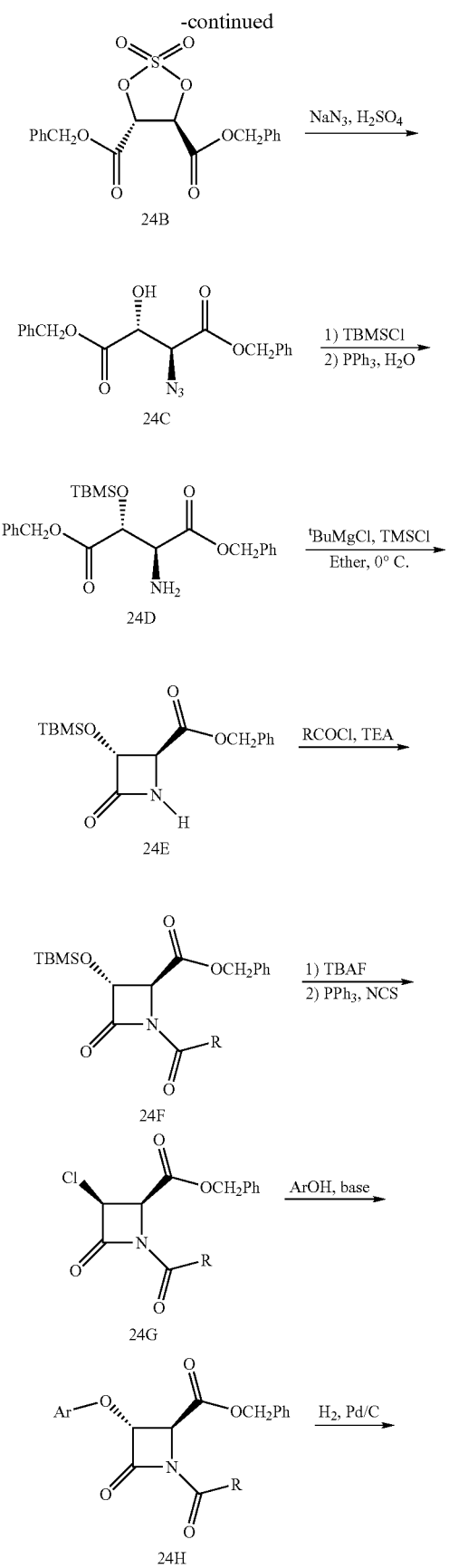

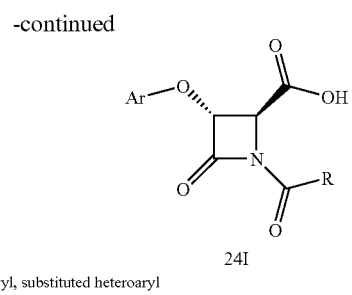

Ar = aryl, substituted aryl, heteroaryl, substituted heteroaryl

One method of synthesizing compounds of the invention with aryloxy substituents is shown in Scheme 24. 24A can be treated with thionyl chloride and then sodium periodate and ruthenium trichloride in order to produce 24B. 24B can be treated with sodium nitrate in sulfuric acid in order to produce 24C. 24C can be treated with TBMSCl and then triphenylphosphine in water in order to produce 24D. 24D can be treated with t-BuMgCl and TMSCl in ether in order to produce 24E. 24E can be treated with an acyl chloride in order to produce 24F. 24F can then be treated with TBAF and then triphenylphosphine and isothiocyanate in order to produce 24G. 24G can be treated with an aryl alcohol (or alternatively a substituted aryl, heteroaryl, or substituted heteroaryl alcohol) and base in order to produce 24H. 24H can be subjected to hydrogenation conditions in order to produce 24I.

IV. g) Heteroaryloxy [pyridinyloxy]

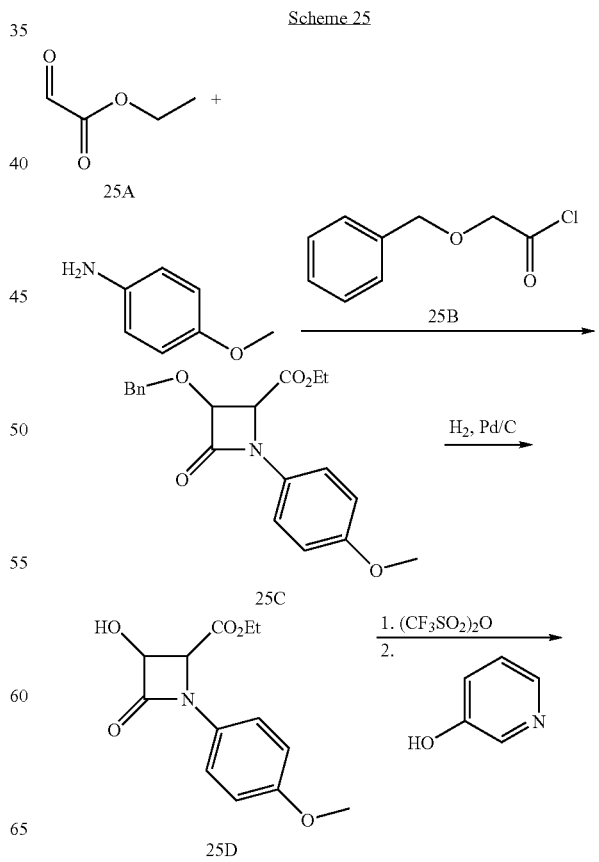

-continued

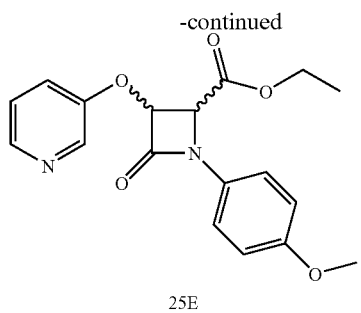

25E

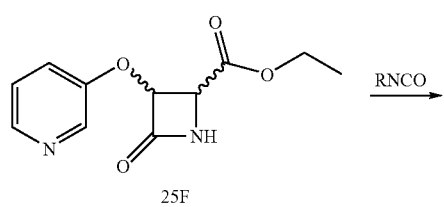

25F

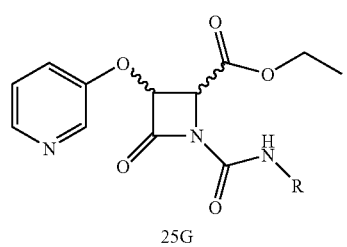

25G

N-Heteroaryloxy substituents on azetidinone compounds can be synthesized as shown in Scheme 25. 25A and 25B can be treated with 4-methoxyaniline under dehydrating conditions to produce an intermediate imine, which is treated with 2-benzyloxyacetylchloride to form compound 25C. 25C can be subjected to catalytic hydrogenation conditions in order to produce 25D. The secondary alcohol of 25D can be activated with $(CF_3SO_2)_2O$ and addition of 3-hydroxypyridine can provide 25E. An alternative path to 23E can be through a Mitsunobu reaction of 25D and 3-hydroxypyridine in the presence of triphenylphosphine and DEAD. 25E can be treated with ceric ammonium nitrate (CAN) in order to produce 25F. 25F can be treated with various isocyanates in order to produce 25G.

IV. h) Heteroarylthio

Scheme 101

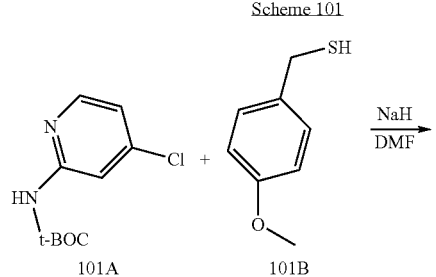

101A   101B

-continued

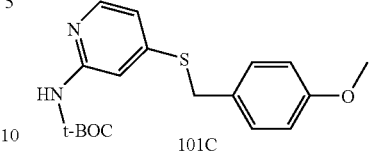

101C

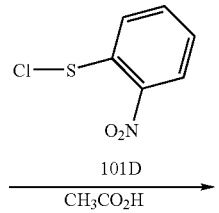

101D

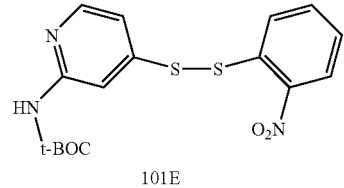

101E

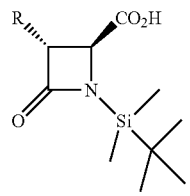

101F

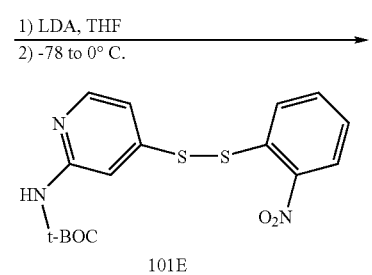

101E

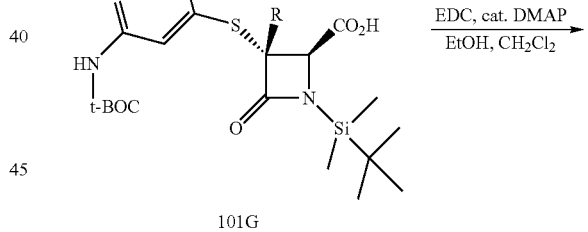

101G

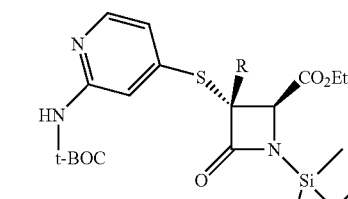

101H

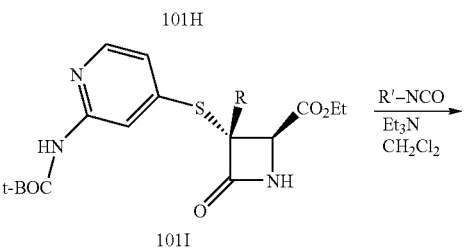

101I

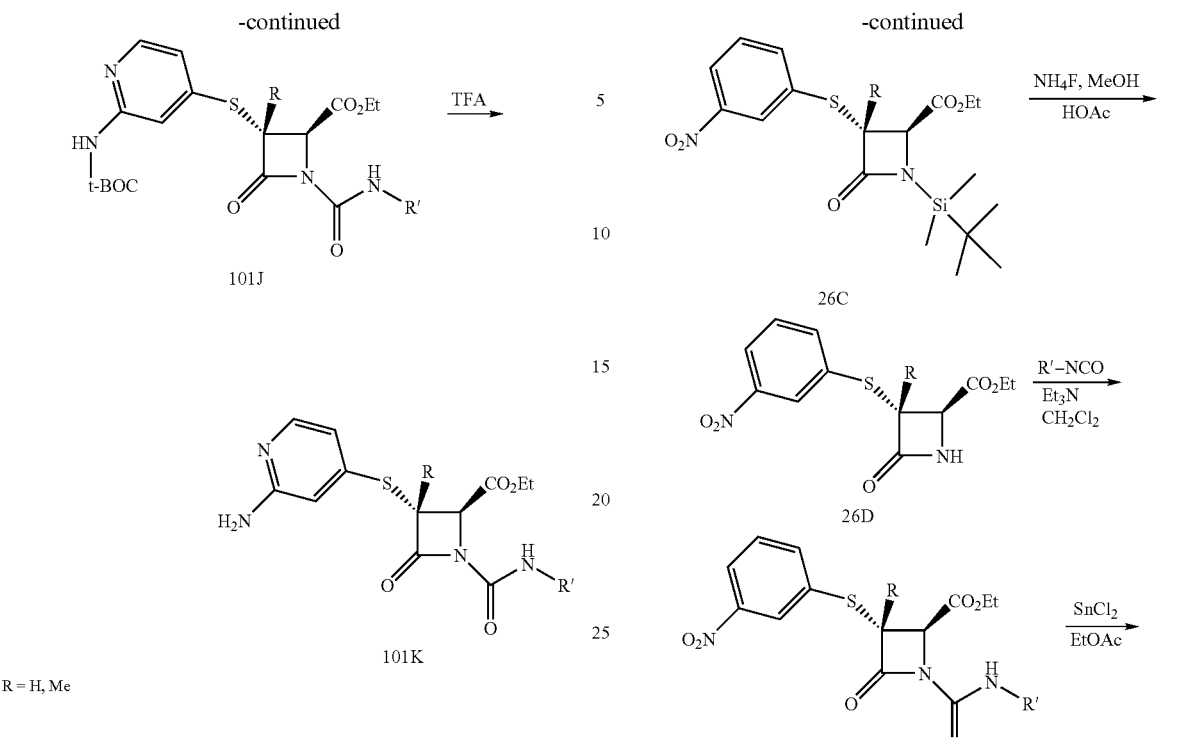

A method of synthesizing heteroarylthio substituents is shown in Scheme 101. Compound 101A can be treated with sulfide 101B to provide thioether 101C. 101C can be treated with sulfenyl chloride 101D to form disulfide 101E. This disulfide can be used to functionalize the dianion of 101F, forming thioether 101G. Esterification with a mixture of ethanol, DMAP, and EDC can provide 101H. The TBDMS group can deprotected using a mixture of ammonium fluoride, acetic acid, and methanol to form 101I. 101I can be treated with various isocyanates in the presence of triethylamine to provide 101J. BOC deprotection with TFA can provide 101K.

IV. i) Arylthio

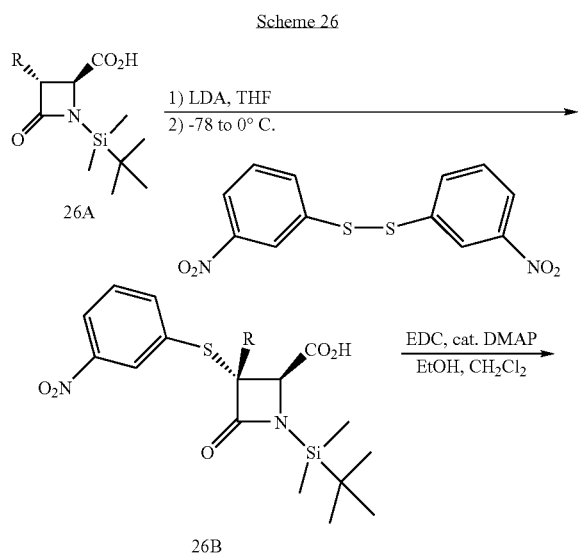

A method of synthesizing arylthio substituents is shown in Scheme 26. Compound 26A can be treated with LDA to form the lithium dianion. Addition of bis-3-nitrophenyldisulfide provides 26B. The carboxylate of 26B can be converted to the ethyl ester using ethanol, DMAP, and EDC. The TBDMS group in the resulting ester 26C can deprotected using ammonium fluoride in methanol. 26D can be treated with various isocyanates in the presence of triethylamine to provide 26E. The nitro group can be reduced using tin (II) chloride to give the aromatic amine 26F.

IV. j) Heteroarylalkoxy

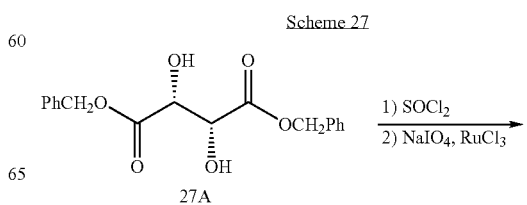

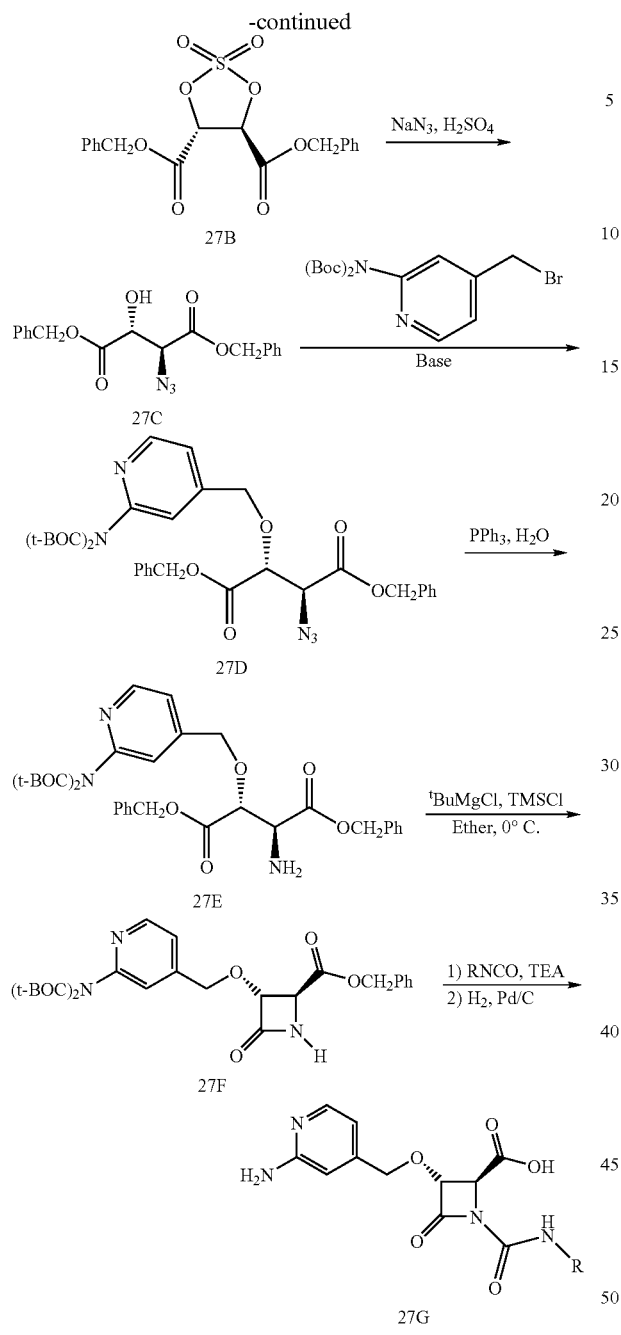

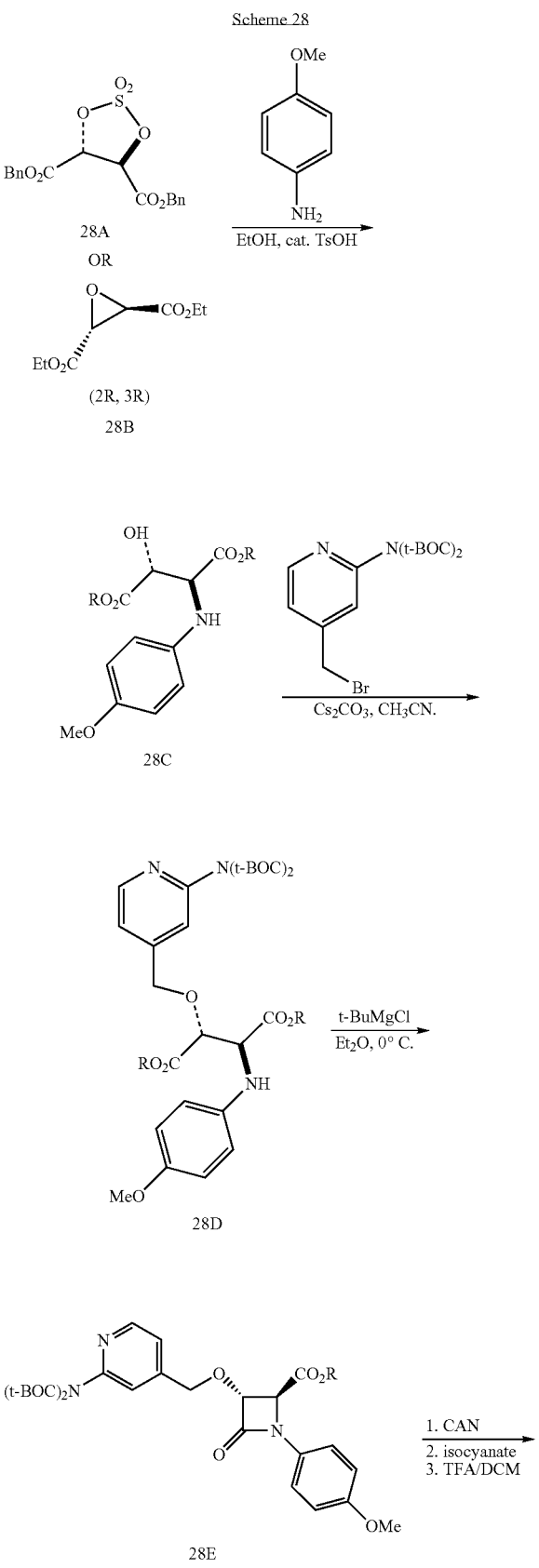

One method of synthesizing compounds of the invention with [2-amino-4-azabenyloxy] substituents is shown in Scheme 27. Dibenzyltartartic acid 27A can be treated with thionyl chloride and then sodium periodate in the presence of ruthenium trichloride in order to produce 27B. 27B can be treated with sodium azide in sulfuric acid in order to produce 27C. Bis-BOC protected-2-amino-4-bromomethyl pyridine can be treated with 27C in the presence of a base in order to produce 27D. The azide group of 27D can be reduced with triphenylphosphine (Staudinger reaction) in the presence of water in order to produce 27E. 27E can be treated with t-BuMgCl and TMSCl in ether to produce 27F. 27F can be treated with an isocyanate and TEA, and then subjected to hydrogenation conditions in order to produce 27G.

-continued

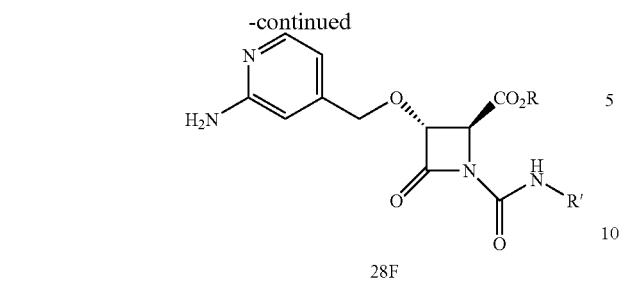

28F

R = Et or CH₂Ph

A method of synthesizing compounds of the invention with [2-amino-pyridinyl] methoxy substituents is shown in Scheme 28. 28A or 28B can be treated with 4-methoxyaniline in ethanol with a catalytic amount of an organic acid in order to produce 28C. 28C can be treated with Bis-BOC protected-2-amino-4-bromomethylpyridine in order to produce 28D. 28D can be treated with t-butylMgCl in ether in order to produce 28E. Deprotection of the 4-methoxyphenyl using CAN followed by reaction with various isocyanates, flowed by BOC removal in TFA/DCM produces 28F.

IV. k) Heteroarylalkylthio

-continued

29F

PMB = para-methoxybenzyl

Heteroarylthio substituents can be synthesized on azetidinone compounds as shown in Scheme 29. 29A can be treated with an equivalent of thiourea, then three equivalents of lithium hydroxide, and then sodium bicarbonate in order to produce 29B. The lithium dianion of 29C can be treated with 29B to provide compound 29E. The carboxylic acid of 29D can be protected as the para-methoxybenzyl ester using para-methoxybenzylalcohol in the presences of EDC and DMAP in order to produce 29E. Deprotection of the TBDMS group of 29E followed by urea formation with isocyanate, and finally TFA deprotection of the BOC groups can produce 29F.

Scheme 29

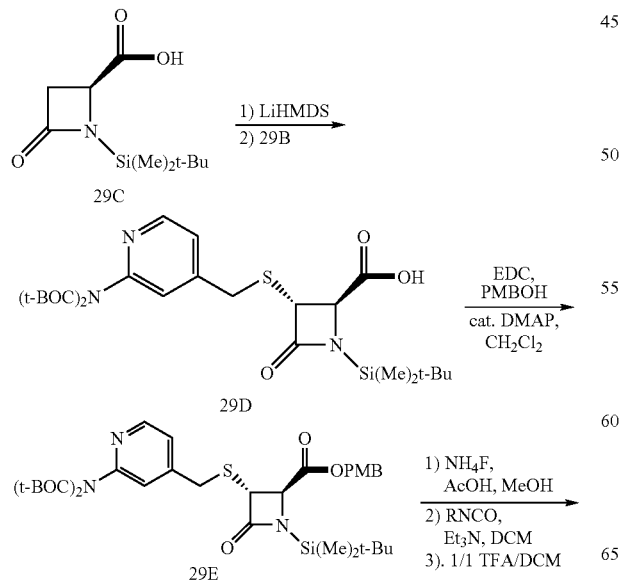

Scheme 30

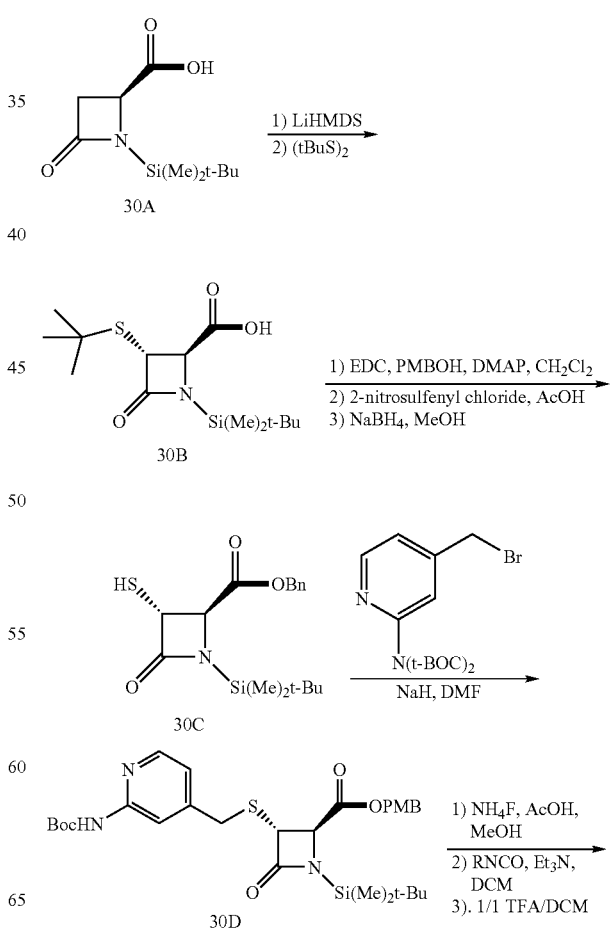

-continued

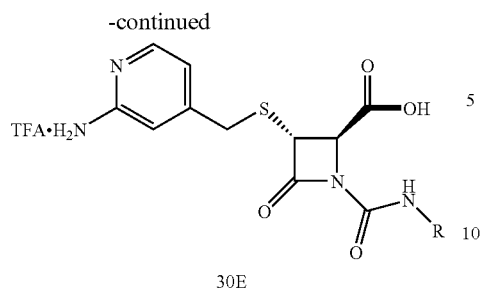

30E

An alternative method of synthesizing heteroarylthio substituents is shown in Scheme 30. 30A can be treated with 2.4 eq. of a lithium reagent to provide the dianion of 30A and then 1.2 eq. of (t-BuS)₂ in order to produce 30B. 30B can be treated with EDC and DMAP in order to produce the benzyl ester 30C. 30C can be treated with Bis-BOC protected-2-amino-4-bromomethylpyridine and sodium hydride in DMF in order to produce 30D. 30D can be treated with ammonium fluoride, then isocyanate and finally TFA in order to produce 30E.

Scheme 31

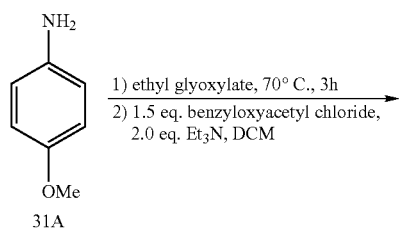

31A

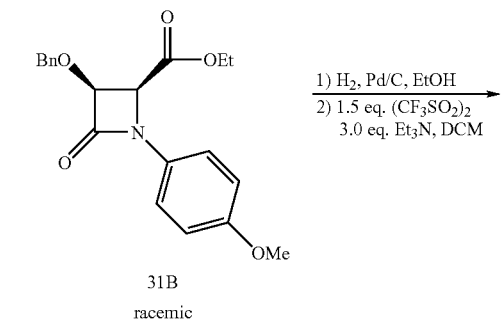

31B
racemic

-continued

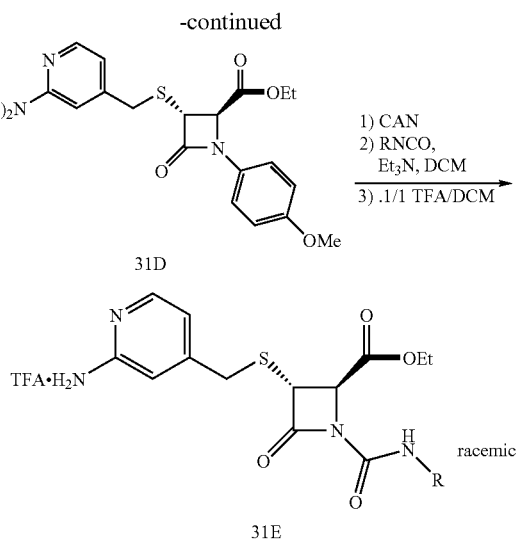

Note: if a chiral isocyanate is used, the two epimers can then be separated

An alternative method of synthesizing heteroarylthio substituents is shown in Scheme 31. 31A can be condensed with ethyl glyoxylate, and the resulting imine can be acylated with an appropriate acid chloride and cyclized to provide 31B. Hydrogenolysis and treatment with triflic anhydride can provide 31C. Displacement of the triflate with an appropriate mercaptan can provide thio ether 31D. Removal of the aryl group with CAN, treatment with an appropriate isocyanate, and deprotection can provide 31E.

IV. 1) Heteroarylalkylamino

Scheme 32

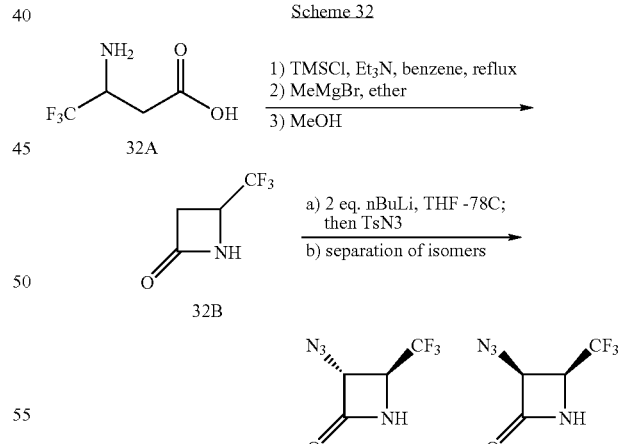

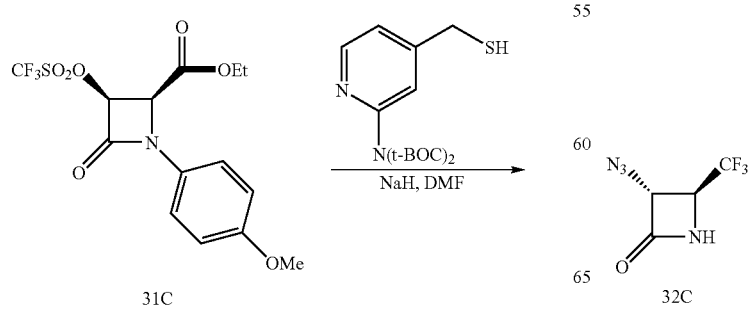

31C

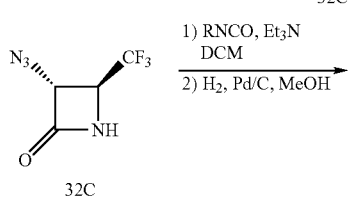

32C

-continued

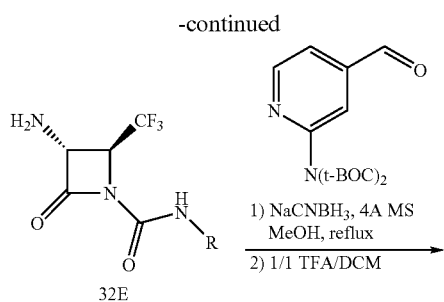

32E

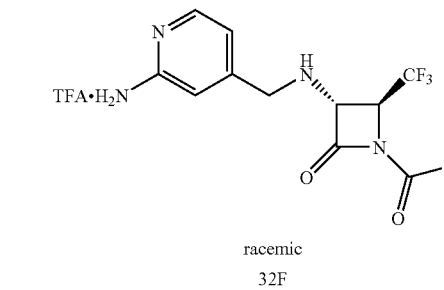

racemic
32F note: if chiral isocyanate is used,
the epimers can be separated

A method of synthesizing compounds with 4-trifluoromethyl substituents is shown in Scheme 32. 32A can be treated with TMS-chloride followed by deprotonation with a Grignard reagent to form 32B. The resulting beta-lactam 32B can be treated with 2 equiv. of n-butyl lithium to provide the dianion with after quenching with tosyl azide to give a mixture of 32C and 32D. Separation of the mixture followed by urea formation and reduction of the azide can provide 32E. 32E can undergo reductive amination with an appropriate aldehyde in the presence of a reducing agent such as NaCNBH$_3$ to provide, after deprotection of the BOC groups with TFA, 32F.

Scheme 33

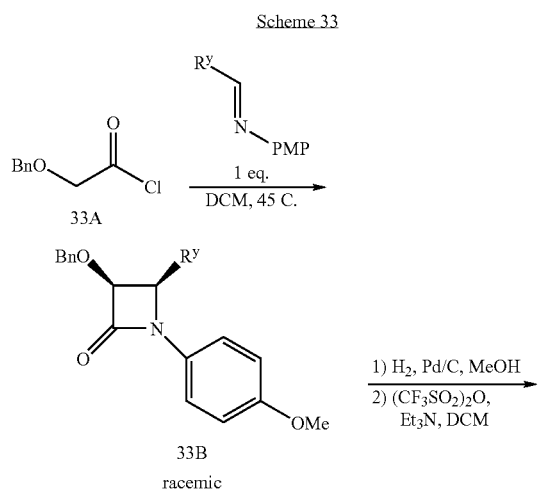

-continued

33C

33D 33E
racemic $R^y$ = CF$_3$, CF$_2$H, CF$_2$Cl

Note: if a chiral isocyanate is used, the two epimers can be separated

A method of synthesizing compounds with halomethyl substituents is shown in Scheme 33. 33B can be prepared by heterocyclization of 33A with various imines. The resulting beta-lactam 33B can be hydrogenolyzed to give the intermediate alcohol with is subsequently activated using trifluoromethanesulfonic anhydride to give triflate 33C. Displacement of the trifluomethanesulfonate with S or O nucleophiles can provide 33D. Deprotection of the para-methoxyphenyl with CAN, urea formation using various isocyanates, and deprotection of the BOC groups with TFA can provide 33E.

IV. m) Thio- β-lactams

Scheme 107

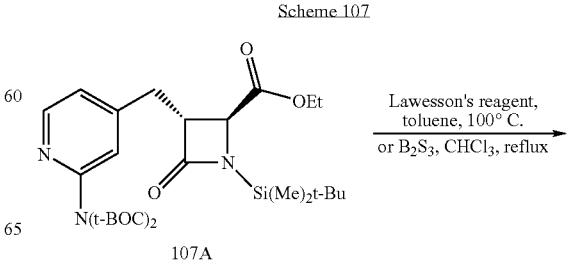

107A

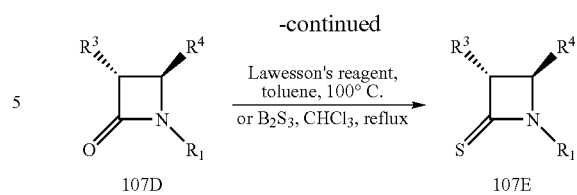

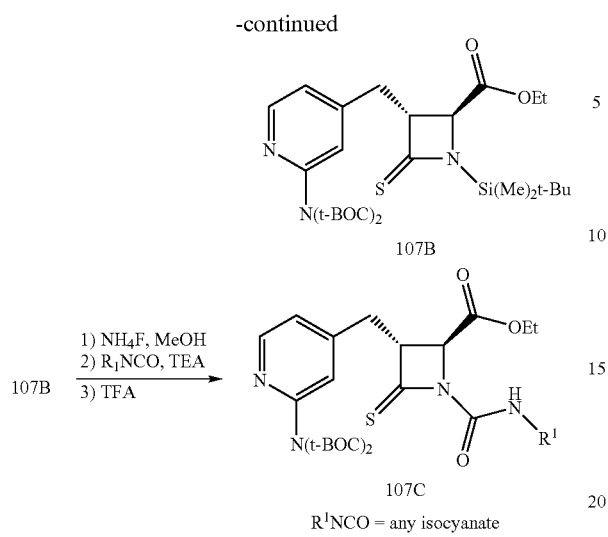

A method of synthesizing thioazetedinones is shown in scheme 107. Beta lactam 107A can be converted to its thio analog 107B. Desilylation, acylation with an appropriate isocyanate, and TFA deprotection can provide 107E. This chemistry may be applied to other beta lactams 107D of this invention to provide thio analogs 107E.

IV. n) Thiourea

Scheme 108

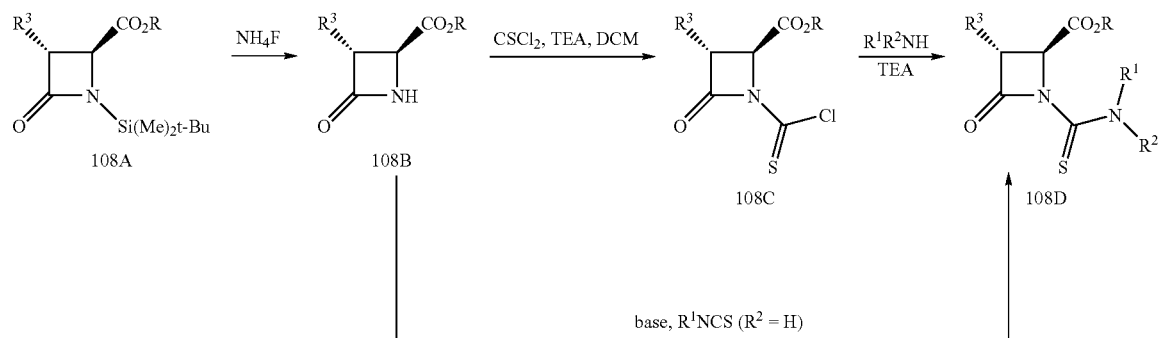

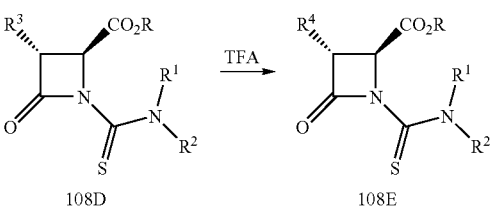

R = H, benzyl, p-methoxybenzyl, alkyl
$R^1$ and $R^2$ = alkyl, aryl, cycloalkyl, etc.

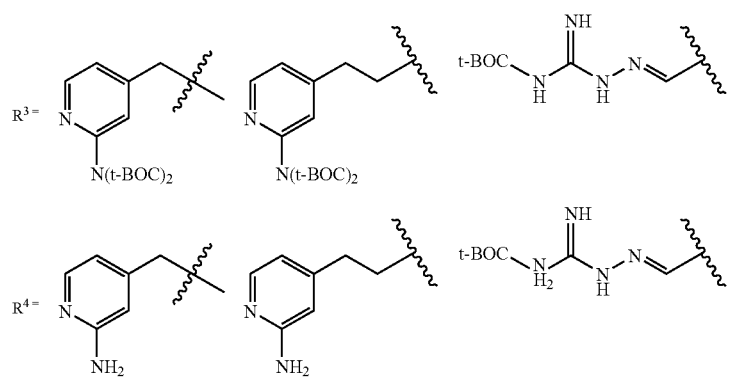

A method of synthesizing azetedinone thioureas is shown in scheme 108. An appropriate ester 108A (see schemes 7 and 11) can be desilylated to provide 108B. 108B can be converted either directed to 108D via a thioisocyanate acylation or in a two step procedure involving intermediate chloride 108C. TFA deprotection can provide 108E.

IV. o) Additional Exemplary Moieties

In another exemplary embodiment, the compounds of the invention comprise a moiety that increases the water-solubility of the parent compound. This moiety can be covalently attached, directly or indirectly, to the 1, 2, 3 or 4 position on the azetidinone ring. Exemplary moieties of use for increasing a compound's water solubility include ethers and polyethers, e.g., a member selected from ethylene glycol, and ethylene glycol oligomers, having a molecular weight of from about 60 daltons to about 10,000 daltons, and more preferably of from about 100 daltons to about 1,000 daltons.

Representative polyether-based substituents include, but are not limited to, the following structures:

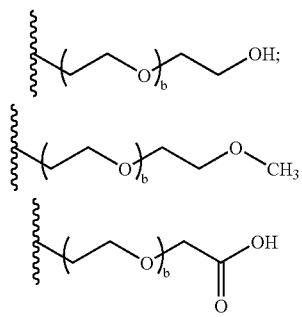

in which b is preferably a number from 1 to 100, inclusive. Other functionalized polyethers are known to those of skill in the art, and many are commercially available from, for example, Shearwater Polymers, Inc. (Alabama).

In another exemplary embodiment, the compounds of the invention comprise a moiety that includes a reactive functional group for conjugating the compound to another molecule or to a surface. This moiety can be attached, directly or indirectly, to the 1, 2, 3 or 4 position on the azetidinone ring. The linkers of use in the compounds of the invention can also include a cleaveable group. In an exemplary embodiment, the cleaveable group is interposed between the azetidinone core and a targeting agent or macromolecular backbone. Representative useful reactive groups are discussed in greater detail in succeeding sections. Additional information on useful reactive groups is known to those of skill in the art. See, for example, Hermanson, BIOCONJUGATE TECHNIQUES, Academic Press, San Diego, 1996.

Reactive Functional Groups

As discussed above, the azetidinone core of the compounds of the invention are optionally tethered to other species by means of bonds formed between a reactive functional group on the azetidinone or a linker attached to the azetidinone, and a reactive functional group of complementary reactivity on the other species. For clarity of illustration the succeeding discussion focuses on the conjugation of representative azetidinones of the invention to polymers, including poly(ethers) and dendrimers, and to targeting agents useful for translocating the azetidinone-targeting agent conjugate across a membrane. The focus exemplifies selected embodiments of the invention from which others are readily inferred by one of skill in the art. No limitation of the invention is implied, by focusing the discussion on the representative embodiments.

Exemplary azetidinones of the invention bear a reactive functional group, which is generally located on the azetidinone ring or on a substituted or unsubstituted alkyl or heteroalkyl chain attached to the ring, allowing their facile attachment to another species. A convenient location for the reactive group is the terminal position of an alkyl or heteroalkyl substituent of the azetidinone core.

Reactive groups and classes of reactions useful in practicing the present invention are generally those that are well known in the art of bioconjugate chemistry. Currently favored classes of reactions available with reactive analogues are those proceeding under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Exemplary reaction types include the reaction of carboxyl groups and various derivatives thereof including, but not limited to, N-hydroxysuccinimide esters, N-hydroxybenzotriazole esters, acid halides, acyl imidazoles, thioesters, p-nitrophenyl esters, alkyl, alkenyl, alkynyl and aromatic esters. Hydroxyl groups can be converted to esters, ethers, aldehydes, etc. Haloalkyl groups are converted to new species by reaction with, for example, an amine, a carboxylate anion, thiol anion, carbanion, or an alkoxide ion. Dienophile (e.g., maleimide) groups participate in Diels-Alder. Aldehyde or ketone groups can be converted to imines, hydrazones, semicarbazones or oximes, or reacted via such mechanisms as Grignard addition or alkyllithium addition. Sulfonyl halides react readily with amines, for example, to form sulfonamides. Amine or sulfhydryl groups are, for example, acylated, alkylated or oxidized. Alkenes can be converted to an array of new species using cycloadditions, acylation, Michael addition, etc. Epoxides react readily with amines and hydroxyl compounds.

Exemplary combinations of reactive functional groups found on a ligand of the invention and on a targeting moiety (or polymer or linker) are set forth in Table 1.

TABLE 1

| Chemical Functionality 1 | Chemical Functionality 2 | Linkage |
|---|---|---|
| Hydroxy | Carboxy | Ester |
|  | Hydroxy | Carbonate |
|  | Amine | Carbamate |
|  | SO$_3$ | Sulfate |
|  | PO$_3$ | Phosphate |
|  | Carboxy | Acyloxyalkyl |
|  | Ketone | Ketal |
|  | Aldehyde | Acetal |
|  | Hydroxy | Anhydride |
| Mercapto | Mercapto | Disulfide |
|  | Carboxy | Acyloxyalkyl |
|  |  | Thioether |
|  | Carboxy | Thioester |
|  | Carboxy | Amino amide |
|  | Mercapto | Thioester |

TABLE 1-continued

| Chemical Functionality 1 | Chemical Functionality 2 | Linkage |
|---|---|---|
| | Carboxy | Acyloxyalkyl ester |
| | Carboxy | Acyloxyalkyl amide |
| | Amino | Acyloxyalkoxy carbonyl |
| | Carboxy | Anhydride |
| | Carboxy | N-acylamide |
| | Hydroxy | Ester |
| | Hydroxy | Hydroxymethyl ketone ester |
| | Hydroxy | Alkoxycarbonyl oxyalkyl |
| Amino | Carboxy | Acyloxyalkylamine |
| | Carboxy | Acyloxyalkylamide |
| | Amino | Urea |
| | Carboxy | Amide |
| | Carboxy | Acyloxyalkoxycarbonyl |
| | Amide | N-Mannich base |
| | Carboxy | Acyloxyalkyl carbamate |
| Phosphate | Hydroxy | Phosphate |
| oxygen ester | Amine | Phosphoramidate |
| | Mercapto | Thiophosphate ester |
| Ketone | Carboxy | Enol ester |
| Sulfonamide | Carboxy | Acyloxyalkyl sulfonamide |
| | Ester | N-sulfonyl-imidate |

One skilled in the art will readily appreciate that many of these linkages may be produced in a variety of ways and using a variety of conditions. For the preparation of esters, see, e.g., March supra at 1157; for thioesters, see, March, supra at 362-363, 491, 720-722, 829, 941, and 1172; for carbonates, see, March, supra at 346-347; for carbanates, see March, supra at 1156-57; for amides, see, March supra at 1152; for ureas and thioureas, see, March supra al 1174; for acetals and ketals, see, Greene et al. supra 178-210 and March supra at 1146; for acyloxyalkyl derivatives, see, PRODRUGS: TOPICAL AND OCULAR DRUG DELIVERY, K. B. Sloan, ed., Marcel Dekker, Inc., New York, 1992; for enol esters, see, March supra at 1160; for N-sulfonylimidates, see, Bundgaard et al., *J. Med. Chem.*, 31:2066 (1988); for anhydrides, see, March supra at 355-56, 636-37, 990-91, and 1154; for N-acylamides, see, March supra at 379; for N-Mannich bases, see, March supra at 800-02, and 828; for hydroxymethyl ketone esters, see, Petracek et al. *Annals NY Acad. Sci.*, 507:353-54 (1987); for disulfides, see, March supra at 1160; and for phosphonate esters and phosphonamidates.

The reactive functional groups can be chosen such that they do not participate in, or interfere with, the reactions necessary to assemble the reactive ligand analogue. Alternatively, a reactive functional group can be protected from participating in the reaction by the presence of a protecting group. Those of skill in the art will understand how to protect a particular functional group from interfering with a chosen set of reaction conditions. For examples of useful protecting groups, see Greene et al., PROTECTIVE GROUPS IN ORGANIC SYNTHESIS, John Wiley & Sons, New York, 1991.

Generally, prior to forming the linkage between the ligand and the targeting (or other) agent, and optionally, the linker group, at least one of the chemical functionalities is activated. One skilled in the art will appreciate that a variety of chemical functionalities, including hydroxy, amino, and carboxy groups, can be activated using a variety of standard methods and conditions. For example, a hydroxyl group of the ligand (or targeting agent) can be activated through treatment with phosgene to form the corresponding chloroformate, or pnitrophenylchloroformate to form the corresponding carbonate.

In an exemplary embodiment, the invention makes use of a targeting agent that includes a carboxyl functionality. Carboxyl groups may be activated by, for example, conversion to the corresponding acyl halide or active ester. This reaction may be performed under a variety of conditions as illustrated in March, supra pp. 388-89. In an exemplary embodiment, the acyl halide is prepared through the reaction of the carboxyl-containing group with oxalyl chloride. The activated agent is combined with a ligand or ligand-linker arm combination to form a conjugate of the invention. Those of skill in the art will appreciate that the use of carboxyl-containing targeting agents is merely illustrative, and that agents having many other functional groups can be conjugated to the ligands of the invention.

Targeting Groups

The compounds of the invention may also be conjugated to an agent that targets the compound to a specific tissue or region of disease. The compound of the invention can be targeted for specific delivery to the cells to be treated by conjugation of the compounds to a targeting agent. The term "targeting agent" refers to a species that serves to deliver the compound of the invention to a specific site. Targeting agents include, for example, molecules that specifically bind molecules present on a cell surface. Such targeting agents useful in the invention include anti-cell surface antigen antibodies; cytokines, including interleukins, factors such as epidermal growth factor (EGF), and the like, are also specific targeting agents known to bind cells expressing high levels of their receptors. Targeting agents include species that are taken up by cells using either active or passive mechanisms.

Particularly useful targeting agents for targeting the compounds of the invention to cells for therapeutic activity include those ligands that bind antigens or receptors present on virus-infected cells to be treated. For example, antigens present on T-cells, such as CD48, can be targeted with antibodies. Antibody fragments, including single chain fragments, can also be used. Other such ligand-receptor binding pairs are known in the scientific literature for targeting antiviral treatments to target cells. Methods for producing conjugates of the compounds of the invention and the targeting moieties are known.

Membrane translocation polypeptides are another exemplary targeting agent. Membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, *Current Opinion in Neurobiology* 6:629-634 (1996)). Another subsequence, the h (hydrophobic) domain of signal peptides, was found to have similar cell membrane translocation characteristics (see, e.g., Lin et al., *J. Biol. Chem.* 270: 14255-14258 (1995)).

Examples of peptide sequences include, but are not limited to: an 11 amino acid peptide of the tat protein of HIV; a 20 residue peptide sequence which corresponds to amino acids 84-103 of the p16 protein (see Fahraeus et al., *Current Biology* 6:84 (1996)); the third helix of the 60-amino acid long homeodomain of Antennapedia (Derossi et al., *J. Biol. Chem.* 269:10444 (1994)); the h region of a signal peptide such as the Kaposi fibroblast growth factor (K-FGF) h region (Lin et al., supra); or the VP22 translocation domain from HSV (Elliot & O'Hare, *Cell* 88:223-233 (1997)). Other suitable chemical moieties that provide enhanced cellular uptake may also be chemically linked to the compounds of the invention.

Such subsequences can be used to translocate compounds of the invention across a cell membrane. Compounds of the invention can be conveniently fused to or derivatized with such sequences. Typically, the translocation sequence is provided as part of a fusion protein. Optionally, a linker as described herein can be used to link the compound of the invention and the translocation sequence. Any suitable linker can be used, e.g., a peptide linker or other chemical linkers.

Toxin molecules also have the ability to transport compounds across cell membranes. Often, such molecules are composed of at least two parts (called "binary toxins"): a translocation or binding domain or polypeptide and a separate toxin domain or polypeptide. Typically, the translocation domain or polypeptide binds to a cellular receptor, and then the toxin is transported into the cell. Several bacterial toxins, including *Clostridium perfringens* iota toxin, diphtheria toxin (DT), *Pseudomonas* exotoxin A (PE), pertussis toxin (PT), *Bacillus anthracis* toxin, and pertussis adenylate cyclase (CYA), have been used in attempts to deliver peptides to the cell cytosol as internal or amino-terminal fusions (Arora et al., *J. Biol. Chem.*, 268: 3334-3341 (1993); Perelle et al., *Infect. Immun.*, 61: 5147-5156 (1993); Stenmark et al., *J. Cell Biol.* 113: 1025-1032 (1991); Donnelly et al., *PNAS U.S.A.* 90: 3530-3534 (1993); Carbonetti et al., *Abstr. Annu. Meet. Am. Soc. Microbiol.* 95: 295 (1995); Sebo et al., *Infect. Immun.* 63:3851-3857 (1995); Klimpel et al., *PNAS U.S.A.* 89:10277-10281 (1992); and Novak et al., *J. Biol. Chem.* 267:17186-17193 (1992)).

Non-covalent protein binding groups are also of use to target the compounds of the invention to specific regions of the body and to increase the half-life of the agent through protein binding.

Macromolecular Conjugates

In an exemplary embodiment, the invention provides a macromolecular, i.e., MW>1000 D, conjugate between the azetidinone core and a macromolecular species. In one embodiment, a macromolecular conjugate of the invention is formed by covalently conjugating an azetidinone to a macromolecule via a reactive functional group. In another embodiment, the macromolecular conjugate is formed by a non-covalent interaction between a azetidinone derivative and a macromolecule, e.g., a serum protein.

In the following discussion, the invention is described by reference to specific macromolecules of use for forming conjugates with the novel azetidinone cores of the invention. Those of skill in the art will appreciate that the focus of the discussion is for clarity of illustration and does not limit the scope of the invention. The invention provides macromolecular conjugates that include components derived from biomolecules and synthetic molecules. Exemplary biomolecules include polypeptides (e.g., antibodies, enzymes, receptors, antigens, immunogens such as KLH (keyhole limpet hemocyanin), BSA (bovine serum albumin) and HSA (human serum albumin); polysaccharides (e.g., starches, inulin, dextran); lectins, nonpeptide antigens and the like. Exemplary synthetic polymers include poly(acrylic acid), poly(l-ysine), poly(glutamic acid), poly(ethylene imine), etc.

Covalent Conjugation

Selection of an appropriate reactive functional group on an azetidinone core of the invention to form a desired macromolecular species is well within the abilities of one of skill in the art. Exemplary reactive functional groups of use in forming the covalent conjugates of the invention are discussed above.

It is well within the abilities of one of skill to select and prepare an azetidinone core of the invention having an appropriate reactive functional group of complementary reactivity to a reactive group on its conjugation partner.

In one embodiment, the bond formed between reactive functional groups of the macromolecule and that of the azetidinone attaches the azetidinone to the macromolecule essentially irreversibly via a "stable bond" between the components. A "stable bond", as used herein, is a bond, which maintains its chemical integrity over a wide range of conditions (e.g., amide, carbamate, carbon-carbon, ether, etc.). In another embodiment, a "cleaveable bond" links the macromolecule and the azetidinone. A "cleaveable bond", as used herein, is a bond that undergoes scission under selected conditions. Cleaveable bonds include, but are not limited to, disulfide, imine, carbonate and ester bonds. As discussed in the preceding sections, the reactive functional group can be located at one or more positions of the azetidinone.

Polysaccharides

In an exemplary embodiment, the present invention provides conjugates between an azetidinone core and saccharides, e.g., polysaccharides. In an exemplary embodiment, the invention provides a conjugate between a azetidinone and inulin. Inulin is a naturally occurring polysaccharide, which has been previously investigated as a carrier for diagnostic moieties (Rongved, P. K., *J. Carbohydr. Res.* 1991, 214, 315; Corsi, D. M. V. E. et al., *Chem. Eur. J.* 2001, 7, 64). The structure of inulin can be described as a mixture of linear β-(2→1)-linked α-D-fructofuranosyl chains with a α-D-glucopyranosyl unit at the terminal end. Inulin is commercially available in a variety of molecular weights and the degree of polymerization varies from 10 to 30, resulting in a molecular weight distribution of 1500 to 5000 Da. The high hydrophilicity, pH stability, low solution viscosity and biocompatability of inulin ensure that its conjugates have favorable pharmacological properties.

Dendrimer-Based Agents

In another aspect, the present invention provides a azetidinone as set forth above, which is attached to a dendrimer via a reactive functional group. Similar to the polymeric group discussed above, the dendrimer has at least two reactive functional groups. In one embodiment, one or more formed azetidinone is attached to the dendrimer. Alternatively, the azetidinone is formed directly on the dendrimer.

In an exemplary embodiment, a water-soluble and bio-adapted polyester (polypropionate) class of dendrimers has been designed to provide favorable pharmacokinetic properties. See., for example, Ihre, H. et al., *Macromolecules* 1998, 31, 4061; Ihre, H. et al., *J. Am. Chem. Soc.* 1996, 118, 6388; Anders, H., Ihre, H., Patent W0/9900440 (Sweden)). In an exemplary embodiment, the termini of the dendrimers are conjugated to a azetidinone core of the invention.

Poly(ethylene glycol)-Based Agents

In another exemplary embodiment, the invention provides a conjugate between a azetidinone core of the invention and poly(ethylene glycol). Poly(ethylene glycol) (PEG) is used in biotechnology and biomedical applications. The use of this agent has been reviewed (POLY(ETHYLENE GLYCOL) CHEMISTRY: BIOTECHNICAL AND BIOMEDICAL APPLICATIONS, J. M. Harris, Ed., Plenum Press, New York, 1992). Modification of enzymes (Chiu et al., *J. Bioconjugate Chem.*, 4: 290-295 (1993)), RGD peptides (Braatz et al., *Bioconjugate Chem.*, 4: 262-267 (1993)), liposomes (Zalipsky, S. *Bioconjugate Chem.*, 4: 296-299 (1993)), and CD4-IgG glycoprotein (Chamow et al.,

*Bioconjugate Chem.*, 4: 133-140 (1993)) are some of the recent advances in the use of polyethylene glycol. Surfaces treated with PEG have been shown to resist protein deposition and have improved resistance to thrombogenicity when coated on blood contacting biomaterials (Merrill, "Poly(ethylene oxide) and Blood Contact: A Chronicle of One Laboratory," in POLY(ETHYLENE GLYCOL) CHEMISTRY: BIOTECHNICAL AND BIOMEDICAL APPLICATIONS, Harris, Ed., Plenum Press, New York, (1992), pp. 199-220).

Many routes are available for attaching an azetidinone core of the invention onto a polymeric or oligomeric species. See, for example, Dunn, R. L., et al., Eds. POLYMERIC DRUGS AND DRUG DELIVERY SYSTEMS, ACS Symposium Series Vol. 469, American Chemical Society, Washington, D.C. 1991; Herren et al., *J. Colloid and Interfacial Science* 115: 46-55 (1987); Nashabeh et al., *J. Chromatography* 559: 367-383 (1991); Balachandar et al., *Langmuir* 6: 1621-1627 (1990); and Burns et al., *Biomaterials* 19: 423-440 (1998).

Many activated derivatives of poly(ethyleneglycol) are available commercially and in the literature. It is well within the abilities of one of skill to choose, and synthesize if necessary, an appropriate activated PEG derivative with which to prepare a conjugate useful in the present invention. See, Abuchowski et al. *Cancer Biochem. Biophys.*, 7: 175-186 (1984); Abuchowski et al., *J. Biol. Chem.*, 252: 3582-3586 (1977); Jackson et al., *Anal. Biochem.*, 165: 114-127 (1987); Koide et al., *Biochem Biophys. Res. Commun.*, 111: 659-667 (1983)), tresylate (Nilsson et al., *Methods Enzymol.*, 104: 56-69 (1984); Delgado et al., *Biotechnol. Appl. Biochem.*, 12: 119-128 (1990)); N-hydroxysuccinimide derived active esters (Buckmann et al., *Makromol. Chem.*, 182: 1379-1384 (1981); Joppich et al., *Makromol. Chem.*, 180: 1381-1384 (1979); Abuchowski et al., *Cancer Biochem. Biophys.*, 7: 175-186 (1984); Katre et al. *Proc. Natl. Acad. Sci. U.S.A.*, 84: 1487-1491 (1987); Kitamura et al., *Cancer Res.*, 51: 4310-4315 (1991); Boccu et al., *Z. Naturforsch.*, 38C: 94-99 (1983), carbonates (Zalipsky et al., POLY(ETHYLENE GLYCOL) CHEMISTRY: BIOTECHNICAL AND BIOMEDICAL APPLICATIONS, Harris, Ed., Plenum Press, New York, 1992, pp. 347-370; Zalipsky et al., *Biotechnol. Appl. Biochem.*, 15: 100-114 (1992); Veronese et al., *Appl. Biochem. Biotech.*, 11: 141-152 (1985)), imidazolyl formates (Beauchamp et al., *Anal. Biochem.*, 131: 25-33 (1983); Berger et al., *Blood*, 71: 1641-1647 (1988)), 4-dithiopyridines (Woghiren et al., *Bioconjugate Chem.*, 4: 314-318 (1993)), isocyanates (Byun et al., *ASAIO Journal*, M649-M653 (1992)) and epoxides (U.S. Pat. No. 4,806,595, issued to Noishiki et al, (1989). Other linking groups include the urethane linkage between amino groups and activated PEG. See, Veronese, et al., *Appl. Biochem. Biotechnol.*, 11: 141-152 (1985).

V. Pharmaceutical Compositions and Methods of Treatment

The pharmaceutical compositions, or pharmaceutical formulations, of the invention can take a variety of forms adapted to the chosen route of administration. In general, they include a compound of the invention and at least one pharmaceutical excipient. Those skilled in the art will recognize various synthetic methodologies that may be employed to prepare non-toxic pharmaceutical formulations incorporating the compounds described herein. Those skilled in the art will recognize a wide variety of non-toxic pharmaceutically acceptable solvents that may be used to prepare solvates of the compounds of the invention, such as water, ethanol, propylene glycol, mineral oil, vegetable oil and dimethylsulfoxide (DMSO).

The compositions of the invention may be administered orally, topically, parenterally, by inhalation or spray or rectally in dosage unit formulations containing conventional non-toxic pharmaceutically acceptable carriers, adjuvants and vehicles. It is further understood that the best method of administration may be a combination of methods. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques.

The pharmaceutical formulations containing compounds of the invention are preferably in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical formulations, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ); and agents to control release such as polyacrylic copolymer (e.g., CARBOPOL 934). Lubricants, glidants, flavors, coloring agents and stabilizers may also be added for ease of fabrication and use.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; and dispersing or wetting agents, which may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical formulations of the invention may also be in the form of oil-in-water emulsions and water-in-oil emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth; naturally-occurring phosphatides, for example soy bean, lecithin, and esters or partial esters derived from fatty acids and hexitol; anhydrides, for example sorbitan monooleate; and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical formulations may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The composition of the invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Alternatively, the compositions can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition containing the therapeutic compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water. The composition can also added as a food or drink supplement for humans.

Dosage levels of the order of from about 5 mg to about 250 mg per kilogram of body weight per day and more preferably from about 25 mg to about 150 mg per kilogram of body weight per day, are useful in the treatment of the above-indicated conditions. The amount of active ingredient that may be combined with the carrier materials to produce a single dosage form will vary depending upon the condition being treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy.

Preferred compounds of the invention will have desirable pharmacological properties that include, but are not limited to, oral bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of laboratory animals that receive the compound intravenously.

Serum protein binding may be predicted from albumin binding assays. Such assays are described in a review by Oravcova, et al. (Journal of Chromatography B (1996) volume 677, pages 1-27).

Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120-1127).

The amount of the composition required for use in treatment will vary not only with the particular compound selected but also with the route of administration, the nature of the condition being treated and the age and condition of the patient and will ultimately be at the discretion of the attendant physician or clinician.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The novel compounds of the invention possess tryptase inhibitory activity. As a result of this tryptase activity, the compounds of the invention as well as an inner salt thereof, a pharmaceutically acceptable salt thereof, a hydrolyzable ester thereof, or a solvate thereof, are useful as antiinflammatory agents particularly in the treatment of chronic asthma and may also be useful in treating or preventing allergic rhinitis, inflammatory bowel disease, psoriasis, conjunctivitis, atopic dermatitis, rheumatoid arthritis, osteoarthritis, and other chronic inflammatory joint diseases, or diseases of joint cartilage destruction. Additionally, these compounds may be useful in treating or preventing myocardial infarction, stroke, angina and other consequences of atherosclerotic plaque rupture. Additionally, these compounds may be useful for treating or preventing diabetic retinopathy, tumor growth and other consequences of angiogenosis. Additionally, these compounds may be useful for treating or preventing fibrotic conditions, for example, fibrosis, scleroderma, pulmonary fibrosis, liver cirrhosis, myocardial fibrosis, neurofibromas and hypertrophic scars.

The compounds of the invention are also inhibitors of Factor Xa and/or Factor VIIa. As a result, the compounds of the invention as well as an inner salt or a pharmaceutically acceptable salt thereof, a hydrolyzable ester thereof, or a solvate thereof may also be useful in the treatment or prevention of thrombotic events associated with coronary artery and cerebrovascular disease, venous or arterial thrombosis, coagulation syndromes, ischemia and angina (stable and unstable), deep vein thrombosis (DVT), disseminated intravascular coagulopathy, Kasacach-Merritt syndrome, pulmonary embolism, myocardial infarction, cerebral infarction, cerebral thrombosis,transient ischemic attacks, atrial fibrillation, cerebral embolism, thromboembolic complications of surgery (such as hip or knee replacement, introduction of artificial heart valves and endarterectomy) and peripheral arterial occlusion and may also be useful in treating or preventing myocardial infarction, stroke, angina and other consequences of atherosclerotic plaque rupture. The compounds of the invention possessing Factor Xa and/or Factor VIIa inhibtion activity may also be useful as inhibitors of blood coagulation such as during the preparation, storage and fractionation of whole blood;

The compounds of the invention are also inhibitors of urokinase-type plasminogen activator. As a result, the compounds of the invention as well as an inner salt or a pharmaceutically acceptable salt thereof, a hydrolyzable ester thereof, or a solvate thereof may be useful in the treatment or prevention of restenosis and aneurysms, in the treatment or prevention of myocardial infarction, stroke, angina and other consequences of atherosclerotic plaque rupture, and may also be useful in the treatment of malignancies, prevention of metastases, prevention of prothrombotic complications of cancer, and as an adjunct to chemotherapy.

The compounds of the invention also possess thrombin and trypsin inhibitory activity. As a result, the compounds of the invention as well as an inner salt or a pharmaceutically acceptable salt thereof, a hydrolyzable ester thereof, or a solvate thereof may be useful in treating or preventing pancreatitis, in the treatment or prevention of thrombotic events as described above, and may also be useful as inhibitors of blood coagulation such as during the preparation, storage, and fractionation of whole blood.

The compounds of the invention are also inhibitors of Factor XIa. As a result, the compounds of the invention as well as an inner salt or a pharmaceutically acceptable salt thereof, a hydrolyzable ester thereof, or a solvate thereof may also be useful in the treatment or prevention of thrombotic events associated with coronary artery and cerebrovascular disease, venous or arterial thrombosis, coagulation syndromes, ischemia and angina (stable and unstable), deep vein thrombosis (DVT), disseminated intravascular coagulopathy, Kasacach-Merritt syndrome, pulmonary embolism, myocardial infarction, cerebral infarction, cerebral thrombosis,transient ischemic attacks, atrial fibrillation, cerebral embolism, thromboembolic complications of surgery (such as hip or knee replacement, introduction of artificial heart valves and endarterectomy) and peripheral arterial occlusion and may also be useful in treating or preventing myocardial infarction, stroke, angina and other consequences of atherosclerotic plaque rupture. The compounds of the invention possessing Factor XIa inhibtion activity may also be useful as inhibitors of blood coagulation such as during the preparation, storage and fractionation of whole blood.

The compounds of the invention as well as an inner salt or a pharmaceutically acceptable salt thereof, a hydrolyzable ester thereof, or a solvate thereof may be administered orally, topically, rectally or parenterally or may be administered by inhalation into the bronchioles or nasal passages. The method of administration will, or course, vary upon the type of disease being treated. The amount of active compound administered will also vary according to the method of administration and the disease being treated. An effective amount will be within the dosage range of about 0.1 to about 100 mg/kg, preferably about 0.2 to about 50 mg/kg and more preferably about 0.5 to about 25 mg/kg per day in a single or multiple doses administered at appropriate intervals throughout the day.

The pharmaceutical composition used in these therapies can be in a variety of forms. These include, for example, solid, semi-solid and liquid dosage forms such as tablets, pills, powders, liquid solutions or suspensions, liposomes, injectable and infusible solutions. Such compositions can include pharmaceutically acceptable excipients, preservatives, stabilizers, and other agents conventionally employed in the pharmaceutical industry.

When the compounds of the invention as well as an inner salt or a pharmaceutically acceptable salt thereof, a hydrolyzable ester thereof, or a solvate thereof are employed to treat asthma or allergic rhinitis they will may be formulated as aerosols. The term "aerosol" includes any gas-borne suspended phase of the active compound which is capable of being inhaled into the bronchioles or nasal passage. Aerosol formulations include a gas-borne suspension of droplets of the active compound as produced in a metered dose inhaler or nebulizer or in a mist sprayer. Aerosol formulations also include a dry powder composition suspended in air or other carrier gas. The solutions of the active compounds of the invention used to make the aerosol formulation will be in a concentration of from about 0.1 to about 100 mg/ml, more preferably 0.1 to about 30 mg/ml, and most preferably from about 1 to about 10 mg/ml. The solution will usually include a pharmaceutically acceptable buffer such as a phosphate or bicarbonate to give a pH of from about 5 to 9, preferably 6.5 to 7.8, and more preferably 7.0 to 7.6. Preservatives and other agents can be included according to conventional pharmaceutical practice.

Other pharmaceutically active agents can be employed in combination with the compounds of the invention depending upon the disease being treated. For example, in the treatment of asthma, β-adrenergic agonists such as albuterol, terbutaline, formoterol, fenoterol or prenaline can be included as can anticholinergics such as ipratropium bromide, anti-inflammatory cortiocosteroids such as beclomethasone, triamcinolone, flurisolide or dexamethasone, and anti-inflammatory agents such as cromolyn and nedocromil.

In addition to the novel compounds of the invention and the methods of use for the compounds of the invention, this invention is also directed to novel intermediates and novel synthetic routes employed in the preparation of such compounds.

FXIa inhibition according to the invention represents a more effective and safer method of inhibiting thrombosis compared to inhibiting other coagulation serine proteases such as thrombin or Factor Xa. Administration of a small molecule FXIa inhibitor should have the effect of inhibiting thrombin generation and clot formation with no or substantially no effect on bleeding times and little or no impairment of haemostasis. These results differ substantially from that of other "direct acting" coagulation protease inhibitors (e.g. active-site inhibitors of thrombin and Factor Xa), which demonstrate prolongation of bleeding time and less separation between antithrombotic efficacy and bleeding time prolongation. A preferred method according to the invention comprises administering to a mammal a pharmaceutical composition containing at least one compound of the invention.

The methods of the present invention are useful for treating or preventing those conditions which involve the action of Factor XIa. Accordingly, the methods of the present invention are useful in treating consequences of atherosclerotic plaque rupture including cardiovascular diseases associated with the activation of the coagulation cascade in thrombotic or thrombophilic states. As used herein, the terms "treating" or "treatment" encompass responsive and/or prophylaxis measures, e.g., measures designed to inhibit or delay the onset of the disease, achieve a full or partial reduction of the symptoms or disease state, and/or to alleviate, lessen, or cure the disease or disorder and/or its symptoms.

More particularly, the methods of the present invention may be used to treat acute coronary syndromes such as coronary artery disease, myocardial infarction, unstable angina (including crescendo angina), ischemia (e.g., ischemia resulting from vascular occlusion), and cerebral infarction. The methods of the present invention further may be useful in treating stroke and related cerebral vascular diseases (including cerebrovascular accident and transient ischemic attack); venous thrombosis and thrombo-embolism, such as deep vein thrombosis (DVT) and pulmonary embolism; thrombosis associated with atrial fibrillation, ventricular enlargement, dilated cardiac myopathy, or heart failure; peripheral arterial disease and intermittent claudication; the formation of atherosclerotic plaques and transplant atherosclerosis; restenosis following arterial injury induced endogenously (by rupture of an atherosclerotic plaque), or exogenously (by invasive cardiological procedures such as vessel wall injury resulting from angioplasty); disseminated intravascular coagulopathy, Kasabach-Merritt syndrome, cerebral thrombosis, cerebral embolism, and disseminated intravascular coagulopathy.

Additionally, the methods of the present invention may be useful in treating thrombo-embolic consequences or complications associated with surgery (such as hip replacement, endarterectomy, introduction of artificial heart valves, vascular grafts, mechanical organs, and implantation or transplantation of organ, tissue or cells); medications (such as oral contraceptives, hormone replacement, and heparin, e.g., for treating heparin-induced thrombocytopenia); and pregnancy or childbirth. The methods of the present invention may be used to treat thrombosis due to confinement (i.e. immobilization, hospitalization, bed rest, limb immobilization, e.g., with immobilizing casts, etc.).

The methods of the present invention also may be useful in preventing thrombosis and complications in patients genetically predisposed to arterial thrombosis or venous thrombosis (including activated protein C resistance, FVleiden, Prothrombin 20210, elevated coagulation factors FVII, FVIII, FIX, FX, FXI, prothrombin, TAFI and fibrinogen), elevated levels of homocystine, and deficient levels of antithrombin, protein C, and protein S. The inventive methods may be used for treating heparin-intolerant patients, including those with congenital and acquired antithrombin III deficiencies, heparin-induced thrombocytopenia, and those with high levels of polymorphonuclear granulocyte elastase. The methods of this invention may be used to treat all forms of thrombophilia.

The methods of the present invention may also be used to maintain blood vessel potency, for example, in patients undergoing transluminal coronary angioplasty, or in connection with vascular surgery such as bypass grafting, arterial reconstruction, atherectomy, vascular grafts, stent patency, and organ, tissue or cell implantation and transplantation. The inventive methods may be used to inhibit blood coagulation in connection with the preparation, storage, fractionation, or use of whole blood. For example, the inventive methods may be used in maintaining whole and fractionated blood in the fluid phase such as required for analytical and biological testing, e.g., for ex vivo platelet and other cell function studies, bioanalytical procedures, and quantitation of blood-containing components, or for maintaining extracorpeal blood circuits, as in dialysis or surgery (e.g., coronary artery bypass surgery).

In addition, the methods of the present invention may be useful in treating and preventing the prothrombotic complications of cancer. The methods may be useful in treating tumor growth, as an adjunct to chemotherapy, for preventing angiogenesis, and for treating cancer, more particularly, cancer of the lung, prostate, colon, breast, ovaries, and bone.

The methods of the present invention also may be used to treat diabetes mellitus, hypertension, or hypercholesterolemia.

In carrying out the methods of the present invention, it may be desired to administer the compounds of the invention (Factor XIa inhibitors) in combination with each other and one or more other agents for achieving a therapeutic benefit such as antithrombotic or anticoagulant agents, anti-hypertensive agents, anti-ischemic agents, anti-arrhythmic agents, platelet function inhibitors, and so forth. More particularly, the inventive methods may be carried out by administering the small molecule Factor XIa inhibitors in combination with aspirin, clopidogrel, ticlopidine or CS-747, warfarin, low molecular weight heparins (such as LOVENOX), GPIIb/GPIIIa blockers, PAI-1 inhibitors such as XR-330 and T-686, P2Y1 and P2Y12 receptor antagonists; thromboxane receptor antagonists (such as ifetroban), prostacyclin mimetics, thromboxane A synthetase inhibitors (such as picotamide), serotonin-2-receptor antagonists (such as ketanserin); compounds that inhibit other coagulation factors such as FVII, FVIII, FIX, FX, prothrombin, TAFI, and fibrinogen, and/or other compounds that inhibit FXI; fibrinolytics such as TPA, streptokinase, PAI-1 inhibitors, and inhibitors of α-2-antiplasmin such as anti-α-2-antiplasmin antibody fibrinogen receptor antagonists, hypolipidemic agents, such as HMG-CoA reductase inhibitors (e.g., pravastatin, simvastatin, atorvastatin, fluvastatin, cerivastatin, AZ4522, and itavastatin), and microsomal triglyceride transport protein inhibitors (such as disclosed in U.S. Pat. Nos. 5,739,135, 5,712,279 and 5,760,246); antihypertensive agents such as angiotensin-converting enzyme inhibitors (e.g., captopril, lisinopril or fosinopril); angiotensin-II receptor antagonists (e.g., irbesartan, losartan or valsartan); ACE/NEP inhibitors (e.g., omapatrilat and gemopatrilat); and/or β-blockers (such as propranolol, nadolol and carvedilol). The inventive methods may be carried out by administering the small molecule Factor XIa inhibitors in combination with anti-arrhythmic agents such as for atrial fibrillation, for example, amiodarone or dofetilide.

In carrying out the methods of the present invention, it may be desired to administer the compounds of the invention (Factor XIa inhibitors) in combination with agents that increase the levels of cAMP or cGMP in cells for a therapeutic benefit. For example, the compounds of the invention may have advantageous effects when used in combination with phosphodiesterase inhibitors, including PDE1 inhibitors (such as those described in Journal of Medicinal Chemistry, Vol. 40, pp. 2196-2210 [1997]), PDE2 inhibitors, PDE3 inhibitors (such as revizinone, pimobendan, or olprinone), PDE4 inhibitors (such as rolipram, cilomilast, or piclamilast), PDE7 inhibitors, or other PDE inhibitors such as dipyridamole, cilostazol, sildenafil, denbutyline, theophylline (1,2-dimethylxanthine), ARIFLOT™ (i.e., cis-4-cyano-4-[3-(cyclopentylox-y)-4-methoxyphenyl]cyclohexane-1-carboxylic acid), arofyline, roflumilast, C-11294A, CDC-801, BAY-19-8004, cipamfylline, SCH351591, YM-976, PD-189659, mesiopram, pumafentrine, CDC-998, IC-485, and KW-4490.

The inventive methods may be carried out by administering the compounds of the invention in combination with pro-thrombolytic agents, such as tissue plasminogen activator (natural or recombinant), streptokinase, reteplase, activase, lanoteplase, urokinase, prourokinase, anisolated streptokinase plasminogen activator complex (ASPAC), animal salivary gland plasminogen activators, and the like.

The inventive methods may be carried out by administering the compounds of the invention in combination with β-adrenergic agonists such as albuterol, terbutaline, formoterol, salmeterol, bitolterol, pilbuterol, or fenoterol; anticholinergics such as ipratropium bromide; anti-inflammatory cortiocosteroids such as beclomethasone, triamcinolone, budesonide, fluticasone, flunisolide or dexamethasone; and anti-inflammatory agents such as cromolyn, nedocromil, theophylline, zileuton, zafirlukast, monteleukast and pranleukast.

The small molecule Factor XIa inhibitors may act synergistically with one or more of the above agents. Thus, reduced doses of thrombolytic agent(s) may be used, therefore obtaining the benefits of administering these compounds while minimizing potential hemorrhagic and other side effects.

The effective amount of a small molecule Factor XIa inhibitor administered according to the present invention may be determined by one of ordinary skill in the art. The specific dose level and frequency of dosage for any particular subject may vary and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. An exemplary effective amount of compounds of the invention may be within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

EXAMPLES

Proton NMR are recorded on Varian AS 300 spectrometer and chemical shifts are reported as δ (ppm) down field from tetramethylsilane. Mass spectra are determined on Micromass Quattro II.

Example 1

General Method A for the Preparation of 3-aminopyridyl Beta-lactam Acids

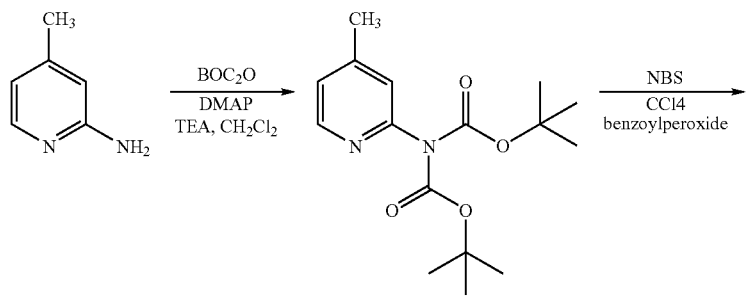

-continued
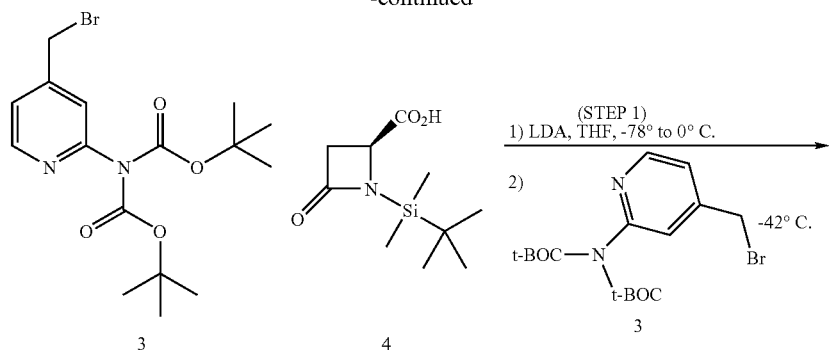
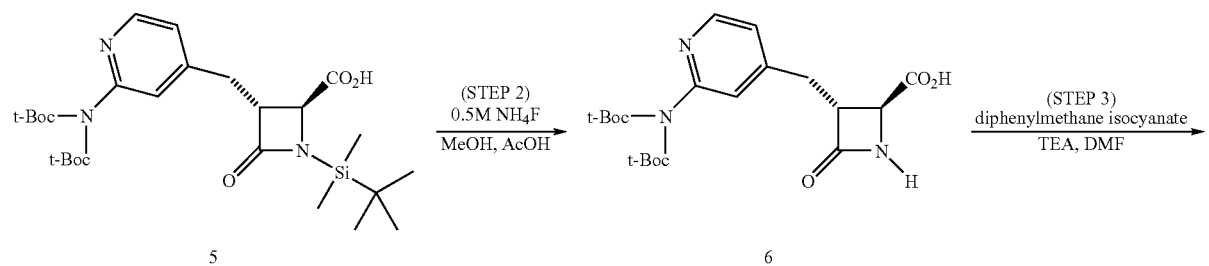
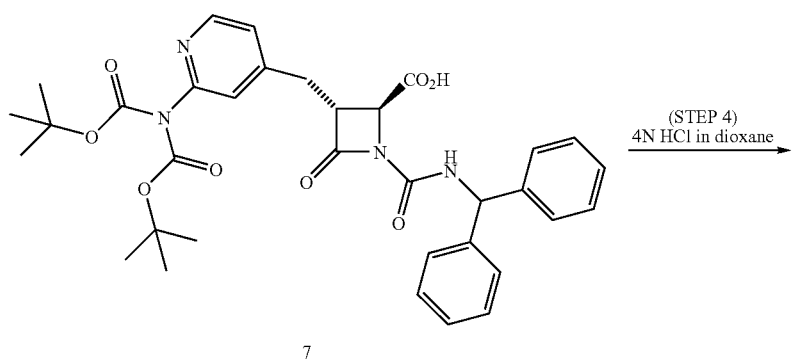
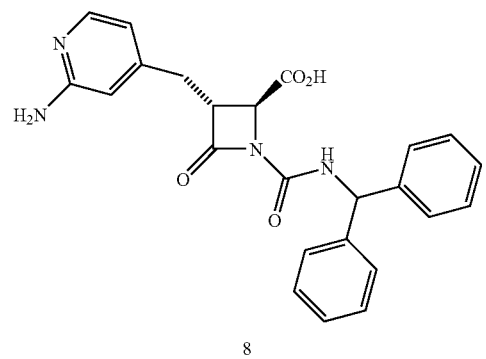

4-Methyl-2-bis(Boc)-aminopyridine (2): Under argon, in a 1-L, 3-necked flask was placed a solution of 2-aminopicoline (16.23 g, 150.1 mmol, 1.0 equiv), triethylamine (41.8 mL, 30.04 g, 300.2 mmol, 2.0 equiv), dimethylaminopyridine (DMAP) (18.3 g, 150 mmol, 1.0 equiv), and $CH_2Cl_2$ (300 mL). The mixture was cooled to 5-7° C. in an ice-water bath with magnetic stirring. A solution of Boc-anhydride (100 g, 458.2 mmol, 3.1 equiv) in $CH_2Cl_2$ (100 mL) was added dropwise over a period of 30 min. The ice bath was removed and the reaction allowed to warm to room temperature with stirring for 4 h. The reaction mixture was worked up by washing the $CH_2Cl_2$ solution with sat. $NH_4Cl$ (2×400 mL) followed by sat. $NaHCO_3$ (2×400 mL), and then passing the solution through silica gel (350 mL fritted glass funnel) (elution with $CH_2Cl_2$, 500 mL). Rotary-evaporation of the solvent and tert-butanol at 5 mm Hg, 70° C., 18 h provided the crude product as a semi-crystalline straw-colored oil. This material was further purified by silica gel chromatography on a 330 g Combi-flash pre-packed cartridge, gradient elution with 100% hexanes to 20% ethyl acetate in hexanes. Fractions containing product were pooled and evaporated to provide 27.6 g, 60% yield of an oil. The oil was transformed into a solid by first dissolving it in $CH_2Cl_2$, then adding hexane and concentrating in vacuo at 25° C. for 30 min, followed by high vacuum produced a free-flowing powder 2. TLC: hexanes/EtOAc [2:1] Rf~0.6.

4-Bromomethyl-2-bis-Boc-aminopyridine (3): To a solution of 4-methyl-2-bis(boc)aminopyridine 2 (26.0 g, 84.4 mmol, 1.0 equiv) in $CCl_4$ (421 mL) was added N-bromosuccinimide (15.0 g, 84.4 mmol, 1.0 equiv) and dibenzoylperoxide (97%) (204 mg, 0.84 mmol, 0.01 equiv). The reaction mixture was quickly heated to reflux (hot plate with assistance from a heat gun) and the reaction was illuminated with a 500-watt halogen work light and two, 175-watt incandescent spotlights (Home Depot). The reaction was monitored at 210 nm and when the reaction had reached completion (1 hr at reflux), the reaction mixture was cooled to room temperature, filtered through celite/fritted glass to remove much of the succinimide. The volatiles were removed to give a crude material which was purified by silica gel chromatography (330 gram Combiflash silica gel) using gradient elution from 1% acetone in $CH_2Cl_2$ to 8% acetone in $CH_2Cl_2$. Fractions containing pure product from each of the four chromatography runs were pooled and evaporated to provide 10 g (31%) of 3 as a yellow foam.

(2S,3R)-1-(tert-butyldimethylsilyl)-3-((2-(di-t-butyloxycarbonylamino)pyridin-4-yl)methyl)-4-oxoazetidine-2-carboxylic acid (5): Commerically available beta-lactam 4 (15.31 mmol, 3.51 g, 1.0 eq.) was dissolved in 40 mL dry THF at room temperature with magnetic stirring, in an oven-dried flask with dry stir bar under dry argon. The solution was cooled to −78° C. and the LDA solution (2.05 eq., 31.38 mmol, 17.4 mL 1.8M solution from Aldrich) was added slowly over 5 minutes by syringe to the cooled stirring solution. The solution was kept at −78° C. for 15 minutes and warmed to 0° C. with an ice bath. The solution was kept at 0° C. for 45 minutes, and then cooled to −42° C. (dry ice-acetonitrile). Bromide 3 (5.34 g, 13.78 mmol, 0.9 eq.) was dissolved in 20 mL of dry THF and cooled to −42° C. (dry ice-acetonitrile). The resulting bromide solution was added dropwise via a dry narrow bore cannula to the enolate solution using balloon pressure, with both vessels cooled to −42° C. during the 30 minute addition. A deep dark blue-black color forms immediately. After the addition was complete, the vial that contained the bromide solution was rinsed with two 2 mL portions of dry THF, which was cooled to −42° C. and added to the enolate solution. The reaction vessel was kept at −42° C. for 4 hours. A quench solution was prepared by adding 50 g of ice to 150 mL of 5% aqueous $KHSO_4$ solution in an Erlenmeyer. The reaction mixture was poured into the quench solution, and the vessel was rinsed with 5×20 mL aliquots of ethyl acetate, which were poured into the quench solution. The two layers were poured into a separatory funnel. The pH of the aqueous layer was 2-3. The organic layer was separated, the organic layer extracted with 3 portions of ethyl acetate, and the combined organic layers were washed with brine and concentrated in vacuo. The residue was dissolved in minimal methylene chloride and put on a 120 g pre-packed ISCO Combiflash silica column. The column was eluted with a dual solvent system: solvent A=hexane, solvent B=2% acetic acid in ethyl acetate. The gradient applied was 0-30% B over 3 minutes, 30% B for 10 minutes, ramped 30 to 50% B over 10 minutes, 50% B for 15 minutes, 50 to 80% B over 10 minutes, 80% for 10 minutes. Product 5 eluted in the 50% B fractions and all pure fractions containing 5 were concentrated in vacuo to yield 5 (4.76 g, 64%) as a crunchy yellow foam. TLC (3:2 EtOAc/hexanes/1% AcOH) Rf=0.2.

(2S,3R)-3-((2-(di-t-butyloxycarbonylamino)pyridin-4-yl)methyl)-4-oxoazetidine-2-carboxylic acid (6): To a solution of pyridyl beta-lactam acid 5 (0.4 g, 1.0 eq.) in 3.4 mL methanol and 0.12 mL acetic acid was added 0.5M ammonium fluoride in methanol (1.5 mL, 1.0 eq.). The solution was stirred for 3 hours until disappearance of all starting material. The reaction was then concentrated in vacuo and put under high vacuum overnight to yield a yellow solid which was taken on to the next step without further purification.

(2S,3R)-1-(benzhydrylcarbamoyl)-3-((2-(di-t-butyloxycarbonylamino)pyridin-4-yl)methyl)-4-oxoazetidine-2-carboxylic acid (7): To a solution of beta-lactam acid 6 (50 mg, 1.0 eq) in dimethylformamide (1.2 mL) was added diphenylmethylisocyanate (100 uL, 4.45 eq.), triethylamine (80 uL, 4.8 eq.). The reaction was stirred at room temperature for 23 hours and then concentrated in vacuo. The crude material was purified by preparative TLC eluting with 9:1:0.2 ethyl acetate:methanol:acetic acid to yield 7 (42 mg, 56%) as a yellow foam.

(2S,3R)-3-((2-aminopyridin-4-yl)methyl)-1-(benzhydrylcarbamoyl)-4-oxoazetidine-2-carboxylic acid (8): To solid 7 (42 mg) was added 4N HCl-dioxane (1.0 mL). The reaction was capped and stirred at room temperature for 5.5 hrs (or until reaction is complete) and then triturated with diethyl ether to yield a crude solid which was further purified via preparative HPLC (C18, acetonitrile/water, 0.1% TFA) to give 8 (10.6 mg, 35%) as a white powder.

(2S,3R)-1-(((1S,2S)-2-(benzyloxy)cyclopentyl)carbamoyl)-3-((2-aminopyridin-4-yl)methyl)-4-oxoazetidine-2-carboxylic acid (9): Compound 9 was synthesized by general method A using (1R,2R)-benzyloxycyclopentyl isocyanate (step 3).

(2S,3R)-3-((2-aminopyridin-4-yl)methyl)-N1,N2-bis ((1S,2S)-2-(benzyloxy)cyclopentyl)-4-oxoazetidine-1,2-dicarboxamide (10): Compound 10 was synthesized by general method A using (1R,2R)-benzyloxycyclopentyl isocyanate (step 3). Note: This compound was a byproduct from step 3 which was independently isolated via the same preparative TLC conditions and deprotected using the same conditions in step 4 (4N HCl-dioxane).

(2S,3R)-3-((2-aminopyridin-4-yl)methyl)-N1,N2-bis(3-benzylphenyl)-4-oxoazetidine-1,2-dicarboxamide (11): Compound 11 was synthesized by general method A using 3-benzylphenylisocyanate (step 3). Note: This compound was a byproduct from step 3 which was independently isolated via the same preparative TLC conditions and deprotected using the same conditions in step 4 (4N HCl-dioxane).

(2S,3R)-3-((2-aminopyridin-4-yl)methyl)-4-oxo-N1,N2-bis(3-phenoxyphenyl)azetidine-1,2-dicarboxamide (12): Compound 12 was synthesized by general method A using 3-phenoxyphenylisocyanate (step 3). Note: This compound was a byproduct from step 7 which was independently isolated via the same preparative TLC conditions and deprotected using the same conditions in step 4 (4N HCl-dioxane).

Example 2
General Method B for the Preparation of 3-aminopyridyl Beta-lactam methyl esters
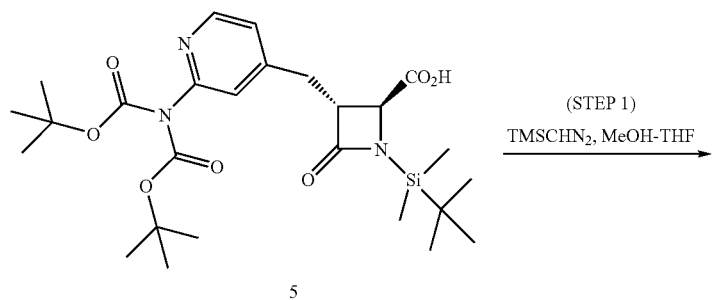
5
(STEP 1)
TMSCHN₂, MeOH-THF
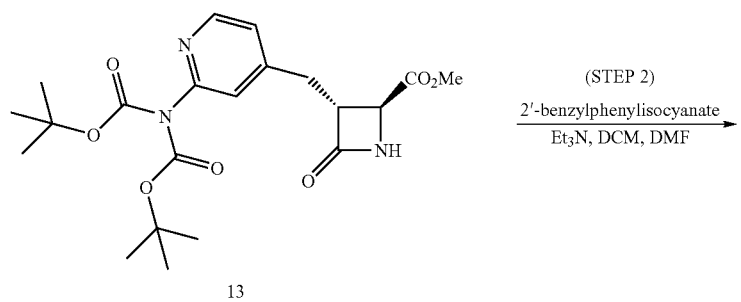
13
(STEP 2)
2'-benzylphenylisocyanate
Et₃N, DCM, DMF
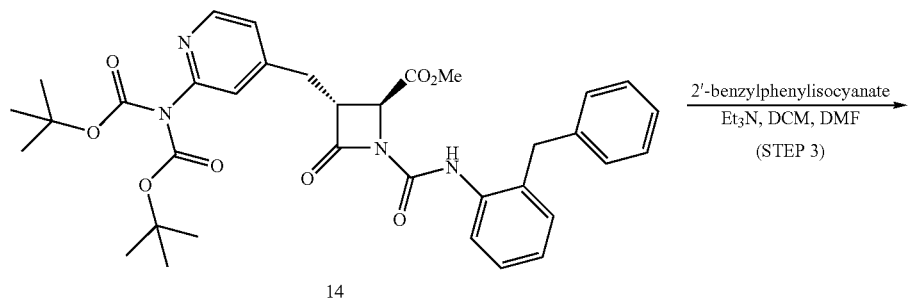
14
2'-benzylphenylisocyanate
Et₃N, DCM, DMF
(STEP 3)
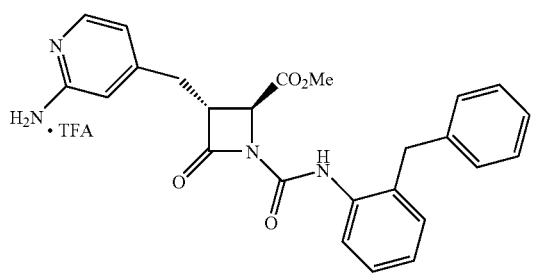
15

(2S,3R)-methyl 3-((2-(di-t-butyloxycarbonylamino)pyridin-4-yl)methyl)-4-oxoazetidine-2-carboxylate (13): To a solution of pyridyl beta-lactam acid 5 (0.1 g, 1.0 eq.) in 3 mL methanol and 1.0 mL tetrahydrofuran was added 2.0M trimethylsilyldiazomethane in hexanes (558 μL, 6.0 eq.). After disappearance of all starting material, the reaction was concentrated in vacuo. The crude material was purified by reverse phase HPLC (C18, acetonitrile/water with 0.1% TFA) to yield 13 (45.5 mg, 56%) as a clear oil.

(2S,3R)-methyl 1-((2-benzylphenyl)carbamoyl)-3-((2-(di-t-butyloxycarbonylamino)pyridin-4-yl)methyl)-4-oxoazetidine-2-carboxylate (14): To a solution of beta-lactam ester 13 (11 mg, 1.0 eq) in dichloromethane (0.75 mL) was added 2'-benzylphenyl isocyanate (10 uL, 2.0 eq.), triethylamine (11 uL, 3.0 eq.) and a few drops of DMF to solubilize any undissolved material. The reaction was stirred at room temperature for 21 hours and then concentrated in vacuo. The crude material was taken on to the next step without further purification.

(2S,3R)-methyl 3-((2-aminopyridin-4-yl)methyl)-1-((2-benzylphenyl)carbamoyl)-4-oxoazetidine-2-carboxylate (15): To crude acylated beta-lactam ester 14 was added 4N HCl in dioxane (2 mL). The reaction was capped and stirred for 4 hours and then concentrated in vacuo. The crude material was purified via reverse phase HPLC (C18, acetonitrile/water with 0.1% TFA) to yield 15 (3.6 mg) as a white solid.

(2S,3R)-methyl 1-(((1S,2R)-2-phenylcyclopropyl)carbamoyl)-3-((2-aminopyridin-4-yl)methyl)-4-oxoazetidine-2-carboxylate trifluoroacetate (16): Compound 16 was synthesized by general method B using trans-2-phenylcyclopropyl isocyanate (step 3) to yield 16 (3.9 mg) as a white solid.

(2S,3R)-methyl 1-(((1R,2R)-2-(benzyloxy)cyclopentyl)carbamoyl)-3-((2-aminopyridin-4-yl)methyl)-4-oxoazetidine-2-carboxylate trifluoroacetate (17): Compound 17 was synthesized by general method B using (1S,2S)-2-benzyloxycyclopentyl isocyanate (step 3) to yield 17 (5.0 mg) as a white solid.

Example 3

General Method C for the Preparation of 3-aminopyridyl Beta-lactam esters and amides

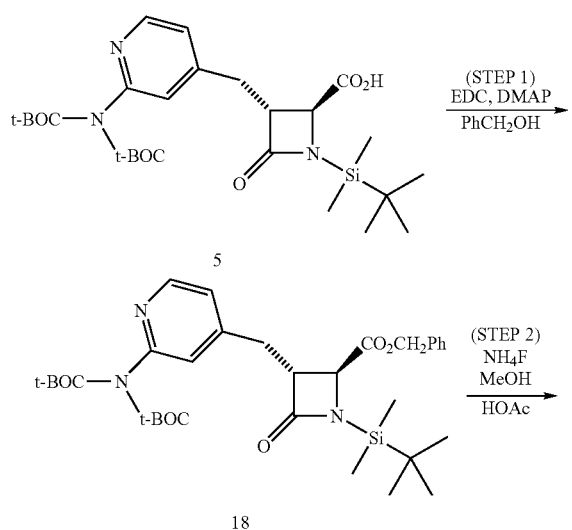

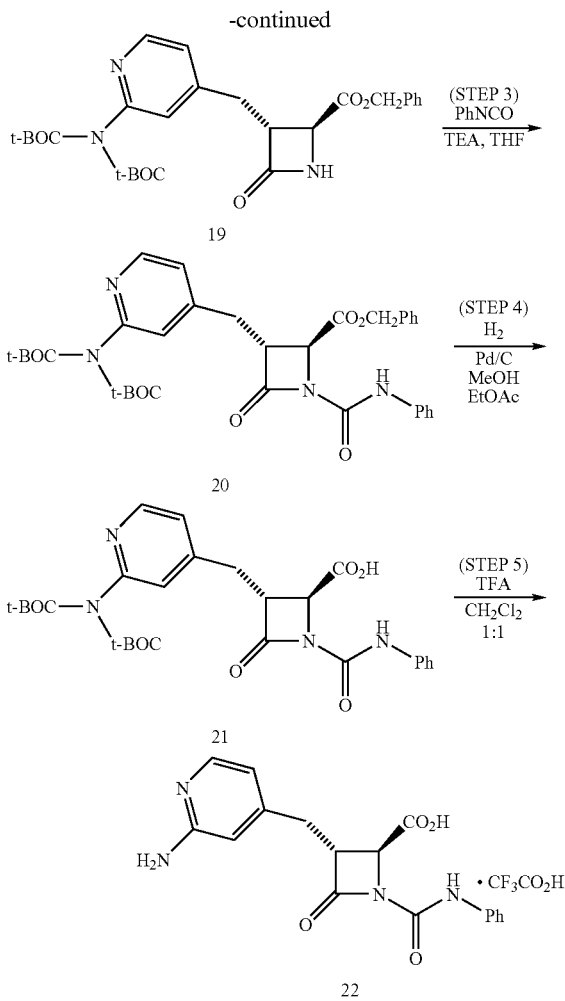

(2S,3R)-benzyl 1-(tert-butyldimethylsilyl)-3-((2-(di-t-butoxycarbonylamino)pyridin-4-yl)methyl)-4-oxoazetidine-2-carboxylate (18): The beta-lactam acid 5 (136 mg, 0.254 mmol) was dissolved in 4 mL dry dichloromethane at room temperature. EDC (73 mg, 3 equiv.), benzyl alcohol (33 mg, 32 uL, 1.2 equiv), and catalytic DMAP (3 mg) were added sequentially. The reaction was stirred overnight under argon, diluted with 20 mL ethyl acetate and 25 mL water. The water layer was washed with 3 portions of ethyl acetate, and the combined organic layers were dried over sodium sulfate, filtered, and concentrated in vacuo. The residue was purified by column chromatography using a gradient of 10 to 30% ethyl acetate in hexane, yielding 18 (72%). MS: 626.3 [M+H]+.

(2S,3R)-benzyl 3-((2-(di-t-butoxycarbonylamino)pyridin-4-yl)methyl)-4-oxoazetidine-2-carboxylate (19): Ester 18 (127 mg, 0.20 mmol) was dissolved in 1 mL dry methanol at room temperature. 1 mL of a 0.5 M solution of ammonium fluoride in methanol (0.5 mmol, 2.5 equiv.) was added, then 60 mg acetic acid (1 mmol, 5 equiv). The reaction was stirred overnight under argon, diluted with 20 mL ethyl acetate and 20 mL saturated sodium bicarbonate solution. The water layer was washed with 3 portions of ethyl acetate, and the combined organic layers were dried over sodium sulfate, filtered, and concentrated in vacuo. The residue was purified by column chromatography eluting with 3:1 methylene chloride/ethyl acetate to yield 19 (72 mg, 69%). MS: 611.2 [M+H]+.

(2S,3R)-benzyl 3-((2-(di-t-butoxycarbonylamino)pyridin-4-yl)methyl)-4-oxo-1-(phenylcarbamoyl)azetidine-2-carboxylate (20): Deprotected lactam 19 (72 mg, 0.14 mmol) was dissolved in 4 mL dry THF at room temperature. Triethylamine (71 mg, 5 equiv.) was added, then 42 mg (2.5 equiv.) of the isocyanate. The reaction was stirred overnight under argon and concentrated in vacuo. The residue was purified by column chromatography eluting with methylene chloride to yield 20 (75 mg, 85%). MS: 631.3. [M+H]+.

(2S,3R)-3-((2-(di-t-butoxycarbonylamino)pyridin-4-yl)methyl)-4-oxo-1-(phenylcarbamoyl)azetidine-2-carboxylic acid (21): Acylated lactam ester 20 (56 mg, 0.089 mmol) was dissolved in 2 mL of 1:1 methanol-ethyl acetate in a 20 mL glass vial. 10% palladium on carbon catalyst (10 mg) was added, and the solution was stirred under an atmosphere of hydrogen at room temperature overnight under argon, filtered, and then concentrated in vacuo. The residue was pure by HPLC/MS and was taken to the next step without purification. MS: 541.1 [M+H]+.

(2S,3R)-3-((2-aminopyridin-4-yl)methyl)-4-oxo-1-(phenylcarbamoyl)azetidine-2-carboxylic acid trifluoroacetate (22): Acylated lactam acid 21 (from the previous step) was dissolved in 2 mL of 1:1 TFA-methylene chloride in a 20 mL glass vial. The solution was stirred for 1 hour at room temperature under argon and then concentrated in vacuo. The residue was purified by preparative HPLC using a C18 column and a gradient of 20-60% water in acetonitrile. All fractions containing the desired product were pooled and concentrated in vacuo. Freeze-drying from 1:1 water:acetonitrile gave 22 (25 mg, 62% for 2 steps). MS: 341.1 [M+H]+.

(2S,3R)-1-(((R)-1-phenylethyl)carbamoyl)-3-((2-aminopyridin-4-yl)methyl)-4-oxoazetidine-2-carboxylic acid trifluoroacetate (23): Compound 23 was synthesized by general method C using α-methylbenzylamine isocyanate (step 3).

(2S,3R)-1-(((R)-1-(naphthalen-1-yl)ethyl)carbamoyl)-3-((2-aminopyridin-4-yl)methyl)-4-oxoazetidine-2-carboxylic acid trifluoroacetate (24): Compound 24 was synthesized by general method C using α-methylnaphthyl isocyanate (step 3).

(2S,3R)-ethyl 1-(((R)-1-(naphthalen-1-yl)ethyl)carbamoyl)-3-((2-aminopyridin-4-yl)methyl)-4-oxoazetidine-2-carboxylate trifluoroacetate (25): Compound 25 was synthesized by general method C using ethyl alcohol (step 1) and α-methylnaphthyl isocyanate (step 3).

(2S,3R)-ethyl 3-((2-aminopyridin-4-yl)methyl)-4-oxo-1-(phenylcarbamoyl)azetidine-2-carboxylate trifluoroacetate (26): Compound 26 was synthesized by general method C using ethyl alcohol (step 1) and phenyl isocyanate (step 3).

(2S,3R)-benzyl 3-((2-aminopyridin-4-yl)methyl)-4-oxo-1-(phenylcarbamoyl)azetidine-2-carboxylate trifluoroacetate (27): Compound 27 was synthesized by general method C using benzyl alcohol (step 1) and phenyl isocyanate (step 3).

(2S,3R)-ethyl 1-(((R)-1-phenylethyl)carbamoyl)-3-((2-aminopyridin-4-yl)methyl)-4-oxoazetidine-2-carboxylate trifluoroacetate (28): Compound 28 was synthesized by general method C using ethyl alcohol (step 1) and α-methylbenzylamine isocyanate (step 3).

(2S,3R)-3-((2-aminopyridin-4-yl)methyl)-N2,N2-diethyl-4-oxo-N1-((R)-1-phenylethyl)azetidine-1,2-dicarboxamide trifluoroacetate (29): Compound 29 was synthesized by general method C using dimethylamine (step 1) and α-methylbenzylamine isocyanate (step 3).

(2S,3R)-3-((2-aminopyridin-4-yl)methyl)-N2-ethyl-N2-methyl-4-oxo-N1-((R)-1-phenylethyl)azetidine-1,2-dicarboxamide trifluoroacetate (30): Compound 30 was synthesized by general method C using N-methyl-N-ethylamine (step 1) and α-methylbenzylamine isocyanate (step 3).

(2S,3R)-3-((2-aminopyridin-4-yl)methyl)-2-(morpholine-4-carbonyl)-4-oxo-N-((R)-1-phenylethyl)azetidine-1-carboxamide trifluoroacetate (31): Compound 31 was synthesized by general method C using morpholine (step 1) and α-methylbenzylamine isocyanate (step 3).

(2S,3R)-3-((2-aminopyridin-4-yl)methyl)-4-oxo-N1-((R)-1-phenylethyl)-N2-(pyridin-3-yl)azetidine-1,2-dicarboxamide trifluoroacetate (32): Compound 32 was synthesized by general method C using 3-aminopyridine (step 1) and α-methylbenzylamine isocyanate (step 3).

(2S,3R)-benzyl 3-(benzofuran-5-ylmethyl)-4-oxoazetidine-2-carboxylate (33) and (2S,3R)-3-(benzofuran-5-ylmethyl)-4-oxo-1-(phenylcarbamoyl)azetidine-2-carboxylic acid (34): Compounds 33 and 34 were synthesized by general method A (step 1) using 5-(bromomethyl)benzofuran as the electrophile instead of 4-bromomethyl-2-bis-Boc-aminopyridine and then the synthesis was completed by following general method C. The compounds were separated via silica gel chromatography eluting with 10-40% ethyl acetate in hexanes. Yield of 33: 56 mg.

(2S,3R)-3-(2-(benzo[d][1,3]dioxol-5-yl)ethyl)-4-oxo-1-(phenylcarbamoyl)azetidine-2-carboxylic acid (35): Compound 35 was synthesized by general method A (step 1) using 5-(2-bromoethyl)benzo[d][1,3]dioxole as the electrophile instead of 4-bromomethyl-2-bis-Boc-aminopyridine. The starting 5-(bromomethyl)benzo[d][1,3]dioxole was made by standard treatment of benzo[d][1,3]dioxol-5-ylmethanol with carbon tetrabromide and triphenylphosphine in toluene. The synthesis was then completed by following general method C.

(2S,3R)-3-(benzo[d][1,3]dioxol-5-ylmethyl)-4-oxo-1-(phenylcarbamoyl)azetidine-2-carboxylic acid (36): Compound 36 was synthesized by general method A (step 1) using 5-(bromomethyl)benzo[d][1,3]dioxole as the electrophile instead of 4-bromomethyl-2-bis-Boc-aminopyridine. The synthesis was then completed by following general method C.

(2S,3R)-3-(3-chlorobenzyl)-4-oxo-1-(phenylcarbamoyl)azetidine-2-carboxylic acid (37): Compound 37 was synthesized by general method A (step 1) by using 1-(bromomethyl)-3-chlorobenzene as the electrophile instead of 4-bromomethyl-2-bis-Boc-aminopyridine. The completion of the synthesis then followed general method C using 4-methoxybenzyl alcohol (step 1). Removal of the PMB group was accomplished by treatment with TFA/DCM at room temperature for one hour to yield the desired acid 37 (45 mg, 100%).

Example 4

General Method D for the Preparation of 3-aminopyridyl Beta-lactam Alcohols

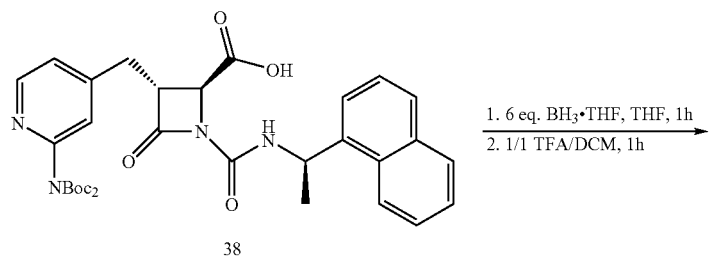

38

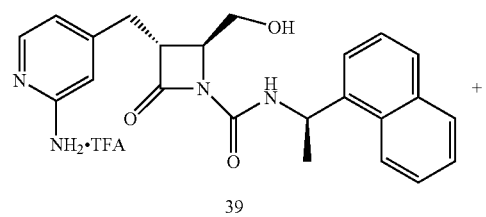

39

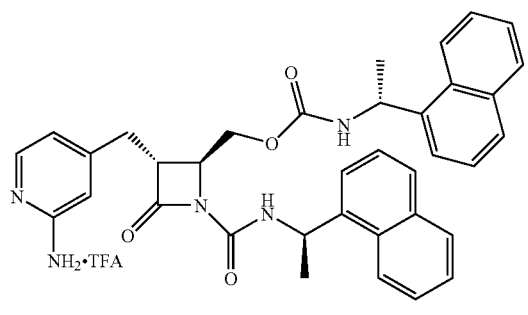

40

(2S,3R)-1-(((R)-1-(naphthalen-1-yl)ethyl)carbamoyl)-3-((2-(di-t-butoxycarbonylamino)pyridin-4-yl)methyl)-4-oxoazetidine-2-carboxylic acid (38): Compound 38 was synthesized by general method C using α-ethylnaphthyl isocyanate.

(2S,3R)-3-((2-aminopyridin-4-yl)methyl)-2-(hydroxymethyl)-N-((R)-1-(naphthalen-1-yl)ethyl)-4-oxoazetidine-1-carboxamide trifluoroacetate (39) and ((2S,3R)-1-(((R)-1-(naphthalen-1-yl)ethyl)carbamoyl)-3-((2-aminopyridin-4-yl)methyl)-4-oxoazetidin-2-yl)methyl(R)-1-(naphthalen-1-yl)ethylcarbamate trifluoroacetate (40): To a solution of compound 38 (0.03 g, 0.048 mmol) in 1 ml anhydrous THF was added 1M borane in THF (0.29 ml, 0.29 mmol) dropwise and the reaction mixture was stirred at room temperature for 1 h. Then the reaction was slowly quenched with water, acidified to pH 1 with 1 N HCl, and then neutralized with sodium bicarbonate solution. The reaction mixture was extracted twice with ethyl acetate and the organic extracts were dried over magnesium sulfate and concentrated in vacuo. The desired product was purified by silica gel chromatography (12 g pre-packed Si column, hexane/ethyl acetate eluents) to yield the Boc protected alcohol (0.008 g, 27% yield; LS/MS M+H 605.1, calc. 605.48). The alcohol (0.008 g, 0.013 mmol) was treated with 1 ml 1/1 TFA/DCM for 1 h at room temperature. Afterwards, the reaction mixture was concentrated in vacuo and the solid washed with ethyl ether (three times) to give the 39 as a TFA salt (2.2 mg). LS/MS M+H 405.12, calc. 405.5 and 40 as a TFA salt (2.5 mg).

(2S,3R)-3-((2-aminopyridin-4-yl)methyl)-2-(hydroxymethyl)-4-oxo-N-((R)-1-phenylethyl)azetidine-1-carboxamide (TFA salt) (41): Compound 41 was synthesized by general method C using α-ethylnaphthyl isocyanate (step 3) and finished following general method D (2.5 mg, white powder) LC/MS M+H 355.2, calc. 355.17.

Example 5

General Method E for the Preparation of N-aryl 3-aminopyridyl Beta-lactams

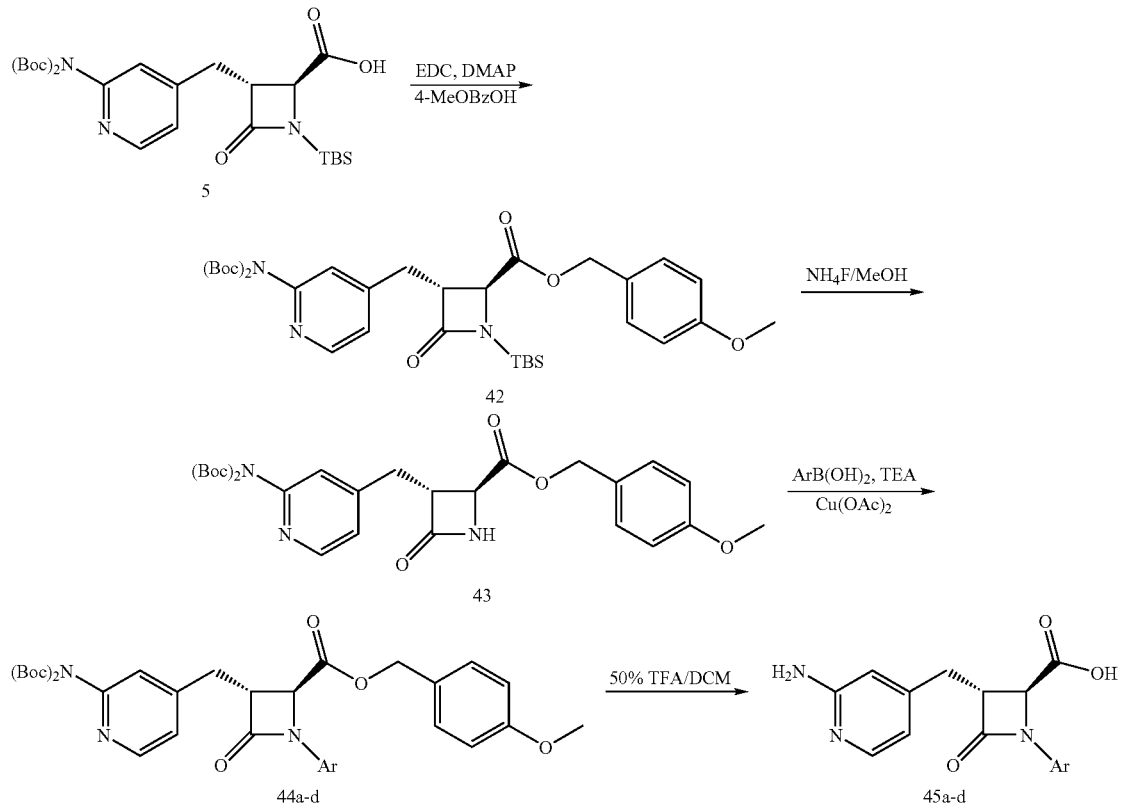

(2S,3R)-4-methoxybenzyl-1-(tert-butyldimethylsilyl)-3-((2-(di-t-butoxycarbonylamino)pyridin-4-yl)methyl)-4-oxoazetidine-2-carboxylate (42): A mixture of 534 mg of crude compound 5 (1.0 mmol), EDC hydrochloride salt (403 mg, 2.1 mmol), DMAP (24 mg, 0.2 mmol) and 4-methoxybenzyl alcohol (416 mg, 3.0 mmol) in dichloromethane (5 Ml) was stirred at room temperature overnight. The solvent was removed in vacuo. The residue was dissolved with ethyl acetate, washed with 5% aqueous $KHSO_4$, water and brine. The organic layer was dried over $Na_2SO_4$, then concentrated to yield a crude material which was purified by ISCO silica gel column using 0-20% ethyl acetate in hexanes to afford 42 (463 mg, 71%): Anal. $C_{34}H_{49}N_3O_8Si$, Mol. Wt.: 655.85. Found: ESI-MS: 656.0 $(M+H)^+$.

(2S,3R)-4-methoxybenzyl-3-((2-(di-t-butoxycarbonylamino)pyridin-4-yl)methyl)-4-oxoazetidine-2-carboxylate (43): A solution of 1.7 Ml of 0.5 M ammonium fluoride in methanol (0.85 mmol) was added to a mixture of compound 42 (463 mg, 0.71 mmol), acetic acid (140 Ul, 2.45 mmol) and methanol (7 Ml). The mixture was stirred at room temperature for 3 h. The solvent was removed and the residue was taken up in toluene (2~3 Ml) to assist removal of AcOH. After solvent was removed, the residue was taken up in DCM. The resulting white solids were filtered off. Concentration of the filtrate gave 43 (0.44 g), which was ready for next step reaction without further purification. Anal. $C_{28}H_{35}N_3O_8$, Mol. Wt.: 541.59. Found: ESI-MS: 541.8 $(M+H)^+$.

Compounds (44a-d): A mixture of β-lactam 43 (30 mg, 0.055 mmol), aryl boronic acid (0.11 mmol), copper acetate (20 mg, 0.11 mmol), triethylamine (31 Ul, 0.22 mmol) and activated 4A molecular sieves (56 mg) in dichloromethane (1.3 Ml) was stirred at room temperature overnight. The reaction mixture was filtered through celite and the filtrate was concentrated. Preparative TLC (20% EtOAc/Hexanes) of the residue gave the desired products 44a-d in 27-78% yield.

Compounds (45a-d): The crude esters 44a-d were treated with 30% TFA in DCM (3 Ml). After two hours, LC-MS analyses indicated completion of the reactions. The solvent was removed and the residue was purified by preparative HPLC (Vydac reverse phase C-18 column, 22×250 mm ID). Mobile phase: A=0.1% TFA in water, B=0.1% TFA in acetonitrile. The flow rate was 12 Ml/min. The gradient time was 5% B to 55% B or 10% B to 60% B over 30 min. The desired products were thus obtained:

(2S,3R)-1-(4-((4-fluorophenyl)carbamoyl)phenyl)-3-((2-aminopyridin-4-yl)methyl)-4-oxoazetidine-2-carboxylic acid (45a): Yield 2.5 mg.

(2S,3R)-1-(3-((4-fluorophenyl)carbamoyl)phenyl)-3-((2-aminopyridin-4-yl)methyl)-4-oxoazetidine-2-carboxylic acid (45b): Yield 3.2 mg.

(2S,3R)-3-((2-aminopyridin-4-yl)methyl)-1-(3-(benzyloxy)phenyl)-4-oxoazetidine-2-carboxylic acid (45c): Yield 2.0 mg.

(2S,3R)-4-methoxybenzyl 3-((2-aminopyridin-4-yl)methyl)-1-(benzofuran-2-yl)-4-oxoazetidine-2-carboxylate (45d): Yield 1.7 mg.

(2S,3R)-3-((2-aminopyridin-4-yl)methyl)-1-(4-(benzyloxy)-2-fluorophenyl)-4-oxoazetidine-2-carboxylic acid (46): Compound 46 was synthesized by general method E using 4-(benzyloxy)-2-fluorophenylboronic acid.

Example 6

General Method F for Synthesis of 3,3-alkyl, methyl Beta-lactams

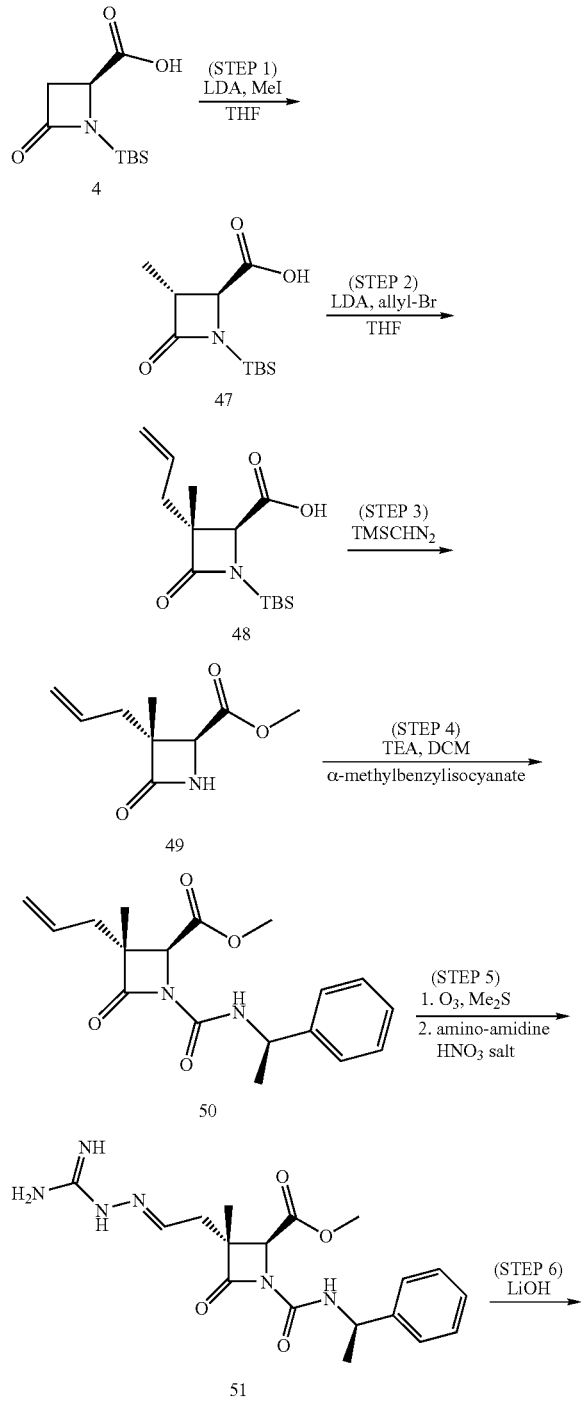

(2S,3R)-1-(tert-butyldimethylsilyl)-3-methyl-4-oxoazetidine-2-carboxylic acid (47): To a solution of (S)-1-(tert-butyldimethylsilyl)-4-oxoazetidine-2-carboxylic acid 4 (2.00 g, 8.73 mmol.) in THF (30 ml) at −78° C. was added LDA (19 ml, 2.0 eq.). After the solution was stirred for 20 min. at −78° C., it was warmed to 0° C. for 5 min. The solution was re-cooled to −78° C. and methyl iodide (3.10 g, 2.5 eq.) in THF (5 ml) was added. The reaction solution was warmed up to room temperature, quenched with aqueous $KHSO_4$ solution (10%, 30 ml), extracted with ethyl acetate (3×). The combined organic layers were washed with brine twice and dried with $MgSO_4$. After concentrating in vacuo, 47 was obtained. $H^1NMR$ ($CDCl_3$): 0.15, 0.35 (s, 6H), 1.14 (s, 9H), 1.35 (d, 3H), 3.71 (d, 1H), 4.14 (m, 1H). $C_{11}H_{21}NO_3Si$, Mol. Wt.: 243.37. Found: 244 (M+1).

(2S,3R)-3-allyl-1-(tert-butyldimethylsilyl)-3-methyl-4-oxoazetidine-2-carboxylic acid (48): To a solution of compound 47 (0.200 g, 0.823 mmol) in THF (5 ml) at −78° C. was added a solution of LDA (1.10 ml, 2.4 eq.). The reaction solution was stirred for 20 min. at that temperature, warmed to −20° C. and allyl bromide (0.138 Ml, 2.0 eq.) was added slowly. Reaction mixture was warmed to 0° C. for 30 min. and quenched with $KHSO_4$ (20 ml, 10%), extracted with ethyl acetate (3×). Combined organic layers were washed with brine twice and dried over $MgSO_4$. After concentrating in vacuo, compound 48 was obtained. $H^1NMR$ ($CDCl_3$): 0.15, 0.37 (s, 6H), 1.16 (s, 9H), 1.33 (s, 3H), 2.50 (m, 2H), 3.98 (s, 1H), 5.22 (m, 2H), 5.88 (m, 1H). $C_{14}H_{25}NO_3Si$, Mol. Wt.: 283.44. Found: 284 (M+1).

(2S,3R)-methyl 3-allyl-3-methyl-4-oxoazetidine-2-carboxylate (49): TMS diazomethane (1.23 Ml, 3.0 eq. 2 M in THF) was added to a solution of the acid compound 48 (260 mg, 0.82 mmol) in methanol (5 Ml) at 0° C. and stirred at room temperature overnight to yield the deprotected product 46. $H^1NMR$ ($CDCl_3$): 1.30 (s, 3H), 2.50 (m, 2H), 3.80 (s, 3H), 4.08 (s, 3H), 5.30 (m, 2H), 5.85 (m, 1H), 5.92 (s, b, 1H). $C_9H_{13}NO_3$, Mol. Wt.: 183.2. Found: 184 (M+1).

(2S,3R)-methyl 1-(((R)-1-phenylethyl)carbamoyl)-3-allyl-3-methyl-4-oxoazetidine-2-carboxylate (50): To a solution of 49 (120 mg, 0.66 mmol) in methylene chloride (15 mL) was added triethylamine (0.27 mL, 3.0 eq.), DMAP (8.0 mg, 10% mmol) and α-methyl-benzyl isocyanate (146 mg, 1.5 eq.). The reaction was stirred overnight and concentrated in vacuo to yield a crude material, which was extracted with ethyl acetate and aqueous $NH_4Cl$. Combined organic layers were washed with brine purified via silica gel chromatography to yield compound 47. $H^1NMR$ ($CDCl_3$): 1.35 (s, 3H), 1.60 (d, 3H), 2.50 (m, 2H), 3.82 (s, 3H), 4.44 (s, 1H), 5.50 (m, 1H), 5.25 (m, 2H), 5.83 (m, 1H), 6.74 (d, b, 1H), 7.40 (m, 5H). $C_{18}H_{22}N_2O_4$, Mol. Wt.: 330.38. Found: 331 (M+1).

(2S,3R)-methyl 1-(((R)-1-phenylethyl)carbamoyl)-3-(2-iminoguanidinoethyl)-3-methyl-4-oxoazetidine-2-carboxylate (51): To a solution of 50 (135 mg) in methylene chloride (5 mL) at −78° C. was bubbled $O_3$ until a blue color was seen.

The reaction was quenched with dimethylsulfide. Removal of solvents gave the desired aldehyde product, which was used in the next step without further purification. To a solution of the freshly prepared aldehyde compound (118 mg, 0.36 mmol) in ethanol (0.75 mL) was added amino amidine (HNO₃ salt, 98 mg, 2.0 eq.) and acetic acid (30 uL, 3.0 eq.). The mixture was stirred for 1.5 h and residual after removal of solvent was purified via reverse-phase HPLC to yield compound 51 (41 mg). $C_{18}H_{24}N_6O_4$, Mol. Wt.: 388.42. Found: 389 (M+1).

(2S,3R)-1-(((R)-1-phenylethyl)carbamoyl)-3-(2-iminoguanidinoethyl)-3-methyl-4-oxoazetidine-2-carboxylic acid (52): To a solution of compound 51 (10 mg) in 1:1:1 THF:methanol:water (1.5 mL total) was added solid LiOH (3.5 eq.). The reaction was stirred at room temperature for 30 min. LCMS showed formation of the desired acid and disappearance of the starting methyl ester. The crude material was purified via reverse-phase HPLC to yield pure 52. C17H22N6O4, Mol. Wt.: 374.39. Found: 375 (M+1).

(2S,3R)-ethyl 1-(((R)-1-phenylethyl)carbamoyl)-3-((6-aminopyridin-3-yl)methyl)-3-methyl-4-oxoazetidine-2-carboxylate (53) and (2S,3R)-1-(((R)-1-phenylethyl)carbamoyl)-3-((6-aminopyridin-3-yl)methyl)-3-methyl-4-oxoazetidine-2-carboxylic acid (54): Compounds 53 and 54 were synthesized by general method F using 4-bromomethyl-2-bis-boc-aminopyridine as the alkylating agent in step 2 and forming the ethyl ester (step 3) analogous to the ester synthesis in general method C.

Example 7

General Method G for the Preparation of N-alkyl amidinohydrazone Beta-lactams

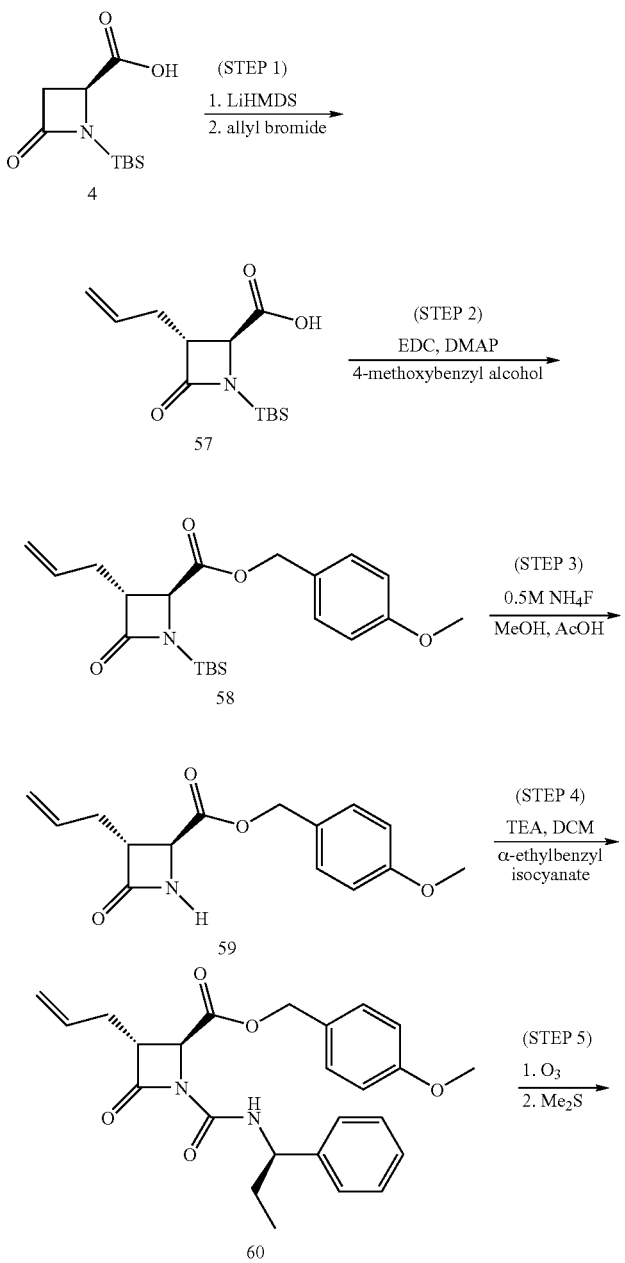

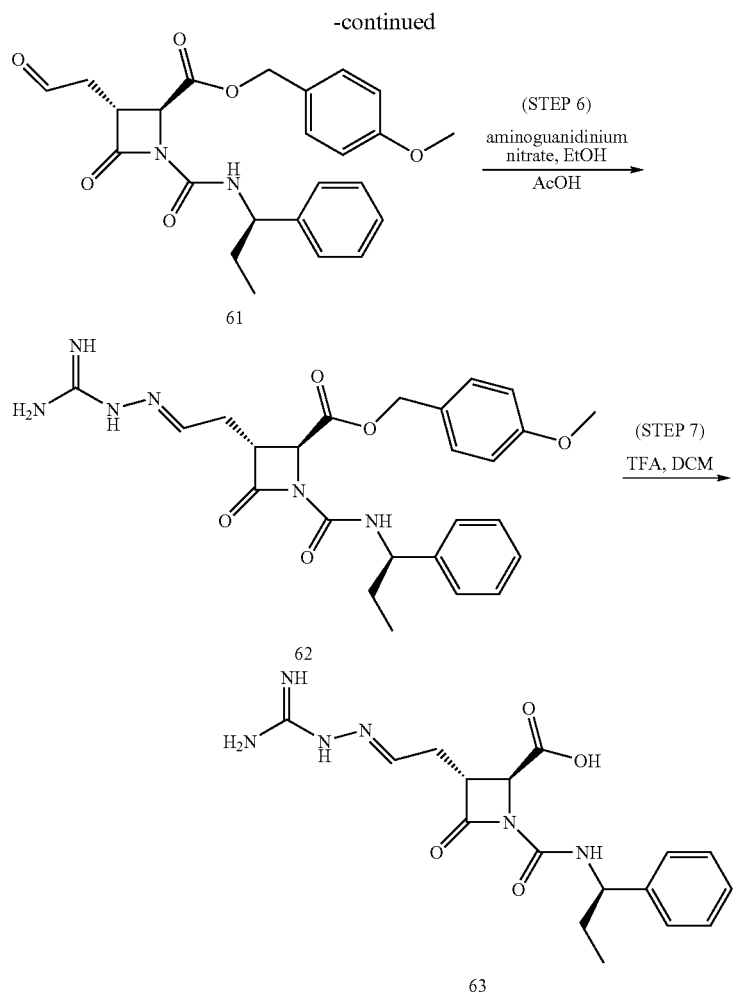

(2S,3R)-3-Allyl-1-(tert-butyl-dimethyl-silanyl)-4-oxo-azetidine-2-carboxylic acid (57): To a solution of (S)-1-(tert-butyldimethylsilyl)-4-oxoazetidine-2-carboxylic acid (4) (2.00 g, 8.73 mmol.) in anhydrous THF (20 mL) at −78° C. was added 1.0 M solution of LiHMDS (20 ml, 20.1 mmol, 2.3 eq.) in THF. After the solution was stirred for 30 min. at −78° C., it was warmed to 0° C. for 10 min. The solution was recooled to −78° C. and allyl bromide (1.28 g, 10.5 mmol, 1.2 eq.) was added slowly. The reaction solution was stirred at −78° C. for 1 h, then warmed up to room temperature and stirred for another hour. The reaction mixture was quenched with aqueous 10% $KHSO_4$ solution (30 ml) and extracted with ethyl acetate (40 mL×3). The combined organic layers were washed with brine twice and dried over $Na_2SO_4$. After removal of solvent, compound 57 was obtained as crystalline solid (2.0 g, 85%); 78% purity by LCMS, $^1$HNMR (300 MHz, $CDCl_3$): 0.12 (s, 3H), 0.30 (s, 3H), 0.95 (s, 9H), 2.55 (m, 2H), 3.41 (m, 1H), 3.80 (d, J=2.61 Hz, 1H), 5.16 (m, 2H), 5.72 (m, 1H). Anal. $C_{13}H_{23}NO_3Si$, Mol. Wt.: 269.41. Found: ESI-MS: 270.0 (M+H)$^+$.

(2S,3R)-3-Allyl-1-(tert-butyl-dimethyl-silanyl)-4-oxo-azetidine-2-carboxylic acid 4-methoxy-benzyl ester (58): A mixture of 900 mg of crude compound 57 (3.34 mmol) above, EDC hydrochloride salt (1.34 g, 7.01 mmol), DMAP (83 mg, 0.67 mmol) and 4-methoxybenzyl alcohol (1.40 g, 10.1 mmol) in dichloromethane (9 mL) was stirred at room temperature overnight. The solvent was removed in vacuo. The residue was dissolved with ethyl acetate, washed with 5% aqueous $KHSO_4$, water (×2) and brine (×1). The organic layer was dried over $Na_2SO_4$, then concentrated to yield the crude 58 with LC purity: 60%. Purification by ISCO silica gel column using 0-20% AcOEt in Hexanes afforded 630 mg of compound 58 (49% yield, 81% purity): $^1$HNMR (300 MHz, $CDCl_3$): 0.13 (s, 3H), 0.32 (s, 3H), 0.95 (s, 9H), 2.56 (m, 2H), 3.43 (m, 1H), 3.81 (d, J=2.60 Hz, 1H), 3.82 (s, 3H), 4.67 (s, 2H), 5.17 (m, 2H), 5.72 (m, 1H), 6.94 (d, 2H), 7.34 (d, 2H). Anal. $C_{21}H_{31}NO_4Si$, Mol. Wt.: 389.56. Found: ESI-MS: 390.0 (M+H)$^+$.

(2S,3R)-3-Allyl-4-oxo-azetidine-2-carboxylic acid 4-methoxy-benzyl ester (59): A solution of 6.2 mL of 0.5 M ammonium fluoride in methanol (3.1 mmol) was added to a mixture of compound 58 (1.0 g, 2.57 mmol), acetic acid (530 uL, 9.0 mmol) and methanol (25 mL). The mixture was stirred at room temperature for 2 h. The solvent was removed and the residue was taken up in toluene (2~3 mL) to assist removal of AcOH. After solvent was removed, the residue was taken up in DCM. The resulting white solids were filtered off. Concentration of the filtrate gave 0.70 g of the crude 59 with purity: 91.1%, $^1$HNMR (300 MHz, $CDCl_3$): 2.60 (m, 2H), 3.38 (m, 1H), 3.87 (s, 3H), 3.98 (d, 1H), 5.22 (m, 4H), 5.83

(m, 1H), 6.15 (b, s, 1H), 6.90 (d, 2H), 7.35 (d, 2H). Anal. C15H17NO4, Mol. Wt.: 275.3. Found: ESI-MS: 275.8 (M+H)+.

(2S,3R)-3-Allyl-4-oxo-1-(1-phenyl-propylcarbamoyl)-azetidine-2-carboxylic acid 4-methoxy-benzyl ester (60): A mixture of compound 59 (41 mg, 0.15 mmol), triethylamine (83 uL, 0.60 mmol), α-ethyl-benzyl isocyanate (29 mg, 0.18 mmol) in methylene chloride (1.2 mL) was stirred overnight. TLC analysis indicated the completion the reaction. Removal of solvents gave the crude material, which was purified by preparative TLC plate (15% EtOAc in hexanes), yielding 38.2 mg of compound 60 (59%): LC-MS purity: 98.1%; $^1$HNMR (300 MHz, CDCl$_3$): 0.95 (t, 3H), 1.92 (m, 2H), 2.69 (m, 2H), 3.30 (m, 1H), 3.83 (s, 3H), 4.22 (d, 1H), 4.85 (q, 1H), 5.18 (m, 4H), 5.80 (m, 1H), 6.85 (br, d, 1H), 7.45 (m, 9H). Anal. C25H28N2O5, Mol. Wt.: 436.5. Found: ESI-MS: 437.1 (M+H)+.

(3S,4R)-4-Oxo-3-(2-oxo-ethyl)-1-(1-phenyl-propylcarbamoyl)-azetidine-2-carboxylic acid 4-methoxy-benzyl ester (61): Ozone was bubbled through a solution of 60 (38.1 mg, 0.087 mmol) in dry methylene chloride (6 mL) at −78 ° C. until a faint blue color persisted. The reaction mixture was quenched with dimethylsulfide (200 uL) at −78 ° C., then the cooling bath was removed. After the solvent was concentrated, the residue was taken up in EtOAc. Removal of solvents gave the desired aldehyde product 61, which was sufficiently pure for next step without further purification. Anal. C$_{24}$H$_{26}$N$_2$O$_6$, Mol. Wt.: 338.47. Found: ESI-MS: 439.0 (M+H)+, 461.0 (M+Na)+.

(2S,3R)-4-Oxo-3-(3-amindinohydrozone-ethyl)-1-(1-phenyl-propylcarbamoyl)-azetidine-2-carboxylic acid 4-methoxy-benzyl ester (62): To a solution of the freshly prepared aldehyde 61 (29 mg, 0.066 mmol) in ethanol (0.5 mL) was added aminoguanidinium nitrate (18 mg, 0.13 mmol) and acetic acid (11 uL, 0.20 mmol). The mixture was stirred at room temperature for 2 h. Concentration of solvent gave the crude desired product 62. Anal. C$_{25}$H$_{30}$N$_6$O$_5$, Mol. Wt.: 494.54. Found: ESI-MS: 495.0 (M+H)+.

(2S,3R)-4-Oxo-3-(3-amindinohydrozone-ethyl)-1-(1-phenyl-propylcarbamoyl)-azetidine-2-carboxylic acid (63): The crude ester 62 was treated with a mixture of TFA/DCM (1.5 mL/2 mL). After one and half hours, LC-MS analysis indicated that no ester was present. The solvent was removed and the residue was purified by preparative HPLC (Vydac reverse phase C-18 column, 22×250 mm ID). Mobil phase: A=0.1% TFA in water; B=0.1% TFA in acetonitrile. The flow rate was 12 mL/min. The gradient time was 5% B to 55% B over 50 min. The peak of interest was eluted at around 27 minutes to give 3.5 mg of the desired product, 63 as a white solid with 95.6% purity. $^1$HNMR (300 MHz, CDCl$_3$): 0.84 (t, 3H), 1.80 (m, 2H), 2.83 (m, 2H), 3.70 (dt, 1H), 4.25 (d, 1H), 4.61 (q, 1H), 6.58 (br s, 1H), 7.15-7.65 (m, 9H), 11.65(s 1H), 13.10 (br s, 1H); Anal. C$_{17}$H$_{24}$N$_6$O$_4$, Mol. Wt.: 374.39. Found: ESI-MS: 375.0 (M+H)+.

(2S,3R)-cyclobutyl 1-(((R)-1-phenylethyl)carbamoyl)-3-(2-iminoguanidinoethyl)-4-oxoazetidine-2-carboxylate (64): Compound 64 was synthesized by general method G using cyclobutyl alcohol (step 2) and α-methylbenzylisocyanate (step 4). Yield: 72.5 mg (48%). Mol. Wt.: 414.46. Found: ESI-MS: 415.0 (M+H)+.

(2S,3R)-methyl 1-(((R)-1-phenylethyl)carbamoyl)-3-(2-iminoguanidinoethyl)-4-oxoazetidine-2-carboxylate (65): Compound 65 was synthesized by general method G with step 2 esterification accomplished via TMSCHN$_2$ in hexanes and using α-methylbenzylisocyanate in step 4.

(2S,3R)-N2,N2-diethyl-3-(2-iminoguanidinoethyl)-4-oxo-N1-((R)-1-phenylethyl)azetidine-1,2-dicarboxamide (66): Compound 66 was synthesized by general method G, using diethylamine in step 2 and α-methylbenzylisocyanate in step 4, to yield 4.1 mg (35%). Mol. Wt.: 415.49. Found: ESI-MS: 416.0 (M+H)+.

(2S,3R)-3-(2-iminoguanidinoethyl)-4-oxo-1-(biphenylcarbamoyl)azetidine-2-carboxylic acid (67): Compound 67 was synthesized by general method G using 4-biphenylisocyanate (step 4). Yield: 1.1 mg (6.8% over 2 steps). Mol. Wt.: 408.41. Found: ESI-MS: 409.0 (M+H)+.

(2S,3R)-methyl 3-(2-iminoguanidinoethyl)-4-oxo-1-(phenylcarbamoyl)azetidine-2-carboxylate (68): Compound 68 was synthesized by general method G with step 2 esterification accomplished via TMSCHN$_2$ in hexanes and using phenylisocyanate in step 4.

(2S,3R)-1-(((R)-1-phenylethyl)carbamoyl)-3-(2-iminoguanidinoethyl)-4-oxoazetidine-2-carboxylic acid (69), (2S,3R)-1-(((R)-1-phenylethyl)carbamoyl)-3-(2-(R)-1-phenylethyl)carbamoyl)-iminoguanidinoethyl)-4-oxoazetidine-2-carboxylic acid (70) and (2S,3R)-3-(2-(R)-1-phenylethyl)carbamoyl)-iminoguanidinoethyl)-4-oxoazetidine-2-carboxylic acid (71): Compounds 69-71 were synthesized by general method G using α-methylbenzylisocyanate (step 4). The compounds were separated via reverse phase HPLC (acetonitrile/water) with 0.1% TFA added to the mobile phase.

(2S,3R)-3-(2-iminoguanidinoethyl)-4-oxo-1-((4-phenoxyphenyl)carbamoyl)azetidine-2-carboxylic acid (72): Compound 72 was synthesized by general method G using 4-phenoxyphenyl isocyanate (step 4).

(2S,3R)-3-(2-iminoguanidinoethyl)-4-oxo-1-(phenylcarbamoyl)azetidine-2-carboxylic acid (73): Compound 73 was synthesized by general method G using phenyl isocyanate (step 4).

(2S,3R)-cyclobutyl 1-(((R)-1-phenylethyl)carbamoyl)-3-(2-imino(methylguanidino)ethyl)-4-oxoazetidine-2-carboxylate (74): Compound 74 was synthesized by general method G using cyclobutyl alcohol (step 2), α-methylbenzyl isocyanate (step 4) and N-methylpimagedine (step 6).

(2S,3R)-benzyl 3-(2-iminoguanidinoethyl)-4-oxo-1-(biphenylcarbamoyl)azetidine-2-carboxylate (75): Compound 75 was synthesized by general method G using benzyl alcohol (step 2) and 4-biphenylisocyanate (step 4).

(2S,3R)-ethyl 1-(((R)-1-phenylethyl)carbamoyl)-3-(2-imino(methylguanidino)ethyl)-4-oxoazetidine-2-carboxylate (76): Compound 76 was synthesized by general method G using ethyl alcohol (step 2), α-methylbenzylisocyanate (step 4) and N-methyl pimagedine (step 6).

(2S,3R)-1-(((R)-1-phenylpropyl)carbamoyl)-3-(2-imino (methylguanidino)ethyl)-4-oxoazetidine-2-carboxylic acid (77): Compound 77 was synthesized by general method G using α-ethylbenzylisocyanate (step 4) and N-methyl pimagedine (step 6).

(2S,3R)-4-methoxybenzyl 1-(((R)-1-phenylethyl)carbamoyl)-3-(2-iminoguanidino ethyl)-4-oxoazetidine-2-carboxylate (78): Compound 78 was synthesized by general method G using α-methybenzylisocyanate (step 4).

(2S,3R)-1-(((R)-1-phenylpropyl)carbamoyl)-3-((E)-2-(2-(4,5-dihydro-1H-imidazol-2-amine)imino)ethyl)-4-oxoazetidine-2-carboxylic acid: Compound 79 was synthesized by general method G using α-ethylbenzylisocyanate (step 4) and 1-(4,5-dihydro-1H-imidazol-2-yl)hydrazine in step 6 (2.7 mg, 88%).

Example 8

General Method H for the Preparation of N-aryl amidinohydrazone Beta-lactams

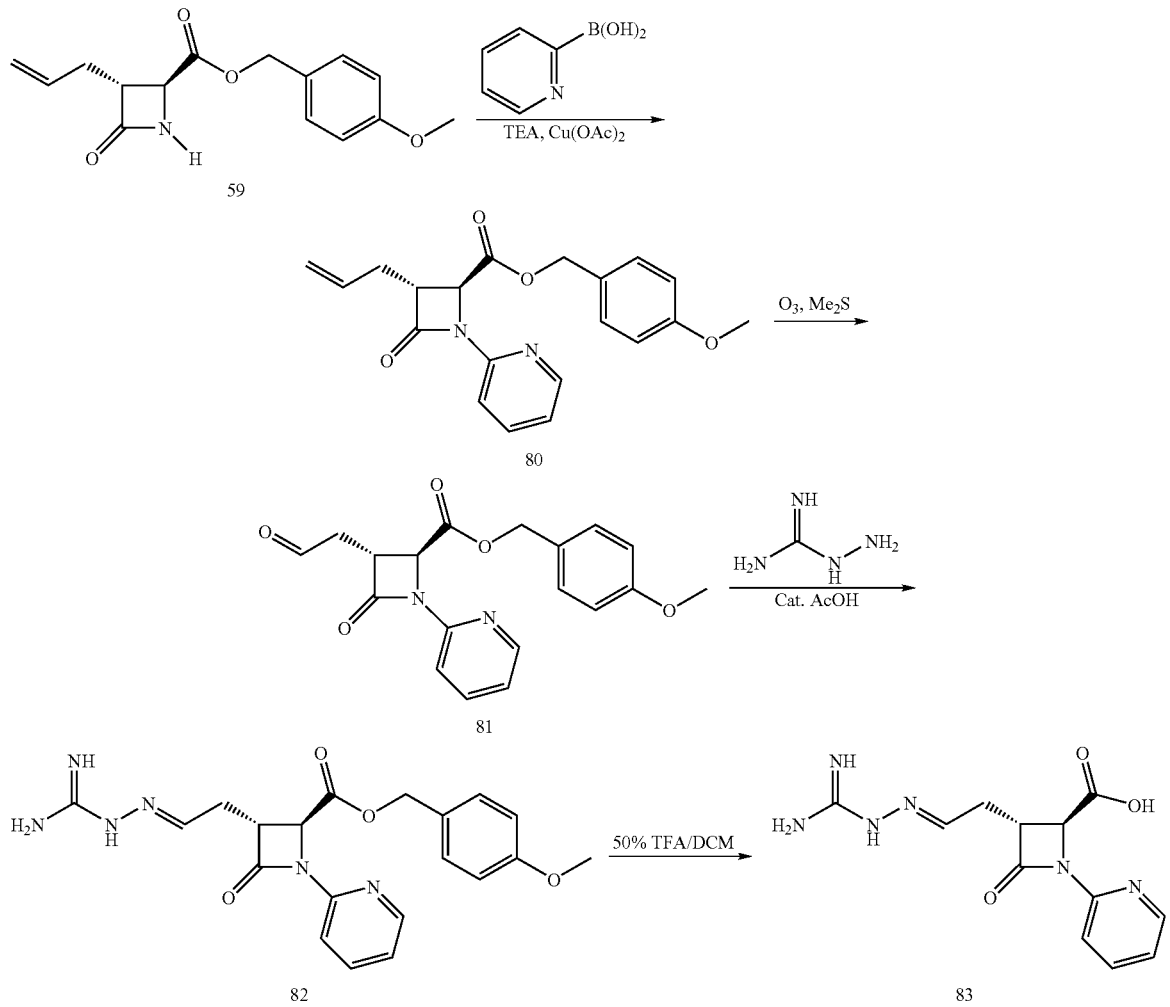

3-Allyl-4-oxo-1-pyridin-2-yl-azetidine-2-carboxylic acid 4-methoxy-benzyl ester (80): A mixture of β-lactam 59 (60 mg, 0.22 mmol), Pyridin-2-boronic acid (81 mg, 0.66 mmol), copper acetate (120 mg, 0.66 mmol), triethylamine (0.153 mL, 1.1 mmol) and activated 4A molecular sieves (270 mg) in dichloromethane (5 mL) was stirred at room temperature for 2 days. The reaction mixture was filtered through celite and the filtrate was concentrated. Preparative TLC (20% EtOAc/Hexanes) of the residue gave the desired product 80 (19.2 mg, 24.8%) $^1$HNMR (300 MHz, CDCl$_3$): 2.60 (m, 2H), 3.49 (m, 1H), 3.81 (s, 3H), 4.41 (d, J=2.61 Hz, 1H), 5.11-5.21 (m, 4H), 5.82 (m, 1H), 6.85 (d, J=8.7 Hz, 2H), 7.01 (m, 1H), 7.22 (d, J=8.1 Hz, 2H), 7.66-7.72 (m, 2H); 8.19 (d, J=4.7 Hz, 1H) Anal. $C_{20}H_{20}N_2O_4$, Mol. Wt.: 352.38. Found: ESI-MS: 352.9 (M+H)$^+$.

4-Oxo-3-(2-oxo-ethyl)-1-pyridin-2-yl-azetidine-2-carboxylic acid 4-methoxy-benzyl ester (81): Ozone was bubbled through a solution of 80 (24.0 mg) in dry methylene chloride (7 mL) at −78° C. until a faint blue color persisted (about 10 min). The reaction mixture was quenched with dimethylsulfide (200 uL) at −78 ° C., then the cooling bath was removed. After the solvent was concentrated, the residue was taken up in EtOAc. Removal of solvents gave the desired aldehyde product 81, which was sufficiently pure to carry on to the next step without further purification. Anal. $C_{19}H_{18}N_2O_5$, Mol. Wt.: 354.36. Found: ESI-MS: 354.9 (M+H)$^+$.

(2S,3R)-4-methoxybenzyl-3-(2-guanidinoiminoethyl)-4-oxo-1-(pyridin-2-yl)azetidine-2-carboxylate (82): To a solution of the freshly prepared aldehyde 81 (32.2 mg, 0.068 mmol) in ethanol (0.85 mL) was added aminoguanidinium nitrate (19 mg, 0.14 mmol) and acetic acid (12 uL, 0.20 mmol). The mixture was stirred at room temperature for 3 h. Concentration of solvent gave the crude desired product 82. Anal. $C_{20}H_{30}N_6O_4$, Mol. Wt.: 410.43. Found: ESI-MS: 411.0 (M+H)$^+$.

(2S,3R)-3-(2-guanidinoiminoethyl)-4-oxo-1-(pyridin-2-yl)azetidine-2-carboxylic acid (83): The crude ester 82 was treated with TFA/DCM (0.75 mL/1 mL). After one and half hours, LC-MS analysis indicated completion of the reaction. The solvent was removed and the residue was purified by preparative HPLC (Vydac reverse phase C-18 column, 22×250 mm ID). Mobil phase: A=0.1% TFA in water, B=0.1% TFA in acetonitrile. The flow rate was 12 mL/min.

The gradient time was 5% B to 50% B over 45 min. The desired product, 83, was obtained as a white solid (5.5 mg). Anal. $C_{19}H_{24}N_6O_4$, Mol. Wt.: 290.28. Found: ESI-MS: 291.0 $(M+H)^+$.

Synthesis of 86 and 87

(2R,3R)-1-(isopropyldimethylsilyl)-3-(3-nitrophenylthio)-4-oxoazetidine-2-carboxylic acid (84): Using glassware, starting materials, and THF that are each rigorously dry is essential for successful alkylation, as well as keeping the reaction mixture under dry argon. Commercially available beta-lactam acid 4 (15.31 mmol, 3.51 g) was dissolved in 40 mL dry THF at room temperature with magnetic stirring, in an oven-dried flask with dry stir bar under dry argon. The solution was cooled to −78° C. and the LDA solution (2.05 equivalent relative to acid, 31.38 mmol, 17.4 mL 1.8M solution from Aldrich) was added slowly over 5 minutes by syringe to the cooled stirring solution. The solution was kept at −78° C. for 15 minutes and warmed to 0° C. with an ice bath. The solution was kept at 0° C. for 45 minutes, and then cooled to −42° C. (dry ice-acetonitrile). The disulfide was dissolved in 20 mL of dry THF and cooled to −42° C. (dry ice-acetonitrile). The disulfide solution was added dropwise via a dry narrow bore cannula to the enolate solution using balloon pressure, with both vessels cooled to −42° C. during the 30 minute addition. After the addition was complete, the vial was rinsed with two 2 mL portions of dry THF, which was cooled to −42° C. and added to the enolate solution also. The reaction vessel was kept at −42° C. for 4 hours and then warmed to 0° C. A quench solution was prepared by adding 50 g of ice to 150 mL of 5% aqueous $KHSO_4$ solution in an Erlenmeyer. The reaction mixture was poured into the quench solution, and the vessel was rinsed with 5×20 mL aliquots of ethyl acetate, which were poured into the quench solution. The two layers were poured into a separatory funnel. The pH of the aqueous layer was 2-3. The organic layer was separated, the aqueous layer was extracted with 3 portions of ethyl acetate, and the combined organic layers were washed with brine and concentrated in vacuo. The solution was warmed to 0° C. and after 4 hours worked up in the standard way ($KHSO_4$ quench). The desired product 84 was purified by column chromatography on silica gel using 50:50:1 hexane:ethyl acetate:acetic acid as eluent. Product MS: 383.1 $[M+H]^+$.

(2R,3R)-ethyl 1-(((R)-1-phenylethyl)carbamoyl)-3-(3-nitrophenylthio)-4-oxoazetidine-2-carboxylate (85a) and (2R,3S)-ethyl 1-(((R)-1-phenylethyl)carbamoyl)-3-(3-nitrophenylthio)-4-oxoazetidine-2-carboxylate (85b). The completion of the synthesis of 85a-b was accomplished by following general method C using ethyl alcohol (step 1), and α-methylbenzylisocyanate (step 3).

(2R,3R)-ethyl 1-(((R)-1-phenylethyl)carbamoyl)-3-(3-aminophenylthio)-4-oxoazetidine-2-carboxylate (86): To a solution of compound 85a (18 mg, 41 umol) in ethyl acetate (1 mL) was added tin chloride monohydrate (2.5 eq.) and the solution was heated to 50° C. After 1 h the solution was concentrated in vacuo. The residue was purified by column chromatography using a gradient of hexane/ethyl acetate 20-100% as eluent to yield 86 (12 mg, 72%). Product MS: 414.1 (M+1).

(2R,3S)-ethyl 1-(((R)-1-phenylethyl)carbamoyl)-3-(3-aminophenylthio)-4-oxoazetidine-2-carboxylate (87): To a solution of 85b (17 mg, 38 umol) in ethyl acetate (1 mL) at room temperature was added tin chloride monohydrate (2.5 eq.) and the solution was heated to 50° C. After 1 h the solution was concentrated in vacuo. The residue was purified by column chromatography using a gradient of hexane/ethyl acetate 20-100% as eluent to yield 87 (10 mg, 63%). Product MS: 414.1 (M+1).

Synthesis of 90

(2S)-ethyl 1-(((R)-1-phenylethyl)carbamothioyl)-3-((2-(tert-butoxycarbonyl)pyridin-4-yl)methyl)-4-oxoazetidine-2-carboxylate (89): Compound 88 was prepared by general method C using ethyl alcohol (step 1). To the solution of 88 (23 mg) in THF was added LiHMDS (0.14 mL, 1M solution in THF) at −78° C. The reaction mixture was warmed up to 0° C. for 5 h and then was quenched with 5% $KHSO_4$ to pH~5. After extraction with ethyl acetate, the organic layer was washed with brine, dried over $Na_2SO_4$ and concentrated in vacuo to yield 89 LC/MS (ESI) m/z 512.8.

(2S)-ethyl 1-(((R)-1-phenylethyl)carbamothioyl)-3-((2-aminopyridin-4-yl)methyl)-4-oxoazetidine-2-carboxylate (90): Compound 89 (crude) was treated with 50% TFA-DCM at 0° C. LCMS was used to monitor the reaction until it was completed. The reaction mixture was condensed and the residue was purified by preparative HPLC with 5-70% acetonitrile-water (with 0.1% TFA) as mobile phase and gradient time 40 min to afford 90 (9 mg, 26% yield). $^1$H NMR (DMSO) δ8.44 (d, 1H), 7.70 (d, 1H), 7.37-7.27 (m, 5H), 7.26 (s, 2H), 6.72 (s, 1H), 6.66 (d, 1H), 5.51 (m, 1H), 4.38 (d, 1H), 4.22 (dd, 2H), 3.40 (d, 1H), 3.14 (m, 2H), 1.62 (d, 3H), 1.22 (t, 3H), LC/MS (ESI) m/z 413.1.

Synthesis of 93

(2S)-4-Methoxybenzyl 3-((2-bis(tert-butoxycarbonyl)-aminopyridin-4-yl)methyl)-4-oxoazetidine-2-carboxylate (91): Compound 91 was prepared by general method C using 4-methoxybenzyl alcohol (step 1).

(2S)-4-Methoxybenzyl 1-(((R)-1-phenylethyl)carbamothioyl)-3-((2-bis(tert-butoxycarbonyl)-aminopyridin-4-yl)methyl)-4-oxoazetidine-2-carboxylate (92): Compound 92 was prepared analogously to the synthesis of 89 and the crude sample was taken on without further purification. LC/MS (ESI) m/z 705.0.

(2S)-1-(((R)-1-phenylethyl)carbamothioyl)-3-((2-aminopyridin-4-yl)methyl)-4-oxoazetidine-2-carboxylic acid (93): Compound 93 was prepared analogously to the synthesis of 90. The crude sample was purified by preparative HPLC with 0-70% acetonitrile-water (with 0.1% TFA) as mobile phase and gradient time 40 min to afford 93 (5.6 mg, 16%). HPLC purity, >96%, $^1$H NMR (DMSO) δ9.04 (d, 1H), 8.00 (br, 2H), 7.90 (d, 1H), 7.41-7.27 (m, 5H), 6.90 (m, 2H), 5.44 (m, 1H), 4.33 (d, 1H), 3.69 (m, 1H), 3.2 (m, 2H), 1.53 (d, J=7.0 Hz, 3H), LC/MS (ESI) m/z 385.1.

Synthesis of 96

(2S,3R)-3-((2-bis(tert-butoxylcarbonyl)aminopyridin-4-yl)methyl)-N-(methylsulfonyl)-4-oxoazetidine-2-carboxamide (94): Compound 5 was prepared by general method A. To a solution of 5 (40 mg, 1 eq.) in dichloromethane (1 mL) was added EDC-HCl (17 mg, 1.2 eq.), HOBt (12 mg, 1.2 eq.), DIEA (16 uL, 1.2 eq.) and methanesulfonamide (9 mg, 1.2 eq.). The reaction was stirred at room temperature for 12 hrs and then concentrated in vacuo. The crude material was redissolved in dichloromethane and washed with saturated $NaHCO_3$ and water, dried over sodium sulfate and concentrated in vacuo to give 22 mg of crude 94 as a tan oil which was taken on to the next step without further purification.

(2S,3R)-3-((2-bis(tert-butoxycarbonyl)aminopyridin-4-yl)methyl)-N2-(methylsulfonyl)-4-oxo-N1-((R)-1-phenylethyl)azetidine-1,2-dicarboxamide (95): To a solution of crude 94 in THF (1 mL) was added DIEA (8 uL, 1.5 eq.) and (R)-(+)-α-methylbenzylisocyanate. The reaction was stirred for 12 hours at room temperature. Ethyl acetate was added to the reaction mixture and washed with water. The organic layer was concentrated in vacuo. The crude product was purified using a silica gel column and a gradient elution from 10% EtOAc/hexanes to 100% EtOAc followed by 10% MeOH in DCM to elute 95. Product fractions were concentrated in vacuo to give 20 mg of compound 95.

(2S,3R)-3-((2-aminopyridin-4-yl)methyl)-N2-(methylsulfonyl)-4-oxo-N1-((R)-1-phenylethyl)azetidine-1,2-dicarboxamide (96): To a solution of 95 in 1 mL dichloromethane was added 300 uL of TFA. The reaction was stirred for 1 hour and then concentrated in vacuo. The crude material was purified via reverse phase HPLC (C18, acetonitrile/water with 0.1% TFA) to yield 0.75 mg of 96. MS [M+H]$^+$=446.0

Synthesis of 101

(2S,3R)-3-((2-bis(tert-butoxycarbonyl)aminopyridin-4-yl)methyl)-1-(tert-butyldimethylsilyl)-N-(4-fluorophenylsulfonyl)-4-oxoazetidine-2-carboxamide (97): Compound 5 was prepared by general method A. To a solution of 5 (50.6 mg, 1.0 eq.) in THF (1 mL) was added carbonyldiimidazole (CDI, 23 mg, 1.5 eq.) and DMAP (17 mg, 1.5 eq.). The reaction was stirred for 1 hour at room temperature. Then 4-fluorobenzenesulfonamide (20 mg, 1.2 eq.) and DBU (15 uL, 1.05 eq.) were added and the capped vial was allowed to stir for 16 hours. The reaction was then concentrated in vacuo to yield crude 97.

(2S,3R)-3-((2-bis(tert-butoxycarbonyl)aminopyridin-4-yl)methyl)-N-(4-fluorophenylsulfonyl)-4-oxoazetidine-2-carboxamide (98): To a solution of crude 97 from above in MeOH:AcOH (900 uL: 100 uL) was added 0.5M NH$_4$F in MeOH (190 uL, 1.0 eq.). After 2 hours and 20 minutes the reaction was concentrated in vacuo and triturated with dichloromethane to yield 98 as a yellow foam which was taken on to the next step without further purification.

(2S,3R)-3-((2-bis(tert-butoxycarbonyl)aminopyridin-4-yl)methyl)-N-(4-fluorophenylsulfonyl)-N-methyl-4-oxoazetidine-2-carboxamide (99): To a solution of 98 (18 mg, 1.0 eq.) in MeOH: THF (1 mL: 300 uL) was added 2.0M TMSCHN$_2$ in hexanes (266 uL, 17 eq.). After 15 minutes, TLC showed complete conversion of starting material. The reaction was poured into ethyl acetate and then washed with 0.2N HCl, 1N NaHCO$_3$ and brine. The organic layer was then dried over sodium sulfate and concentrated in vacuo. The product was then purified via reverse phase HPLC (C18, acetonitrile/water with 0.1% TFA) to yield 99 (11.9 mg, 65%) as a clear oil.

(2S,3R)-3-((2-bis(tert-butoxycarbonyl)aminopyridin-4-yl)methyl)-N2-(4-fluorophenylsulfonyl)-N2-methyl-4-oxo-N1-((R)-1-phenylethyl)azetidine-1,2-dicarboxamide (100): To a solution of 99 in DMF (0.75 mL) was added (R)-α-methylbenzylisocyanate (6 uL, 2.0 eq.) and TEA (8.5 uL, 3.0 eq.). The reaction was stirred under an atmosphere of argon for 20 hours. The reaction was then concentrated in vacuo and taken on to the next step without further purification.

(2S,3R)-3-((2-aminopyridin-4-yl)methyl)-N2-(4-fluorophenylsutfonyl)-N2-methyl-4-oxo-N1-((R)-1-phenylethyl)azetidine-1,2-dicarboxamide (101): To crude 100 from above was added 4N HCl in dioxane (2 mL). The reaction was capped, stirred for 4 hours, concentrated in vacuo and triturated with diethyl ether. The crude product was dissolved in acetonitrile/methanol, filtered and purified via reverse phase HPLC (C18, acetonitrile/water with 0.1% TFA) to yield 101 (1.7 mg).

Synthesis of 106

(2S,3R)-benzyl 3-((2-(bis-N,N-t-butoxycarbonyl)aminopyridin-4-yl)methyl)-1-(tert-butyldimethylsilyl)-4-oxoazetidine-2-carboxylate (102): Compound 102 was synthesized by general method C using α-methylbenzyl isocyanate (step 3).

(3R,4S)-3-((2-(bis-N,N-t-butoxycarbonyl)aminopyridin-4-yl)methyl)-1-(tert-butyldimethylsilyl)-4-(hydroxymethyl)azetidin-2-one (103): To a solution of compound 102 (0.35 g, 0.56 mmol) in 10 ml anhydrous methanol was added sodium borohydride (0.128 g, 3.36 mmol) in several bacthes. The reaction was stirred at room temperature for 2 hr, then slowly quenched with water and acidified with 1N HCl. The reaction mixture was extracted with ethyl acetate (three times), dried over magnesium sulfate and concentrated in vacuo. The viscous oil was triturated with ether to give the alcohol 103 as a white solid (0.184 g, 63%). LS/MS M+H 522.3, calc. 522.29.

((2S,3R)-3-((2-(bis-N,N-t-butoxycarbonyl)aminopyridin-4-yl)methyl)-1-(tert-butyldimethylsilyl)-4-oxoazetidin-2-yl) methyl methanesulfonate (104): To a solution of alcohol 103 (0.047 mmol) in 2 ml of dichloromethane was added methanesulfonyl chloride (0.071 mmol) and triethylamine (0.141 mmol) dropwise and the reaction was stirred at room temperature overnight. Afterwards, it was concentrated in vacuo, diluted with ethyl acetate and washed with sodium bicarbonate. The layers were separated and the organic layer was dried over magnesium sulfate and concentrated in vacuo to give compound 104 as a yellow oil (85%). LS/MS M+H 600.3, calc. 600.22.

((2S,3R)-3-((2-(bis-N,N-t-butoxycarbonyl)-aminopyridin-4-yl)methyl)-4-oxoazetidin-2-yl)methyl methanesulfonate (105): To a solution of compound 104 (0.04 mmol) in 1 ml anhydrous methanol were added ammonium fluoride (0.048 mmol, 0.5 M in methanol) and acetic acid (0.144 mmol) and the reaction was stirred at room temperature for 2 h. Afterwards, it was concentrated in vacuo and the residual acetic acid was azeotroped with toluene. The solid was diluted with dichloromethane and was filtered through a syringe filter. The solution was concentrated in vacuo to give compound 105 as a clear oil (quantitative yield) LS/MS M+H 486.5, calc. 486.13.

((2S,3R)-1-(((R)-1-phenylethyl)carbamoyl)-3-((2-aminopyridin-4-yl)methyl)-4-oxoazetidin-2-yl)methyl methanesulfonate TFA salt (106): To a solution of compound 105 (0.04 mmol) in 2 ml anhydrous methylene chloride was added isocyanate (0.06 mmol) and triethyl amine (0.12 mmol) dropwise and the reaction mixture was stirred at room temperature for 5 h. Afterwards, the reaction mixture was concentrated in vacuo, diluted with ethyl acetate and washed with sodium bicarbonate. The layers were separated and the organic layer was dried over magnesium sulfate and concentrated in vacuo. Column chromatography purification (silica, hexane/ethyl acetate) gave the product in 70% yield. (LS/MS M+H 633.4, calc. 633.2). The product was treated with 1 ml TFA:dichloromethane for 1 h at room temperature. Afterwards, it was concentrated in vacuo and washed with ethyl ether (five times). Compound 106 was obtained as a white solid (76%). LS/MS M+H 433.3, calc. 433.15.

Synthesis of 112

(2S,3S)-ethyl 3-(benzyloxy)-1-(4-methoxyphenyl)-4-oxoazetidine-2-carboxylate (108): To a solution of p-anisidine (107, 5.4 mmol) in 10 ml anhydrous dichloromethane and 2 ml toluene were added ethyl glyoxylate (8.0 mmol, 50% solution in toluene) and anhydrous magnesium sulfate (3.0 g). The reaction mixture was heated at 70° C. for 3 h. Afterwards, the mixture was filtered and cooled to 0° C. with an ice/water bath. Triethylamine (10.8 mmol) and benzyloxyacetyl chloride (8.1 mmol) were added dropwise and the reaction mixture was stirred at room temperature for 18 h. Afterwards, it was concentrated in vacuo and triturated with ethyl ether and hexane to give compound 108 as a tan solid (69% yield). LS/MS M+H 356.2, calc. 356.12.

(2S,3S)-ethyl 1-(4-methoxyphenyl)-4-oxo-3-(trifluoromethylsulfonyloxy)azetidine-2-carboxylate (109): Palladium hydroxide (0.186 mmol, 20% on carbon, wet) was added to a round bottom flask. The flask was evacuated and backfilled with hydrogen (three times). Afterwards a solution of compound 108 (3.72 mmol) in anhydrous methanol (30 ml) was added to the flask and the reaction was stirred for 18 h at room temperature under a positive atmosphere of hydrogen. Afterwards, the mixture was filtered through celite and concentrated in vacuo to give the free alcohol as a white solid. To a cold (0° C.) solution of the alcohol (0.377 mmol) in anhydrous dichloromethane (2 ml) were added triethylamine (1.13 mmol) and trifluoromethanesulfonyl chloride (0.57 mmol) dropwise and the reaction was stirred at 0° C. for 30 min. Afterwards, it was diluted with ethyl acetate and washed with sodium bicarbonate. The layers were separated and the organic layer was dried over magnesium sulfate and concentrated in vacuo. Compound 109 was obtained as an orange solid (quant.yield). LS/MS M+H 398.5, calc. 398.3.

(2R,3R)-ethyl 3-mercapto-1-(4-methoxyphenyl)-4-oxoazetidine-2-carboxylate (110): To a solution of triisopropylsilane thiol (0.91 mmol) in anhydrous THF (2 ml) was added sodium hydride (0.68 mmol, 60% in mineral oil) and the reaction mixture was stirred at room temperature for 15 min. Afterwards, compound 109 (0.45 mmol, dissolved in 2 ml THF) was added to the reaction and the mixture was stirred at room temperature for 1 h. Then it was concentrated in vacuo, diluted with ethyl acetate and washed with sodium bicarbonate. The layers were separated and the organic layer was dried over magnesium sulfate and concentrated in vacuo. Column chromatography purification (12 g pre-packed silica column, hexane/ethyl acetate) afforded the protected thiol. The thiol (0.126 mmol) was then diluted with anhydrous methanol (2 ml) and ammonium fluoride (0.15 mmol, 0.5 M in methanol) and acetic acid (0.454 mmol) were added to the reaction and the mixture was stirred at room temperature for 2 h. Afterwards, it was concentrated in vacuo and the residual acetic acid was azeotroped with toluene. The solid was diluted with dichloromethane and was filtered through a syringe filter. The solution was concentrated in vacuo to give compound 110 as a clear oil (23% yield for both steps). LS/MS M+H 282.3, calc. 282.1.

(2R,3R)-ethyl 3-((2-bis(butoxycarbonyl)aminopyridin-4-yl)methylthio)-4-oxoazetidine-2-carboxylate (111): To a solution of compound 110 (0.05 mmol) in anhydrous THF (2 ml) was added sodium hydride (0.07 mmol, 60% in mineral oil) and the reaction mixture was stirred at room temperature for 15 min. Afterwards, bromide A was added (0.08 mmol) and the reaction was stirred at room temperature for 1 h. Then it was concentrated in vacuo, diluted with ethyl acetate and washed with sodium bicarbonate. The layers were separated and the organic layer was dried over magnesium sulfate and concentrated in vacuo. Column chromatography purification (4 g pre-packed silica column, hexane/ethyl acetate) afforded the product as a yellow oil (48% yield). The product was then diluted with acetonitrile (1 ml) and water (0.5 ml) and cooled to 0° C. with an ice water bath. Ceric ammonium nitrate (0.08 mmol) dissolved in water (0.5 ml) was added and the reaction was stirred at 0° C. for 30 min. Afterwards, the reaction was concentrated in vacuo and diluted with ethyl acetate and sodium bicarbonate. The aqueous layer was extracted with ethyl acetate (three times), dried over magnesium sulfate and concentrated in vacuo. Compound 111 was obtained was a clear oil (96% yield). LS/MS M+H 482.3, calc. 482.2.

(2R,3R)-ethyl 1-(((R)-1-phenylethyl)carbamoyl)-3-((2-aminopyridin-4-yl)methylthio)-4-oxoazetidine-2-carboxylate (112): To a solution of compound 111 (0.025 mmol) in 2 ml anhydrous methylene chloride were added isocyanate B (0.038 mmol) and triethylamine (0.075 mmol) dropwise and the reaction mixture was stirred at room temperature for 5 h. Afterwards, the reaction mixture was concentrated in vacuo, diluted with ethyl acetate and washed with sodium bicarbonate. The layers were separated and the organic layer was dried over magnesium sulfate and concentrated in vacuo. The product was treated with 1 ml TFA/dichloromethane for 1 h at room temperature. Afterwards, it was concentrated in vacuo and washed with ethyl ether. The two diastereomers were separated on reverse phase HPLC (acetonitrile/water as eluents). Compound 112 was obtained as a white solid (0.001 mg). LS/MS M+H 429.62, calc. 429.5

(2R,3R)-ethyl 3-((2-aminopyridin-4-yl)methylthio)-1-(4-methoxyphenyl)-4-oxoazetidine-2-carboxylate (113) and (2R,3S)-ethyl 3-((2-aminopyridin-4-yl)methylthio)-1-(4-methoxyphenyl)-4-oxoazetidine-2-carboxylate (114): Compound 113 and 114 were synthesized by the same method used to synthesis 112 with the omission of the $NH_4F$/AcOH/MeOH deprotection step. The final TFA deprotection yielded the mixture of the 113 and 114. The isomers were separated via reverse phase HPLC (acetonitrile/water) with 0.1% TFA added to the mobile phase.

Synthesis of 119

(3R,4S)-3-((2-bis(t-butoxycarbonyl)-aminopyridin-4-yl)methyl)-1-(tert-butyldimethylsilyl)-4-(2-diazoacetyl)azetidin-2-one (115): To a solution of compound 5 (100 mg, 0.186 mmol) in THF (1 mL) at −15° C. was added triethylamine (27.8 uL, 0.2 mmol) and ethyl chloroformate (20 uL, 0.2 mmol). The reaction mixture was then stirred at −15° C. for 30 minutes and the ppt was then filtered off under an atmosphere of argon. To the crude anhydride was then added acetonitrile (1 mL) and 2.0M $TMSCHN_2$ in hexanes (0.2 mL, 0.4 mmol). The reaction was stirred at 4° C. for 48 h, at which point LCMS showed complete conversion of starting material. Diethyl ether (25 mL) was added to the reaction and washed with 10% $NaHSO_4$ (25 mL), saturated $NaHCO_3$ (25 mL) and brine (25 mL). The crude material was purified by Combiflash silica gel chromatography (0-3 min: 100% hexanes, 3-10 min: 40% EtOAc in hexanes) to yield 115 (32 mg). Exact mass. 559.28. Found ES MS [M+H]⁺559.9.

(3R,4S)-3-((2-bis(t-butoxycarbonyl)-aminopyridin-4-yl)methyl)-4-(2-diazoacetyl)azetidin-2-one (116): To a solution of 115 (50 mg, 0.089 mmol) in methanol (1 mL) at room temperature was added 0.5 M ammonium fluoride (178 uL, 0.089 mmol) and acetic acid (14 uL, 0.257 mmol). The reaction was stirred for 16 hours and then purified with Combiflash silica gel chromatography (0-10 min: 100% ethyl acetate) to yield 116 (39 mg).

(2S,3R)-3-((2-bis(t-butoxycarbonyl)-aminopyridin-4-yl)methyl)-2-(2-diazoacetyl)-4-oxo-N-((R)-1-phenylethyl)azetidine-1-carboxamide (117): To a solution of 116 (39 mg, 0.089 mmol) in anhydrous DCM (2 mL) was added (R)-(+)-methylbenzylamine (30 mg, 2 eq.) and triethylamine (36 uL, 3 eq.). The reaction was stirred for 16 hours and the crude mixture was purified via preparative TLC (70% EtOAc in hexanes) to yield 117 (43.4 mg).

Ethyl 2-((2R,3R)-1-(((R)-1-phenylethyl)carbamoyl)-3-((2-bis(t-butoxycarbonyl)-aminopyridin-4-yl)methyl)-4-oxoazetidin-2-yl)acetate (118): To a solution of 117 (10 mg, 0.016 mmol) in ethanol (2 mL) was added silver benzoate (1 mg, 10% w/w) and the mixture was stirred at room temperature for 16 hours. The crude material was then purified by preparative TLC (70% EtOAc in hexanes) to yield 118 (4 mg). Exact mass. 610.3. Found ES MS [M+H]+610.9.

Ethyl 2-((2R,3R)-1-(((R)-1-phenylethyl)carbamoyl)-3-((2-aminopyridin-4-yl)methyl)-4-oxoazetidin-2-yl)acetate (119): Compound 118 was dissolved in 1:1 TFA:DCM (2 mL) and the reaction stirred for 2 hours and then concentrated in vacuo to yield a crude material which was purified by reverse phase HPLC (acetonitrile/water with 0.1% TFA) to yield 119 (1.2 mg).

Synthesis of 123

Alkylating Agent Synthesis

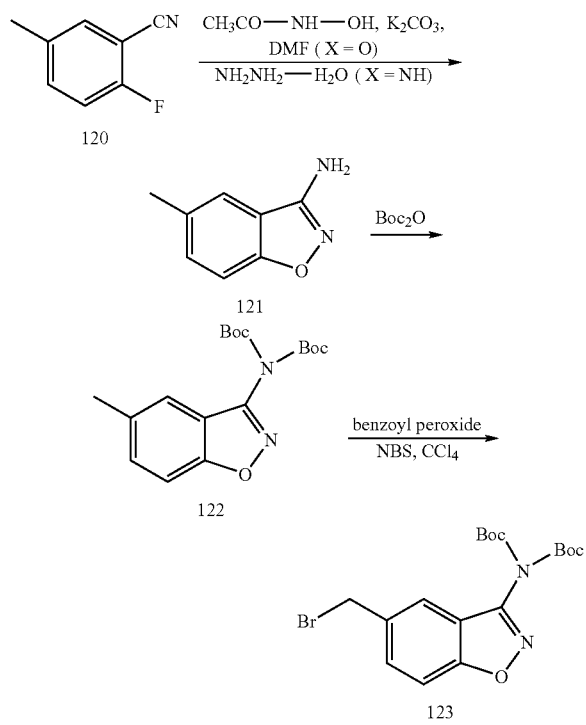

5-Methyl-benzo[d]isoxazoll-3-ylamine (121) Acetohydroxamic acid (1.69 g, 22.5 mmol) in DMF (45 mL) was stirred with $K_2CO_3$ and several drops of water at RT for 30 min, the 2-fluoro-5-methylbenzonitrile (120) (1.35 g, 10 mmol) in DMF (5 mL) was added and the reaction mixture was stirred at RT for 3 days. The reaction was diluted with water and the mixture was extracted with ethyl acetate. The organic layer was dried over $Na_2SO_4$ and concentrated in vacuo to provide 121 (878 mg, 60%). LC-MS (ESI) m/z 149.2.

Benzo[d]isoxazol-3-bis(N,N-t-butoxycarbonyl)amine (122): To a solution of 121 (148 mg, 1 mmol) in DCM (2 mL) was added di-t-butyldicarbonate (546 mg, 2.5 mmol), DIEA (0.348 mL, 2 mmol), and DMAP (22.2 mg, 1 mmol) at 0° C. The reaction was warmed up to RT and stirred for 4 hr and then diluted with ethyl acetate and treated with aqueous ammonium chloride to pH 6. The organic layer was separated and washed with brine and concentrated in vacuo. The residue purified by silica gel chromatography using 100% hexane as the eluent to yield 122 (347 mg, 100%), LC-MS (ESI) m/z 348.8.

5-(Bromomethyl)benzo[d]isoxazol-3-(bis(t-butoxycarbonyl))amine (123): To a solution of 122 (1.37 g, 3.9 mmol) in $CCl_4$ was added N-bromosuccinimide (700 mg, 1 eq.) and benzoyl peroxide (54 mg, 0.04 eq.). The mixture was heated to 85° C. for 4 hours and then filtered after cooling to room temperature. The filtrated was concentrated in vacuo and purified via silica gel chromatography eluting with 0-10% EtOAc in hexanes to provide 123 (630 mg).

Synthesis of 129

(S)-benzyl 4-oxo-1-(phenylcarbamoyl)azetidine-2-carboxylate (125) A solution of aniline (124) (0.186 mL, 2 mmol) and triethylamine (0.28 mL, 2 mmol) in dichloromethane (5 mL) was dropped into a phosgene solution (1.27 mL, 20% in toluene) at 0° C. and stirred for 30 min. Then (S)-benzyl 4-oxoazetidine-2-carboxylate (531 mg, 2.6 mmol) in THF (5 mL) was added. The resultant reaction mixture was stored in a refrigerator overnight and then filtered. The filtrate was condensed and the residue was purified by medium pressure chromatography (silica gel column) with dichloromethane as the eluent to provide 125 (474 mg, 73%). $^1$H NMR ($CDCl_3$) δ8.28 (br, 1H), 7.48-7.29 (m, 9H), 7.14-7.09 (m, 1H), 5.25 (s, 2H), 4.62-4.57 (m, 1H), 3.43-3.35 (m, 1H), 3.12-3.05 (m, 1H), LC-MS (ESI) m/z 324.0.

(S)-4-oxo-1-(phenylcarbamoyl)azetidine-2-carboxylate acid (126) Compound 125 was dissolved in a methanol-ethanol solution and 10% Pd-C catalyst was added. The reaction vessel was then evacuated and flushed with hydrogen. The reaction was stirred under an atmosphere of hydrogen until all the starting material was consumed as evidenced by LCMS to yield 126 (quantitative yield). $^1$H NMR (MeOD) δ7.63-7.46 (m, 2H), 7.34-7.29 (m, 2H), 7.13-7.08 (m, 1H), 4.54-4.51 (m, 1H), 3.48 (dd, J=6.4, 15.8 Hz, 1H), 3.09 (dd, J=2.3, 16.8 Hz, 1H), LC-MS (ESI) m/z 234.9.

(2S,3R)-3-((3-di-Boc-aminobenzo[d]isoxazol-5-yl)methyl)-4-oxo-1-(phenylcarbamoyl)azetidine-2-carboxylic acid (128) A solution of 126 (41 mg, 0.174 mmol) in THF was added to 1.0M LiHMDS in THF (0.635 mL) at –78° C. and the reaction mixture was stirred for 30 min and then slowly warmed up to room temperature over 1 h. The reaction mixture was cooled back to –78° C. followed by addition of compound 127 (44 mg, 0.103 mmol) dissolved in THF. After 30 min, the reaction mixture was warmed up to 0° C. for one hour and then to room temperature for another hour. The reaction was quenched with aqueous ammonia chloride and extracted with ethyl acetate. The organic layer was dried over $Na_2SO_4$ and concentrated in vacuo. The residue was purified by preparative TLC to afford 128 (32 mg, 54%), LC/MS (ESI) m/z 581.0.

(2S,3R)-3-((3-aminobenzo[d]isoxazol-5-yl)methyl)-4-oxo-1-(phenylcarbamoyl)-azetidine-2-carboxylic acid (129): Compound 128 (32 mg) was treated with 20% TFA-DCM for 20 min at room temperature. The reaction was concentrated in vacuo and the residue was purified by preparative HPLC (Vydac, Protein & Peptide C18 column, 0-60% $H_2O$-acetonitrile w/0.1% TFA, gradient change in 50 min) to afford 129 (7.2 mg, 26%), $^1$H NMR (DMSO) δ8.95 (s, 1H), 7.77 (s, 1H), 7.55 (d, J=8.3 Hz, 3H), 7.43 (d, J=8.55 Hz, 1H), 7.36 (t, J=7.7 Hz, 2H), 7.13 (t, J=7.4 Hz, 1H), 4.35 (d, J=2.8 Hz, 1H), 3.76 (m, 1H), 3.27 (d, J=7.7 Hz, 2H), LC-MS (ESI) m/z 381.1.

(2S,3R)-3-((3-amino-1H-indazol-5-yl)methyl)-4-oxo-1-(phenylcarbamoyl)azetidine-2-carboxylic acid (130): Compound 130 was prepared analogously to 129 using hydrazine instead of acetohydroxamic acid in the synthesis of the alkylating agent. Yield 2.3 mg. $^1$H NMR (DMSO) δ11.60 (br, 1H), 8.90 (s, 1H), 7.63 (s, 1H), 7.51 (d, J=6.0 Hz, 2H), 7.35-7.20 (m, 5H), 7.09 (t, J=6.9 Hz, 1H), 6.45 (br, 2H), 4.28 (d, J=2.7 Hz, 1H), 3.69 (dt, J=2.7, 7.3 Hz, 1H), 3.17 (d, J=7.4 Hz, 2H), LC-MS (ESI) m/z 380.1.

Example 9

General Method J for the Synthesis of 3-Substituted-amino Beta-lactams

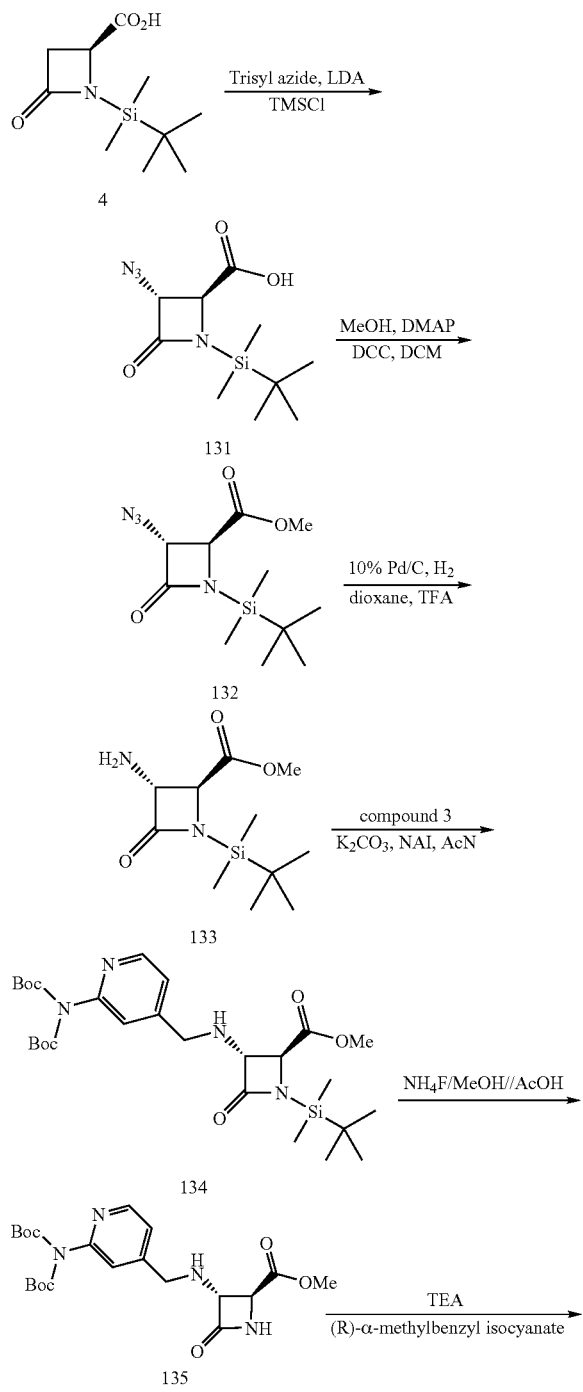

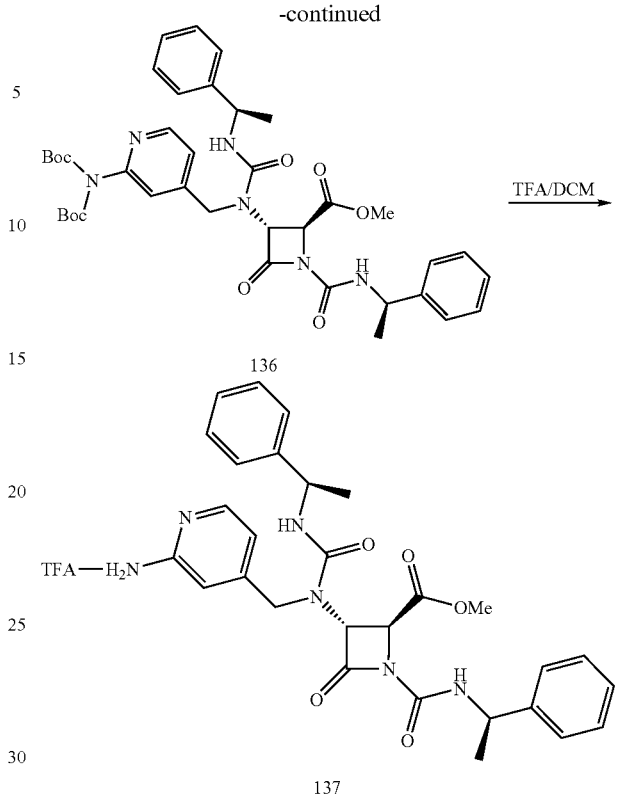

(2S,3R)-3-azido-1-(tert-butyldimethylsilyl)-4-oxoazetidine-2-carboxylic acid (131): To LDA (1.8M, 4.99 mL) and THF (10 mL) at −78° C. was added dropwise (S)-1-t-butyldimethylsilyl-4-oxo-2-azetidinecarboxylic acid (4, 1.0 g) in THF (15 mL). The resulting solution was warmed to −30° C. or −10° C. for 30 min. If a slurry formed, additional THF was added to solublize the azetidine. After 30 min., the solution was cooled to −78° C. A pre-cooled solution (−10° C.) of trisyl azide (1.61 g) in THF (10 mL) was added slowly. The reaction mixture was stirred for one hour before quenching with TMSCl (0.82 mL). The cold bath was then removed and the solution allowed to stir for an additional hour. Saturated sodium bicarbonate (100 mL) was added and the aqueous layer was extracted with diethyl ether (2×100 mL). The organic extracts were discarded. The aqueous layer was then brought to pH=7 by slow addition of 1N HCl and extracted with Et$_2$O (2×100 mL) and the organic layers were discarded. The aqueous layer was then brought to pH=3 by slow addition of 1N HCl and extracted with EtOAc (3×100 mL). The combined organic layers were dried over MgSO$_4$ and concentrated in vacuo to yield 131 which was taken on to the next step without further purification.

(2S,3R)-methyl 3-azido-1-(tert-butyldimethylsilyl)-4-oxoazetidine-2-carboxylate (132): To a solution of crude 131 (1.58 g) in CH$_2$Cl$_2$ (25 mL) was added methanol (0.26 mL, 6.43 mmol). DCC (1.45 g, 7.02 mmol) and catalytic DMAP. The solution was stirred at room temperature overnight. The solution was then filtered through Celite and concentrated in vacuo. The crude product was purified by silica gel column chromatography, eluting with 20% EtOAc in hexanes, to yield pure 132.

(2S,3R)-methyl 3-amino-1-(tert-butyldimethylsilyl)-4-oxoazetidine-2-carboxylate (133): To a solution of 132 (5.85 mmol) in 3:1 methanol:dioxane (25 mL) was added a few drops of TFA and 10% Pd/C (10 wt %). The reaction was stirred under atmospheric hydrogen for one hour and then filtered through Celite. The solvent was removed and the residue triturated with diethyl ether to afford 133, which was used in the next step without further purification.

(2S,3R)-methyl 1-(tert-butyldimethylsilyl)-3-((2-(di-(t-butoxycarbonyl)-amino)pyridin-4-yl)methylamino)-4-oxoazetidine-2-carboxylate (134): To a solution of 133 and 3 in acetonitrile was added potassium carbonate and catalytic NaI. The resultant solution was heated at reflux until complete by TLC (~1-2 h.) The solution was then cooled and the solvent removed in vacuo. The residue was taken up in ethyl acetate and the organic layer was washed with water (2×X mL) and brine (×mL.). The organic layer was then dried over MgSO$_4$, and concentrated in vacuo. The product was then purified by silica gel chromatography, eluting with 50-100% ethyl acetate in hexanes, to yield pure 134.

(2S,3R)-methyl 3-((2-(di-(t-butoxycarbonyl)-amino)pyridin-4-yl)methylamino)-4-oxoazetidine-2-carboxylate (135): Compound 135 was synthesized following the procedure outlined in steps 2 of General method C.

(2S,3R)-methyl 1-(((R)-1-phenylethyl)carbamoyl)-3-(1-((2-(di-(t-butoxycarbonyl)-amino)pyridin-4-yl)methyl)-3-((R)-1-phenylethyl)ureido)-4-oxoazetidine-2-carboxylate (136): Compound 136 was synthesized following the procedure outlined in steps 3 of General method C.

(2S,3R)-methyl 1-(((R)-1-phenylethyl)carbamoyl)-3-(1-((2-aminopyridin-4-yl)methyl)-3-((R)-1-phenylethyl)ureido)-4-oxoazetidine-2-carboxylate (137), TFA salt: Compound 137 was synthesized following the procedure outlined in steps 5 of General method C.

Example 10

General Method K for the Preparation of geminal dimethyl Beta-lactams

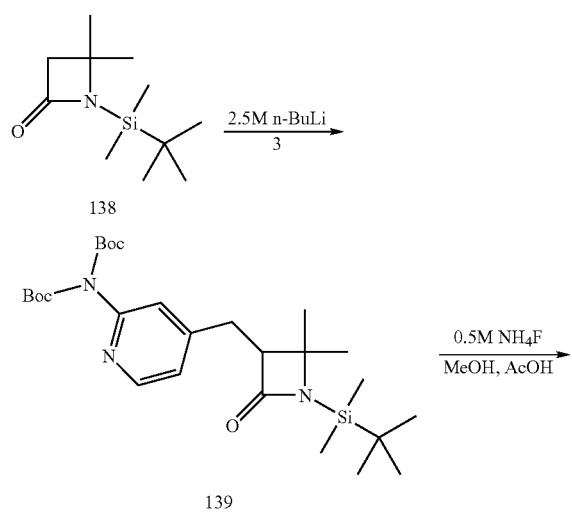

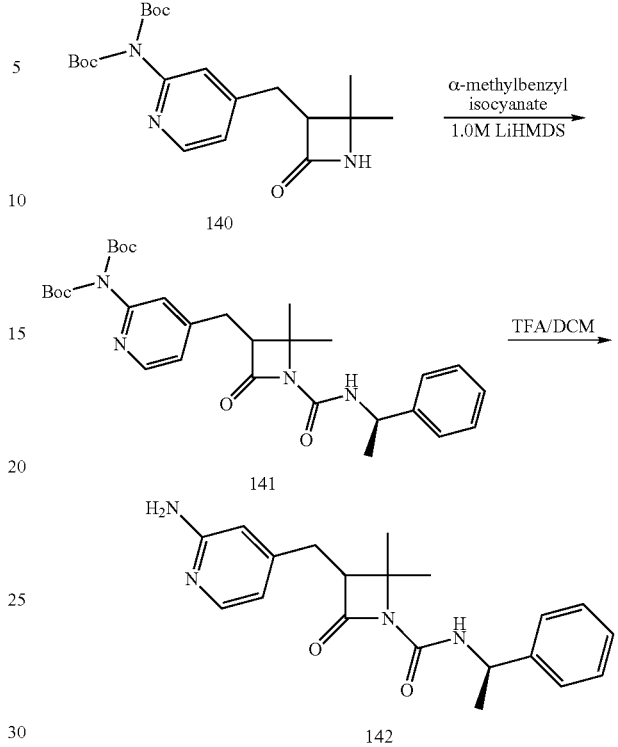

1-(Tert-butyldimethylsilyl)-3-(3-chloropropyl)-4,4-dimethylazetidin-2-one (138): 4,4-dimethylazetidin-2-one was prepared as described in *J. Medicinal Chemistry* 1994, 37, 897-906 and then as described in U.S. Pat. No. 6,335,324.

3-((2-(N,N-bis-tert-butoxycarbonyl)-aminopyridin-4-yl)methyl)-1-(tert-butyldimethylsilyl)-4,4-dimethylazetidin-2-one (139): The alkylation procedure from patent U.S. Pat. No. 6,335,324, p. 22 except a) 3,4-bromomethyl-2-bis-Boc-aminopyridine, was used as the alkylating agent instead of 3-chloropropyl iodide and b) the reaction was allowed to warm up to room temperature after the addition of the 3.

3-((2-(N,N-bis-tert-butoxycarbonyl)-aminopyridin-4-yl)methyl)-4,4-dimethylazetidin-2-one (140): To 139 (31 mg) was added 0.5M NH$_4$F in methanol (143 uL) and acetic acid (11 uL) and stirred until disappearance of the starting material. The reaction was concentrated in vacuo and re-dissolved in DCM. After 2 hr, the precipitate was filtered and the filtrate purified via preparative TLC (50% ethyl acetate in hexanes) to yield 140 (20 mg, 84%).

3-((2-(N,N-bis-tert-butoxycarbonyl)-aminopyridin-4-yl)methyl)-2,2-dimethyl-4-oxo-N-((R)-1-phenylethyl)azetidine-1-carboxamide (141): To a solution of 140 (0.03 mmol) in anhydrous THF (1 mL) was cooled to −78° C. and then 1.0 M LiHMDS (1.2 eq) was added slowly via syringe. After stirring for 30 minutes at −78° C., α-methylbenzyl isocyanate (1.2 eq.) was added via syringe. The reaction was then allowed to warm up to 0° C. over 30 minutes (or until LCMS showed no starting material). The reaction was then quenched with saturated ammonium chloride, extracted with ethyl acetate, and the organic layer was dried over sodium sulfate. The reaction was concentrated in vacuo and taken on without further purification.

3-((2-aminopyridin-4-yl)methyl)-2,2-dimethyl-4-oxo-N-((R)-1-phenylethyl)azetidine-1-carboxamide (142): A solution of crude 141 in DCM (1 mL) was cooled to 0° C. and then TFA (200 uL) was added. After 4 hr, the reaction was concentrated in vacuo and the crude material purified via reverse phase HPLC (acetonitrile/water) with 0.1% TFA to yield 142 (13.3 mg) as the TFA salt.

Example 11
General Method L for the Preparation of
3-propylguanidine Beta-lactams
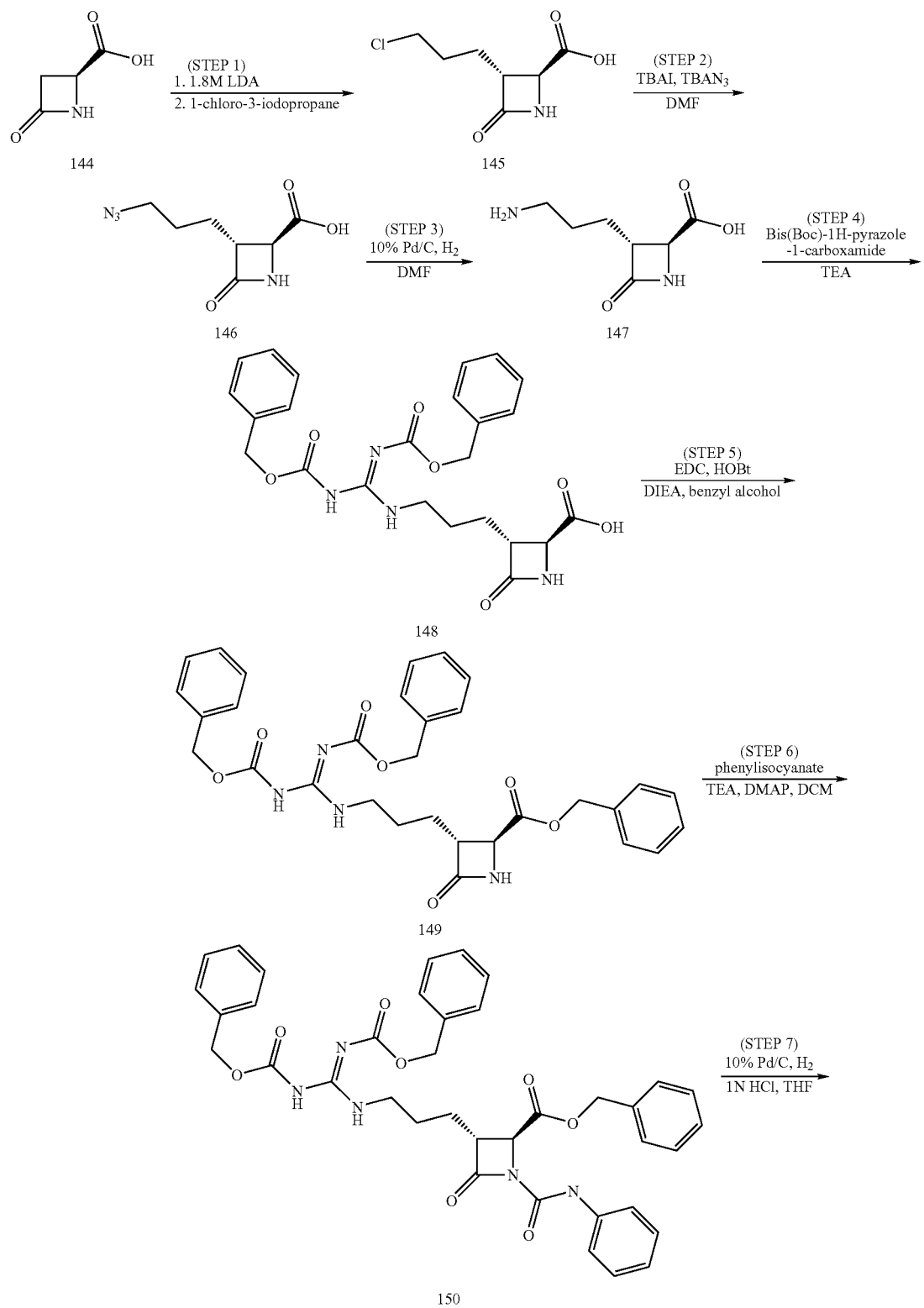

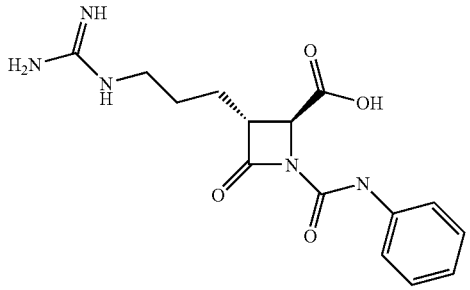

151

4(2S,3R)-3-(3-chloropropyl)-4-oxoazetidine-2-carboxylic acid (145): Commercially available beta-lactam acid 144 (1 g, 1.0 eq.) was dissolved in anhydrous THF (15 mL) and the solution was cooled to −78° C. under an atmosphere of argon. 1.8M LDA in heptane/THF/ethylbenzene (5.9 mL, 2.4 eq.) was added slowly to the cooled solution via syringe. The reaction was stirred for 20 minutes at −78° C. and then 1-chloro-3-iodopropane (0.6 mL, 1.2 eq.) was slowly added to the cooled solution. The reaction was stirred a further hour at −78° C., warmed to room temperature and poured into 1:1 cold 1N HCl: brine (75 mL). The aqueous phase was extracted with ethyl acetate (2×75 mL) and the organic layers were combined and washed with saturated NaHCO$_3$ (2×25 mL). The basic layer was then washed again with ethyl acetate (75 mL). The basic aqueous layer was then acidified with 1N HCl-brine and extracted with ethyl acetate (2×50 mL) and the organic layers were combined and dried over sodium sulfate. Concentration in vacuo yielded 145 (0.88 g) as a dark yellow oil.

(2S,3R)-3-(3-azidopropyl)-4-oxoazetidine-2-carboxylic acid (146): To a solution of 145 (1.0 g, 1.0 eq.) in anhydrous DMF (5 mL) was added tetrabutylammonium iodide (60 mg, 0.05 eq.) and tetrabutylammonium azide (1.1 g, 1.2 eq.). The reaction was stirred at room temperature for 72 hours and the poured into 1N HCl-brine and extracted with ethyl acetate (2×20 mL). Then the organic layers were extracted with saturated NaHCO$_3$ (3 15 mL). The combined basic aqueous layers were then acidified with 1N-HCl:brine and then the acidic solution was extracted with ethyl acetate (3×20 mL). These last organic layers were combined, dried over magnesium sulfate and concentrated in vacuo to yield 146 (0.59 g ) as a brown oil.

(2S,3R)-3-(3-aminopropyl)-4-oxoazetidine-2-carboxylic acid (147): To a solution of 146 (0.59 g, 1.0 eq.) in DMF (5 mL) and acetic acid (1 mL) was added 10% Pd/C (300 mg). The flask was evacuated and flushed with hydrogen. The reaction was then stirred at room temperature under an atmosphere of hydrogen for 16 hours. The reaction was then filtered through Celite and crude amine 147 was immediately used in the next step as a solution in DMF.

(2S,3R,E)-3-(3-(2,3-bis(3-phenylpropanoyl)guanidino)propyl)-4-oxoazetidine-2-carboxylic acid (148): To the DMF solution of amine 147 (330 mg of amine) was added N,N'bis(benzyloxycarbonyl)-1H-pyrazole-1-carboxamide (718 mg, 1.0 eq.) and DIEA (1.5 mL). The reaction was stirred at room temperature for 6 hours and then poured into 1N HCl:brine and extracted with ethyl acetate (2×30 mL). The organic layers were combined and extracted with saturated NaHCO$_3$ (2×25 mL). The basic aqueous layers were then acidified with 1N HCl:brine and extracted with ethyl acetate (2×25 mL). These last organic layers were dried over sodium sulfate and concentration in vacuo yielded a crude material (200 mg) as a colorless oil. The crude material was purified via silica gel chromatography eluting with a gradient elution from ethyl acetate to 1% acetic acid in EtOAc to give 148 (74 mg).

(2S,3R,E)-benzyl 3-(3-(2,3-bis(3-phenylpropanoyl)guanidino)propyl)-4-oxoazetidine-2-carboxylate (149): To a solution of 148 (74 mg, 1.0 eq.) in DMF (1.5 mL) was added benzyl alcohol (19 uL, 1.2 eq.), EDC-HCl (35 mg, 1.2 eq.), HOBt (24 mg, 1.2 eq.) and DIEA (60 µL eq.). The reaction was stirred at room temperature for 16 hours and then diluted with ethyl acetate and washed with 1N HCl. The aqueous layer was then washed with ethyl acetate (2×10 mL). The combined organics were then washed with saturated NaHCO$_3$ (2×10 mL), water (10 mL), dried over magnesium sulfate and concentrated in vacuo to give the crude product (55 mg) as a colorless oil. The product was purified by silica gel chromatography using a gradient elution from 20% EtOAc in hexanes to 50% EtOAc in hexanes to yield 149 (50 mg).

(2S,3R,E)-benzyl 3-(3-(2,3-bis(3-phenylpropanoyl)guanidino)propyl)-4-oxo-1-(phenylcarbamoyl)azetidine-2-carboxylate (150): To a solution of 149 (50 mg, 1.0 eq.) in DCM (2 mL) was added phenylisocyanate (29 µL, 3.0 eq.), triethylamine (12 µL, 1 eq.) and DMAP (1 mg). The reaction was stirred for 18 hours at room temperature and then diluted with dichloromethane and washed with 1N HCl and water. The organic layer was then concentrated in vacuo and purified via silica gel chromatography eluting with 15% EtOAc in hexanes to give 150 (10 mg).

(2S,3R)-3-(3-guanidinopropyl)-4-oxo-1-(phenylcarbamoyl)azetidine-2-carboxylic acid (151): To a solution of 150 (10 mg, 1.0 eq.) in THF (3 mL) and 1N HCl (0.5 mL) was added 10% Pd/C (20 mg). The reaction flask was then evacuated and flushed with hydrogen and stirred under an atmosphere of hydrogen for 18 hours. The reaction was then filtered through Celite and concentrated in vacuo. The crude material was purified via HPLC (C18, acetonitrile/water, 0.1% TFA) to yield 151 (0.5 mg).

(2S,3R)-Ethyl 3-(3-guanidinopropyl)-4-oxo-1-(phenylcarbamoyl)azetidine-2-carboxylate (152): Compound 152 was synthesized by general method L using ethyl alcohol (step 5) and phenyl isocyanate (step 6) to yield 152.

(2S,3R)-1-((4-Methoxybenzyl)carbamoyl)-3-(3-guanidinopropyl)-4-oxoazetidine-2-carboxylic acid (153): Compound 153 was synthesized by general method L using 4-methoxylbenzylisocyanate (step 6) to yield 153 (6.8 mg).

(2S,3R)-1-((4-Methoxyphenethyl)carbamoyl)-3-(3-guanidinopropyl)-4-oxoazetidine-2-carboxylic acid (154): Compound 154 was synthesized by general method L using 4-methoxyphenethylisocyanate (step 6) to yield 154 (23 mg).

(2S,3R)-1-(((R)-1-(Naphthalen-1-yl)ethyl)carbamoyl)-3-(3-guanidinopropyl)-4-oxoazetidine-2-carboxylic acid (155): Compound 155 was synthesized by general method L using (R)-1-naphthylethylisocyanate (step 6) to yield 155 (31.1 mg, 66%).

(2S,3R)-1-((3-Ethylphenyl)carbamoyl)-3-(3-guanidinopropyl)-4-oxoazetidine-2-carboxylic acid (156): Compound 156 was synthesized by general method L using 4-ethylphenylisocyanate (step 6) to yield 156 (25.1 mg, 61%).

(2S,3R)-1-(((S)-1-Phenylethyl)carbamoyl)-3-(3-guanidinopropyl)-4-oxoazetidine-2-carboxylic acid (157): Compound 157 was synthesized by general method L using (S)-1-methylbenzylisocyanate (step 6) to yield 157.

(2S,3R)-1-(((S)-1-(naphthalen-1-yl)ethyl)carbamoyl)-3-(3-guanidinopropyl)-4-oxoazetidine-2-carboxylic acid (158): Compound 158 was synthesized by general method L using (S)-1-naphthylethylisocyanate (step 6) to yield 158 (25.3 mg, 77%).

(2S,3R)-1-((4-ethylphenyl)carbamoyl)-3-(3-guanidinopropyl)-4-oxoazetidine-2-carboxylic acid (159): Compound 159 was synthesized by general method L using 4-ethylphenylisocyanate (step 6) to yield 159 (24.8 mg, 63%).

(2S,3R)-1-(((R)-1-phenylethyl)carbamoyl)-3-(3-guanidinopropyl)-4-oxoazetidine-2-carboxylic acid (160): Compound 160 was synthesized by general method L using (R)-1-methylbenzylisocyanate (step 6) to yield 160.

What is claimed is:

1. A compound according to the following structure:

wherein
A is a member selected from $CR^1R^2$, O and S
wherein
$R^1$ is H,
$R^2$ is H,
B is a member independently selected from unsubstituted alkyl, —S—, and —O—;
m is an integer selected from 0 to 2;
C is a member selected from a bond and —O—;
D is a member selected from X is a member selected from S and O;
Y is a member selected from a bond, C=O, and $SO_2$;
$R_a$ is a member selected from $NR^7R^8$ and substituted and unsubstituted heteroaryl
wherein
$R^7$ is a member selected from H, substituted or unsubstituted alkyl, substituted or unsubstituted cycloalkyl, substituted or unsubstituted aryl, and substituted or unsubstituted heteroaryl; and
$R^8$ is a member selected from substituted or unsubstituted alkyl, substituted or unsubstituted cycloalkyl, substituted or unsubstituted aryl, and substituted or unsubstituted heteroaryl;
$R_c$ is a member selected from H and substituted or unsubstituted alkyl;
$R_d$ is a member selected from $R^{16}$ and $(CR^{14}R^{15})_pR^{16}$
wherein
p is 1;
$R^{14}$ is H;
$R^{15}$ is H; and
$R^{16}$ is a member selected from $C(O)R^{18}$, OH, and wherein
$R^{18}$ is a member from $OR^{21}$, $NR^{19}R^{20}$, and $NR^{19}SO_2R^{20}$
wherein
$R^{21}$ is a member selected from H, substituted or unsubstituted alkyl, substituted or unsubstituted cycloalkyl, and substituted or unsubstituted aryl;
$R^{19}$ is a member selected from H and substituted or unsubstituted alkyl; and
$R^{20}$ is a member selected from H, substituted or unsubstituted alkyl, substituted or unsubstituted heteroalkyl, substituted or unsubstituted cycloalkyl, substituted or unsubstituted aryl, and substituted or unsubstituted heteroaryl; and
$R^{19}$ and $R^{20}$ can be optionally joined, together with the atoms to which they are attached, to form a 6 membered ring; and
$R_d$ is H;
with the proviso for the compound, or salts thereof, that if:
Y is a member selected from C=O and $SO_2$;
ABC, in combination, form unsubstituted alkyl; and
D is substituted or unsubstituted guanidine;

then $R_c$ cannot be a member selected from $CH_3$ and $CH_2CH_3$; and $R_d$ and $R_d'$ cannot be members selected from H and $COOR^{1a}$; and H and $CONR^{19}R^{20}$;

wherein $R^{1a}$ is a member independently selected from H, substituted or unsubstituted alkyl, substituted or unsubstituted cycloalkyl, and substituted or unsubstituted aryl;

$R^{19}$ is selected from H and substituted or unsubstituted alkyl; and $R^{20}$ is selected from H, substituted or unsubstituted alkyl, substituted or unsubstituted heteroalkyl, substituted or unsubstituted cycloalkyl, substituted or unsubstituted aryl, and substituted or unsubstituted heteroaryl.

2. The compound according to claim 1, wherein at least one of said $R^7$, $R^8$, $R^{16}$, $R^{18}$, $R^{19}$, $R^{20}$, and $R^{21}$ is a member selected from substituted or unsubstituted arylalkyl and substituted or unsubstituted heteroarylalkyl.

3. The compound according to claim 2, wherein at least one of said $R^{1a}$, $R^{16}$, $R^{18}$, $R^{19}$, $R^{20}$, $R^{21}$, and $R_a$ is a member selected from substituted or unsubstituted arylalkyl and substituted or unsubstituted heteroarylalkyl.

4. The compound according to claims 1 or 2, wherein $AB_mCD$, in combination, form a member selected from

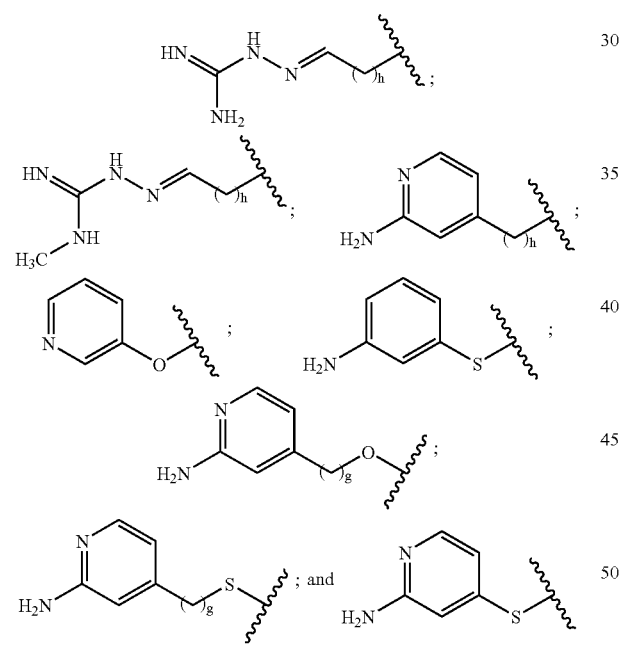

wherein g is an integer selected from 1 and 2; and h is an integer selected from 1 to 3.

5. The compound according to claim 1 or 2, wherein $R_d$ is a member selected from

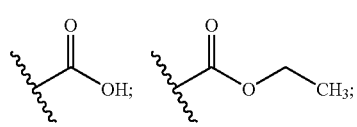

-continued

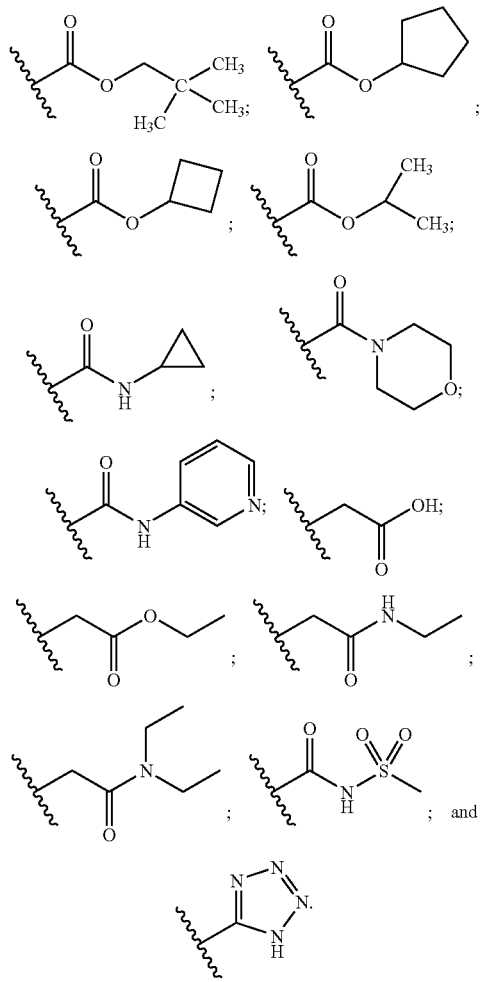

6. The compound according to claim 1 or 2, wherein —Y—$R_a$, in combination, form a member selected from

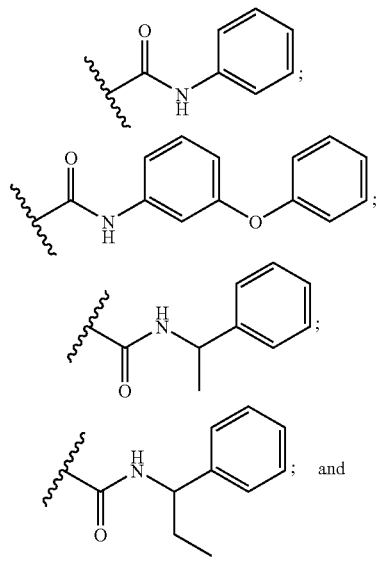

-continued

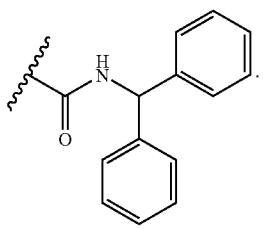

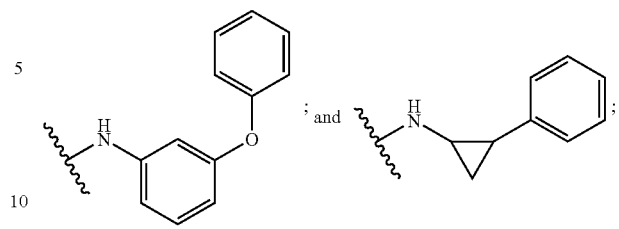

7. The compound according to claim 1, wherein $R_c$ is a member selected from H, methyl and ethyl.

8. The compound according to claim 1 or 4 or 5 or 6 or 7, wherein X is S.

9. The compound according to claim 1, wherein $R_a$ is a member selected from $R_d$ is a member selected from

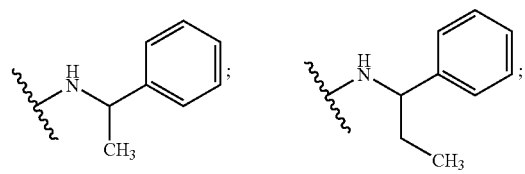

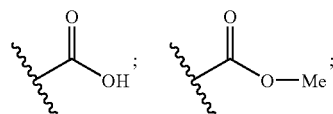

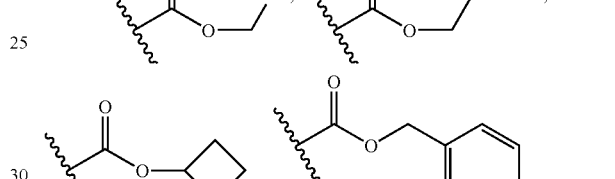

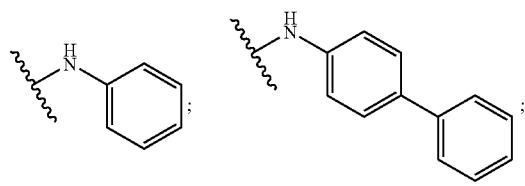

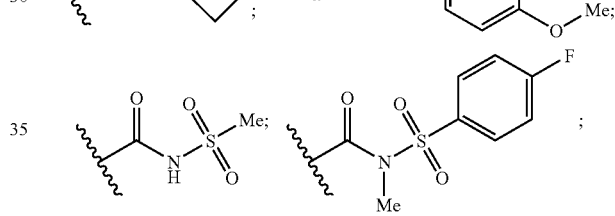

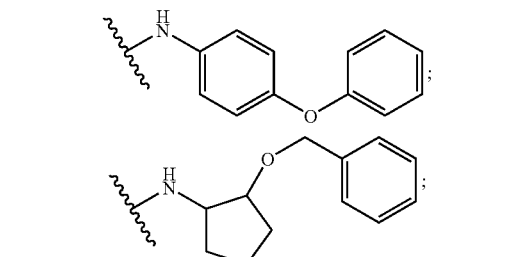

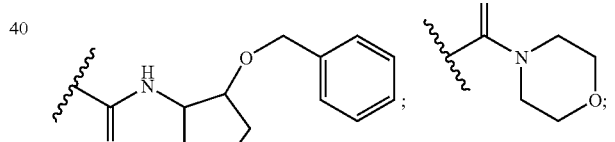

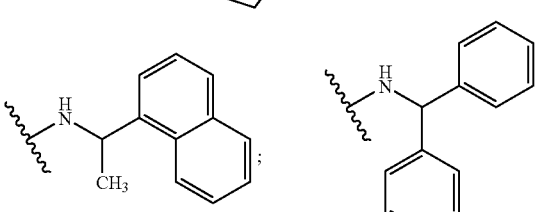

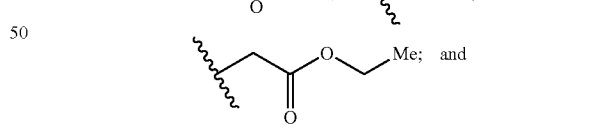

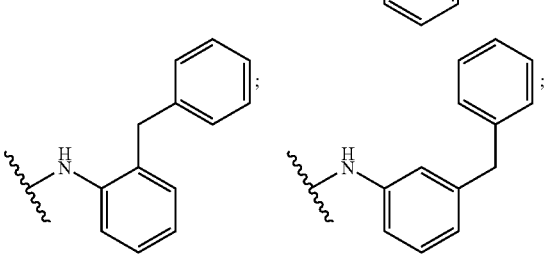

Y is a member selected from C(O) and S(O)$_2$, wherein Me is methyl.

10. The compound according to claim 9, wherein AB$_m$CD, in combination, form a member selected from

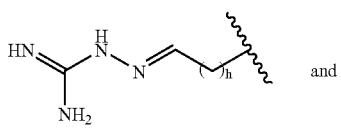

-continued

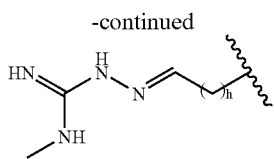

wherein h is an integer selected from 1 to 3.

11. The compound according to claim 9, wherein $AB_mCD$, in combination, form a member selected from

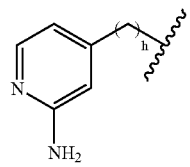

wherein h is an integer selected from 1 to 3;

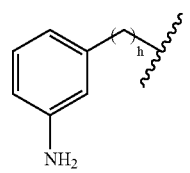

wherein h is an integer selected from 1 to 3;

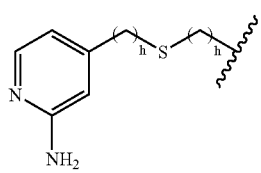

wherein h is an integer selected from 0 and 1;

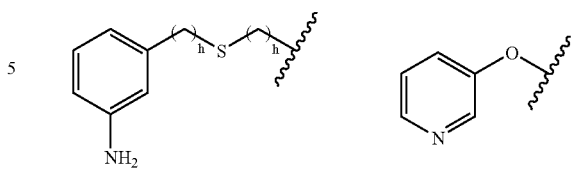

wherein h is an integer selected from 0 and 1; and.

12. A pharmaceutical composition comprising an effective amount of a compound of claim 1 including an inner salt or a pharmaceutically acceptable salt thereof, or a hydrolysable ester thereof and one or more pharmaceutically acceptable excipients.

13. The pharmaceutical composition according to claim 12, wherein said composition is useful for enhancing thrombolyis or treating thrombosis, asthma, chronic asthma, or allergic rhinitis.

14. A method for treating asthma, chronic asthma or allergic rhinitis in a mammalian species comprising administering an effective amount of the composition of claim 1.

15. A method of inhibiting tryptase in a mammal by administration of a compound according to claim 1.

16. A method of enhancing thrombolysis or treating thrombosis in a mammalian species comprising administering an effective amount of the composition of claim 1.

17. A method of inhibiting Factor XIa in a mammal by administration of a compound according to claim 1.

* * * * *

UNITED STATES PATENT AND TRADEMARK OFFICE
CERTIFICATE OF CORRECTION

PATENT NO. : 7,501,404 B2  Page 1 of 1
APPLICATION NO. : 11/398438
DATED : March 10, 2009
INVENTOR(S) : Thomas Bannister et al.

It is certified that error appears in the above-identified patent and that said Letters Patent is hereby corrected as shown below:

In claim 1, column 146, lines 12-13, that portion of the text reading "substituted and unsubstituted" should read --substituted or unsubstituted--.

In claim 1, column 146, line 62, that portion of the text reading "$R_d$" should read --$R_d'$--.

In claim 9, column 150, lines 46-49, cancel the following structure:

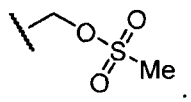

In claim 11, column 152, lines 1-13, remove the structure:

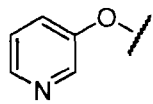

above the text beginning with "wherein h is" and insert the same structure between the text ending "from 0 and 1; and" and the period in column 152, line 13.

Signed and Sealed this
Seventh Day of June, 2011

David J. Kappos
*Director of the United States Patent and Trademark Office*